US012790314B2

(12) United States Patent
Pourashraf et al.

(10) Patent No.: US 12,790,314 B2
(45) Date of Patent: *Nov. 10, 2026

(54) SUBSTITUTED BENZIMIDAZOLES, THEIR PREPARATION AND THEIR USE AS PHARMACEUTICALS

(71) Applicant: EPIGENETIX, INC., Delray Beach, FL (US)

(72) Inventors: Mehrnaz Pourashraf, Montreal (CA); Guillaume Jacquemot, Montreal (CA); Stephen Claridge, Montreal (CA); Malken Bayrakdarian, Montreal (CA); Shawn Johnstone, Montreal (CA); Jeffrey S. Albert, Montreal (CA); Andrew Griffin, Montreal (CA)

(73) Assignee: EPIGENETIX, INC., Delray Beach, FL (US)

( * ) Notice: Subject to any disclaimer, the term of this patent is extended or adjusted under 35 U.S.C. 154(b) by 166 days.

This patent is subject to a terminal disclaimer.

(21) Appl. No.: 18/629,321

(22) Filed: Apr. 8, 2024

(65) Prior Publication Data

US 2024/0425481 A1 Dec. 26, 2024

Related U.S. Application Data

(63) Continuation of application No. 17/743,792, filed on May 13, 2022, now Pat. No. 11,981,657, which is a continuation of application No. 16/881,803, filed on May 22, 2020, now Pat. No. 11,365,186, which is a continuation of application No. 15/751,801, filed as application No. PCT/CA2016/050952 on Aug. 12, 2016, now Pat. No. 10,703,740.

(60) Provisional application No. 62/358,101, filed on Jul. 4, 2016, provisional application No. 62/204,178, filed on Aug. 12, 2015.

(51) Int. Cl.

| | |
|---|---|
| ***C07D 401/14*** | (2006.01) |
| ***A61P 1/00*** | (2006.01) |
| ***A61P 17/06*** | (2006.01) |
| ***A61P 19/02*** | (2006.01) |
| ***A61P 35/00*** | (2006.01) |
| ***C07D 401/04*** | (2006.01) |
| ***C07D 405/14*** | (2006.01) |

(52) U.S. Cl.

CPC .............. *C07D 401/14* (2013.01); *A61P 1/00* (2018.01); *A61P 17/06* (2018.01); *A61P 19/02* (2018.01); *A61P 35/00* (2018.01); *C07D 401/04* (2013.01); *C07D 405/14* (2013.01)

(58) Field of Classification Search

CPC .................................................... C07D 401/14
USPC .......................................................... 514/394
See application file for complete search history.

(56) References Cited

U.S. PATENT DOCUMENTS

| | | | | |
|---|---|---|---|---|
| 4,550,166 | A | 10/1985 | Moran et al. | |
| 4,785,005 | A | 11/1988 | Campbell et al. | |
| 5,401,738 | A | 3/1995 | Mederski et al. | |
| 6,162,804 | A | 12/2000 | Bilodeau et al. | |
| 6,465,484 | B1 | 10/2002 | Bilodeau et al. | |
| 8,557,841 | B2 | 10/2013 | Yu et al. | |
| 8,987,250 | B2 | 3/2015 | Babaoglu et al. | |
| 10,703,740 | B2 * | 7/2020 | Pourashraf | C07D 405/14 |
| 11,365,186 | B2 * | 6/2022 | Pourashraf | A61P 19/02 |
| 11,981,657 | B2 * | 5/2024 | Pourashraf | C07D 401/14 |
| 2005/0153985 | A1 | 7/2005 | Kehrli, Jr. et al. | |
| 2008/0280917 | A1 | 11/2008 | Albrecht et al. | |
| 2014/0094456 | A1 | 4/2014 | Buckman et al. | |
| 2014/0349990 | A1 | 11/2014 | Blank et al. | |
| 2015/0051208 | A1 | 2/2015 | Engelhardt et al. | |
| 2015/0148342 | A1 | 5/2015 | Yue et al. | |
| 2015/0148375 | A1 | 5/2015 | Yue et al. | |

FOREIGN PATENT DOCUMENTS

| | | | |
|---|---|---|---|
| CA | 2098243 | A1 | 12/1993 |
| CA | 2657327 | A1 | 1/2008 |
| CA | 2701355 | A1 | 4/2009 |
| CA | 2760084 | A1 | 11/2010 |
| CA | 2874953 | A1 | 12/2013 |
| CA | 2875016 | A1 | 12/2013 |
| CA | 2895404 | A1 | 6/2014 |
| CA | 2917562 | A1 | 1/2015 |
| CA | 2932030 | A1 | 6/2015 |
| CA | 2982588 | A1 | 10/2016 |
| WO | WO-0012089 | A1 | 3/2000 |
| WO | WO-2005089763 | A1 | 9/2005 |

(Continued)

OTHER PUBLICATIONS

Andrieu, "Clinical Trials for BET Inhibitors Run Ahead of the Science," Drug Discovery Today: Technologies, 2016, vol. 19, pp. 45-50.

Aurora Fine Chemicals, 3(2H)-Pyridazinone, 5-(aminomethyl)-2-methyl-6-(1-methyl-1H-benzimidazol-5-yl)-. STN Files: Chemcats, CAS RN: 1782034-46-1 (Jun. 17, 2015).

Aurora Fine Chemicals, 4-Pyridazinecarbonitrile, 1,6-dihydro-1-methyl-3-(1-methyl-1H-benzimidazol-5-yl)-6-oxo-. STN Files: CHEMCATS, CAS RN: 1781658-56-7 (Jun. 17, 2015).

Banker et al., Prodrugs, Modern Pharmaceutics, 3rd edition, Revised and Expanded, 1986, pp. 451 and 596.

Basheer et al., "BET bromodomain inhibitors in leukemia," Experimental Hematology, 43, pp. 718-731 (2015).

Bernstein et al. Polymorphism in Molecular Crystals. Oxford: Clarendon Press pp. 115-118 and 272 (2002).

(Continued)

*Primary Examiner* — Niloofar Rahmani

(74) *Attorney, Agent, or Firm* — Young Basile Hanlon & MacFarlane, P.C.

(57) ABSTRACT

This application relates to substituted benzimidazoles, compositions comprising them and their uses in the treatment of diseases and conditions in which inhibition of a bromodomain is indicated. For example, the application relates to substituted benzimidazoles and to their use as bromodomain inhibitors. The present application is also related to the treatment or prevention of proliferative disorders, autoimmune disorders, inflammatory disorders, dermal disorders, and neoplasms, including tumors and/or cancers.

16 Claims, No Drawings

(56) References Cited

FOREIGN PATENT DOCUMENTS

| | | | |
|---|---|---|---|
| WO | WO-2008078091 | A1 | 7/2008 |
| WO | WO-2009050183 | A2 | 4/2009 |
| WO | WO-2011054846 | A1 | 5/2011 |
| WO | WO-2011060235 | A1 | 5/2011 |
| WO | WO-2012082689 | A1 | 6/2012 |
| WO | WO-2013024104 | A1 | 2/2013 |
| WO | WO-2013186229 | A1 | 12/2013 |
| WO | WO-2014051698 | A1 | 4/2014 |
| WO | WO-2014055548 | A1 | 4/2014 |
| WO | WO-2014096965 | A2 | 6/2014 |
| WO | WO-2014128655 | A1 | 8/2014 |
| WO | WO-2014145051 | A1 | 9/2014 |
| WO | WO-2014152029 | A2 | 9/2014 |
| WO | WO-2014159837 | A1 | 10/2014 |
| WO | WO-2014191896 | A1 | 12/2014 |
| WO | WO-2015002754 | A2 | 1/2015 |
| WO | WO-2015004533 | A2 | 1/2015 |
| WO | WO-2015004534 | A2 | 1/2015 |
| WO | WO-2015022332 | A1 | 2/2015 |
| WO | WO-2015049629 | A1 | 4/2015 |
| WO | WO-2015086526 | A1 | 6/2015 |
| WO | WO-2015104653 | A1 | 7/2015 |
| WO | WO-2015153683 | A1 | 10/2015 |
| WO | WO-2015164480 | A1 | 10/2015 |
| WO | WO-2016077656 | A2 | 5/2016 |
| WO | WO-2016087936 | A1 | 6/2016 |
| WO | WO-2016097863 | A1 | 6/2016 |
| WO | WO-2016097870 | A1 | 6/2016 |
| WO | WO-2016139292 | A1 | 9/2016 |
| WO | WO-2016146738 | A1 | 9/2016 |
| WO | WO-2016168682 | A2 | 10/2016 |
| WO | WO-2016170323 | A1 | 10/2016 |
| WO | WO-2016170324 | A1 | 10/2016 |

OTHER PUBLICATIONS

Bilodeau et al., "Design and Synthesis of 1,5-Diarylbenzimidazoles as Inhibitors of the VEGF-Receptor KDR," Bioorganic & Medicinal Chemistry Letters, 2003, vol. 13, pp. 2485-2488.
Braga, et al. Making crystals from crystals: a green route to crystal engineering and polymorphism. Chemical Communications 29:3635-3645 (2005).
Brand et al. Small Molecule Inhibitors of Bromodomain-Acetyl-lysine Interactions, ACS Chem. Biol., vol. 10: pp. 22-39. (2015).
Bundgaard, Design of Prodrugs, chapter 1, p. 1. (1985).
CAS Registry No. 1238376-75-4. Database Registry [Online] (Aug. 25, 2010).
CAS Registry No. 1781658-56-7. Database Registry [Online] (Jun. 17, 2015).
CAS Registry No. 1782034-46-1. Database Registry [Online] (Jun. 17, 2015).
Chambers et al. Dissemination and Growth of Cancer Cells in Metastatic Sites. Nature Reviews 2:663-672 (2002).
Davidovich et al. Detection of Polymorphism by Powder X-Ray Diffraction: Interference by Preferred Orientation. American Pharmaceutical Review 7:10-17 (2004).
Dean. Section 10. Analytical Chemistry Handbook. pp. 10.24-10.26 (1995).
Ember, et al. Acetyl-lysine Binding Site of Bromodomain-Containing Protein 4 (BRD4) Interacts with Diverse Kinase Inhibitors, ACS Chem. Biol, vol. 9: pp. 1160-1171. (2014).
Ettmayer, et al. Lessons learned from marketed and investigational prodrugs. Journal of medicinal chemistry. 2004, 47.10: 2393-2404.
European Search Report dated Jan. 8, 2019 for corresponding EP Application No. 16834372.1.
Garnier et al. BET bromodomain inhibitors: a patent review. Expert Opinion Therapeutic Patents, 24(2):185-199. (2014).
Golub, T. R. et al. Molecular classification of cancer: class discovery and class prediction by gene expression monitoring. Science 286(5439):531-537 (1999).
Guillory. In Polymorphism in Pharmaceutical Solids (Brittain ed.). pp. 1-2, 125-181, 183-226 (1999).
Gura. Cancer Models: Systems for identifying new drugs are often faulty. Science 278(5340):1041-42 (Nov. 1997).
Hackam, et al., Translation of Research Evidence From Animals to Humans; JAMA, 296(14), 2006, 1731-1732.
Hay et al., "Discovery and Optimization of Small-Molecule Ligands for the CBP/p300 Bromodomains" Journal of the American Chemical Society, 2014, vol. 136, pp. 9308-9319.
Ivanisevic et al. Use of X-ray Powder Diffraction In the Pharmaceutical Industry. Pharmaceutical Sciences Encyclopedia: Drug Discovery, Development, and Manufacturing pp. 1-42 (2010).
Jain, et al. Polymorphism in Pharmacy. Indian Drugs 23(6):315-329 (1986).
Johnson et al., Relationships between drug activity in NCI preclinical in vitro and in vivo models and early clinical trials. British Journal of Cancer 84(10):1424-1431 (2001).
Johnstone et al."EG-04. Development of Highly Potent, Selective Bet Bromodomain inhibitors that are CNS Penetrant and Effective in Rodent Models of Brain Cancer", Neuro- Oncology, 2014, 16: supplement 5, Epigenetics EG-04. Abstracts from the 19th Annual Scientific Meeting of the Society for Neuro-Oncology, Miami, Florida, Nov. 13-16, 2014.
Jordan, "Tamoxifen: A Most Unlikely Pioneering Medicine," Nature Reviews 2:205-213, Mar. 2003.
Kharenko, "Novel Approaches to Targeting BRD4," Drug Discovery Today: Technologies, 2017, vol. 24, pp. 19-24.
Kirk-Othmer. Crystallization. Encyclopedia of Chemical Technology 8:95-147 (2002).
Klein, et al. Bromodomain protein inhibition: a novel therapeutic strategy in rheumatic diseases, RMD Open, 4:e000744 (2018).
Klein, et al. Evaluating the bromodomain protein BRD1 as a therapeutic target in rheumatoid arthritis, Scientific Reports, 8(11125), pp. 1-7 (2018).
Mirguit, et al., From ApoA1 upregulation to BET family bromodomain inhibition: Discovery of I-BET151. Bioorg. Med. Chem. Lett. 22 (8):2963-2967. (2012).
Nakamura et al., "Enantioselective Synthesis and Enhanced Circularly Polarized Luminescence of S-Shaped Double Azahelicenes", Journal of the American Chemical Society, 2014, vol. 136, pp. 5555-5558.
PCT/CA2016/050952 International Preliminary Report on Patentability dated Feb. 13, 2018.
Pervaiz, "Bromodomain Drug Discovery—the Past, the Present, and the Future," The Chemical Record, 2018, vol. 18, pp. 1808-1817.
Picaud et al., "PFI-1, a Highly Selective Protein Interaction Inhibitor, Targeting BET Bromodomains", Therapeutics, Targets, and Chemical Biology, Cancer Research, 73(11), 2013, pp. 3336-3346.
Ramadoss, "Targeting the Cancer Epigenome: Synergistic Therapy with Bromodomain Inhibitors," Drug Discover Today, 2018, vol. 23, pp. 76-89.
Romero, et al. Disrupting Acetyl-Lysine Recognition: Progress in the Development of Bromodomain Inhibitors. Journal of Medicinal Chemistry 59(4):1271-1298 (2016).
Rooney et al. A Series of Potent CREBBP Bromodomain Ligands Reveals an Induced-Fit Pocket Stabilized by a Cation-TT Interaction, Angew. Chem. Int. Ed., 53: pp. 6126-6130. (2014).
Sastry et al., "Synthesis of 6-(1,4,5,6-tetrahydro-6-oxo-3-pyridazinyl)-2H-1,4-benzoxazin-3(4H)-ones as possible cardiotonic agents", Indian Journal of Chemistry, vol. 28B, 1989, pp. 882-884.
Seal et al., Identification of a novel series of BET family bromodomain inhibitors: Binding mode and profile of 1-BET151 (GSK1210151A). Bioorganic & Medicinal Chemistry Letters, 22:2968-2972 (2012).
Seddon. Pseudopolymorph: A Polemic. Crystal Growth & Design 4(6): 108 (2004) (2 pgs. from internet).
Shi, et al.: The mechanisms behind the therapeutic activity of BET bromodomain inhibition. Molecular Cell. 54(5):728-736 (2014).
Silverman, Richard B. Chapter 8: Prodrugs and Drug Delivery Systems. The Organic Chemistry of Drug Design and Drug Action, Academic Press 352-401 (1992).
Oncology:Introduction, Cecil Textbook of Medicine, ed Bennett et al. W.B.Saunders Co. 20th ed, vol. 1, 1996, pp. 1004-1010.

(56) References Cited

OTHER PUBLICATIONS

Stathis et al., "BET Proteins as Targets for Anticancer Treatment," Cancer Discovery, pp. 24-36 (2018).
Stella et al. Prodrugs as therapeutics. Expert Opin. Ther. Patents 14(3):277-280 (2004).
Swords et al., "Novel BET Bromodomain Inhibitors EP31670, EP11313 and EP11336 Have Potent Anti-Leukemic Activity in Acute Myeloid Leukemia (AML) and Augment the Effects of All-Trans-Retinoic Acid (ATRA) in Vitro", ASH 57th Annual Meeting, Orlando, FL, Dec. 5-8, 2015.
Testa, "Prodrug Research: Futile or Fertile?," Biochemical Pharmacology, 2004, vol. 68, pp. 2097-2106.
U.S. Appl. No. 16/881,803 Notice of Allowance dated Feb. 16, 2022.
U.S. Appl. No. 17/743,792 Notice of Allowance dated Jan. 10, 2024.
Venkatesh et al. Role of the Development Scientist in Compound Lead Selection and Optimization. J. Pharm. Sci. 89(2):145-154 (Feb. 2000).
Vidler et al. Discovery of Novel Small-Molecule Inhibitors of BRD4 Using Structure-Based Virtual Screening, Journal of Medicinal Chemistry, vol. 56: pp. 8073-8088. (2013).
Vippagunta, Sudha R. et al. Crystalline solids. Advanced Drug Delivery Reviews 48(1):3-26 (2001).
Wells et al., "The dormancy dilemma: Quiescence versus balanced proliferation," Cancer Res., pp. 3811-3816 (2013).
West, Solid State Chemistry and Its Applications, John Wiley & Sons. (1984).
White, et al. Emerging roles of and therapeutic strategies targeting BRD4 in cancer, Cellular Immunology, 337, pp. 48-53 (2019).
Wolff. Burger's Medicinal Chemistry and Drug Discovery. 5th Ed. Part 1, pp. 975-977 (1995).
Wolff, ed., Burger's Medicinal Chemistry and Drug Discovery, 5th edition, NY: John Wiley & Sons, 1996, vol. 1, pp. 949-976.
Yamanaka et al., "Imidazo (1,2-a]pyridines. III. Synthesis and Bradycardic Activity of New 5-Imidazo[1,2-a]pyridin-6-ylpyridine Derivatives", Chem. Pharm. Bull., 1992, vol. 40, No. 6, pp. 1486-1493.
Yamanaka et al., "Imidazo (1,2-a]pyridines.I. Synthesis and Inotropic Activity of New 5-Imidazo(1,2-a]pyridinyl-2(1H)-pyridinone Derivatives", Chem. Pharm. Bull., 1991, vol. 39. No. 6, pp. 1556-1567.
Yu et al. Physical characterization of polymorphic drugs: an integrated characterization strategy. PSTT 1(3):118-127 (1998).
Zaragoza, "Side Reactions in Organic Synthesis: A Guide to Successful Synthesis Design," Weinheim: Wiley-VCH Verlag GmbH & Co. KGaA, 2005, Preface pp. IX-X.
Zaware, et al. Bromodomain biology and drug discovery, Nature Structural Molecular Biology, 26, pp. 870-879: (2019).

* cited by examiner

SUBSTITUTED BENZIMIDAZOLES, THEIR PREPARATION AND THEIR USE AS PHARMACEUTICALS

CROSS-REFERENCE TO RELATED APPLICATIONS

This application is a continuation of U.S. application Ser. No. 17/743,792, filed May 13, 2022, now U.S. Pat. No. 11,981,657, issued May 14, 2024, which is a continuation of U.S. application Ser. No. 16/881,803, filed May 22, 2020, now U.S. Pat. No. 11,365,186, issued Jun. 21, 2022, which is a continuation of U.S. application Ser. No. 15/751,801, filed Feb. 9, 2018, now U.S. Pat. No. 10,703,740, issued Jul. 7, 2020, which is a U.S. National Stage application of International Application No. PCT/CA2016/050952, filed Aug. 12, 2016, which claims the benefit of U.S. provisional application No. 62/204,178 filed on Aug. 12, 2015 and to U.S. provisional application No. 62/358,101 filed on Jul. 4, 2016, the contents of which are incorporated herein by reference in their entirety for all purposes.

TECHNICAL FIELD

The technical field generally compounds, compositions and their uses in the treatment of diseases and conditions in which inhibition of bromodomains is indicated. For example, the application relates to benzimidazoles, to pharmaceutical compositions comprising the same, and to their use as bromodomain inhibitors. The present application is also related to the treatment or prevention of proliferative disorders, auto-immune disorders, inflammatory disorders, dermal disorders, and neoplasms, including tumors and/or cancers.

BACKGROUND

Bromodomains are found in a variety of mammalian DNA-binding proteins. The bromodomain, which is the conserved structural module in chromatin-associated proteins and histone acetyltransferases, is known to recognize acetyl-lysine residues on proteins. Bromodomain inhibitors are believed to be useful in the treatment of a variety of diseases or conditions, such as cancer as well as chronic autoimmune and inflammatory conditions. There is therefore a need for compounds that could inhibit bromodomains.

SUMMARY

According to one aspect, the present application relates to compounds of Formula I, and pharmaceutically acceptable salts, solvates, esters or prodrugs thereof:

Formula I

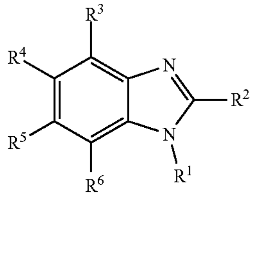

wherein, $R^1$ is:

a) an unsubstituted $C_1$-$C_6$alkyl;

b) a $C_1$-$C_6$alkyl substituted with one or more group(s) selected from halogen (such as fluorine), CN, $NO_2$, $C(O)NHR^{11}$, $C(O)N(R^{11})_2$, $CO_2H$, $SO_2R^{11}$, $SO_2NHR^{11}$, and $SO_2N(R^1)_2$;

c) a $C_2$-$C_6$alkyl group substituted with a group selected from $OR^{11}$, halogenated $OC_1$-$C_6$alkyl, SH, $SR^{11}$, $NH_2$, $NHR^{11}$, $N(R^{11})_2$, $NHC(O)R^{11}$, and $N(R^{11})C(O)R^{11}$; or d) a group selected from $C(O)R^{11}$, $C(O)NHR^{11}$, $C(O)N(R^{11})_2$, $SO_2R^{11}$, $SO_2NHR^{11}$, and $SO_2N(R^{11})_2$;

$R^2$ is selected from hydrogen and a substituted or unsubstituted group selected from $C_1$-$C_6$alkyl, $C_2$-$C_6$alkenyl, $C_2$-$C_6$alkynyl, $C_3$-$C_{10}$cycloalkyl, $C_3$-$C_{10}$heterocycloalkyl, $C(O)R^{12}$, $NH_2$, $NHR^{12}$, $N(R^{12})_2$, $C(O)NH_2$, $C(O)NHR^{12}$, $C(O)N(R^{12})_2$, $NHC(O)R^{12}$, $SO_2R^{12}$, $SO_2NHR^{12}$, $SO_2N(R^{12})_2$, $NHSO_2R^{12}$, $N(R^{12})SO_2R^{12}$, $NHSO_2NHR^{12}$, $N(R^{12})SO_2NHR^{12}$, $NHSO_2N(R^{12})_2$, and $N(R^{12})SO_2N(R^{12})_2$;

$R^3$ and $R^6$ are each independently H or a substituted or unsubstituted group selected from $C_1$-$C_6$alkyl, $C(O)R^{11}$, $NH_2$, $NHR^{11}$, $N(R^{11})_2$, $C(O)NH_2$, $C(O)NHR^{11}$, $C(O)N(R^{11})_2$, $NHC(O)R^{11}$—; and one of $R^4$ and $R^5$ is H or a substituted or unsubstituted group selected from $C_1$-$C_6$alkyl, $C(O)R^{11}$, $NH_2$, $NHR^{11}$, $N(R^{11})_2$, $C(O)NH_2$, $C(O)NHR^{11}$, $C(O)N(R^{11})_2$, and $NHC(O)R^{11}$; the other of $R^4$ and $R^5$ is a group of Formula II:

Formula II

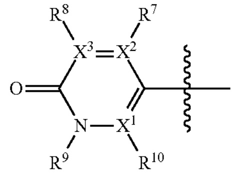

wherein, $R^7$, $R^8$, and $R^{10}$ are each independently H, halogen (such as F, Cl), CN, or a substituted or unsubstituted $C_1$-$C_6$alkyl or $C_3$-$C_6$cycloalkyl group, $OR^{11}$, $SR^{11}$, $NHR^{11}$, $N(R^{11})_2$, $NHC(O)R^{11}$, and $N(R^{11})C(O)R^{11}$, provided that at least one of $R^7$, $R^8$, and $R^{10}$ is other than H;

$R^9$ is a substituted or unsubstituted $C_1$-$C_3$alkyl or $C_3$-$C_5$cycloalkyl group;

$R^{11}$ is, independently in each occurrence, a substituted or unsubstituted $C_1$-$C_6$alkyl group;

$R^{12}$ is, independently in each occurrence, a substituted or unsubstituted $C_1$-$C_6$alkyl, $C_2$-$C_6$alkenyl, $C_2$-$C_6$alkynyl, $C_3$-$C_{10}$cycloalkyl, and $C_3$-$C_{10}$heterocycloalkyl;

$X^1$, $X^2$, and $X^3$ are each selected from N or C, wherein when $X^1$, $X^2$, or $X^3$ is N, then the $R^7$, $R^8$, or $R^{10}$ attached thereto is absent, provided that at least two of $X^1$, $X^2$, and $X^3$ is C;

wherein when any of the foregoing group contains an alkyl group, then said alkyl is a linear or branched acyclic alkyl group.

According to one embodiment, the compound is of Formula I, wherein $R^4$ is a group of Formula II, preferably wherein said $R^5$ is hydrogen or a substituted or unsubstituted $C_1$-$C_3$ alkyl. According to another embodiment, the compound is of Formula I, wherein $R^5$ is a group of Formula II, preferably wherein said $R^4$ is hydrogen or a substituted or unsubstituted $C_1$-$C_3$ alkyl.

In one embodiment, in Formula II, groups $X^1$, $X^2$ and $X^3$ are all carbon atoms. In another embodiment, $X^1$ is a nitrogen atom and $R^{10}$ is absent, and $X^2$ and $X^3$ are carbon atoms. For instance, the group of Formula II may be defined as a group of Formula II(a):

Formula II(a)

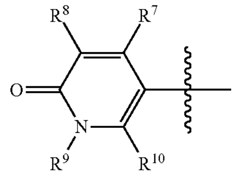

wherein $R^7$, $R^8$, $R^9$ and $R^{10}$ are as herein defined.

In one embodiment, $R^9$ is an unsubstituted $C_1$-$C_3$alkyl or $C_3$-$C_5$cycloalkyl group, for instance a methyl, ethyl, n-propyl, isopropyl or cyclopropyl group. In another embodiment, $R^7$ and $R^{10}$ are each hydrogen atoms and $R^8$ is selected from Cl, CN, $NHR^{11}$ and a substituted or unsubstituted $C_1$-$C_6$alkyl or $C_3$-$C_6$cycloalkyl group.

Another embodiment of the application relates to compounds of Formula I(a), and pharmaceutically acceptable salts, solvates, esters or prodrugs thereof:

Formula I(a)

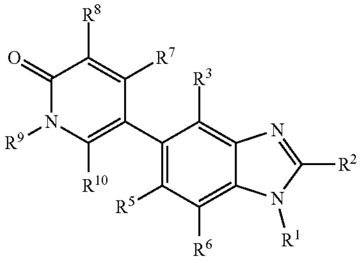

wherein, $R^1$, $R^2$, $R^3$, $R^5$, $R^6$, $R^7$, $R^8$, $R^9$, and $R^{10}$ are as herein defined.

According to another embodiment, the application also relates to compounds of Formula I(b), and pharmaceutically acceptable salts, solvates, esters or prodrugs thereof:

Formula I(b)

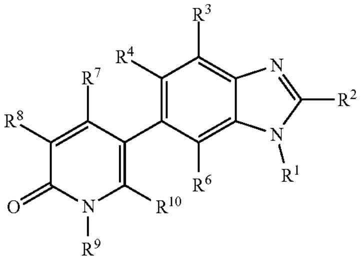

wherein, $R^1$, $R^2$, $R^4$, $R^3$, $R^6$, $R^7$, $R^8$, $R^9$, and $R^{10}$ are as herein defined.

In one embodiment, the application relates to compounds as herein defined wherein $R^3$ is H or a substituted or unsubstituted $C_1$-$C_6$alkyl group, preferably $R^3$ is H. In another embodiment, the application relates to compounds as herein defined wherein $R^6$ is H or a substituted or unsubstituted $C_1$-$C_6$alkyl group, preferably $R^6$ is H.

In another embodiment, the present application relates to compounds of Formula III, and pharmaceutically acceptable salts, solvates, esters or prodrugs thereof:

Formula III

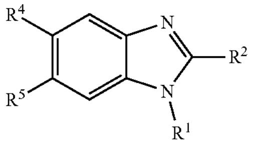

wherein, $R^1$, $R^2$, $R^4$ and $R^5$ are as herein defined.

Another embodiment of the application relates to compounds of Formula III(a), and pharmaceutically acceptable salts, solvates, esters or prodrugs thereof:

Formula III(a)

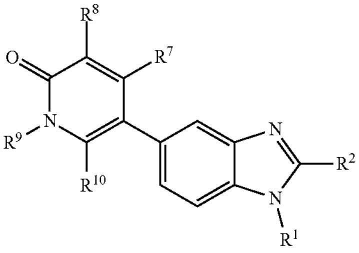

wherein $R^1$, $R^2$, $R^7$, $R^8$, $R^9$, and $R^{10}$ are as herein defined.

According to another embodiment, the application also relates to compounds of Formula III(b), and pharmaceutically acceptable salts, solvates, esters or prodrugs thereof:

Formula III(b)

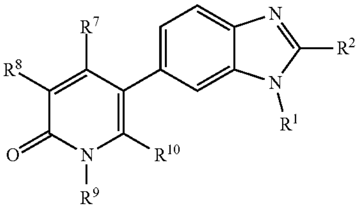

wherein $R^1$, $R^2$, $R^7$, $R^8$, $R^9$, and $R^{10}$ are as herein defined.

According to one embodiment, the application relates to compounds of Formula III(a) or III(b) as herein defined, wherein $R^9$ is an unsubstituted $C_1$-$C_3$alkyl or $C_3$-$C_5$cycloalkyl group, or $R^9$ is a fluorine-substituted $C_1$-$C_3$alkyl or $C_3$-$C_5$cycloalkyl group, for instance, $R^9$ is selected from methyl, trifluoromethyl, ethyl, n-propyl, isopropyl and cyclopropyl. In another embodiment, the application relates to compounds of Formula III(a) or III(b), wherein said $R^7$ and $R^{10}$ are each hydrogen atoms and $R^8$ is selected from Cl, CN, $NHR^{11}$ and a substituted or unsubstituted $C_1$-$C_6$alkyl or $C_3$-$C_6$cycloalkyl group. In a further embodiment, $R^8$ and $R^9$ are each independently a methyl, ethyl, isopropyl, fluoromethyl, difluoromethyl, trifluoromethyl, cyclopropyl, or difluorocyclopropyl group.

In yet another embodiment, the present application relates to a compound of Formula I, I(a), I(b), III, III(a) or III(b) as herein defined, wherein $R^2$ is hydrogen or a substituted or unsubstituted group selected from $C_1$-$C_6$alkyl, $C_3$-$C_{10}$cycloalkyl, or $C_3$-$C_{10}$heterocycloalkyl group. For instance, $R^2$ is a substituted or unsubstituted $C_1$-$C_3$alkyl, $C_3$-$C_6$cycloalkyl, or $C_3$-$C_6$heterocycloalkyl group, or is a substituted or unsubstituted group selected from methyl, ethyl, propyl, isopropyl, butyl, isobutyl, tert-butyl, cyclopropyl, cyclobutyl, cyclopentyl, tetrahydrofuranyl, tetrahydropyranyl, dioxolanyl, piperidinyl, and pyrrolidinyl.

According to a further embodiment, the compound of the present application is a compound of Formula I, I(a), I(b), III, III(a) or III(b) as herein defined, wherein $R^1$ is a branched or linear $C_2$-$C_6$alkyl substituted with a group selected from fluorine, $OC_1$-$C_6$alkyl, and halogenated $OC_1$-$C_6$alkyl. For instance, $R^1$ is a branched or linear $C_2$-$C_3$alkyl substituted with a group selected from fluorine, $OC_1$-$C_6$alkyl, and halogenated $OC_1$-$C_6$alkyl. In an alternate embodiment, $R^1$ is selected from fluoromethyl, difluoromethyl, trifluoromethyl, 2,2,2-trifluoroethyl, 2-methoxyethyl, 2-ethoxyethyl, 2-(fluoromethoxy)ethyl, 2-(difluoromethoxy)ethyl, 2-(trifluoromethoxy)ethyl, 3,3,3-trifluoro-1-propyl, 3-methoxy-1-propyl, 3-ethoxy-1-propyl, 3-(fluoromethoxy)-1-propyl, 3-(difluoromethoxy)-1-propyl, 3-(trifluoromethoxy)-1-propyl, 1-methoxy-2-propyl, 1-ethoxy-2-propyl, 1-(fluoromethoxy)-2-propyl, 1-(difluoromethoxy)-2-propyl, 1-(trifluoromethoxy)-2-propyl, 2-methoxy-1-propyl, 2-ethoxy-1-propyl, 2-(fluoromethoxy)-1-propyl, 2-(difluoromethoxy)-1-propyl, or 2-(trifluoromethoxy)-1-propyl, for instance, $R^1$ is 2-methoxyethyl, 2-(trifluoromethoxy)ethyl, 1-methoxy-2-propyl, 1-(trifluoromethoxy)-2-propyl, 2-methoxy-1-propyl, or 2-(trifluoromethoxy)-1-propyl. In another embodiment, $R^1$ is methyl, trifluoromethyl, ethyl, 2,2,2-trifluoroethyl, n-propyl, 3,3,3-trifluoro-1-propyl, isopropyl, n-butyl, isobutyl, or t-butyl.

In a further embodiment, this application relates to a compound selected from Compounds 1 to 67 as herein defined, or a pharmaceutically acceptable salt, solvate, or prodrug thereof, for instance, any of these compounds or their isomers, or a pharmaceutically acceptable salt, solvate, or prodrug thereof, taken individually or as sub-groups.

Another aspect related to pharmaceutical composition, comprising a compound as defined in the present application, together with a pharmaceutically acceptable carrier, diluent or excipient.

A further aspect relates to the use of a compound as defined in the present application, or such a compound for use, in the treatment or prevention of a disease or condition for which a bromodomain inhibitor is indicated. Similarly, this aspect relates to the use of a compound of the present application in the manufacture of a medicament for the treatment or prevention of a disease or condition for which a bromodomain inhibitor is indicated. This aspect also further relates to a method for treating a disease or condition for which a bromodomain inhibitor is indicated, which comprises administering to a subject in need thereof, a therapeutically effective amount of a compound as herein defined. In one embodiment, the disease or condition for which a bromodomain inhibitor is indicated is an auto-immune disorder, an inflammatory disorder (such as rheumatoid arthritis, irritable bowel syndrome, or psoriasis), a dermal disorder, or cancer (for instance, brain cancer, pancreatic cancer, breast cancer, lung cancer, or prostate cancer). For instance the disease or condition is brain cancer, such as glioblastoma multiforme.

According to a further aspect, the application relates to the use of a compound as herein defined, or such a compound for use, in the treatment of a disease or condition selected from auto-immune disorders, inflammatory disorders, dermal disorders, and neoplasms. This aspect also relates to a method for the treatment or prevention of a disease or condition selected from auto-immune disorders, inflammatory disorders, dermal disorders, and neoplasms, which comprises administering to a subject in need thereof, a therapeutically effective amount of a compound as herein defined. For instance, the inflammatory disorder is rheumatoid arthritis, irritable bowel syndrome, or psoriasis. For example, the disease or condition is a neoplasm which is brain cancer (e.g. glioblastoma multiforme), pancreatic cancer, breast cancer, lung cancer, or prostate cancer.

Additional objects and features of the present compounds, compositions, methods and uses will become more apparent upon reading of the following non-restrictive description of exemplary embodiments, which should not be interpreted as limiting the scope of the invention.

DESCRIPTION

All technical and scientific terms used herein have the same meaning as commonly understood by one ordinary skilled in the art to which the present technology pertains. For convenience, the meaning of certain terms and phrases used herein are provided below.

To the extent the definitions of terms in the publications, patents, and patent applications incorporated herein by reference are contrary to the definitions set forth in this specification, the definitions in this specification control. The section headings used herein are for organizational purposes only, and are not to be construed as limiting the subject matter disclosed.

i. Definitions

The terminology used herein is for the purpose of describing particular embodiments only and is not intended to be limiting. It should be noted that, the singular forms "a", "an", and "the" include plural forms as well, unless the content clearly dictates otherwise. Thus, for example, reference to a composition containing "a compound" also contemplates a mixture of two or more compounds. It should also be noted that the term "or" is generally employed in its sense including "and/or" unless the content clearly dictates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the terms "compounds herein described", "compounds of the present application" and equivalent expressions refer to compounds described in the present application, e.g., those encompassed by structural Formulae such as Formula I, I(a), I(b), III, III(a), and III(b), optionally with reference to any of the applicable embodiments, and also includes exemplary compounds, for example, Compounds 1-36, as well as their pharmaceutically acceptable salts, solvates, esters, and prodrugs when applicable. When a zwitterionic form is possible, the compound may be drawn as its neutral form for practical purposes, but the compound is understood to also include its zwitterionic form. Embodiments herein may also exclude one or more of the compounds. Compounds may be identified either by their chemical structure or their chemical name. In a case where the chemical structure and chemical name would conflict, the chemical structure will prevail.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the present description. Unless otherwise stated, all tautomeric forms of the compounds are within the scope of the present description. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of the present description. Such compounds are useful, for example, as analytical tools, as probes in biological assays, or as therapeutic agents in accordance with the present description.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions*, p. 268 (E. L. Eliel, Ed., Univ. of Notre Dame Press, Notre Dame, IN 1972).

Definitions of specific functional groups and chemical terms are described in more detail below. For purposes of the present description, the chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* $5^{th}$, Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* $3^{rd}$ Edition, Cambridge University Press, Cambridge, 1987.

The number of carbon atoms in a hydrocarbyl substituent can be indicated by the prefix "$C_x$-$C_y$," where x is the minimum and y is the maximum number of carbon atoms in the substituent. However, when the prefix "$C_x$-$C_y$" is associated with a group incorporating one or more heteroatom(s) by definition (e.g. heterocycloalkyl, heteroaryl, etc), then x and y define respectively the minimum and maximum number of atoms in the cycle, including carbons as well as heteroatom(s).

The prefix "halo" indicates that the substituent to which the prefix is attached is substituted with one or more independently selected halogen radicals. More specifically, the terms "halo" and "halogen" as used herein refer to an atom selected from fluorine (fluoro, —F), chlorine (chloro, —Cl), bromine (bromo, —Br), and iodine (iodo, —I). For example, "haloalkyl" means an alkyl substituent wherein at least one hydrogen radical is replaced with a halogen radical.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl).

As used herein a "direct bond" or "covalent bond" refers to a single, double or triple bond. In certain embodiments, a "direct bond" or "covalent bond" refers to a single bond.

Abbreviations may also be used throughout the application, unless otherwise noted, such abbreviations are intended to have the meaning generally understood by the field. Examples of such abbreviations include Me (methyl), Et (ethyl), Pr (propyl), i-Pr (isopropyl), Bu (butyl), t-Bu (tert-butyl), i-Bu (iso-butyl), s-Bu (sec-butyl), c-Bu (cyclobutyl), Ph (phenyl), Bn (benzyl), Bz (benzoyl), CBz or Cbz or Z (carbobenzyloxy), Boc or BOC (tert-butoxycarbonyl), and Su or Suc (succinimide). For greater certainty, examples of abbreviations used in the present application are listed in a table in the Examples section.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Aliphatic groups include, but are not limited to, alkyl, alkenyl, alkynyl, carbocycle. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein, refers to a saturated, straight- or branched-chain hydrocarbon radical typically containing from 1 to 20 carbon atoms. For example, "$C_1$-$C_8$ alkyl" contains from one to eight carbon atoms. Examples of alkyl radicals include, but are not limited to, methyl, ethyl, propyl, isopropyl, w-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_2$-$C_8$ alkynyl" contains from two to eight carbon atoms. Representative alkynyl groups include, but are not limited to, for example, ethynyl, 1-propynyl, 1-butynyl, heptynyl, octynyl and the like.

The terms "cycloalkyl", "alicyclic", "carbocyclic" and equivalent expressions refer to a group comprising a saturated or partially unsaturated (non aromatic) carbocyclic ring in a monocyclic or polycyclic ring system, including spiro (sharing one atom), fused (sharing at least one bond) or bridged (sharing two or more bonds) carbocyclic ring systems, having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl" refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

As used herein, the terms "heterocycle", "heterocycloalkyl", "heterocyclyl", "heterocyclic radical", and "heterocyclic ring" are used interchangeably and refer to a chemically stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). A heterocyclic ring can be attached to its pendant group at any heteroatom or carbon atom that results in a chemically stable structure and any of the ring atoms can be optionally substituted. Examples of heterocycloalkyl groups include, but are not limited to, 1,3-dioxolanyl, pyrrolidinyl, pyrrolidonyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, tetrahydrofuranyl, tetrahydropyranyl, tetrahydrothiopyranyl, tetrahydrodithienyl, tetrahydrothienyl, thiomorpholino, thioxanyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, 2H-pyranyl, 4H-pyranyl, dioxanyl, dithianyl, dithiolanyl, dihydropyranyl, dihydrothienyl, dihydrofuranyl, 3-azabicyclo[3,1,0]hexanyl, 3-azabicyclo[4,1,0]heptanyl, quinolizinyl, quinuclidinyl, tetrahydroquinolinyl, tetrahydroisoquinolinyl, decahydroquinolinyl, and the like. Heterocyclic groups also include groups in which a heterocyclic ring is fused to one or more aryl, heteroaryl, or cycloaliphatic rings, such as indolinyl, 3H-indolyl, chromanyl, chromenyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "aryl" used alone or as part of a larger moiety as in "aralkyl", "aralkoxy", or "aryloxyalkyl", refers to a monocyclic moiety or to a bicyclic or tricyclic fused ring system having a total of six to 15 ring members, wherein at least one ring in the system is aromatic and wherein each ring in the system contains three to seven ring members. The term "aryl" may be used interchangeably with the term "aryl ring". In certain embodiments of the present description, "aryl" refers to an aromatic ring system which includes, but not limited to, phenyl, biphenyl, naphthyl, azulenyl, anthracyl and the like, which may bear one or more substituents. The term "aralkyl" or "arylalkyl" refers to an alkyl residue attached to an aryl ring. Examples of aralkyl include, but are not limited to, benzyl, phenethyl, 1-phenylethyl, and the like. Also included within the scope of the term "aryl", as it is used herein, is a group in which an aromatic ring is fused to one or more non-aromatic rings, such as indanyl, indenyl, phthalimidyl, naphthimidyl, fluorenyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 18 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. Heteroaryl groups include, without limitation, thienyl, furanyl (furyl), thienyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, triazinyl, furopyridinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, 3H-indolyl, isoindolyl, benzothienyl (benzothiophenyl), benzofuranyl, dibenzofuranyl, indazolyl, benzimidazolyl, benzoxazolyl, benzothiazolyl, quinolyl (quinolinyl), isoquinolyl (isoquinolinyl), quinolonyl, isoquinolonyl, cinnolinyl, phthalazinyl, quinazolinyl, quinoxalinyl, 4H-quinolizinyl, carbazolyl, acridinyl, phenanthridinyl, phenazinyl, phenothiazinyl, phenoxazinyl, tetrahydroquinolinyl, tetrahydroisoquinolinyl, and pyrido[2, 3-b]-1,4-oxazin-3 (4H)-one. A heteroaryl group may be mono- or bicyclic. Heteroaryl groups include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like.

The term "bivalent hydrocarbon" refers to a bivalent saturated or unsaturated hydrocarbon group. Such bivalent hydrocarbon groups include alkylene, alkenylene, and alkynylene groups.

The term "alkylene" refers to a divalent group derived from a straight or branched saturated hydrocarbyl chain typically containing from 1 to 20 carbon atoms, more typically from 1 to 8 carbon atoms. Examples of an "alkylene" include a polymethylene group, i.e., $-(CH_2)n-$, wherein n is a positive integer, preferably from 1 to 6, from 1 to 4, from 1 to 3, from 1 to 2, or from 2 to 3; or $-CH_2-$, $-CH_2CH_2-$, $-CH_2CH_2CH_2-$, $-CH_2CH_2CH_2CH_2-$, and $-CH_2CH(CH_3)CH_2-$. A substituted alkylene chain is a polymethylene group in which one or more methylene hydrogen atoms are replaced with a substituent. Suitable substituents include those described below for a substituted aliphatic group.

The term "alkenylene" refers to a divalent unsaturated hydrocarbyl group which may be linear or branched and which has at least one carbon-carbon double bond. An alkenylene group typically contains 2 to 20 carbon atoms, more typically from 2 to 8 carbon atoms. Non-limiting examples of alkenylene groups include $-C(H){=}C(H)-$, $-C(H){=}C(H)-CH_2-$, $-C(H){=}C(H)-CH_2-CH_2-$, $-CH_2-C(H){=}C(H)-CH_2-$, $-C(H){=}C(H)-CH(CH_3)-$, and $-CH_2-C(H){=}C(H)-CH(CH_2CH_3)-$.

The term "alkynylene" refers to a divalent unsaturated hydrocarbon group which may be linear or branched and which has at least one carbon-carbon triple bond. Examples of alkynylene groups include, without limitation, $-C{\equiv}C-$, $-C{\equiv}C-CH_2-$, $-C{\equiv}C-CH_2-CH_2-$, $-CH_2-C{\equiv}C-CH_2-$, $-C{\equiv}C-CH(CH_3)-$, and $-CH_2-C{\equiv}C-CH(CH_2CH_3)-$.

As described herein, compounds of the present description may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under the present description are preferably those that result in the formation of chemically stable or chemically feasible compounds. The term "chemically stable", as used herein, refers to compounds that are not substantially altered when subjected to conditions to allow for their production, detection, and, in certain embodiments, their recovery, purification, and use for one or more of the purposes disclosed herein.

The terms "optionally substituted", "optionally substituted alkyl," "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with substituents including, but not limited to F, Cl, Br, I, OH, $CO_2H$, alkoxy, oxo, thiooxo, $NO_2$, CN, $CF_3$, $NH_2$, protected amino, NHalkyl, NHalkenyl, NHalkynyl, NHcycloalkyl, NHaryl, NHheteroaryl, NHheterocyclic, dialkylamino, diarylamino, diheteroarylamino, O-alkyl, O-alkenyl, O-alkynyl, O-cycloalkyl, O-aryl, O-heteroaryl, O-haloalkyl, O-heterocyclic, C(O)alkyl, C(O)alkenyl, C(O)alkynyl, C(O)cycloalkyl, C(O)aryl, C(O)heteroaryl, C(O)heterocycloalkyl, $CO_2$alkyl, $CO_2$alkenyl, $CO_2$alkynyl, $CO_2$cycloalkyl, $CO_2$aryl, $CO_2$heteroaryl, $CO_2$heterocycloalkyl, OC(O)alkyl, OC(O)alkenyl, OC(O)alkynyl, OC(O)cycloalkyl, OC(O)aryl, OC(O)heteroaryl, OC(O)heterocycloalkyl, C(O)$NH_2$, C(O)NHalkyl, C(O)NHalkenyl, C(O)NHalkynyl, C(O)NHcycloalkyl, C(O)NHaryl, C(O)NHheteroaryl, C(O)NHheterocycloalkyl, $OCO_2$alkyl, $OCO_2$alkenyl, $OCO_2$alkynyl, $OCO_2$cycloalkyl, $OCO_2$aryl, $OCO_2$heteroaryl, $OCO_2$heterocycloalkyl, OC(O)$NH_2$, OC(O)NHalkyl, OC(O)NHalkenyl, OC(O)NHalkynyl, OC(O)NHcycloalkyl, OC(O)NHaryl, OC(O)NHheteroaryl, OC(O)NHheterocycloalkyl, NHC(O)alkyl, NHC(O)alkenyl, NHC(O)alkynyl, NHC(O)cycloalkyl, NHC(O)aryl, NHC(O)heteroaryl, NHC(O)heterocycloalkyl, $NHCO_2$alkyl, $NHCO_2$alkenyl, $NHCO_2$alkynyl, $NHCO_2$cycloalkyl, $NHCO_2$aryl, $NHCO_2$heteroaryl, $NHCO_2$heterocycloalkyl, NHC(O)$NH_2$, NHC(O)NHalkyl, NHC(O)NHalkenyl, NHC(O)NHalkenyl, NHC(O)NHcycloalkyl, NHC(O)NHaryl, NHC(O)NHheteroaryl, NHC(O)NHheterocycloalkyl, NHC(S)$NH_2$, NHC(S)NHalkyl, NHC(S)NHalkenyl, NHC(S)NHalkynyl, NHC(S)NHcycloalkyl, NHC(S)NHaryl, NHC(S)NHheteroaryl, NHC(S)NHheterocycloalkyl, NHC(NH)$NH_2$, NHC(NH)NHalkyl, NHC(NH)NHalkenyl, NHC(NH)NHalkenyl, NHC(NH)NHcycloalkyl, NHC(NH)NHaryl, NHC(NH)NHheteroaryl, NHC(NH)NHheterocycloalkyl, NHC(NH)alkyl, NHC(NH)alkenyl, NHC(NH)alkenyl, NHC(NH)cycloalkyl, NHC(NH)aryl, NHC(NH)heteroaryl, NHC(NH)heterocycloalkyl, C(NH)NHalkyl, C(NH)NHalkenyl, C(NH)NHalkynyl, C(NH)NHcycloalkyl, C(NH)NHaryl, C(NH)NHheteroaryl, C(NH)NHheterocycloalkyl, S(O)alkyl, S(O)alkenyl, S(O)alkynyl, S(O)cycloalkyl, S(O)aryl, $S(O)_2$alkyl, $S(O)_2$alkenyl, $S(O)_2$alkynyl, $S(O)_2$cycloalkyl, $S(O)_2$aryl, S(O)heteroaryl, S(O)heterocycloalkyl, $SO_2NH_2$, $SO_2$NHalkyl, $SO_2$NHalkenyl, $SO_2$NHalkynyl, $SO_2$NHcycloalkyl, $SO_2$NHaryl, $SO_2$NHheteroaryl, $SO_2$NHheterocycloalkyl, $NHSO_2$alkyl, $NHSO_2$alkenyl, $NHSO_2$alkynyl, $NHSO_2$cycloalkyl, $NHSO_2$aryl, $NHSO_2$heteroaryl, $NHSO_2$heterocycloalkyl, $CH_2NH_2$, $CH_2SO_2CH_3$, alkyl, alkenyl, alkynyl, aryl, arylalkyl, heteroaryl, heteroarylalkyl, heterocycloalkyl, cycloalkyl, carbocyclic, heterocyclic, polyalkoxyalkyl, polyalkoxy, methoxymethoxy, methoxyethoxy, SH, S-alkyl, S-alkenyl, S-alkynyl, S-cycloalkyl, S-aryl, S-heteroaryl, S-heterocycloalkyl, or methylthiomethyl.

In certain embodiments, suitable monovalent substituents on a substitutable carbon atom of an "optionally substituted" group are independently halogen; $(CH_2)_{0-4}R^\circ$; $(CH_2)_{0-4}OR^\circ$; $O(CH_2)_{0-4}C(O)OR^\circ$; $(CH_2)_{0-4}CH(OR^\circ)_2$; $(CH_2)_{0-4}SR^\circ$; $(CH_2)_{0-4}Ph$, which may be substituted with $R^\circ$; $(CH_2)_{0-4}O(CH_2)_{0-4}Ph$ which may be substituted with $R^\circ$; $-CH{=}CHPh$, which may be substituted with $R^\circ$; $NO_2$; CN; $N_3$; $(CH_2)_{0-4}N(R^\circ)_2$; $(CH_2)_{0-4}N(R^\circ)C(O)R^\circ$; $N(R^\circ)C(S)R^\circ$; $(CH_2)_{0-4}N(R^\circ)C(O)NR^\circ_2$; $N(R^\circ)C(S)NR^\circ_2$; $(CH_2)_{0-4}N(R^\circ)C(O)OR^\circ$; $N(R^\circ)N(R^\circ)C(O)R^\circ$; $N(R^\circ)N(R^\circ)C(O)NR^\circ_2$; $N(R^\circ)N(R^\circ)C(O)OR^\circ$; $(CH_2)_{0-4}C(O)R^\circ$; $C(S)R^\circ$; $(CH_2)_{0-4}C(O)OR^\circ$; $(CH_2)_{0-4}C(O)SR^\circ$; $(CH_2)_{0-4}C(O)$ $OSiR°_3$; $(CH_2)_{0-4}OC(O)R°$; $OC(O)(CH_2)_{0-4}SR$—, SC(S) SR°; $(CH_2)_{0-4}SC(O)R°$; $(CH_2)_{0-4}C(O)NR°_2$; $C(S)NR°_2$; C(S)SR°; SC(S)SR°, $(CH_2)_{0-4}OC(O)NR°_2$; C(O)N(OR°) R°; C(O)C(O)R°; $C(O)CH_2C(O)R°$; C(NOR°)R°; $(CH_2)_{0-4}$ SSR°; $(CH_2)_{0-4}S(O)_2R°$; $(CH_2)_{0-4}(O)_2OR°$; $(CH_2)_{0-4}OS(O)_2$ R°; $S(O)_2NR°_2$; $(CH_2)_{0-4}S(O)R°$; $N(R°)S(O)_2NR°_2$; $N(R°)S(O)_2R°$; N(OR°)R°; $C(NH)NR°_2$; $P(O)_2R°$; $P(O)R°_2$; $OP(O)R°_2$; $OP(O)(OR°)_2$; $SiR°_3$; (straight or branched $C_{1-4}$alkylene)O—$N(R°)_2$; or (straight or branched $C_{1-4}$alkylene)C(O)O—$N(R°)_2$, wherein each R° may be substituted as defined below and is independently hydrogen, $C_{1-6}$aliphatic, $CH_2Ph$, $O(CH_2)_{0-1}Ph$, or a 5-6-membered saturated, partially unsaturated, or aromatic ring having 0-4 heteroatoms independently selected from nitrogen, oxygen, or sulfur, or, notwithstanding the definition above, two independent occurrences of R°, taken together with their intervening atom(s), may form a 3 to 12 membered saturated, partially unsaturated, or aryl mono- or bicyclic ring having 0 to 4 heteroatoms independently selected from nitrogen, oxygen, or sulfur, which may be substituted as defined below.

Examples of monovalent substituents on R° (or the ring formed by taking two independent occurrences of R° together with their intervening atoms), are independently halogen, —$(CH_2)_{0-2}R^*$, -(haloR*), —$(CH_2)_{0-2}OH$, —$(CH_2)_{0-2}OR^*$, —$(CH_2)_{0-2}CH(OR^*)_2$, —O(haloR'), —CN, —$N_3$, —$(CH_2)_{0-2}C(O)R^*$, —$(CH_2)_{0-2}C(O)OH$, —$(CH_2)_{0-2}C(O)OR^*$, —$(CH_2)_{0-2}SR^*$, —$(CH_2)_{0-2}SH$, —$(CH_2)_{0-2}NH_2$, —$(CH_2)_{0-2}NHR^*$, —$(CH_2)_{0-2}NR^*_2$, —$NO_2$, —$SiR^*_3$, —$OSiR^*_3$, —C(O)SR*—($C_{1-4}$ straight or branched alkylene)C(O)OR*, or —SSR*, wherein each R* is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Examples of divalent substituents on a saturated carbon atom of an "optionally substituted" group include the following: ═O, ═S, ═$NNR^*_2$, ═NNHC(O)R*, ═NNHC(O)OR*, ═$NNHS(O)_2R^*$, ═NR*, ═NOR*, —$O(C(R^*_2))_{2-30}$—, or —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR_2)_{2-30}$—, wherein each independent occurrence of R is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Examplary substituents on the aliphatic group of R* include halogen, —R*, -(haloR*), —OH, —OR*, —O(haloR'), —CN, —C(O)OH, —C(O)OR*, —$NH_2$, —NHR*, —$NR^*_2$, or —$NO_2$, wherein each R* is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The expression "pharmaceutically acceptable salt" refers to those salts of the compounds formed by the process of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). The salts can be prepared in situ during the final isolation and purification of the compounds of the present description, or separately by reacting a free base function of the compound with a suitable organic or inorganic acid (acid addition salts) or by reacting an acidic function of the compound with a suitable organic or inorganic base (base-addition salts). Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative base addition alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate.

The term "solvate" refers to a physical association of one of the present compounds with one or more solvent molecules. This physical association includes hydrogen bonding. In certain instances, the solvate will be capable of isolation, for example when one or more solvent molecules are incorporated in the crystal lattice of a crystalline solid. "Solvate" encompasses both solution-phase and isolable solvates. Exemplary solvates include, without limitation, hydrates, hemihydrates, ethanolates, hemiethanolates, n-propanolates, iso-propanolates, 1-butanolates, 2-butanolate, and solvates of other physiologically acceptable solvents, such as the Clas 3 solvents described in the *International Conference on Harmonization* (*ICH*), *Guide for Industry, Q3C Impurities: Residual Solvents* (1997). The compounds as herein described also include each of their solvates and mixtures thereof.

As used herein, the term "pharmaceutically acceptable ester" refers to esters of the compounds formed by the process of the present description which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The expression "pharmaceutically acceptable prodrugs" as used herein refers to those prodrugs of the compounds formed by the process of the present description which are, within the scope of sound medical judgment, suitable for use in contact with the tissues of humans and lower animals with undue toxicity, irritation, allergic response, and the like, commensurate with a reasonable benefit/risk ratio, and effective for their intended use. "Prodrug", as used herein means a compound which is convertible in vivo by metabolic means (e.g. by hydrolysis) to afford any compound delineated by the formulae of the instantdescription. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "*Design and Application of Prodrugs, Textbook of Drug Design and Development*", Chapter 5, 113-191 (1991); Bundgaard, et al., *Journal of Drug Deliver Reviews,* 8:1-38 (1992); Bundgaard, *J. of Pharmaceutical Sciences,* 77:285 et seq. (1988); Higuchi and Stella (eds.) *Prodrugs as Novel Drug Delivery Systems*, American Chemical Society (1975); and Bernard Testa & Joachim Mayer, "*Hydrolysis In Drug And Prodrug Metabolism: Chemistry. Biochemistry And Enzymology*", John Wiley and Sons, Ltd. (2002). Combinations of substituents and variables envisioned by the present description are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

ii. Compounds

The compounds of the present application may be prepared by conventional chemical synthesis, such as exemplified in Scheme 1 and in Examples 1 to 60. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired products of the present description. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof. The synthesized compounds can be separated from a reaction mixture and further purified by standard methods such as column chromatography, high pressure liquid chromatography, or recrystallization.

The compounds of the present description may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof. As such, the following embodiments are present alone or in combination if applicable:

The present application provides substituted benzimidazole compounds of general Formula I, as well as their pharmaceutically acceptable salts, solvates, esters or prodrugs thereof:

Formula I

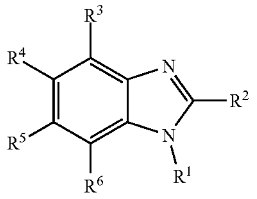

wherein, $R^1$ is:

a) an unsubstituted $C_1$-$C_6$alkyl;

b) a $C_1$-$C_6$alkyl substituted with one or more group(s) selected from halogen (such as fluorine), CN, $NO_2$, $C(O)NHR^{11}$, $C(O)N(R^{11})_2$, $CO_2H$, $SO_2R^{11}$, $SO_2NHR^{11}$, and $SO_2N(R^{11})_2$;

c) a $C_2$-$C_6$alkyl group substituted with a group selected from $OR^{11}$, halogenated $OC_1$-$C_6$alkyl, SH, $SR^{11}$, $NH_2$, $NHR^{11}$, $N(R^{11})_2$, $NHC(O)R^{11}$, and $N(R^{11})C(O)R^{11}$; or d) a group selected from $C(O)R^{11}$, $C(O)NHR^{11}$, $C(O)N(R^1)_2$, $SO_2R^{11}$, $SO_2NHR^{11}$, and $SO_2N(R^{11})_2$;

$R^2$ is selected from hydrogen and a substituted or unsubstituted group selected from $C_1$-$C_6$alkyl, $C_2$-$C_6$alkenyl, $C_2$-$C_6$alkynyl, $C_3$-$C_{10}$cycloalkyl, $C_3$-$C_{10}$heterocycloalkyl, $C(O)R^{12}$, $NH_2$, $NHR^{12}$, $N(R^{12})_2$, $C(O)NH_2$, $C(O)NHR^{12}$, $C(O)N(R^{12})_2$, $NHC(O)R^{12}$, $SO_2R^{12}$, $SO_2NHR^{12}$, $SO_2N(R^{12})_2$, $NHSO_2R^{12}$, $N(R^{12})SO_2R^{12}$, $NHSO_2NHR^{12}$, $N(R^{12})SO_2NHR^{12}$, $NHSO_2N(R^{12})_2$, and $N(R^{12})SO_2N(R^{12})_2$;

$R^3$ and $R^6$ are each independently H or a substituted or unsubstituted group selected from $C_1$-$C_6$alkyl, $C(O)R^{11}$, $NH_2$, $NHR^{11}$, $N(R^{11})_2$, $C(O)NH_2$, $C(O)NHR^{11}$, $C(O)N(R^{11})_2$, $NHC(O)R^{11}$; and one of $R^4$ and $R^5$ is H or a substituted or unsubstituted group selected from $C_1$-$C_6$alkyl, $C(O)R^{11}$, $NH_2$, $NHR^{11}$, $N(R^{11})_2$, $C(O)NH_2$, $C(O)NHR^{11}$, $C(O)N(R^{11})_2$, and $NHC(O)R^{11}$, and the other of $R^4$ and $R^5$ is a group of Formula II:

Formula II

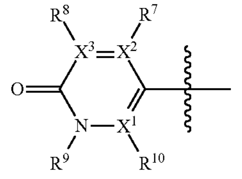

wherein, $R^7$, $R^8$, and $R^{10}$ are each independently H, halogen (such as F, Cl), CN, or a substituted or unsubstituted $C_1$-$C_6$alkyl or $C_3$-$C_6$cycloalkyl group, $OR^{11}$, $SR^{11}$, $NHR^{11}$, $N(R^{11})_2$, $NHC(O)R^{11}$, and $N(R^{11})C(O)R^{11}$, provided that at least one of $R^7$, $R^8$, and $R^{10}$ is other than H;

$R^9$ is a substituted or unsubstituted $C_1$-$C_3$alkyl or $C_3$-$C_6$cycloalkyl group;

$R^{11}$ is, independently in each occurrence, a substituted or unsubstituted $C_1$-$C_6$alkyl group;

$R^{12}$ is, independently in each occurrence, a substituted or unsubstituted $C_1$-$C_6$alkyl, $C_2$-$C_6$alkenyl, $C_2$-$C_6$alkynyl, $C_3$-$C_{10}$cycloalkyl, and $C_3$-$C_{10}$heterocycloalkyl;

$X^1$, $X^2$, and $X^3$ are each selected from N or C, wherein when $X^1$, $X^2$, or $X^3$ is N, then the $R^7$, $R^8$, or $R^{10}$ attached thereto is absent, provided that at least two of $X^1$, $X^2$, and $X^3$ is C;

wherein when any of the foregoing group contains an alkyl group, then said alkyl is a linear or branched acyclic alkyl group.

In one embodiment, $R^8$ is halogen (such as F, Cl), CN, or a substituted or unsubstituted $C_1$-$C_6$alkyl or $C_3$-$C_6$cycloalkyl group, $OR^{11}$, $SR^{11}$, $NHR^{11}$, $N(R^{11})_2$, NHC(O)$R^{11}$, or $N(R^{11})C(O)R^{11}$.

According to one embodiment, $R^4$ may be a group of Formula II and $R^5$ is hydrogen or a substituted or unsubstituted $C_1$-$C_3$ alkyl. In another embodiment, wherein $R^5$ is a group of Formula II, for instance, when $R^4$ is hydrogen or a substituted or unsubstituted $C_1$-$C_3$ alkyl. In one embodiment, $R^4$ is hydrogen.

In one embodiment, in Formula II, groups $X^1$, $X^2$ and $X^3$ are all carbon atoms. In another embodiment, $X^1$ is a nitrogen atom and $R^{10}$ is absent, and $X^2$ and $X^3$ are carbon atoms. For instance, the group of Formula II may be defined as a group of Formula II(a):

Formula II(a)

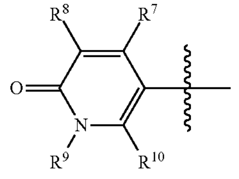

wherein $R^7$, $R^8$, $R^9$ and $R^{10}$ are as herein defined.

In one embodiment, $R^9$ is an unsubstituted $C_1$-$C_3$alkyl or $C_3$-$C_5$cycloalkyl group, such as a methyl, ethyl, n-propyl, isopropyl or cyclopropyl group, for instance, $R^9$ is a methyl group, or $R^9$ is a fluorine-substituted $C_1$-$C_3$alkyl or $C_3$-$C_5$cycloalkyl group, such as trifluoromethyl or difluorocyclopropyl. In another embodiment, $R^7$ and $R^{10}$ are each hydrogen atoms and $R^8$ is selected from Cl, CN, $NHR^{11}$ and a substituted or unsubstituted $C_1$-$C_6$alkyl or $C_3$-$C_6$cycloalkyl group.

Another embodiment relates to compounds of Formula I(a), and pharmaceutically acceptable salts, solvates, esters or prodrugs thereof:

Formula I(a)

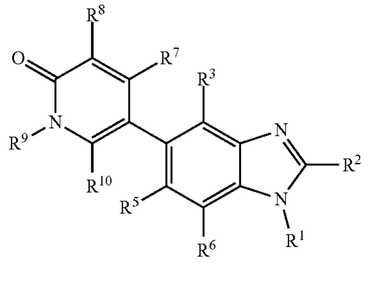

wherein $R^1$, $R^2$, $R^3$, $R^5$, $R^6$, $R^7$, $R^8$, $R^9$, and $R^{10}$ are as herein defined.

According to another embodiment, the application also relates to compounds of Formula I(b), and pharmaceutically acceptable salts, solvates, esters or prodrugs thereof:

Formula I(b)

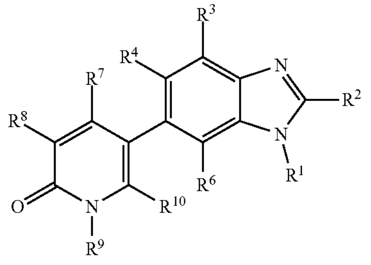

wherein $R^1$, $R^2$, $R^4$, $R^3$, $R^6$, $R^7$, $R^8$, $R^9$, and $R^{10}$ are as herein defined with respect to any of the applicable embodiments.

In one embodiment, the application relates to compounds as herein defined wherein $R^3$ is H or a substituted or unsubstituted $C_1$-$C_6$alkyl group, preferably $R^3$ is H. In another embodiment, the application relates to compounds as herein defined wherein $R^6$ is H or a substituted or unsubstituted $C_1$-$C_6$alkyl group, preferably $R^6$ is H.

In another embodiment, the present application relates to compounds of Formula III, and pharmaceutically acceptable salts, solvates, esters or prodrugs thereof:

Formula III

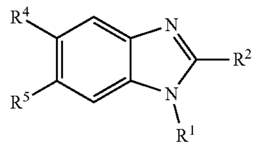

wherein $R^1$, $R^2$, $R^4$ and $R^5$ are as herein defined with respect to any of the applicable embodiments.

Another embodiment of the application relates to compounds of Formula III(a), and pharmaceutically acceptable salts, solvates, esters or prodrugs thereof:

Formula III(a)

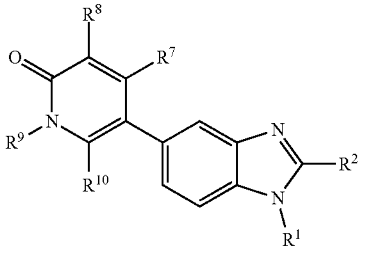

wherein $R^1$, $R^2$, $R^7$, $R^8$, $R^9$, and $R^{10}$ are as herein defined.

According to another embodiment, the application also relates to compounds of Formula III(b), and pharmaceutically acceptable salts, solvates, esters or prodrugs thereof:

Formula III(b)

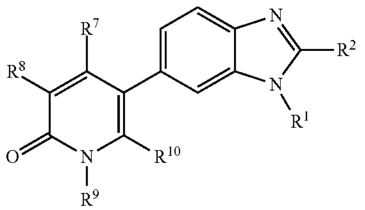

wherein $R^1$, $R^2$, $R^7$, $R^8$, $R^9$, and $R^{10}$ are as herein defined.

According to one embodiment, the application relates to compounds of Formula III(a) or III(b) as herein defined, wherein $R^9$ is an unsubstituted $C_1$-$C_3$alkyl or $C_3$-$C_5$cycloalkyl group, or $R^9$ is a fluorine-substituted $C_1$-$C_3$alkyl or $C_3$-$C_5$cycloalkyl group. For instance, $R^9$ is selected from methyl, trifluoromethyl, ethyl, n-propyl, isopropyl and cyclopropyl, for instance, or $R^9$ is a methyl group. In another embodiment, the application relates to compounds of Formula III(a) or III(b), wherein $R^7$ and $R^{10}$ are each hydrogen atoms and $R^8$ is selected from Cl, CN, $NHR^{11}$ and a substituted or unsubstituted $C_1$-$C_6$alkyl or $C_3$-$C_6$cycloalkyl group. In a further embodiment, $R^8$ and $R^9$ are each independently a methyl, ethyl, isopropyl, fluoromethyl, difluoromethyl, trifluoromethyl, cyclopropyl, or difluorocyclopropyl group.

In yet another embodiment, the present application relates to a compound of Formula I, I(a), I(b), III, III(a) or III(b) as herein defined with respect to any one of the applicable embodiments, wherein $R^2$ is hydrogen or a substituted or unsubstituted group selected from $C_1$-$C_6$alkyl, $C_3$-$C_{10}$cycloalkyl, or $C_3$-$C_{10}$heterocycloalkyl group. For instance, $R^2$ is a substituted or unsubstituted $C_1$-$C_3$alkyl, $C_3$-$C_6$cycloalkyl, or $C_3$-$C_6$heterocycloalkyl group, or is a substituted or unsubstituted group selected from methyl, ethyl, propyl, isopropyl, butyl, isobutyl, tert-butyl, cyclopropyl, cyclobutyl, cyclopentyl, tetrahydrofuranyl, tetrahydropyranyl, dioxolanyl, piperidinyl, and pyrrolidnyl.

According to a further embodiment, the compound of the present application is a compound of Formula I, I(a), I(b), III, III(a) or III(b) as herein defined including any of their respective embodiments, wherein $R^1$ is a branched or linear $C_2$-$C_6$alkyl substituted with a group selected from fluorine, $OC_1$-$C_6$alkyl, and halogenated $OC_1$-$C_6$alkyl. For instance, $R^1$ is a branched or linear $C_2$-$C_3$alkyl substituted with a group selected from fluorine, $OC_1$-$C_6$alkyl, and halogenated $OC_1$-$C_6$alkyl. In an alternate embodiment, $R^1$ is selected from fluoromethyl, difluoromethyl, trifluoromethyl, 2,2,2-trifluoroethyl, 2-methoxyethyl, 2-ethoxyethyl, 2-(fluoromethoxy)ethyl, 2-(difluoromethoxy)ethyl, 2-(trifluoromethoxy)ethyl, 3,3,3-trifluoro-1-propyl, 3-methoxy-1-propyl, 3-ethoxy-1-propyl, 3-(fluoromethoxy)-1-propyl, 3-(difluoromethoxy)-1-propyl, 3-(trifluoromethoxy)-1-propyl, 1-methoxy-2-propyl, 1-ethoxy-2-propyl, 1-(fluoromethoxy)-2-propyl, 1-(difluoromethoxy)-2-propyl, 1-(trifluoromethoxy)-2-propyl, 2-methoxy-1-propyl, 2-ethoxy-1-propyl, 2-(fluoromethoxy)-1-propyl, 2-(difluoromethoxy)-1-propyl, or 2-(trifluoromethoxy)-1-propyl, for instance, $R^1$ is 2-methoxyethyl, 2-(trifluoromethoxy)ethyl, 1-methoxy-2-propyl, 1-(trifluoromethoxy)-2-propyl, 2-methoxy-1-propyl, or 2-(trifluoromethoxy)-1-propyl. In another embodiment, $R^1$ is methyl, trifluoromethyl, ethyl, 2,2,2-trifluoroethyl, n-propyl, 3,3,3-trifluoro-1-propyl, isopropyl, n-butyl, isobutyl, or t-butyl.

Examples of the compounds of the present application include, without limitation:

Compound 1

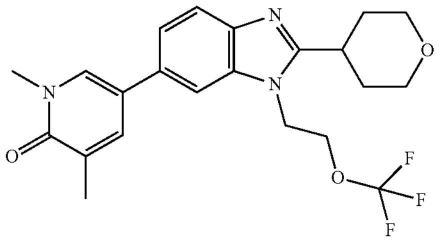

Compound 2

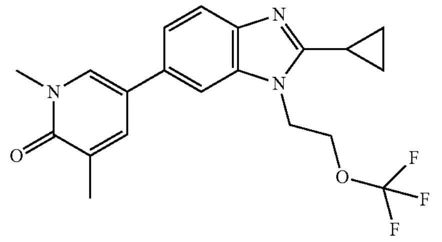

Compound 3

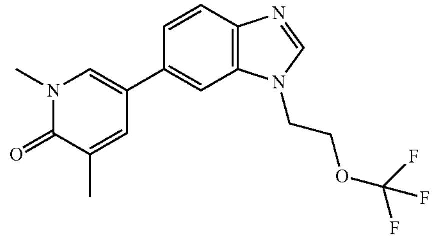

Compound 4

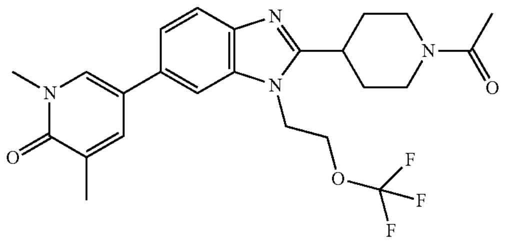

-continued
Compound 5
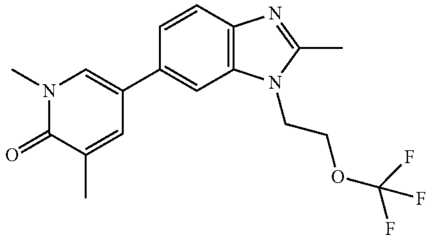
Compound 6
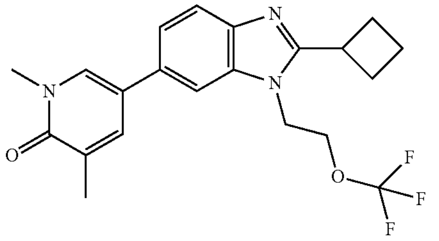
Compound 7
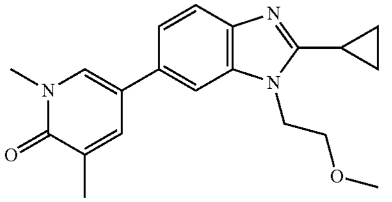
Compound 8
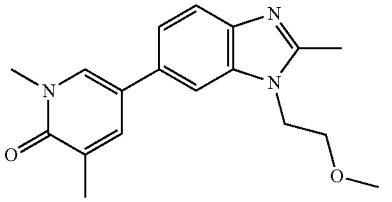
Compound 9
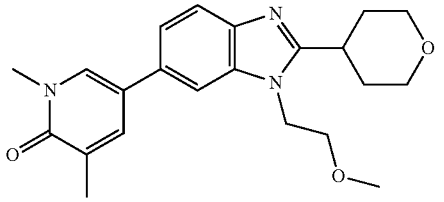
Compound 10
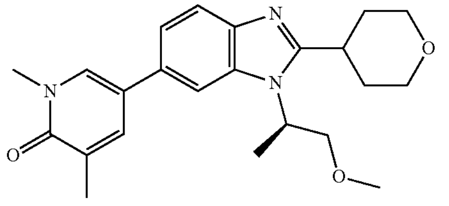
Compound 11
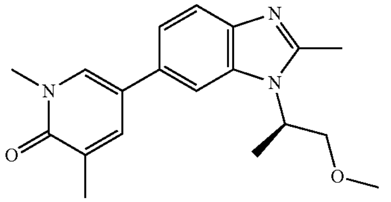
-continued
Compound 12
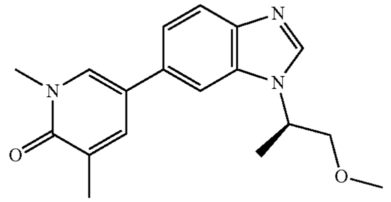
Compound 13
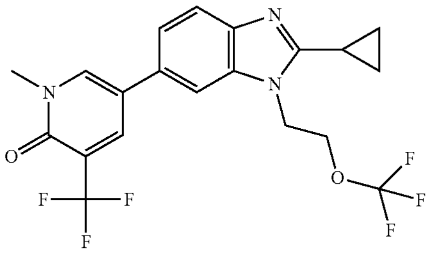
Compound 14
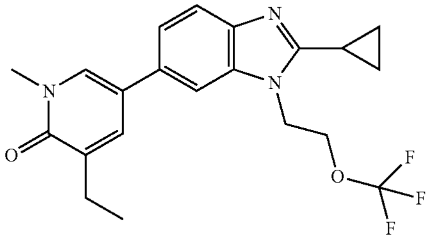
Compound 15
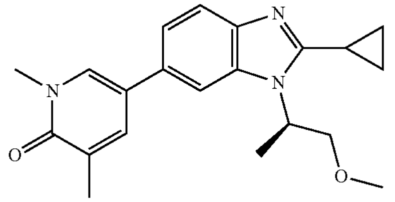
Compound 16
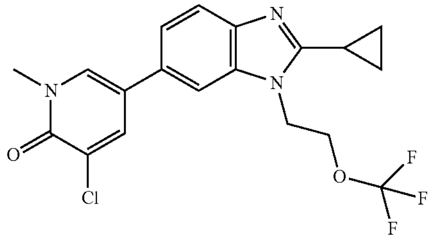
Compound 17
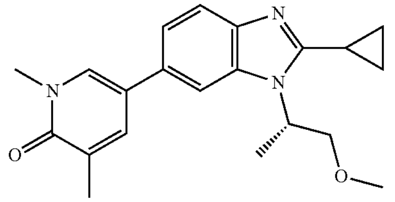
Compound 18
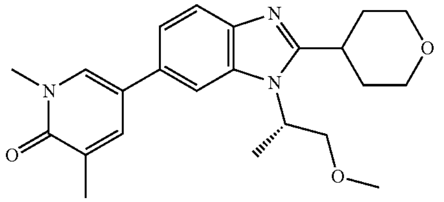

-continued
Compound 19
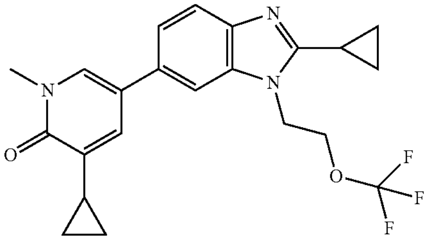
Compound 20
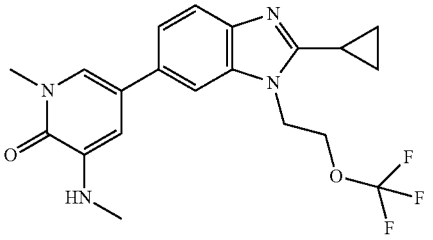
Compound 21
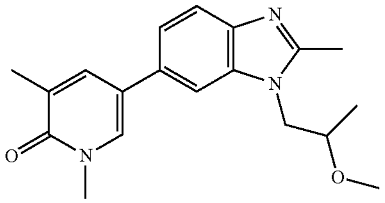
(and isomers 21a and 21b)
Compound 22
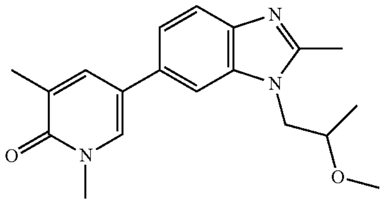
(and isomers 22a and 22b)
Compound 23
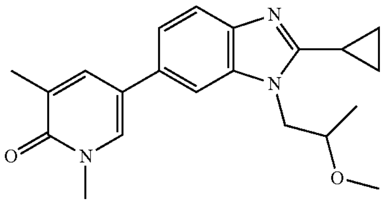
(and isomers 23a and 23b)
Compound 24
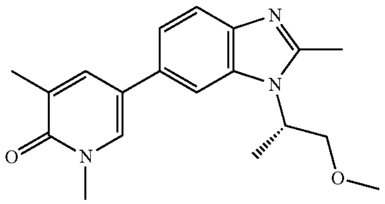
-continued
Compound 25
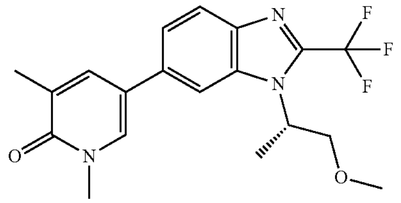
Compound 26
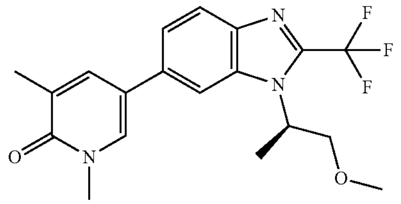
Compound 27
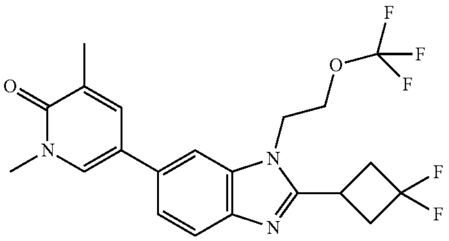
Compound 28
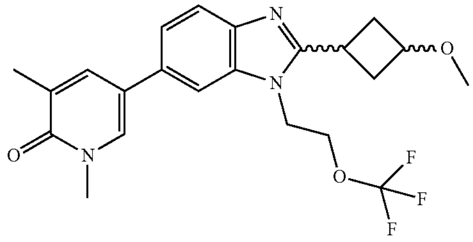
Compound 28a
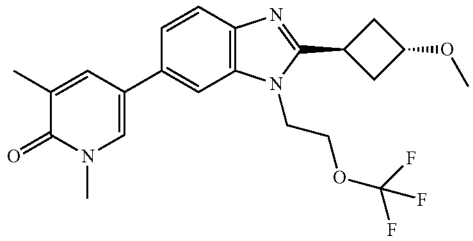
Compound 28b
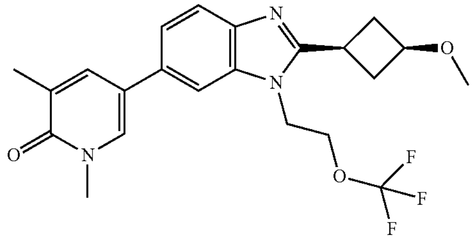

-continued
Compound 29
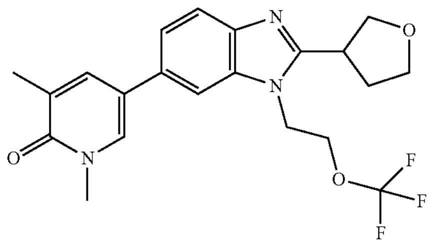
(and isomers 29a and 29b)
Compound 30
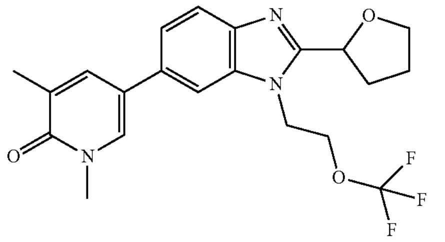
(R/S)
Compound 30a
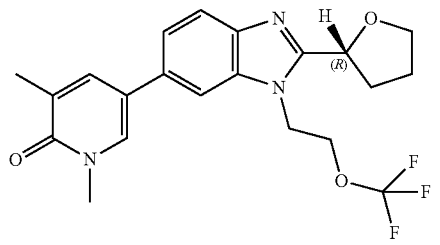
Compound 30b
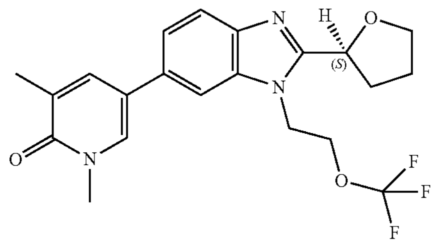
Compound 31
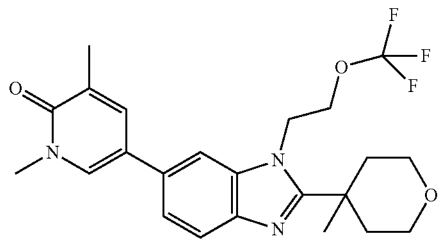
Compound 32
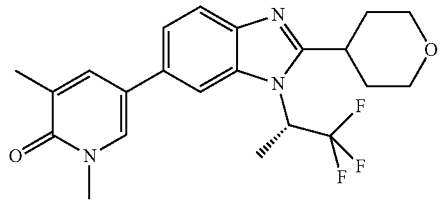
-continued
Compound 33
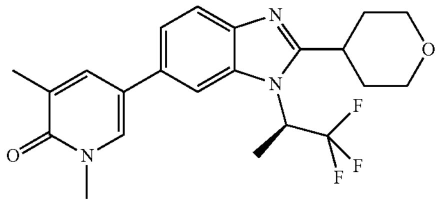
Compound 34
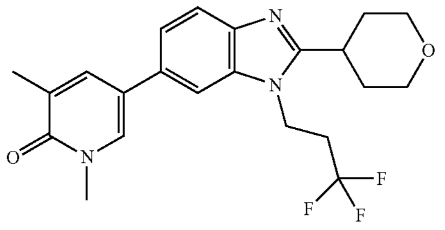
Compound 35
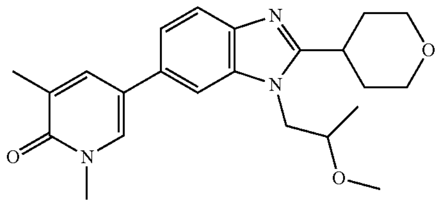
(and isomers 35a and 35b)
Compound 36
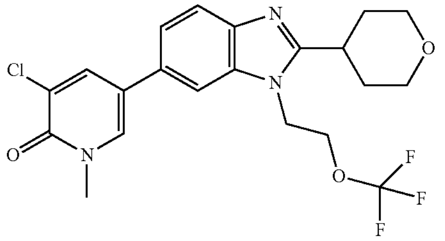
Compound 37
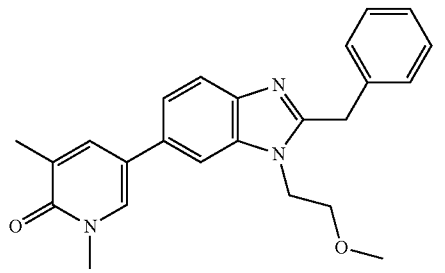
Compound 38
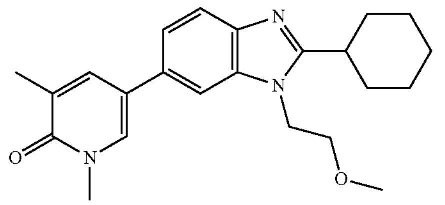

-continued
Compound 39
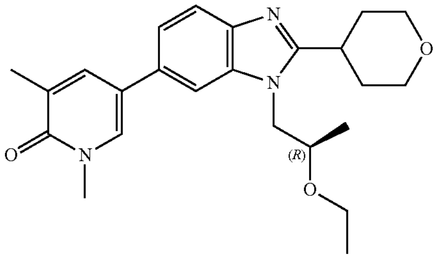
Compound 40
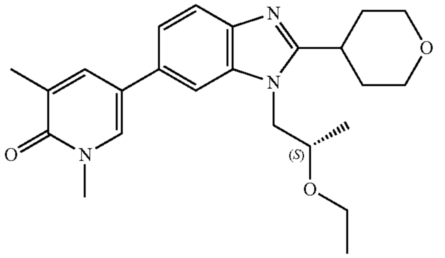
Compound 41
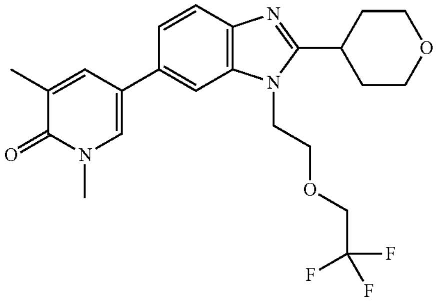
Compound 42
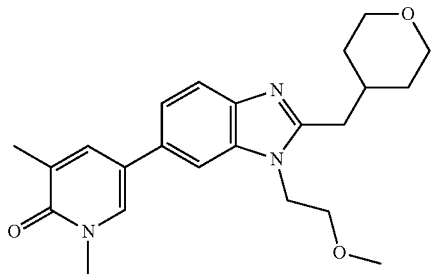
Compound 43
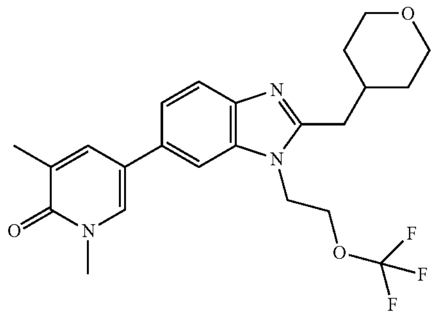
-continued
Compound 44
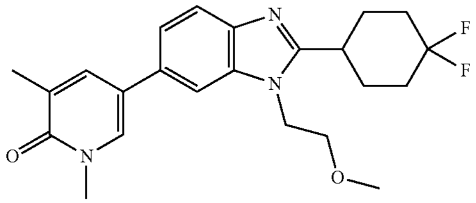
Compound 45
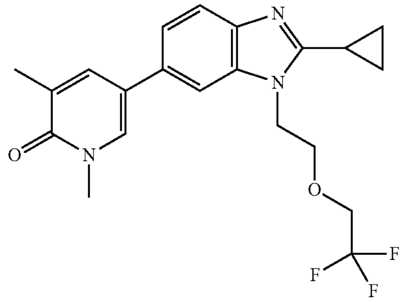
Compound 46
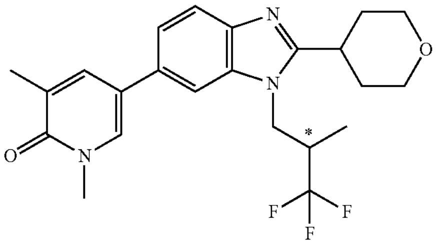
(and isomers 46a and 46b)
Compound 47
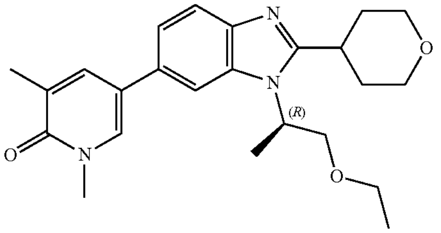
Compound 48
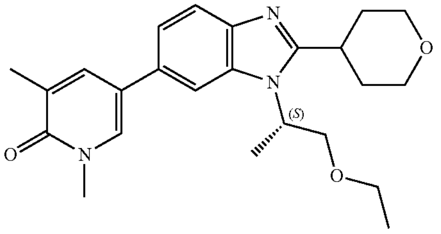
Compound 49
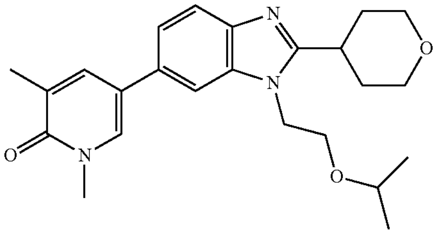

-continued
Compound 50
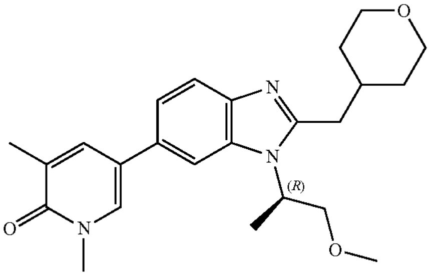
Compound 51
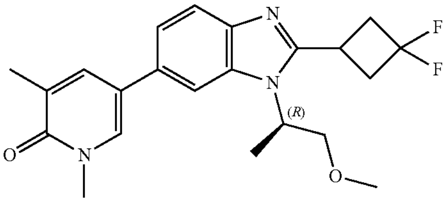
Compound 52
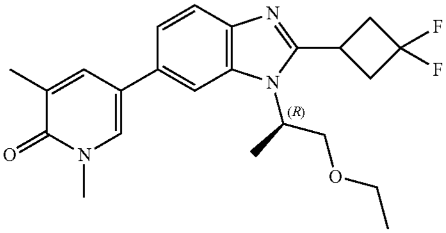
Compound 53
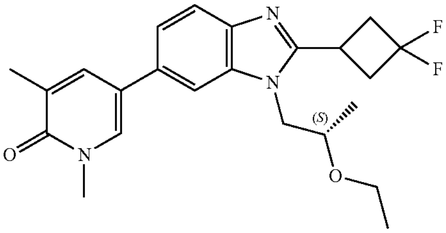
Compound 54
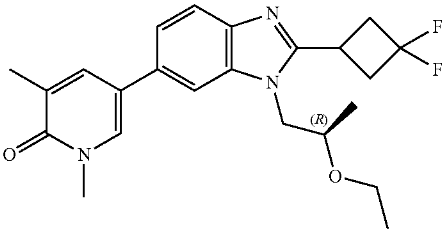
Compound 55
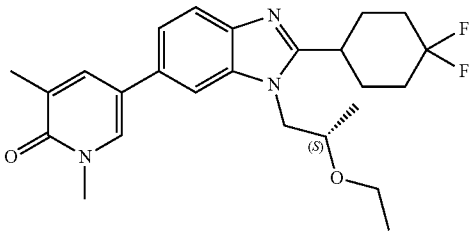
-continued
Compound 56
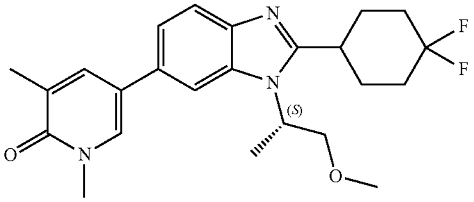
Compound 57
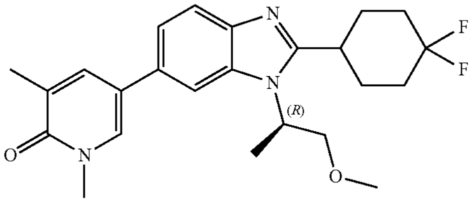
Compound 58
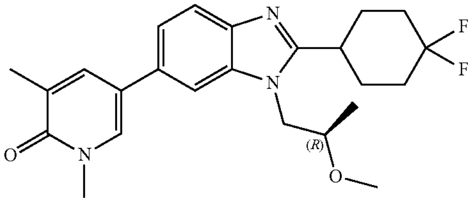
Compound 59
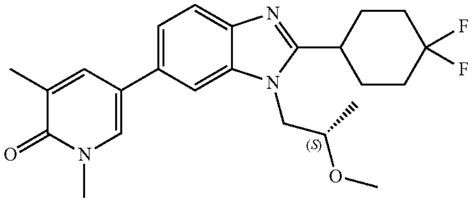
Compound 60
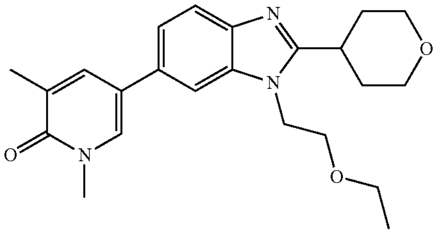
Compound 61
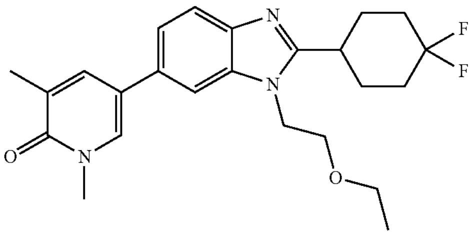

-continued

Compound 62

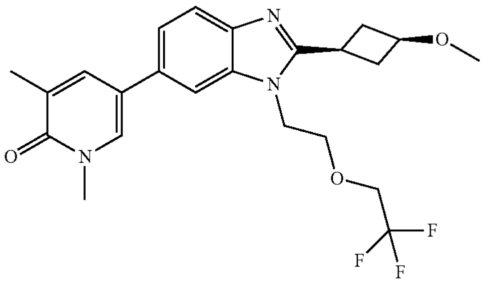

Compound 63

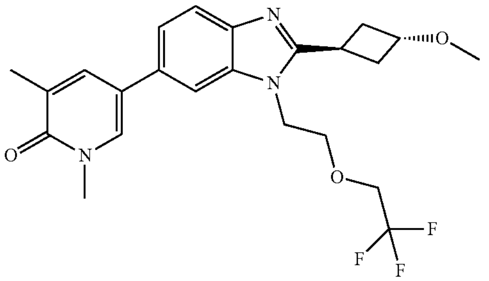

Compound 64

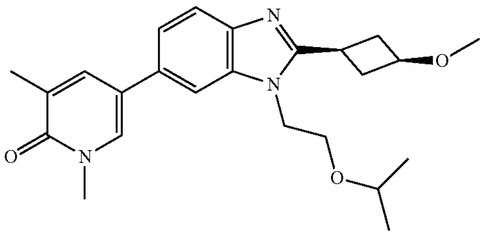

Compound 65

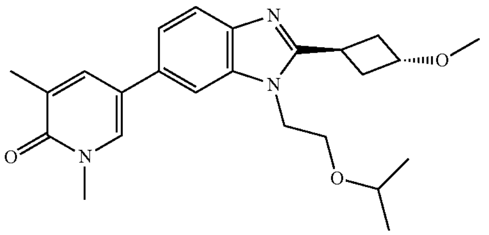

Compound 66

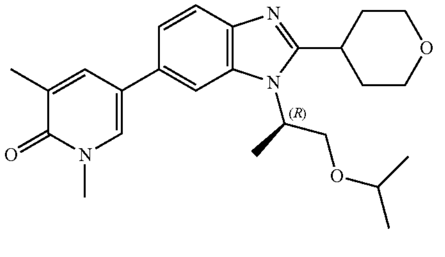

Compound 67

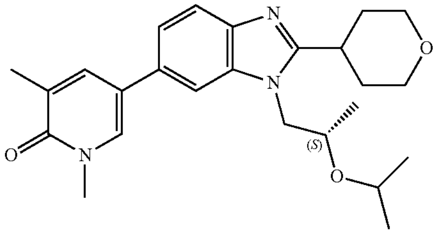

or a pharmaceutically acceptable salt, solvate or prodrug thereof.

In a further embodiment, this application relates to a compound selected from Compounds 1 to 67 as herein defined, or a pharmaceutically acceptable salt, solvate, or prodrug thereof.

iii. Methods, Uses, Formulations and Administration

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in treatment, healing, prevention, or amelioration of a disease, disorder, or side effect, or a decrease in the rate of advancement of a disease or disorder. The term also includes within its scope amounts effective to enhance normal physiological function.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, the term "bromodomain inhibitor" denotes a compound which inhibits the binding of a bromodomain with its cognate acetylated proteins. In one embodiment the bromodomain inhibitor is a compound which inhibits the binding of a bromodomain to acetylated lysine residues. In a further embodiment the bromodomain inhibitor is a compound which inhibits the binding of a bromodomain to acetylated lysine residues on histones, particularly histones H3 and H4.

In a particular embodiment the bromodomain inhibitor is a compound that inhibits the binding of BET family bromodomains to acetylated lysine residues (hereafter referred to as a "BET family bromodomain inhibitor"). The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction.

As used herein, the term "inhibitor" is defined as a compound that binds to and/or inhibits the target bromodomain-containing protein (such as a BET protein, e.g., BRD2, BRD3, BRD4, and/or BRDT) with measurable affinity.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

The term "patient or subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

In some embodiments, the disease or condition can be an auto-immune disorder, an inflammatory disorder, a dermal disorder, or cancer. In some optional embodiments, the disease or condition can be an auto-immune disorder. In some other optional embodiments, the disease or condition can be an inflammatory disorder. In further optional embodiments, the inflammatory disorder can be rheumatoid arthritis, irritable bowel syndrome, or psoriasis.

In some other optional embodiments, the disease or condition can be cancer. In further optional embodiments, the cancer can be brain cancer, pancreatic cancer, breast cancer, lung cancer, or prostate cancer. In further optional embodiments, the cancer can be brain cancer. In further optional embodiments, the brain cancer is glioblastoma multiforme.

In some embodiments, the cancer is selected from the group consisting of: brain (gliomas), glioblastomas, leukemias, lymphomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, gastric, bladder, head and neck, kidney, lung, liver, melanoma, renal, ovarian, pancreatic, prostate, sarcoma, osteosarcoma, giant cell tumor of bone and thyroid.

In some embodiments, the disorder can be a proliferative disorder, inflammatory disease, sepsis, autoimmune disease, or viral infection. In some optional embodiments, the proliferative disorder can be cancer.

The term "proliferative disorder" refers to cells having the capacity for autonomous growth, i.e., an abnormal state of condition characterized by rapidly proliferating cell growth which generally forms a distinct mass that show partial or total lack of structural organization and functional coordination with normal tissue.

The terms "neoplasm", "neoplastic disorder", "neoplasia" "cancer," and "tumor" are meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (related to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures, including external epithelia (e.g., skin and linings of the gastrointestinal tract, lungs, and cervix), and internal epithelia that line various glands (e.g., breast, pancreas, thyroid). Examples of neoplasms include leukemia, and hepatocellular cancers, sarcoma, vascular endothelial cancers, breast cancers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastrointestinal cancers, melanomas, ovarian and endometrial cancer, renal and bladder cancer, liver cancer, endocrine cancer (e.g. thyroid), and pancreatic cancer.

In some aspects, examples of cancers treated using the compounds and methods described herein include, but are not limited to, acinic cell carcinoma, acoustic neuroma, acral lentiginous melanoma, acrospiroma, acute eosinophilic leukemia, acute erythroid leukemia, acute lymphoblastic leukemia, acute lymphocytic leukemia, acute megakaryoblastic leukemia, acute monocytic leukemia, acute myelogenous leukemia, acute myelognous leukemia, acute promyelocytic leukemia, adrenal cancer, adenocarcinoma, adenoid cystic carcinoma, adenoma, adenomatoid odontogenic tumor, adenosquamous carcinoma, adipose tissue neoplasm, adrenal cancer, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, Bannayan-Zonana syndrome, basal cell carcinoma, B-cell chronic lymphocytic leukemia, B-cell lymphoma, B-cell prolymphocytic leukemia, biliary tract cancer, bladder, bladder cancer, blastoma, bone cancer, brain (gliomas), brain cancer, breast, breast cancer, Brenner tumor, Brown tumor, Burkitt's lymphoma, carcinoma, carcinoma in situ, carcinosarcoma, cartilage tumor, cementoma, cervical cancer, chondroma, chordoma, choriocarcinoma, choroid plexus papilloma, chronic lymphocytic leukemia, clear-cell sarcoma of the kidney, colon, colorectal cancer, Cowden disease, craniopharyngioma, cutaneous T-cell lymphoma, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, ependymoma, esophageal cancer, Ewing's sarcoma, fetus in fetu, fibroma, fibrosarcoma, follicular lymphoma, follicular thyroid cancer, gallbladder cancer, ganglioneuroma, gastric, gastric cancer, gastrointestinal cancer, germ cell tumor, gestational choriocarcinoma, giant cell fibroblastoma, giant cell tumor of bone and thyroid, giant cell tumor of the bone, glial tumor, glioblastoma multiforme, glioblastomas, glioma, gliomatosis cerebri, glucagonoma, gonadoblastoma, granulosa cell tumor, gynandroblastoma, hairy cell leukemia, head and neck, head and neck cancer, hemangioblastoma, hemangiopericytoma, hematological malignancy, hepatoblastoma, hepatosplenic T-cell lymphoma, Hodgkin's lymphoma, inflammatory breast cancer, intestinal cancer, invasive lobular carcinoma, kidney, kidney cancer, laryngeal cancer, lentigo maligna, lethal midline carcinoma, leukemia, leukemias, leydig cell tumor, Lhermitte-Duclos disease, liposarcoma, liver, liver cancer, lung, lung cancer, lymphangio sarcoma, lymphangioma, lymphoepithelioma, lymphoma, lymphomas, malignant fibrous histiocytoma, malignant peripheral nerve sheath tumor, malignant triton tumor, MALT lymphoma, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myeloid sarcoma, myxoid liposarcoma, myxoma, myxosarcoma, nasopharyngeal carcinoma, neurinoma, neuroblastoma, neurofibroma, neuroma, nodular melanoma, non-Hodgkin's lymphoma, non-small cell lung cancer, ocular cancer, oligoastrocytoma, oligodendroglioma, oncocytoma, optic nerve sheath meningioma, optic nerve tumor, oral cancer, osteosarcoma, ovarian, ovarian cancer, Pancoast tumor, pancreatic, pancreatic cancer, papillary thyroid cancer, paraganglioma, pharyngeal cancer, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate, prostate cancer, pseudomyxoma peritonei, rectal cancer, renal, renal cell carcinoma, renal medullary carcinoma, retinoblastoma, rhabdomyoma, Rhabdomyosarcoma, Richter's transformation, sarcoma, Schwannomatosis, seminoma, Sertoli cell tumor, sex cord-gonadal stromal tumor, Sezary's disease, signet ring cell carcinoma, skin cancer, small blue round cell tumors, small cell carcinoma, small cell lung cancer, small intestine cancer, soft tissue sarcoma, somatostatinoma, soot wart, spinal tumor, splenic marginal zone lymphoma, squamous carcinoma, squamous cell carcinoma, stomach cancer, synovial sarcoma, T-cell lymphoma, testicular cancer, thecoma, throat cancer, thyroid cancer, transitional cell carcinoma, urachal cancer, urogenital cancer, urothelial carcinoma, uterine cancer, uveal melanoma, vaginal cancer, verrucous carcinoma, visual pathway glioma, vulvar cancer, Waldenstrom's macroglobulinemia, Warthin's tumor, and Wilm's tumor.

In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor. In some other embodiments, the cancer can be acute myelognous leukemia or Burkitt's lymphoma.

In some embodiments, the autoimmune and inflammatory diseases or conditions can involve an inflammatory response to infections with bacteria, viruses, fungi, parasites or their toxins, as well as viruses. In some other embodiments, the autoimmune and inflammatory diseases or conditions can be selected from the group consisting of acute lung injury, acute pancreatitis, acute renal failure, ARDS (adult respiratory distress syndrome), burns, coronavirus, encephalitis, endotoxaemia, fulminant hepatitis, herpes simplex, herpes zoster, Herxheimer reactions, malaria and SIRS associated with viral infections such as influenza, meningitis, multi-organ dysfunction syndrome, myelitis, post-surgical syndromes, sarcoidosis, sepsis, sepsis syndrome, septic shock, systemic inflammatory response syndrome (SIRS), toxic shock syndrome.

In some embodiments, the present description provides a method of treating other conditions. Such other conditions include, but are not limited to, acne, acute inflammatory responses (such as acute respiratory distress syndrome and ischemia/reperfusion injury, glioblastoma, Graves' disease, HIV, HPV, inflammatory disease, keloids and related scarring, lung cancer, meningitis (bacterial and viral), multiple sclerosis, neoplasm, neuroblastoma, pancreatic cancer, scleroderma, skin cancer, toxic shock, viral infections, viral infections and diseases.

In some embodiments, the present description provides a method of treating a benign proliferative disorder. Such benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, prolactinoma, pseudotumor cerebri, pyogenic granuloma, and juvenile polyposis syndrome.

The present description further relates to a method for treating infectious and noninfectious inflammatory events and autoimmune and other inflammatory diseases by administration of an effective amount of a provided compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholecystitis, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleracierma, mycosis fungoides, acute inflammatory responses (such as acute respiratory distress syndrome and ischemia/reperfusion injury), and Graves' disease. Other examples of infectious and noninfectious inflammatory events, autoimmune and other inflammatory diseases include, but are not limited to, Addison's disease, agammaglobulinemia, allergic rhinitis, allergy, Alzheimer's disease, appendicitis, asthma, atherosclerosis, atopic dermatitis, autoimmune alopecia, autoimmune hemolytic and thrombocytopenic states, autoimmune hypopituitarism, autoimmune polyglandular disease (also known as autoimmune polyglandular syndrome), Behcet's disease, cholecystitis, chronic idiopathic thrombocytopenic purpura, chronic obstructive pulmonary disease (COPD), Crohn's disease, degenerative joint disease, dermatitis, dermatomyositis, encephalitis, enteritis, gastritis, gingivitis, glomerulonephritis, Goodpasture's syndrome, Guillain-Barre syndrome, Hashimoto's thyroiditis, hepatitis, hyperacute rejection of transplanted organs, inflammatory pelvic disease, irritable bowel syndrome, juvenile arthritis, meningitis, multiple sclerosis, myasthenia gravis, mycosis fungoides, myocarditis, myositis, nephritis, osteoarthritis, osteomyelitis, pancreatitis, Parkinson's disease, pernicious anemia, pneumonitis, psoriasis, psoriatic arthritis, rheumatoid arthritis, scleraciermа, scleroderma, septic shock, sinusitis, Sjogren's disease, skin sunburn, systemic lupus erythematosus (SLE), tissue graft rejection, Type I diabetes, ulcerative colitis, urethritis, vasculitis, vitiligo, and Waldenstrom macroglobulinemia.

In some embodiments, the present description provides a method of treating systemic inflammatory response syndromes such as LPS-induced endotoxic shock and/or bacteria-induced sepsis by administration of an effective amount of a provided compound to a mammal, in particular a human in need of such treatment.

The present description further relates to a method for treating viral infections and diseases by administration of an effective amount of a provided compound to a mammal, in particular a human in need of such treatment. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

The present description further relates to a method of treating a subject, such as a human, suffering from one of the abovementioned conditions, illnesses, disorders or diseases. The method comprises administering a therapeutically effective amount of one or more provided compounds, which function by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The present description further provides a therapeutic method of modulating protein methylation, gene expression, cell proliferation, cell differentiation and/or apoptosis in vivo in diseases mentioned above, in particular cancer, inflammatory disease, and/or viral disease comprising administering to a subject in need of such therapy a pharmacologically active and therapeutically effective amount of one or more provided compounds.

The present description further provides a method of regulating endogenous or heterologous promoter activity by contacting a cell with a provided compound.

In certain embodiments, the present description provides a method of treating a disorder (as described herein) in a subject, comprising administering to the subject identified as in need thereof, a compound of the present description. The identification of those patients who are in need of treatment for the disorders described above is well within the ability and knowledge of one skilled in the art. Certain of the methods for identification of patients which are at risk of developing the above disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a disorder by methods well known in the art (e.g., determining tumor size or screening for tumor markers where the cell proliferative disorder is cancer) and then administering a therapeutically effective amount of a compound of the present description, to the subject. After an appropriate period of time after the administration of the compound (e.g., 1 day, 1 week, 2 weeks, one month, six months), the extent of the disorder is determined again.

The modulation (e.g., decrease) of the extent or invasiveness of the disorder indicates efficacy of the treatment. The extent or invasiveness of the disorder may be determined periodically throughout treatment. For example, the extent or invasiveness of the disorder may be checked every few hours, days or weeks to assess the further efficacy of the treatment. A decrease in extent or invasiveness of the disorder indicates that the treatment is efficacious. The method described may be used to screen or select patients that may benefit from treatment with a compound of the present description.

According to one aspect, there is provided a method for identifying compounds for use in treating autoimmune and inflammatory diseases or conditions which comprises the step of determining whether the compound inhibits the binding of a bromodomain with its cognate acetylated protein.

According to another embodiment, the description provides a method of inhibiting a bromodomain-containing protein (such as a BET protein, e.g., BRD2, BRD3, BRD4, and/or BRDT) using a composition comprising a compound of the present description or a pharmaceutically acceptable derivative thereof and a pharmaceutically acceptable carrier, adjuvant, or vehicle. The amount of a compound of the present description in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, the amount of compound in a provided composition is such that is effective to measurably inhibit one or more bromodomain-containing proteins (such as a BET protein, e.g., BRD2, BRD3, BRD4, and/or BRDT), or a mutant thereof, in a biological sample or in a patient. In certain embodiments, a provided composition is formulated for administration to a patient in need of such composition. In some embodiments, a provided composition is formulated for oral administration to a patient.

In some embodiments, the therapeutically effective amount of a compound as defined herein can be administered to a patient alone or admixed with a pharmaceutically acceptable carrier, adjuvant, or vehicle.

The expression "pharmaceutically acceptable carrier, adjuvant, or vehicle" and equivalent expressions, refer to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester, prodrug, salt of a prodrug, or other derivative of a compound of the present description that, upon administration to a recipient, is capable of providing, either directly or indirectly, a compound of the present description or an inhibitory active metabolite or residue thereof.

As used herein, the term "inhibitory active metabolite or residue thereof" means that a metabolite or residue thereof is also an inhibitor of one or more bromodomain-containing protein(s) (such as a BET protein, e.g., BRD2, BRD3, BRD4, and/or BRDT), or a mutant thereof.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intraarticular, intrasynovial, intrasternal, intrathecal, intrahepatic, intralesional and intracranial injection or infusion techniques. Other modes of administration also include intradermal or transdermal administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of the present description with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone (PVP), sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of the present description include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of the present description. Additionally, the description contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Compounds or compositions described herein may be administered using any amount and any route of administration effective for treating or lessening the severity of the disorders or diseases as contemplated herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Compounds and compositions described herein are generally useful for the inhibition of activity of one or more proteins involved in epigenetic regulation. Thus, in some embodiments, the present description provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a provided compound or composition.

Examples of proteins inhibited by the compounds and compositions described herein and against which the methods described herein are useful include bromodomain-containing proteins, such as BET proteins, such as BRD2, BRD3, BRD4, and/or BRDT, or an isoform or mutant thereof.

The activity of a provided compound, or composition thereof, as an inhibitor of a bromodomain-containing protein, such as a BET protein, such as BRD2, BRD3, BRD4, and/or BRDT, or an isoform or mutant thereof, may be assayed in vitro, in vivo, or in a cell line. In vitro assays include assays that determine inhibition of bromodomain-containing proteins, such as BET proteins, such as BRD2, BRD3, BRD4, and/or BRDT, or a mutant thereof. Alternatively, inhibitor binding may be determined by running a competition experiment where a provided compound is incubated with a bromodomain-containing protein, such as a BET protein, such as BRD2, BRD3, BRD4, and/or BRDT bound to known ligands, labeled or unlabeled. Detailed conditions for assaying a provided compound as an inhibitor of a bromodomain-containing protein, such as a BET protein, such as BRD2, BRD3, BRD4, and/or BRDT or a mutant thereof.

The present description provides for a method of treating a subject with a MYC-dependent cancer, comprising: identifying a subject in need of treatment; administering to the subject a BET inhibitor; determining at least one of MYC mRNA expression, MYC protein expression and tumor mass, and wherein following administration, there is a decrease in at least one of MYC mRNA expression, MYC protein expression and tumor mass, thereby treating the disease.

In one embodiment, the identification step comprises determining whether the subject has at least one of a MYC translocation, a genetic rearrangement of MYC, MYC amplification, MYC over-expression and at least one cellular function that facilitates cellular and/or tumor growth and is altered upon reduction of MYC mRNA or protein expression.

The present description also provides for a method of treating a subject with a MYC-dependent cancer, comprising: determining at least one of MYC mRNA expression, MYC protein expression and tumor mass; administering to the subject a BET inhibitor; and comparing at least one of MYC mRNA expression, MYC protein expression and tumor mass in the subject before and after administration of the BET inhibitor.

The present description also provides a method of treating a subject with a MYC-dependent cancer, comprising: administering to the subject a BET inhibitor that is identified as capable of decreasing at least one of MYC mRNA expression, MYC protein expression and tumor mass; and determining at least one of MYC mRNA expression, MYC protein expression and tumor mass; wherein following the administration, there is a decrease in at least one of MYC mRNA expression, MYC protein expression and tumor mass, thereby treating the disease.

The present description also provides for a method of treating a subject with a disease, comprising: administering a BET inhibitor that is identified as capable of decreasing at least one of MYC mRNA expression, MYC protein expression and tumor mass, wherein following the administration, there is a decrease in at least one of MYC mRNA expression, MYC protein expression and tumor mass, thereby treating the disease.

Acetylated histone recognition and bromodomain-containing proteins (such as BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/GI, including growth-associated genes, and remains bound to chromatin throughout the cell cycle (Dey, et al. (2009) *Mol. Biol. Cell* 20:4899-4909). BRD4 also physically associates with Mediator and P-TEFb (CDK9/cyclin TI) to facilitate transcriptional elongation (Yang, et al. (2005) *Oncogene* 24:1653-1662; Yang, et al. (2005) *Mol. Cell* 19:535-545). CDK9 is a validated target in chronic lymphocytic leukemia (CLL), and is linked to c-MYC-dependent transcription (Phelps, et al. *Blood* 113:2637-2645; Rahl, et al. (2010) *Cell* 141:432-445).

BRD4 is translocated to the NUT protein in patients with lethal midline carcinoma, an aggressive form of human squamous carcinoma (French, et al. (2001) *Am. J. Pathol.* 159:1987-1992; French, et al. (2003) *Cancer Res.* 63:304-307). In vitro analysis with RNAi supports a causal role for BRD4 in this recurrent t(15;19) chromosomal translocation. Pharmacologic inhibition of the BRD4 bromodomains results in growth arrest/differentiation of BRD4-NUT cell lines in vitro and in vivo (Filippakopoulos, et al. "Selective Inhibition of BET Bromodomains," *Nature* (published online Sep. 24, 2010)).

Bromodomain-containing proteins (such as BET proteins) have also been implicated in inflammatory diseases. BET proteins {e.g., BRD2, BRD3, BRD4, and BRDT) regulate assembly of histone acetylation-dependent chromatin complexes that control inflammatory gene expression (Hargreaves, et al. (2009) *Cell* 138:129-145; LeRoy, et al. (2008) *Mol. Cell* 30:51-60; Jang, et al. (2005) *Mol. Cell* 19:523-534; Yang, et al. (2005) *Mol. Cell* 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme, et al. "Suppression of Inflammation by a Synthetic Histone Mimic," *Nature* (published online Nov. 10, 2010)).

Bromodomain-containing proteins (such as BET proteins) also play a role in viral disease. For example, BRD4 is implicated in human papilloma virus (HPV). In the primary phase of HPV infection of basal epithelia, the viral genome is maintained in an extra-chromosomal episome. In some strains of HPV, BRD4 binding to the HPV E2 protein functions to tether the viral genome to chromosomes. E2 is critical for both the repression of E6/E7 and te activation of HPV viral genes. Disruption of BRD4 or the BRD4-E2 interaction blocks E2-dependent gene activation. BRD4 also functions to tether other classes of viral genomes to host chromatin (e.g., Herpesvirus, Epstein-Barr virus).

In certain embodiments, a provided compound inhibits one or more of BRD2, BRD3, BRD4, BRDT, and/or another member of the bromodomain-containing proteins, or a mutant thereof. In some embodiments, a provided compound inhibits two or more of BRD2, BRD3, BRD4, BRDT, and/or another member of the bromodomain-containing proteins, or a mutant thereof. Provided compounds are inhibitors of one of more of the bromodomain-containing proteins, such as BRD2, BRD3, BRD4, and/or BRDT and are therefore useful for treating one or more disorders associated with activity of one or more of the bromodomain-containing proteins, such as BRD2, BRD3, BRD4, and/or BRDT. Thus, in certain embodiments, the present description provides a method for treating an bromodomain-containing protein-mediated disorder, such as a BET-mediated, a BRD2-mediated, a BRD3-mediated, a BRD4-mediated disorder, and/or a BRDT-mediated disorder comprising the step of inhibiting a bromodomain-containing protein, such as a BET protein, such as BRD2, BRD3, BRD4, and/or BRDT, or a mutant thereof, by administering to a patient in need thereof a provided compound, or a pharmaceutically acceptable composition thereof.

As used herein, the terms "bromodomain-containing protein-mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role.

In some embodiments, the BET family bromodomain can be BRD2, BRD3 or BRD4.

Accordingly, another embodiment of the present description relates to treating or lessening the severity of one or more diseases in which one or more of the bromodomain-containing proteins, such as BET proteins, such as BRD2, BRD3, BRD4, and/or BRDT, or a mutant thereof, are known to play a role.

Diseases and conditions treatable according to the methods of the present description include, but are not limited to, cancer and other proliferative disorders, inflammatory diseases, sepsis, autoimmune disease, and viral infection. Thus one aspect is a method of treating a subject having a disease, disorder, or symptom thereof the method including administration of a compound or composition herein to the subject.

In one embodiment, a human patient is treated with a compound of the present description and a pharmaceutically acceptable carrier, adjuvant, or vehicle, wherein said compound is present in an amount to measurably inhibit bromodomain-containing protein activity (such as BET protein, e.g., BRD2, BRD3, BRD4, and/or BRDT) in the patient.

The present description further relates to the use of provided compounds for the production of pharmaceutical compositions which are employed for the treatment and/or prophylaxis and/or amelioration of the diseases, disorders, illnesses and/or conditions as mentioned herein.

The present description further relates to the use of provided compounds for the production of pharmaceutical compositions which are employed for the treatment and/or prophylaxis of diseases and/or disorders responsive or sensitive to the inhibition of bromodomain-containing proteins, particularly those diseases mentioned above, such as e.g. cancer, inflammatory disease, viral disease.

According to some embodiments, the present description relates to a method of inhibiting bromodomain-containing proteins in a biological sample comprising the step of contacting said biological sample with a provided compound, or a composition thereof.

According to some embodiments, the present description relates to a method of inhibiting a bromodomain-containing protein, such as a BET protein, such as BRD2, BRD3, BRD4 and/or BRDT, or a mutant thereof, activity in a biological sample comprising the step of contacting said biological sample with a provided compound, or a composition thereof.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of activity of a protein, e.g., a bromodomain-containing protein such as a BET protein (e.g. BRD2, BRD3, BRD4 and/or BRDT), or a mutant thereof, in a biological sample is useful for a variety of purposes that are known to one of skill in the art. Examples of such purposes include, but are not limited to, blood transfusion, organ-transplantation, biological specimen storage, and biological assays.

According to another embodiment, the present description relates to a method of inhibiting activity of one or more bromodomain-containing protein, such as a BET protein, such as BRD2, BRD3, BRD4, and/or BRDT, or a mutant thereof, in a patient comprising the step of administering to said patient a provided compound, or a composition comprising said compound. In certain embodiments, the present description provides a method for treating a disorder mediated by one or more bromodomain-containing proteins, such as a BET protein, such as BRD2, BRD3, BRD4, and/or BRDT, or a mutant thereof, in a patient in need thereof, comprising the step of administering to said patient a provided compound or pharmaceutically acceptable composition thereof. Such disorders are described in detail herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the composition of a compound or compounds described herein can be in combination with an additional therapeutic agent.

In some embodiments, the additional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

Other therapies, chemotherapeutic agents, or other anti-proliferative agents may be combined with a provided compound to treat proliferative diseases and cancer. Examples of therapies or anticancer agents that may be used in combination with compounds herein described include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effects (e.g., an antiemetic), and any other approved chemotherapeutic drug.

A provided compound may also be used to advantage in combination with one or more antiproliferative compounds. Such antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carotenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Exemplary aromatase inhibitors include steroids, such as atamestane, exemestane and formestane, and non-steroids, such as aminoglutethimide, rogletimide, pyridoglutethimide, trilostane, testolactone, ketoconazole, vorozole, fadrozole, anastrozole and letrozole.

Exemplary anti-estrogens include tamoxifen, fulvestrant, raloxifene and raloxifene hydrochloride. Anti-androgens include, but are not limited to, bicalutamide. Gonadorelin agonists include, but are not limited to, abarelix, goserelin and goserelin acetate.

Exemplary topoisomerase I inhibitors include topotecan, gimatecan, irinotecan, camptothecin and its analogues, 9-nitrocamptothecin and the macromolecular camptothecin conjugate PNU-166148. Topoisomerase II inhibitors include, but are not limited to, the anthracyclines such as doxorubicin, daunorubicin, epirubicin, idarubicin and nemorubicin, the anthraquinones mitoxantrone and losoxantrone, and the podophillotoxins etoposide and teniposide.

Exemplary microtubule active agents include microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof.

Exemplary alkylating agents include cyclophosphamide, ifosfamide, melphalan or nitrosoureas such as carmustine and lomustine.

Exemplary cyclooxygenase inhibitors include Cox-2 inhibitors, 5-alkyl substituted 2-arylaminophenylacetic acid and derivatives, such as celecoxib, rofecoxib, etoricoxib, valdecoxib or a 5-alkyl-2-arylaminophenylacetic acid, such as lumiracoxib.

Exemplary matrix metalloproteinase inhibitors ("MMP inhibitors") include collagen peptidomimetic and non-peptidomimetic inhibitors, tetracycline derivatives, batimastat, marimastat, prinomastat, metastat, BMS-279251, BAY 12-9566, TAA211, MM1270B, and AAJ996.

Exemplary mTOR inhibitors include compounds that inhibit the mammalian target of rapamycin (mTOR) and possess antiproliferative activity such as sirolimus, everolimus, CCI-779, and ABT578.

Exemplary antimetabolites include 5-fluorouracil (5-FU), capecitabine, gemcitabine, DNA demethylating compounds, such as 5-azacytidine and decitabine, methotrexate and edatrexate, and folic acid antagonists such as pemetrexed.

Exemplary platin-containing compounds include carboplatin, cisplatin, nedaplatin, and oxaliplatin.

Exemplary methionine aminopeptidase inhibitors include bengamide or a derivative thereof and PPI-2458.

Exemplary bisphosphonates include etidronic acid, clodronic acid, tiludronic acid, pamidronic acid, alendronic acid, ibandronic acid, risedronic acid and zoledronic acid.

Exemplary antiproliferative antibodies include trastuzumab, trastuzumab-DMI, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary heparanase inhibitors include compounds that target, decrease or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras; for example, a farnesyl transferase inhibitor such as L-744832, DK8G557, tipifarnib, and lonafarnib.

Exemplary telomerase inhibitors include compounds that target, decrease or inhibit the activity of telomerase, such as compounds which inhibit the telomerase receptor, such as telomestatin.

Exemplary proteasome inhibitors include compounds that target, decrease or inhibit the activity of the proteasome including, but not limited to, bortezomib.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransylcytosine (ara-c) and busulfan; and ALK inhibitors, which are compounds which target, decrease or inhibit anaplastic lymphoma kinase.

Exemplary Flt-3 inhibitors include PKC412, midostaurin, a staurosporine derivative, SU11248 and MLN518.

Exemplary HSP90 inhibitors include compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing or inhibiting the activity of the platelet-derived growth factor-receptors (PDGFR), such as a compound which targets, decreases, or inhibits the activity of PDGFR, such as an N-phenyl-2-pyrimidine-amine derivatives, such as imatinib, SU101, SU6668 and GFB-111; b) a compound targeting, decreasing or inhibiting the activity of the fibroblast growth factor-receptors (FGFR); c) a compound targeting, decreasing or inhibiting the activity of the insulin-like growth factor receptor I (IGF-IR), such as a compound which targets, decreases, or inhibits the activity of IGF-IR; d) a compound targeting, decreasing or inhibiting the activity of the Trk receptor tyrosine kinase family, or ephrin B4 inhibitors; e) a compound targeting, decreasing or inhibiting the activity of the Axl receptor tyrosine kinase family; f) a compound targeting, decreasing or inhibiting the activity of the Ret receptor tyrosine kinase; g) a compound targeting, decreasing or inhibiting the activity of the Kit/SCFR receptor tyrosine kinase, such as imatinib; h) a compound targeting, decreasing or inhibiting the activity of the c-Kit receptor tyrosine kinases, such as imatinib; i) a compound targeting, decreasing or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; ISIS 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) a compound targeting, decreasing or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, CI-1033, EKB-569, GW-2016, antibodies ELI, E2.4, E2.5, E6.2, E6.4, E2.I I, E6.3 and E7.6.3, and 7H-pyrrolo-[2,3-d]pyrimidine derivatives; and m) a compound targeting, decreasing or inhibiting the activity of the c-Met receptor.

Exemplary compounds that target, decrease or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g. thalidomide and TNP-470.

Additional exemplary chemotherapeutic compounds, one or more of which may be used in combination with provided compounds, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, I-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugen; FLT-4 inhibitors, FLT-3 inhibitors, VEGFR-2 IgGI antibody, RPI 4610, bevacizumab, porfimer sodium, anecortave, triamcinolone, hydrocortisone, 11α-epihydrocotisol, cortexolone, 17α-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA or siRNA, or a miscellaneous compound or compound with other or unknown mechanism of action.

For a more comprehensive discussion of updated cancer therapies see: *The Merck Manual,* $17^{th}$ Ed. 1999. See also the National Cancer Institute (CNI) website (www.nci.nih.gov) and the Food and Drug Administration (FDA) website for a list of the FDA approved oncology drugs.

Other examples of additional therapeutic agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon {e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

The above-mentioned compounds, one or more of which can be used in combination with a provided compound, can be prepared and administered as described in the art.

Provided compounds can be administered alone or in combination with one or more other therapeutic compounds, possible combination therapy taking the form of fixed combinations or the administration of a provided compound and one or more other therapeutic compounds being staggered or given independently of one another, or the combined administration of fixed combinations and one or more other therapeutic compounds. Provided compounds can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a composition containing a provided compound, as part of a multiple dosage regimen. Alternatively, those agents may be part of a single dosage form, mixed together with a provided compound in a single composition. If administered as part of a multiple dosage regimen, the two active agents may be submitted simultaneously, sequentially or within a period of time from one another normally within five hours from one another.

Upon improvement of a subject's condition, a maintenance dose of a compound, composition or combination of the present description may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present description will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of the present description administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present description comprise administration to a patient in need of such treatment from about 10 mg to about 1000 mg of the compound(s) of the present description per day in single or multiple doses.

As used herein, the term "combination," "combined," and related terms refers to the simultaneous or sequential administration of therapeutic agents in accordance with the present description. For example, a provided compound may be administered with another therapeutic agent simultaneously or sequentially in separate unit dosage forms or together in a single unit dosage form. Accordingly, an embodiment of the present description provides a single unit dosage form comprising a provided compound, an additional therapeutic agent, and a pharmaceutically acceptable carrier, adjuvant, or vehicle for use in the methods of the present description.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 g/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a provided compound. Implantable devices coated with a compound of the present description are another embodiment of the present description.

In another aspect, the present description provides a method of method of synthesizing a compound of any of the formulae herein. Another embodiment is a method of making a compound of any of the formulae herein using any one, or combination of, reactions delineated herein. The method can include the use of one or more intermediates or chemical reagents delineated herein.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The Examples set forth herein below provide syntheses and experimental results obtained for certain exemplary compounds. Unless otherwise indicated, all numbers expressing quantities of ingredients, reaction conditions, concentrations, properties, stabilities, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

The following is to be construed as merely illustrative, and not limitations of the preceding disclosure in any way whatsoever. Those skilled in the art will promptly recognize appropriate variations from the procedures both as to reactants and as to reaction conditions and techniques. In some cases, starting materials or intermediates may be commercially available. Commercial material may be generally available from known sources, for example, Sigma-Aldrich, Bachem, Lancaster, Alfa Aesar, etc.

Chemical Synthesis of Exemplary Compounds

General:

All temperatures are in degrees Celsius (° C.) and are uncorrected. Reagent grade chemicals and anhydrous solvent were purchased from commercial sources and unless otherwise mentioned, were used without further purification The names of the products were determined using the naming software included in the Contour Software AB electronic lab notebook iLabber version 4.11.3075.18678. Flash chromatography was performed on Teledyne Isco instruments using pre-packaged disposable $SiO_2$ stationary phase columns with eluent flow rate range of 5 to 300 mL/min, UV detection (254 and 280 nm). HPLC purifications were performed, for instance, on a Gilson HPLC with a Phenomenex Gemini column, $C_{18}$, 150:30 mm, 5 micron, eluting at 40 mL/min with mixtures of MeOH and water containing 0.1% $(NH_4)_2CO_3$ (high pH), or mixtures of MeCN and water containing 0.1% formic acid (low pH). Chiral isomer separation were performed, for instance, on a Minigram Semi-Preperative SFC from Mettler-Toledo. The analytical HPLC chromatograms were performed using an Agilent 1100 series instrument. The mass spectra were recorded with a Waters Micromass ZQ detector at 120° C. The mass spectrometer was equipped with an electrospray ion source (ESI) operated in a positive ion mode and was set to scan between m/z 150-750 with a scan time of 0.3 s. Products and intermediates were analyzed by HPLC/MS on a X-Bridge $C_{13}$, (3.5 μM, 2.10×30 mm) using a high pH buffer gradient of 5% to 95% of MeOH in $H_2O$ (0.03% $(NH_4)_2CO_3$/0.375% $NH_4OH$) over 4.5 min at 1 mL/min for a 6 min run. The $^1H$ NMR spectra were recorded on a Bruker UltraShield 500 MHz/54 mm instrument (BZH 43/500/70B, D221/54-3209) or on a Bruker Ultra Shield Avance 400 MHz/5 mm Probe (BBFO). The chemical shifts are reported in part-per-million from a tetramethylsilane standard.

As used herein, the following abbreviations may have the following meanings:

| Abbreviation | Term |
|---|---|
| AcOH | Acetic acid |
| $CDCl_3$ | Deuterated-chloroform |
| $Cs_2CO_3$ | Cesium carbonate |
| d | Day(s) |
| DCM | Dichloromethane |
| DEA | Diethylamine |
| DIPEA | N,N-Diisopropylethylamine |
| DME | 1,2-dimethoxyethane |
| DMF | N,N-dimethyl formamide |
| DMSO | Dimethyl sulfoxide |
| $Et_2O$ | Diethylether |
| EtOAc | Ethyl acetate |
| EtMgBr | Ethyl magnesium bromide |
| h | Hour(s) |
| HATU | (dimethylamino)-N,N-dimethyl(3H-[1,2,3]triazolo[4,5-b]pyridin-3-yloxy) methaniminium hexafluorophosphate |
| HCl | hydrochloric acid |
| HPLC | High-performance liquid chromatography |
| IPA | Isopropanol |
| $K_2CO_3$ | Potassium carbonate |
| KOAc | Potassium acetate |
| MS | Mass spectrometry |
| min | Minute(s) |
| MeCN | Acetonitrile |
| MeOD | Deuterated methanol |
| MeOH | Methanol |
| $MgSO_4$ | Magnesium sulfate |
| $N_2$ | Nitrogen |
| $Na_2CO_3$ | Sodium carbonate |
| $NaHCO_3$ | Sodium bicarbonate |
| $Na_2SO_4$ | Sodium sulfate |
| NMP | N-Methyl-2-pyrrolidone |
| NMR | Nuclear magnetic resonance |
| $PdCl_2(dppf)•CH_2Cl_2$ | 1,1'-Bis(diphenylphosphino)ferrocene]dichloropalladium(II) complex with dichloromethane |
| $Pd(PPh_3)_4$ | Tetrakis(triphenylphosphine)palladium(0) |
| pTSA | p-Toluenesulfonic acid |
| rt | room temperature |
| SFC | Supercritical fluid chromatography |
| TEA | Triethylamine |
| TFA | Trifluoroacetic acid |
| THF | Tetrahydrofuran |
| T3P ™ | 2,4,6-tripropyl-1,3,5,2,4,6-trioxatriphosphorinane-2,4,6-trioxide |

Scheme 1. Preparation of the benzimidazole core

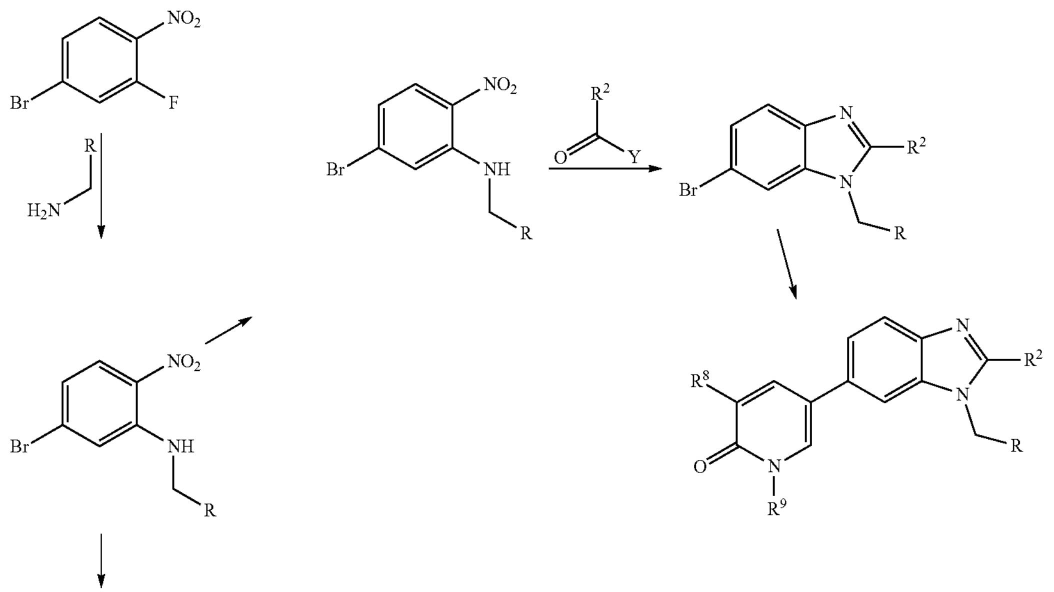

-continued

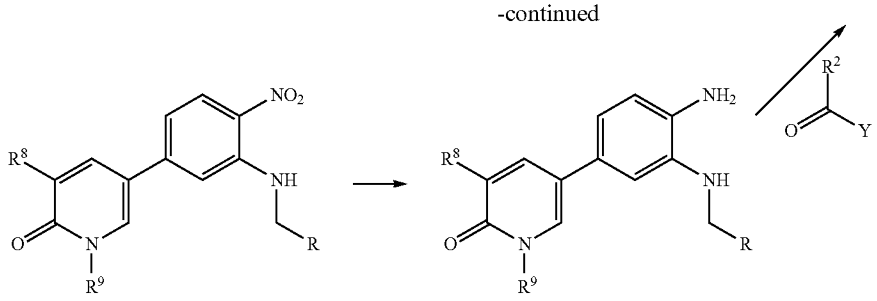

wherein $R^2$, $R^8$ and $R^9$ are as herein defined, $CH_2R$ represents $R^1$ as defined, for instance, in items (a) to (c) of Formula I, and Y is, for example, H, OH, Cl.

Intermediate 1 (4-bromo-N2-[2-(trifluoromethoxy)ethyl]benzene-1,2-diamine)

Step 1: Preparation of 5-bromo-2-nitro-N-[2-(trifluoromethoxy)ethyl]aniline

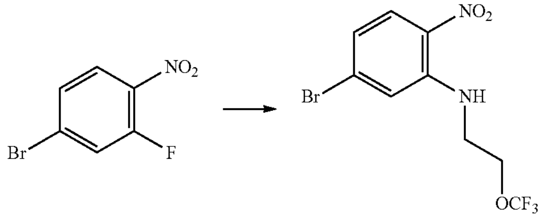 [SMILES: O=[N+]([O-])c1ccc(Br)cc1F ; O=[N+]([O-])c1ccc(Br)cc1NCCOC(F)(F)F]

To a solution of 2-(trifluoromethoxy)ethanamine (0.41 g, 3.18 mmol) in DMSO (6 mL), DIPEA (1.66 mL, 9.55 mmol) was added and the mixture was stirred 10 min at rt and then 4-bromo-2-fluoro-1-nitrobenzene (0.7 g, 3.18 mmol) was added by portion. The mixture was then stirred at rt for 2 h and then water was added. In the alternative, the reaction mixture is transferred into ice/water. The precipitate was collected by filtration and the solid was dried under reduced pressure to provide title compound which was used in the next step without any further purification (0.86 g, 82%). MS (ESI) $[M+H]^+$ 329.1, 331.1. $^1H$ NMR (400 MHz, $CDCl_3$) δ ppm 8.22 (s, 1H), 8.08 (d, J=8.8 Hz, 1H), 7.30 (d, J=2 Hz, 1H), 6.87 (dd, J=2 and 9.2 Hz, 1H), 4.25 (t, J=5.2 Hz, 2H), 3.66 (dd, J=5.2 and 5.6 Hz, 2H).

Step 2: Preparation of Intermediate 1

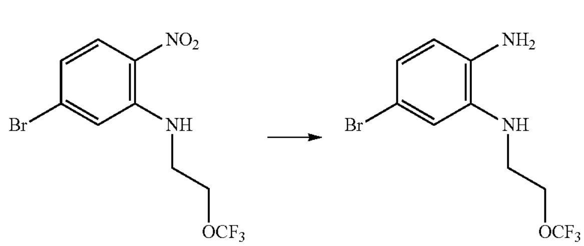 [SMILES: O=[N+]([O-])c1ccc(Br)cc1NCCOC(F)(F)F ; Nc1ccc(Br)cc1NCCOC(F)(F)F]

To a solution of 5-bromo-2-nitro-N-[2-(trifluoromethoxy)ethyl]aniline (0.86 g, 2.61 mmol) in MeOH (5 mL) was added acetic acid (0.45 mL, 7.84 mmol) and zinc powder (1.71 g, 26.13 mmol) at rt. The suspension was stirred at rt for 45 min and was then heated at 60° C. for 30 min. The mixture was then cooled, filtered and evaporated under reduced pressure. The residue was diluted in EtOAc (50 mL) and saturated $NaHCO_3$ (15 mL) was added. The phases were separated and aqueous phase was extracted with EtOAc (2×30 mL). The combined organic phases were washed with brine, dried over $Na_2SO_4$ and evaporated under reduced pressure to provide Intermediate 1, which was used in the next step without any further purification (0.77 g, 98%). MS (ESI) $[M+H]^+$ 299.1, 301.1.

Intermediate 2 (5-[4-amino-3-(2-methoxyethylamino)phenyl]-1,3-dimethyl-pyridin-2-one)

Step 1: Preparation of 5-bromo-N-(2-methoxyethyl)-2-nitro-aniline

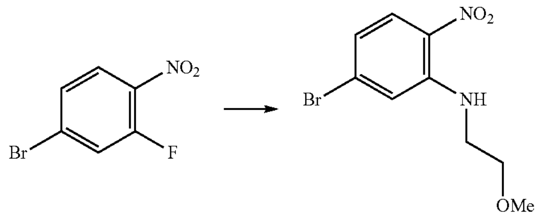 [SMILES: O=[N+]([O-])c1ccc(Br)cc1F ; COCCNc1cc(Br)ccc1[N+](=O)[O-]]

2-methoxyethanamine (1 mL, 13.64 mmol) was dissolved in DMSO (5 mL) and DIPEA (0.79 mL, 4.55 mmol) was added and the mixture was then stirred for 5 min at rt. 4-bromo-2-fluoro-1-nitro-benzene (1 g, 4.55 mmol) was then added and the reaction mixture was stirred for 18 h at rt. Water (10 mL) was added and the solid was collected by filtration and then was dried under reduced pressure to afford title compound (1 g, 80%). MS (ESI) $[M+H]^+$ 275.0, 277.0.

Step 2: Preparation of 5-[3-(2-methoxyethylamino)-4-nitro-phenyl]-1,3-dimethyl-pyridin-2-one

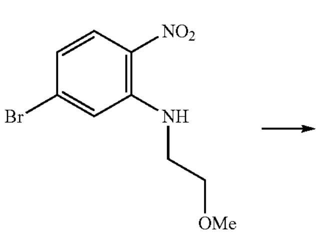

-continued

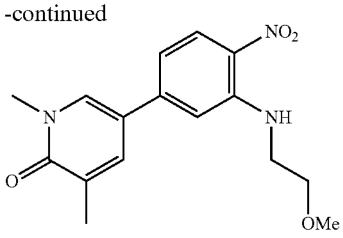

To a solution of 5-bromo-N-(2-methoxyethyl)-2-nitroaniline (320 mg, 1.16 mmol) and 1,3-dimethyl-5-(4,4,5,5-tetramethyl-1,3,2-dioxaborolan-2-yl)pyridin-2-one (prepared using the procedure described in US20130053362, 348 mg, 1.396 mmol) in DME (8 mL) and water (0.4 mL) was degassed by bubbling $N_2$ for 10 min. $Cs_2CO_3$ (0.796 g, 2.44 mmol) and $Pd(PPh_3)_4$ (134 mg, 0.12 mmol) were then added and the mixture was degassed by bubbling $N_2$ for 10 more min. The resulting mixture was heated to 85° C. for 18 h overnight and then cooled to rt. To the mixture, saturated $NaHCO_3$ (10 mL) and EtOAc (50 mL) were added and the aqueous phase was extracted with EtOAc (3×20 mL). The combined organic phases were dried over $MgSO_4$, filtered, and concentrated under reduced pressure. The material was purified by flash chromatography on silica gel using a mixture of EtOAc in hexane as eluent to provide title compound (340 mg, 92%). $^1$H NMR (500 MHz, $CDCl_3$) δ 8.35 (bs, 1H), 8.23 (d, J=8.9 Hz, 1H), 7.50 (dd, J=12.9, 2.0 Hz, 2H), 6.85 (d, J=1.9 Hz, 1H), 6.72 (dd, J=8.9, 1.9 Hz, 1H), 3.74 (t, J=5.4 Hz, 2H), 3.67 (s, 3H), 3.58 (dd, J=10.6, 5.2 Hz, 2H), 3.48 (s, 3H), 2.26 (s, 3H). MS (ESI) $[M+H]^+$ 318.2.

Step 3: Preparation of Intermediate 2

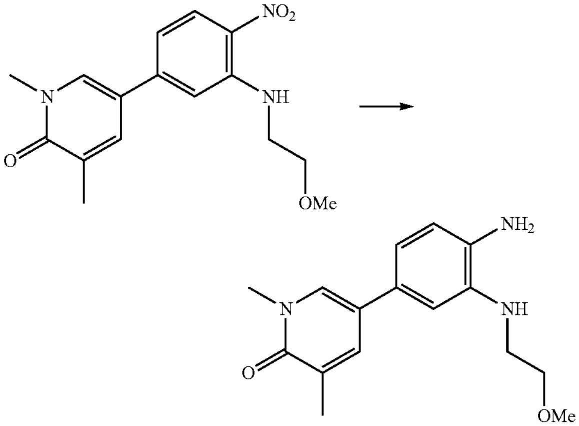

AcOH (0.184 mL, 3.21 mmol) and Zn (0.70 g, 10.71 mmol) were added to a solution of 5-[3-(2-methoxyethylamino)-4-nitro-phenyl]-1,3-dimethyl-pyridin-2-one (0.34 g, 1.07 mmol) in MeOH (7 mL) and the suspension was stirred at rt for 30 min. The mixture was filtered through Celite™, washed with EtOAc (10 mL), and then concentrated under reduced pressure. To the residue, EtOAc (50 mL) and saturated $NaHCO_3$ (30 mL) were added and the aqueous phase was extracted with EtOAc (2×30 mL). The combined organic phases were washed with brine, dried over $Na_2SO_4$, filtered and concentrated under reduced pressure to provide Intermediate 2, which was used in the next step without further purification. (0.29, 94%). MS (ESI) $[M+H]^+$ 288.2.

Intermediate 3 (5-[4-amino-3-[[(1R)-2-methoxy-1-methyl-ethyl]amino]phenyl]-1,3-dimethyl pyridin-2-one)

Step 1: Preparation of 5-bromo-N-[(1R)-2-methoxy-1-methyl-ethyl]-2-nitro-aniline

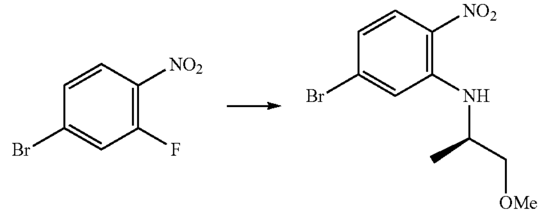 [SMILES: O=[N+]([O-])c1ccc(Br)cc1F ; COC[C@@H](C)Nc1cc(Br)ccc1[N+](=O)[O-]]

To a solution of (2R)-1-methoxypropan-2-amine hydrochloride (343 mg, 2.73 mmol) in DMSO (3 mL), DIPEA (0.95 mL, 5.45 mmol) was added and the mixture was stirred 10 min at rt and then a solution of 4-bromo-2-fluoro-1-nitrobenzene (400 mg, 1.828 mmol) in DMSO (3 mL) was added dropwise and the reaction mixture was then stirred at rt. After 2 h, starting material was still observed and more (2R)-1-methoxypropan-2-amine hydrochloride (114 mg, 0.91 mmol) and DIPEA (0.63 mL, 3.64 mmol) were added and the mixture was stirred at 50° C. for 1 h. To the mixture, saturated $NaHCO_3$ (50 mL) and EtOAc (50 mL) were added and the aqueous phase was extracted with EtOAc (3×50 mL). The combined organic phases were dried over $Na_2SO_4$, filtered, and concentrated under reduced pressure. The material was purified by flash chromatography on silica gel using a mixture of EtOAc in hexane as eluent to provide title compound (484 mg, 92%). 1H NMR (500 MHz, CDCl3) δ 8.19 (d, J=6.4 Hz, 1H), 8.02 (d, J=9.1 Hz, 1H), 7.07 (d, J=2.0 Hz, 1H), 6.73 (dd, J=9.1, 2.0 Hz, 1H), 3.88-3.79 (m, 1H), 3.48 (dd, J=5.0, 1.2 Hz, 2H), 3.41 (s, 3H), 1.33 (d, J=6.5 Hz, 3H). MS (ESI) $[M+H]^+$ 291.0.

Step 2: Preparation of 5-[3-[[(1R)-2-methoxy-1-methyl-ethyl]amino]-4-nitro-phenyl]-1,3-dimethyl-pyridin-2-one

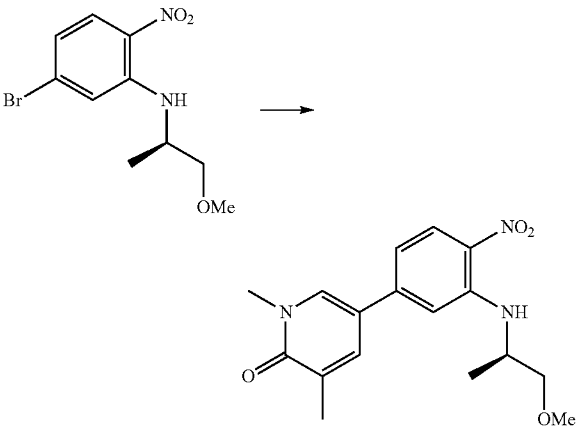

$Pd(PPh_3)_4$ (194 mg, 0.167 mmol) was added to a degassed solution of 5-bromo-N-[(1R)-2-methoxy-1-methyl-ethyl]-2-nitro-aniline (484 mg, 1.674 mmol), 1,3-dimethyl-5-(4,4,5,5-tetramethyl-1,3,2-dioxaborolan-2-yl)pyridin-2-one (prepared using described procedure in US20130053362, 542 mg, 2.18 mmol), and $Cs_2CO_3$ (1.36 g, 4.19 mmol) in mixture of DME (20 mL) and water (2 mL) under $N_2$ and the resulting mixture was heated to 80° C. for 20 h. The mixture was cooled to rt and saturated $NaHCO_3$ (50 mL) and EtOAc (50 mL) were added, and the aqueous phase was extracted with EtOAc (3×50 mL). The combined organic phases were dried over $Na_2SO_4$, filtered through Celite™ and concentrated under reduced pressure. The product was purified by flash chromatography on silica gel using a mixture of EtOAc in hexane as eluent to provide title compound (561 mg, 99%). $^1$H NMR (500 MHz, $CDCl_3$) δ 8.29 (d, J=7.6 Hz, 1H), 8.20 (d, J=8.9 Hz, 1H), 7.71-7.63 (m, 1H), 7.48-7.46 (m, 1H), 6.87 (d, J=1.8 Hz, 1H), 6.66 (dd, J=8.9, 1.9 Hz, 1H), 4.02-3.94 (m, 1H), 3.65 (s, 3H), 3.57-3.48 (m, 2H), 3.43 (d, J=4.5 Hz, 3H), 2.24 (t, J=0.8 Hz, 3H), 1.37 (d, J=6.5 Hz, 3H). MS (ESI) $[M+H]^+$ 332.2.

Step 3: Preparation of Intermediate 3

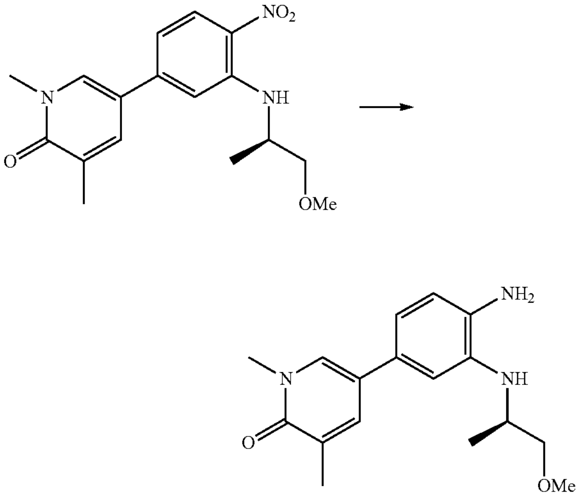

AcOH (0.29 mL, 5.08 mmol) and Zn (1.11 g, 16.93 mmol) were added to a solution of 5-[3-[[(1R)-2-methoxy-1-methyl-ethyl]amino]-4-nitro-phenyl]-1,3-dimethyl-pyridin-2-one (561 mg, 1.69 mmol) in MeOH (10 mL) and the resulting suspension was stirred at rt for 30 min. The mixture was then filtered through Celite™, washed with EtOAc (10 mL) and concentrated under reduced pressure. To the residue, EtOAc (50 mL) and saturated $NaHCO_3$ (30 mL) were added and the aqueous phase was extracted with EtOAc (2×30 mL). The combined organic phases were washed with brine, dried over $Na_2SO_4$, filtered and concentrated under reduced pressure to provide Intermediate 3 (505 mg, 99%), which was used in the next step without further purification. $^1$H NMR (500 MHz, $CDCl_3$) δ 7.70-7.64 (m, 1H), 7.45 (dd, J=2.5, 1.2 Hz, 1H), 7.27 (d, J=2.5 Hz, 1H), 6.72 (dd, J=7.3, 2.2 Hz, 2H), 3.69 (dd, J=11.3, 5.3 Hz, 1H), 3.61 (s, 3H), 3.46 (dd, J=5.1, 2.6 Hz, 2H), 3.40 (s, 3H), 2.22 (s, 3H), 1.26 (d, J=6.4 Hz, 3H). MS (ESI) $[M+H]^+$: 302.2.

Intermediate 4: (1-methyl-5-(4,4,5,5-tetramethyl-1,3,2-dioxaborolan-2-yl)-3-(trifluoromethyl) pyridin-2-one)

Step 1: Preparation of 5-bromo-1-methyl-3-(trifluoromethyl)pyridin-2-one

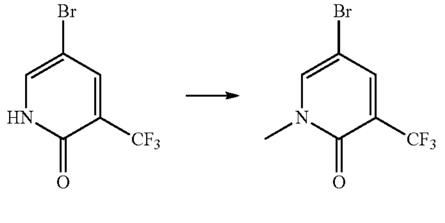

Methyl iodide (0.12 mL, 1.88 mmol) and $Cs_2CO_3$ (0.942 g, 2.89 mmol) were added to a solution of 5-bromo-3-(trifluoromethyl)-1H-pyridin-2-one (0.350 g, 1.45 mmol) in DMF (3 mL) and the resulting mixture was stirred for 18 h at rt. The solvent was evaporated under reduced pressure, water (10 ml) was added to the residue and the aqueous phase was extracted with EtOAc (2×30 mL). The combined organic phases were washed with brine and dried over $MgSO_4$, filtered and concentrated under reduced pressure. The material was triturated with ether then dried to afford title compound, which was used in the next step without any further purification (0.32 g, 86%). $^1$H NMR (500 MHz, $CDCl_3$) δ 7.78 (d, J=2.1 Hz, 1H), 7.64 (d, J=2.7 Hz, 1H), 3.59 (s, 3H).

Step 2: Preparation of Intermediate 4

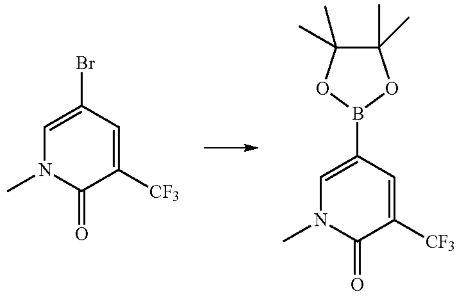 [SMILES: Cn1cc(Br)cc(C(F)(F)F)c1=O ; Cn1cc(B2OC(C)(C)C(C)(C)O2)cc(C(F)(F)F)c1=O]

4,4,4',4',5,5,5',5'-octamethyl-2,2'-bi(1,3,2-dioxaborolane) (0.31 g, 1.23 mmol), $PdCl_2(dppf)\cdot CH_2Cl_2$ (0.07 g, 0.082 mmol) and KOAc (0.24 g, 2.46 mmol) were added to a degassed solution of 5-bromo-1-methyl-3-(trifluoromethyl) pyridin-2-one (0.21 g, 0.82 mmol) in dioxane (7 mL) under $N_2$ and the resulting mixture was refluxed for 20 h. The solution was cooled to rt and filtered through Celite™, washed with EtOAc and concentrated under reduced pressure. The material was purified by flash chromatography on silica gel using a mixture of EtOAc in hexane and then triturated with ether to afford Intermediate 4 (43 mg, 17%). $^1$H NMR (500 MHz, $CDCl_3$) δ 8.02 (d, J=1.0 Hz, 1H), 7.93 (d, J=1.9 Hz, 1H), 3.60 (s, 3H), 1.31 (s, 12H). MS (ESI) $[M+H]^+$ 304.2.

Intermediate 5: 3-ethyl-1-methyl-5-(4,4,5,5-tetramethyl-1,3,2-dioxaborolan-2-yl)pyridin-2-one Step 1: Preparation of 3,5-dibromo-1-methyl-pyridin-2-one

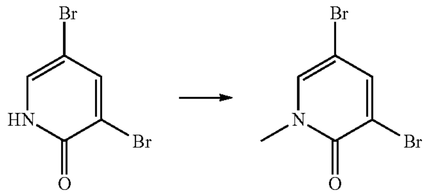

A solution of 3,5-dibromo-1H-pyridin-2-one (5 g, 19.8 mmol) in DMF (170 ml), $K_2CO_3$ (6.01 g, 43.5 mmol) was added and the suspension was stirred for 15 min. To the mixture, MeI (1.36 mL, 21.8 mmol) was added and the reaction mixture was stirred for 18 h at rt. To the mixture, water (200 ml) was added and the aqueous layer was then extracted with EtOAc (3×200 ml). The combined organic layers were dried over $Na_2SO_4$, filtered and concentrated under reduced pressure. The resultant solid was triturated with $Et_2O$ to afford 2 g of the title compound. The filtrate was evaporated under reduced pressure and a second crop of product (2.0 g) was obtained after trituration with $Et_2O$. The filtrate was concentrated and the material was purified by flash chromatography on silica gel using a mixture of EtOAc and hexane as eluent to afford title compound (total amount 4.5 g, 85%). $^1$H NMR (500 MHz, $CDCl_3$) δ 7.78 (d, J=2.5 Hz, 1H), 7.42 (d, J=2.5 Hz, 1H), 3.59 (s, 3H). MS (ESI) $[M+H]^+$ 266.01, 267.99, 269.99.

Step 2: Preparation of 5-bromo-3-ethyl-1-methyl-pyridin-2-one

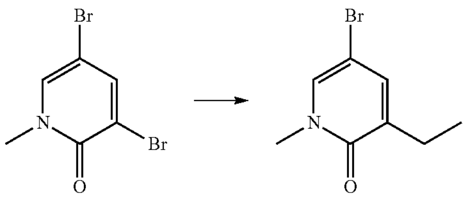

3,5-dibromo-1-methyl-pyridin-2-one (1.2 g, 4.19 mmol) and $Fe(acac)_3$ (55.6 mg, 0.15 mmol) were added to a flask and the air was evacuated with $N_2$ (3×) and then THF (25 ml) and NMP (5 ml) were added. The mixture was cooled to 0° C. and EtMgBr (1.68 ml, 5.03 mmol) was added dropwise and the reaction mixture was stirred for 1 h. To the mixture, 1M HCl solution (10 ml) was added and the aqueous layer was extracted with EtOAc (3×10 mL). The combined organic phases were, dried over $MgSO_4$, filtered and concentrated under reduced pressure. The material was purified by flash chromatography on silica gel using a mixture of EtOAc and hexane as eluent to afford title compound (275 mg, 30%). $^1$H NMR (500 MHz, $CDCl_3$) δ 7.23 (d, J=2.7 Hz, 1H), 7.13 (dt, J=2.4, 1.1 Hz, 1H), 3.47 (d, J=12.3 Hz, 3H), 2.49 (qd, J=7.5, 6.6 Hz, 2H), 1.14-1.04 (m, 3H).

Step 3: Preparation of Intermediate 5

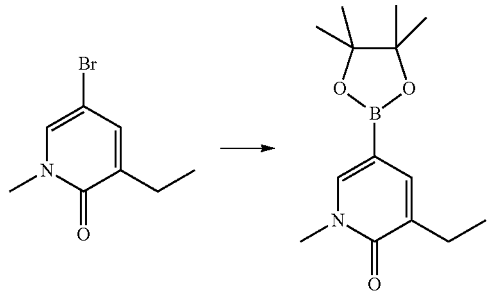 [SMILES: CCc1cc(Br)cn(C)c1=O ; CCc1cc(B2OC(C)(C)C(C)(C)O2)cn(C)c1=O]

4,4,4',4',5,5,5',5'-octamethyl-2,2'-bi(1,3,2-dioxaborolane) (352.6 mg, 1.39 mmol), $PdCl_2$(dppf) (47.2 mg, 0.058 mmol) and KOAc (283.9 mg, 2.89 mmol) were added to a degassed solution of 5-bromo-3-ethyl-1-methyl-pyridin-2-one (250 mg, 1.16 mmol) in dioxane (3 mL) under N2. The solution was heated to 90° C. in a sealed tube for 18 h. The reaction mixture was cooled to rt and EtOAc (20 ml) and water (10 ml) were added. The organic phase was separated and dried over $Na_2SO_4$, filtered and concentrated under reduced. The material was purified by flash chromatography on silica gel using a mixture of EtOAc and hexane as eluent to afford Intermediate 5 (152 mg, 50%), which was used in the next step without any further purification. $^1$H NMR (500 MHz, $CDCl_3$) δ 7.66 (d, J=1.9 Hz, 1H), 7.48-7.41 (m, 1H), 3.55 (s, 3H), 2.55 (q, J=7.4 Hz, 2H), 1.36-1.22 (m, 12H), 1.19 (t, J=7.5 Hz, 3H).

Intermediate 6: 5-[4-amino-3-(2-methoxypropylamino)phenyl]-1,3-dimethyl-pyridin-2-one

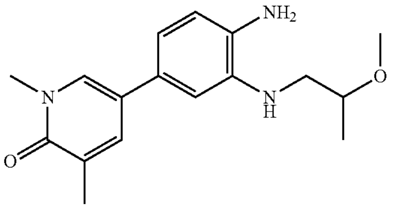 [SMILES: COC(C)CNc1cc(-c2cc(C)c(=O)n(C)c2)ccc1N]

Step 1: Preparation of 5-bromo-N-(2-methoxypropyl)-2-nitro-aniline

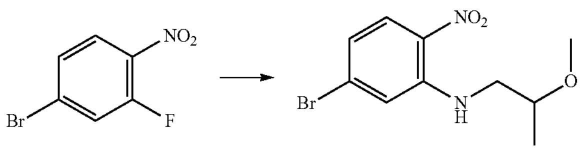 [SMILES: O=[N+]([O-])c1ccc(Br)cc1F ; COC(C)CNc1cc(Br)ccc1[N+](=O)[O-]]

To a solution of 4-bromo-2-fluoro-1-nitro-benzene (752 mg, 3.41 mmol) in dry DMF (7 ml) was added $K_2CO_3$ (945 mg, 6.84 mmol) and 2-methoxypropan-1-amine (365 mg, 4.1 mmol) and the reaction mixture was heated to 40° C. for 2 h. The mixture was cooled to rt, diluted with EtOAc (20 mL) and washed with water (3×10 mL). The organic phase was collected, dried over $Na_2SO_4$, filtered and concentrated under reduced pressure. The material was purified by flash chromatography on silica gel using a mixture of MeOH in DCM as eluent to afford title compound (852 mg, 86%) as solid. $^1H$ NMR (500 MHz, $CDCl_3$) δ 8.24 (s, 1H), 8.01 (d, J=9.1 Hz, 1H), 7.00 (d, J=2.0 Hz, 1H), 6.74 (dd, J=9.1, 2.0 Hz, 1H), 3.68-3.59 (m, 1H), 3.41 (s, 3H), 3.34 (ddd, J=12.8, 5.7, 4.0 Hz, 1H), 3.21 (ddd, J=12.8, 7.3, 4.4 Hz, 1H), 1.26 (dd, J=6.1, 2.5 Hz, 3H).

Step 2: Preparation of 5-[3-(2-methoxypropylamino)-4-nitro-phenyl]-1,3-dimethylpyridin-2-one

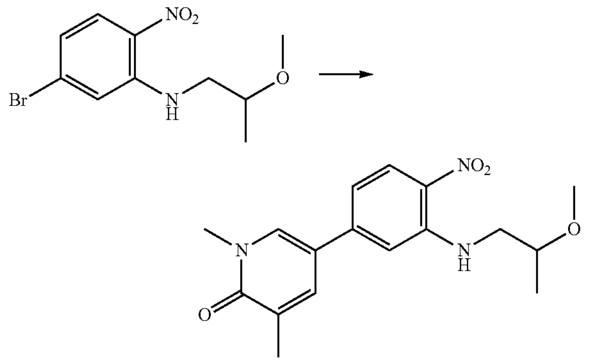

To a suspension of 5-bromo-N-(2-methoxypropyl)-2-nitro-aniline (450 mg, 1.56 mmol) in DME (4 ml) was added 1,3-dimethyl-5-(4,4,5,5-tetramethyl-1,3,2-dioxaborolan-2-yl)pyridin-2-one (prepared using the procedure described in US20130053362, 465 mg, 1.87 mmol), $Cs_2CO_3$ (1.27 g, 3.89 mmol), $Pd(PPh_3)_4$ (180 mg, 0.16 mmol) and water (0.5 ml) and the reaction mixture was degassed by bubbling $N_2$ for 5 min then heated in a sealed tube to 90° C. for 18 h. The mixture was diluted with EtOAc (10 mL) and washed with water (10 mL). The organic phase was collected, dried over $Na_2SO_4$, filtered and concentrated under reduced pressure. The resulting solid (466 mg, 90%) was triturated with $Et_2O$ and to afford title compound, which was used in the next step without further purification. $^1H$ NMR (500 MHz, DMSO) δ 8.32 (t, J=5.0 Hz, 1H), 8.23 (d, J=2.6 Hz, 1H), 8.09 (d, J=9.0 Hz, 1H), 7.93-7.80 (m, 1H), 7.13 (d, J=1.9 Hz, 1H), 6.95 (dd, J=9.1, 1.9 Hz, 1H), 3.67 (dddd, J=13.2, 9.5, 7.8, 5.1 Hz, 2H), 3.54 (d, J=3.9 Hz, 3H), 3.39 (ddd, J=13.2, 6.6, 4.6 Hz, 1H), 3.34 (s, 3H), 2.10 (s, 3H), 1.22 (d, J=6.1 Hz, 3H). MS (ESI) $[M+H]^+$ 332.1.

Step 3: Preparation of Intermediate 6

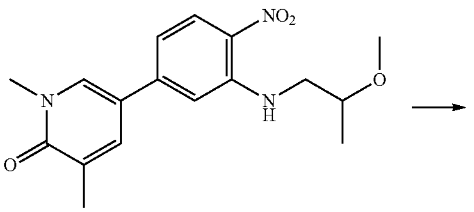

-continued

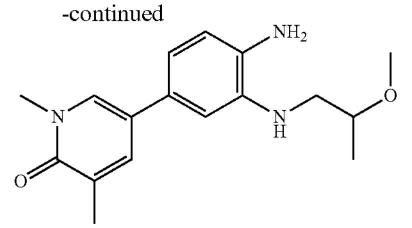

To a solution of 5-[3-(2-methoxypropylamino)-4-nitro-phenyl]-1,3-dimethylpyridin-2-one (466 mg, 1.41 mmol) in MeOH (6 mL) was added acetic acid (0.24 ml, 4.21 mmol) and zinc powder (919 mg, 14.06 mmol) at rt and the resulting suspension was stirred at rt for 45 min. The mixture was filtered through a pad of Celite™ and concentrated under reduced pressure. The residue was diluted in EtOAc (10 mL) and saturated $NaHCO_3$ (10 mL). The phases were separated and the aqueous phase was extracted with EtOAc (2×30 mL). The combined organic phases were washed with brine, dried over $Na_2SO_4$ and concentrated under reduced pressure to afford Intermediate 6 (389 mg, 89%), which was used in the next step without further purification. MS (ESI) $[M+H]^+$ 302.3.

Intermediate 7: 5-[4-amino-3-[[(1S)-2-methoxy-1-methyl-ethyl]amino]phenyl]-1,3-dimethyl pyridin-2-one

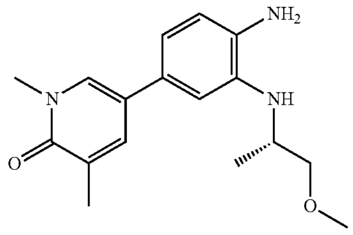 [SMILES: COC[C@H](C)Nc1cc(-c2cc(C)c(=O)n(C)c2)ccc1N]

Step 1: Preparation of 5-bromo-N-[(1S)-2-methoxy-1-methyl-ethyl]-2-nitro-aniline

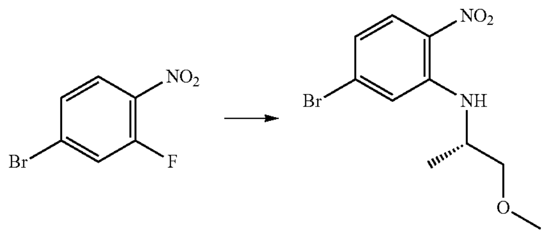 [SMILES: O=[N+]([O-])c1ccc(Br)cc1F ; COC[C@H](C)Nc1cc(Br)ccc1[N+](=O)[O-]]

(2S)-1-methoxypropan-2-amine (384 μL, 3.64 mmol) was dissolved in DMSO (3 mL) and DIPEA (0.95 mL, 5.45 mmol) was added. The mixture was stirred 10 min at rt and then 4-bromo-2-fluoro-1-nitro-benzene (400 mg, 1.82 mmol) in DMSO (3 mL) was added dropwise. The reaction mixture was stirred at 50° C. for 3 h. The mixture was diluted with saturated $NaHCO_3$ (50 mL) and EtOAc (50 mL), and the aqueous phase was extracted with EtOAc (3×50 mL). The combined organic phases were dried over $Na_2SO_4$, filtered, and concentrated under reduced pressure.

The material was purified by flash chromatography on silica gel using a mixture of EtOAc in hexane as eluent to provide the title compound (466 mg, 89%). $^1$H NMR (500 MHz, $CDCl_3$) δ 8.19 (d, J=6.5 Hz, 1H), 8.02 (d, J=9.1 Hz, 1H), 7.07 (d, J=1.9 Hz, 1H), 6.73 (dd, J=9.1, 2.0 Hz, 1H), 3.89-3.78 (m, 1H), 3.48 (dd, J=5.0, 1.2 Hz, 2H), 3.41 (s, 3H), 1.33 (d, J=6.5 Hz, 3H). MS (ESI) $[M+H]^+$ 291.0.

Step 2: Preparation of 5-[3-[[(1S)-2-methoxy-1-methyl-ethyl]amino]-4-nitrophenyl]-1,3-dimethyl pyridin-2-one

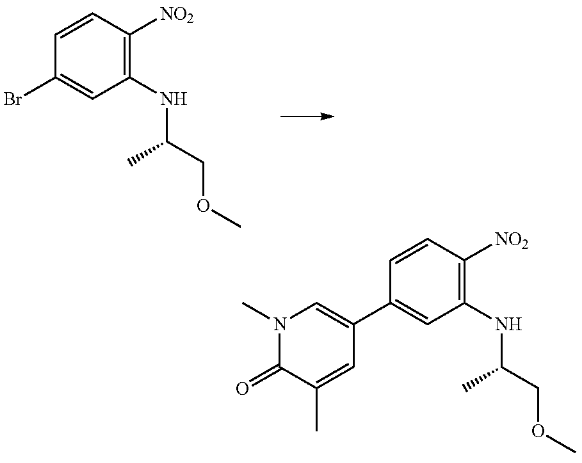

$Pd(PPh_3)_4$ (186 mg, 0.161 mmol) was added to a degassed solution of 5-bromo-N-[(1S)-2-methoxy-1-methyl-ethyl]-2-nitro-aniline (466 mg, 1.61 mmol), 1,3-dimethyl-5-(4,4,5,5-tetramethyl-1,3,2-dioxaborolan-2-yl)pyridin-2-one (prepared using the procedure described in US20130053362, 522 mg, 2.09 mmol), and $Cs_2CO_3$ (1.31 g, 4.03 mmol) in DME (20 mL) and water (2 mL) under $N_2$. The reaction mixture was heated to 80° C. for 18 h and then cooled to rt. The mixture was diluted with saturated $NaHCO_3$ (50 mL) and EtOAc (50 mL), and the aqueous phase was extracted with EtOAc (3×50 mL). The combined organic phases were dried over $Na_2SO_4$, filtered through Celite™ and concentrated under reduced pressure. The material was purified by flash chromatography on silica gel using a mixture of EtOAc in hexane as eluent to provide the title compound (603 mg, 99%) as a solid. $^1$H NMR (500 MHz, $CDCl_3$) δ 8.29 (d, J=7.6 Hz, 1H), 8.20 (d, J=8.9 Hz, 1H), 7.47 (d, J=0.8 Hz, 2H), 6.87 (d, J=1.8 Hz, 1H), 6.66 (dd, J=8.9, 1.9 Hz, 1H), 4.03-3.92 (m, 1H), 3.65 (s, 3H), 3.57-3.48 (m, 2H), 3.43 (s, 3H), 2.24 (t, J=0.8 Hz, 3H), 1.37 (d, J=6.5 Hz, 3H). MS (ESI) $[M+H]^+$ 332.2.

Step 3: Preparation of Intermediate 7

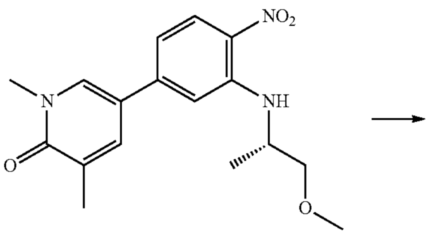

-continued

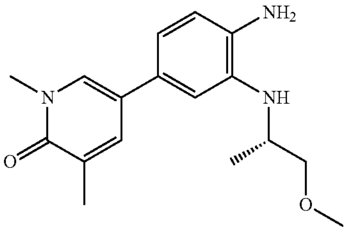

AcOH (0.28 mL, 4.84 mmol) and zinc (1.05 g, 16.12 mmol) were added to a solution of 5-[3-[[(1S)-2-methoxy-1-methyl-ethyl]amino]-4-nitro-phenyl]-1,3-dimethyl-pyridin-2-one (534 mg, 1.61 mmol) in MeOH (10 mL) and the suspension was stirred at rt for 30 min. The mixture was then filtered through Celite™, washed with EtOAc (10 mL) and concentrated under reduced pressure. The residue was diluted in EtOAc (50 mL) and saturated $NaHCO_3$ (30 mL) and then the aqueous phase was extracted with EtOAc (2×30 mL). The combined organic phases were washed with brine, dried over $Na_2SO_4$, filtered and concentrated under reduced pressure to provide Intermediate 7 (535 mg, 99%) as solid. $^1$H NMR (500 MHz, $CDCl_3$) δ 7.64-7.57 (m, 1H), 7.39-7.37 (m, 1H), 7.20 (d, J=2.4 Hz, 1H), 6.67-6.65 (m, 1H), 6.64 (s, 1H), 3.65-3.59 (m, 1H), 3.54 (s, 3H), 3.38 (dd, J=5.1, 2.4 Hz, 2H), 3.33 (s, 3H), 2.16-2.12 (m, 3H), 1.18 (d, J=6.4 Hz, 3H). MS (ESI) $[M+H]^+$ 302.2.

Intermediate 8: 5-(4-amino-3-((2-(trifluoromethoxy) ethyl)amino)phenyl)-1,3-dimethylpyridin-2 (1H)-one

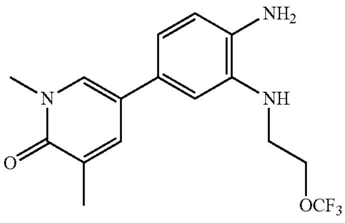 [SMILES: Cc1cc(-c2ccc(N)c(NCCOC(F)(F)F)c2)cn(C)c1=O]

Step 1: Preparation of 1,3-dimethyl-5-(4-nitro-3-((2-(trifluoromethoxy)ethyl)amino)phenyl)pyridin-2 (1H)-one

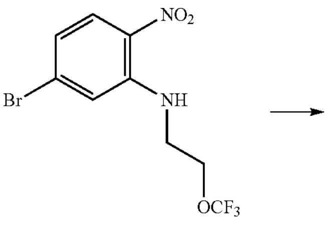

-continued

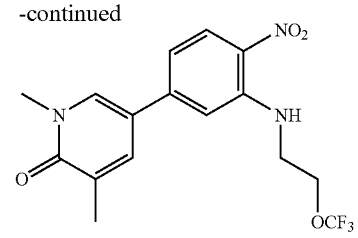

A solution of 5-bromo-2-nitro-N-[2-(trifluoromethoxy) ethyl]aniline (Intermediate 1, step 1; 320 mg, 1.16 mmol), 1,3-dimethyl-5-(4,4,5,5-tetramethyl-1,3,2-dioxaborolan-2-yl)pyridin-2-one (prepared as in US20130053362, 348 mg, 1.40 mmol) in DME (8 mL) and water (0.4 mL) was degassed by bubbling for 10 min. $Cs_2CO_3$ (0.80 g, 2.44 mmol) and $Pd(PPh_3)_4$ (134 mg, 0.116 mmol) were then added and the mixture was degassed by bubbling $N_2$ for 10 more min. The resulting mixture was heated to 85° C. for 18 h and then cooled to rt. The mixture was diluted with saturated $NaHCO_3$ (10 mL) and EtOAc (50 mL), and then the aqueous phase was extracted with EtOAc (3×20 mL). The combined organic phases were dried over $MgSO_4$, filtered, and concentrated under reduced pressure. The material was purified by flash chromatography on silica gel using a mixture of EtOAc in hexane as eluent to provide title compound (340 mg, 92%). MS (ESI) $[M+H]^+$ 372.17.

Step 2: Preparation of Intermediate 8

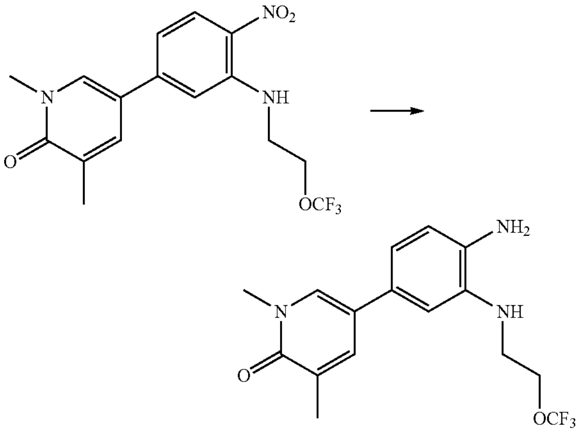

AcOH (0.184 mL, 3.21 mmol) and zinc powder (0.70 g, 10.71 mmol) were added to a solution of 1,3-dimethyl-5-(4-nitro-3-((2-(trifluoromethoxy)ethyl)amino)phenyl)pyridin-2 (1H)-one (0.34 g, 1.07 mmol) in MeOH (7 mL) and the suspension was stirred at rt for 30 min. The mixture was then filtered through Celite™, washed with EtOAc (10 mL) and concentrated under reduced pressure. The residue was diluted in EtOAc (50 mL) and saturated $NaHCO_3$ (30 mL) and then the aqueous phase was extracted with EtOAc (2×30 mL). The combined organic phases were washed with brine, dried over $Na_2SO_4$, filtered and concentrated under reduced pressure to provide Intermediate 8, which was used for the next step without any further purification. (0.29, 94%). $^1$H NMR (500 MHz, $CDCl_3$) δ7.47-7.42 (m, 1H), 7.27 (d, J=4.4 Hz, 1H), 6.77 (s, 2H), 6.66 (s, 1H), 4.23 (t, J=5.3 Hz, 2H), 3.61 (s, 3H), 3.54-3.42 (m, 5H), 2.22 (s, 3H). MS (ESI) $[M+H]^+$ 342.34.

Intermediate 9: 3-chloro-1-methyl-5-(4,4,5,5-tetramethyl-1,3,2-dioxaborolan-2-yl)pyridin-2 (1H)-one

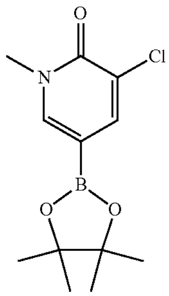 [SMILES: Cn1cc(B2OC(C)(C)C(C)(C)O2)cc(Cl)c1=O]

Step 1: Preparation of 5-bromo-3-chloro-1-methylpyridin-2(1H)-one

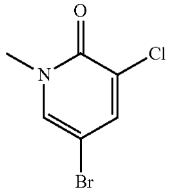

To a rt stirred solution of 5-bromo-3-chloropyridin-2 (1H)-one (4 g, 19.19 mmol) in MeOH (80 mL) was added $K_2CO_3$ (7.94 g, 57.57 mmol), followed by the addition of methyl iodide (3.6 mL, 57.57 mmol). The reaction mixture was heated to 70° C. for 3 h. The mixture was concentrated under pressure, diluted with water (200 mL), and the aqueous layer was extracted with DCM (3×150 mL). The combined organic layers were washed with brine (100 mL), dried over $Na_2SO_4$, filtered and concentrated under reduced pressure to afford the title compound (4 g, 93%) as a solid. MS (ESI) $[M+H]^+$ 223.5.

Step 2: Preparation of Intermediate 9

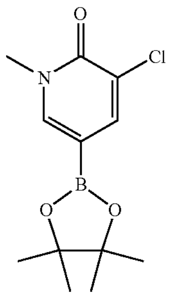 [SMILES: Cn1cc(B2OC(C)(C)C(C)(C)O2)cc(Cl)c1=O]

A stirred solution of 5-bromo-3-chloro-1-methylpyridin-2 (1H)-one (4 g, 18 mmol) and potassium acetate (5.3 g, 54 mmol) in dioxane (80 mL) was purged with nitrogen for 15 min. Bis(pinacolato)diborane (6.85 g, 27 mmol) was added to the reaction mixture, which was again purged with nitrogen for 30 min. $Pd(dppf)Cl_2{\cdot}CH_2Cl_2$ (0.73 g, 0.09 mmol) was added and the resulting mixture was heated at 110° C. for 16 h. The mixture was cooled and filtered through Celite™ and washed with EtOAc (3×50 mL). The organic layer was dried over $Na_2SO_4$, filtered and concentrated under reduced pressure. The material was purified by flash chromatography on silica gel using a gradient (0-3%) of MeOH in DCM as eluent and then triturated with $Et_2O$ to afford Intermediate 9 (1.5 g, 31%) as a solid. $^1$H NMR (400 MHz, DMSO) δ ppm 7.81 (d, J=1.6 Hz, 1H), 7.71 (d, J=1.6 Hz, 1H), 3.63 (s, 3H), 1.32 (s, 12H). MS (ESI) $[M+H]^+$ 270.2.

Intermediate 10: 5-[4-amino-3-(3,3,3-trifluoropropylamino)phenyl]-1,3-dimethyl-pyridin-2-one

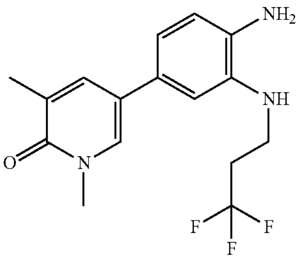 [SMILES: Cc1cc(-c2ccc(N)c(NCCC(F)(F)F)c2)cn(C)c1=O]

Step 1: Preparation of 5-(3-fluoro-4-nitro-phenyl)-1,3-dimethyl-pyridin-2-one

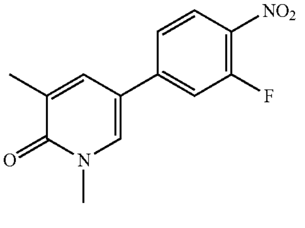 [SMILES: Cc1cc(-c2ccc([N+](=O)[O-])c(F)c2)cn(C)c1=O]

To a solution of 4-bromo-2-fluoro-1-nitrobenzene (2.0 g, 9.09 mmol) in DME (20 mL) was added 1,3-dimethyl-5-(4,4,5,5-tetramethyl-1,3,2-dioxaborolan-2-yl)pyridin-2-one (prepared as in US20130053362, 4.53 g, 18.18 mmol), $Cs_2CO_3$ (2.96 g, 9.09 mmol), $Pd(PPh_3)_4$ (1.05 g, 0.909 mmol) and water (2 mL). The reaction mixture was degassed for 5 min and then heated to 80° C. for 1 h. The mixture was cooled to rt. The solid was collected by filtration and washed with water. The title compound (2.2 g, 92%) was dried under reduced pressure and used in the next step without further purification. $^1$H NMR (500 MHz, DMSO) δ 8.36 (d, J=2.7 Hz, 1H), 8.19 (t, J=8.5 Hz, 1H), 7.92 (dd, J=2.7, 1.1 Hz, 1H), 7.86 (dd, J=13.6, 2.0 Hz, 1H), 7.69 (dd, J=8.7, 1.8 Hz, 1H), 3.54 (s, 3H), 2.09 (s, 3H). MS (ESI) $[M+H]^+$ 263.2.

Step 2: Preparation of 1,3-dimethyl-5-[4-nitro-3-(3,3,3-trifluoropropylamino)phenyl]pyridin-2-one

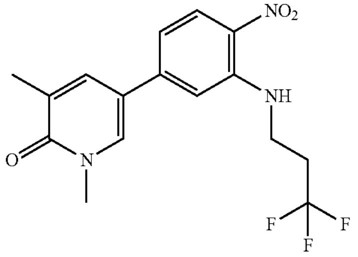 [SMILES: Cc1cc(-c2ccc([N+](=O)[O-])c(NCCC(F)(F)F)c2)cn(C)c1=O]

To a solution of 5-(3-fluoro-4-nitrophenyl)-1,3-dimethylpyridin-2-one (350 mg, 1.335 mmol) in DMF (7 mL) were added $K_2CO_3$ (461.1 mg, 3.34 mmol) and 3,3,3-trifluoropropan-1-amine (196.2 mg, 1.735 mmol) and the reaction mixture was heated to 50° C. for 18 h. The mixture was diluted with EtOAc (20 mL) and water (10 mL). The organic layer was washed with water (2×10 mL), dried over $MgSO_4$, filtered and concentrated under reduced pressure. The resulting solid was triturated with $Et_2O$ to afford the title compound (272 mg, 57%) as a solid. $^1$H NMR (500 MHz, $CDCl_3$) δ 8.29-8.20 (m, 2H), 7.49 (dt, J=2.6, 1.8 Hz, 2H), 6.77 (dt, J=5.8, 1.9 Hz, 2H), 3.74-3.58 (m, 5H), 2.58 (dt, J=10.5, 7.1 Hz, 2H), 2.25 (s, 3H). MS (ESI) $[M+H]^+$ 356.2.

Step 3: Preparation of Intermediate 10

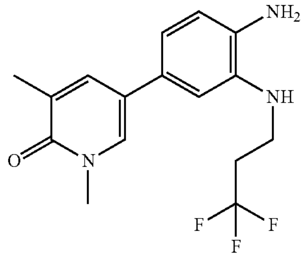 [SMILES: Cc1cc(-c2ccc(N)c(NCCC(F)(F)F)c2)cn(C)c1=O]

To a solution of 1,3-dimethyl-5-[4-nitro-3-(3,3,3-trifluoropropylamino)phenyl]pyridin-2-one (270 mg, 0.76 mmol) in MeOH (6 mL) was added acetic acid (0.13 mL, 2.28 mmol) and zinc powder (497 mg, 7.60 mmol) and the suspension was stirred at rt for 45 min. The mixture was filtered through Celite™ and the filtrate was concentrated under reduced pressure. The residue was dissolved in EtOAc (10 mL) and saturated $NaHCO_3$ (10 mL) was added. The phases were separated and the aqueous layer was extracted with EtOAc (2×30 mL). The combined organic layers were washed with brine, dried over $Na_2SO_4$, filtered and concentrated under reduced pressure to afford Intermediate 10 (244 mg, 99%) as a solid. MS (ESI) $[M+H]^+$ 326.2.

Intermediate 11: (R)-2-ethoxypropan-1-amine hydrochloride

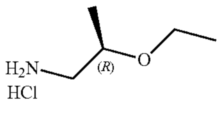

Step 1: Preparation of tert-butyl (R)-(2-ethoxypropyl)carbamate

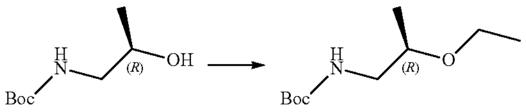

To a suspension of NaH (60% in mineral oil, 0.43 g, 10.7 mmol) in THF (10 mL), tert-butyl (R)-(2-hydroxypropyl) carbamate (1.5 g, 8.56 mmol) in THF (10 mL) was added dropwise at 0° C. and stirred at this temperature for 30 min. Iodoethane (1.7 g, 10.7 mmol) was added dropwise at 0° C. and the reaction mixture was stirred at rt for 2 h. The reaction mixture was then diluted with water (100 mL) and extracted with EtOAc (100 mL×3). The combined organic layers were washed with brine (100 mL), dried over anhydrous $Na_2SO_4$, filtered and concentrated to afford the title compound (1 g, 57%) as an oil, which was used for next step without any further purification.

Step 2: Preparation of Intermediate 11

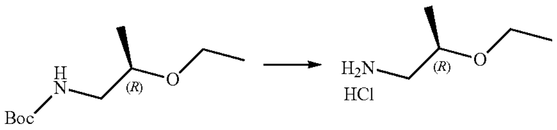

To a stirred solution of tert-butyl (R)-(2-ethoxypropyl) carbamate (1 g, 4.92 mmol) in DCM (10 mL) was added 6M HCl in dioxane (3 mL) at 10° C. under nitrogen. The reaction mixture was stirred at rt for 16 h. The reaction mixture was then evaporated to afford Intermediate 11 (0.9 g), which was used in the next step without further purification.

Intermediate 12: (S)-2-ethoxypropan-1-amine hydrochloride

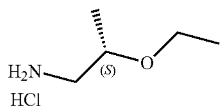

Step 1: Preparation of tert-butyl (S)-(2-ethoxypropyl)carbamate

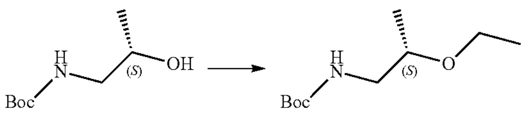

The procedure depicted in step 1 of Intermediate 11 was followed using (S)-(2-hydroxypropyl)carbamate to afford the title compound (1 g, 57%) as an oil, which was used for next step without any further purification.

Step 2: Preparation of Intermediate 12

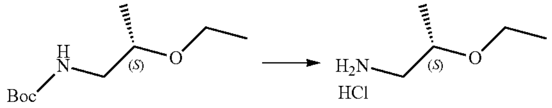

The procedure of step 2 of Intermediate 11 was followed using tert-butyl (S)-(2-ethoxypropyl)carbamate (1 g, 4.92 mmol) to afford the Intermediate 12 (0.8 g), which was used in the next step without further purification.

Example 1: Synthesis of 1,3-dimethyl-5-[2-tetrahydropyran-4-yl-3-[2-(trifluoromethoxy)ethyl]benzimidazol-5-yl]pyridin-2-one (Compound 1)

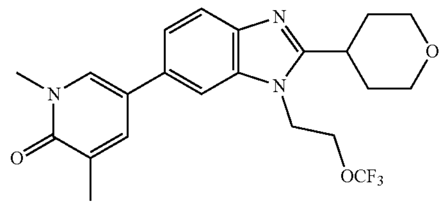 [SMILES: Cc1cc(-c2ccc3nc(C4CCOCC4)n(CCOC(F)(F)F)c3c2)cn(C)c1=O]

Procedure A

Step 1: Preparation of 6-bromo-2-tetrahydropyran-4-yl-1-[2-trifluoromethoxy)ethyl]benzimidazole

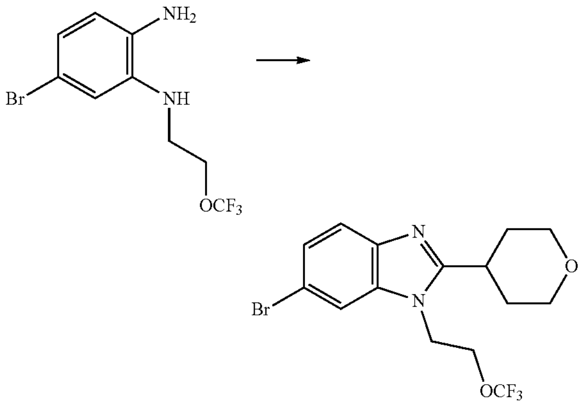

To a solution of 4-bromo-N2-[2-(trifluoromethoxy)ethyl] benzene-1,2-diamine (Intermediate 1, 150 mg, 0.50 mmol) in DCM (5 mL) and tetrahydropyran-4-carbonyl chloride (78.2 mg, 0.527 mmol) was added at rt. The reaction mixture was stirred for 1 h then quenched by addition of water. The mixture diluted in EtOAc (50 mL) and saturated $NaHCO_3$ (10 mL) was added. The phases were separated and aqueous phase was extracted with EtOAc (2×20 mL). The combined organic phases were washed with brine, dried over $Na_2SO_4$ and evaporated under reduced pressure to afford the amide, which was used for the next step without any further purification. MS (ESI) $[M+H]^+$ 411.1, 413.1

To the above compound in toluene (10 mL) and pTSA (86.3 mg, 0.50 mmol) was added and the reaction mixture was heated to 120° C. for 18 h. The mixture was then cooled to rt and evaporated under reduced pressure. The residue was diluted in EtOAc (50 mL) and saturated $NaHCO_3$ (10 mL) was added. The phases were separated and aqueous phase was extracted with EtOAc (2×20 mL). The combined organic phases were washed with brine, dried over $Na_2SO_4$ and evaporated under reduced pressure. The material was purified by flash chromatography on silica gel using a mixture of EtOAc in hexane as eluent to provide the title compound (140 mg, 64%). MS (ESI) $[M+H]^+$ 393.1, 395.0.

Step 2: Preparation of Compound 1

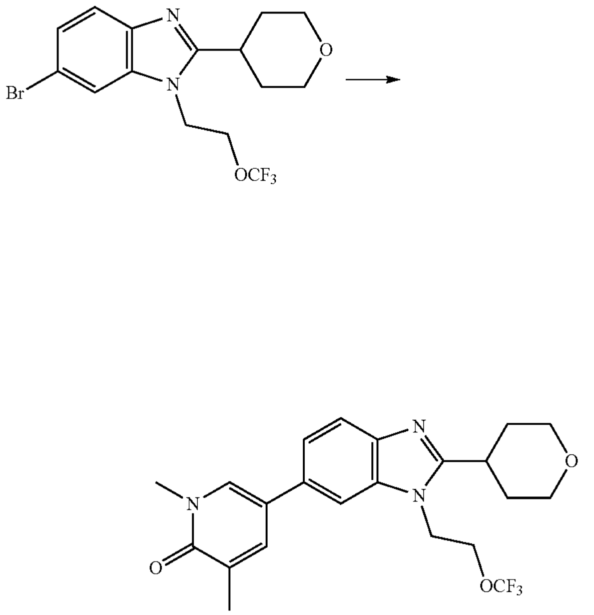

6-Bromo-2-tetrahydropyran-4-yl-1-[2-(trifluoromethoxy)ethyl]benzimidazole (70 mg, 0.18 mmol), 1,3-dimethyl-5-(4,4,5,5-tetramethyl-1,3,2-dioxaborolan-2-yl)pyridin-2-one (prepared using the procedure described in US20130053362, 53 mg, 0.21 mmol), and $Cs_2CO_3$ (122 mg, 0.37 mmol) in a mixture of DME (2 mL) and water (0.2 mL) were degassed by bubbling $N_2$ for 10 min. $Pd(PPh_3)_4$ (21 mg, 0.018 mmol) was then added and the reaction mixture was degassed by bubbling $N_2$ for 10 min. The resulting mixture was heated to 85° C. for 3 h and then cooled to rt. The mixture was diluted with saturated $NaHCO_3$ (10 mL) and EtOAc (30 mL). The phases were separated and the aqueous phase was extracted with EtOAc (2×15 mL). The combined organic phases were washed with brine, dried over $Na_2SO_4$ and evaporated under reduced pressure. The material was purified by flash chromatography on silica gel using a mixture of EtOAc in hexane as eluent, and followed by preparative HPLC to provide Compound 1 (23 mg, 30%). $^1H$ NMR (500 MHz, $CDCl_3$) δ 7.81 (d, J=8.3 Hz, 1H), 7.56 (dd, J=2.6, 1.1 Hz, 1H), 7.41 (d, J=2.5 Hz, 1H), 7.34 (dd, J=8.3, 1.7 Hz, 1H), 7.29-7.28 (m, 1H), (4.54 (t, J=5.4 Hz, 2H), 4.35 (t, J=5.3 Hz, 2H), 4.17 (dd, J=11.7, 2.6 Hz, 2H), 3.67 (s, 3H), 3.60 (td, J=11.9, 1.9 Hz, 2H), 3.21-3.00 (m, 1H), 2.28 (s, 3H), 2.38-2.16 (m, 2H), 1.87 (d, J=11.4 Hz, 2H). MS (ESI) $[M+H]^+$ 436.2.

Procedure B

Step 1: Preparation of N-(4-(1,5-dimethyl-6-oxo-1,6-dihydropyridin-3-yl)-2-((2-(trifluoromethoxy)ethyl)amino)phenyl)tetrahydro-2H-pyran-4-carboxamide

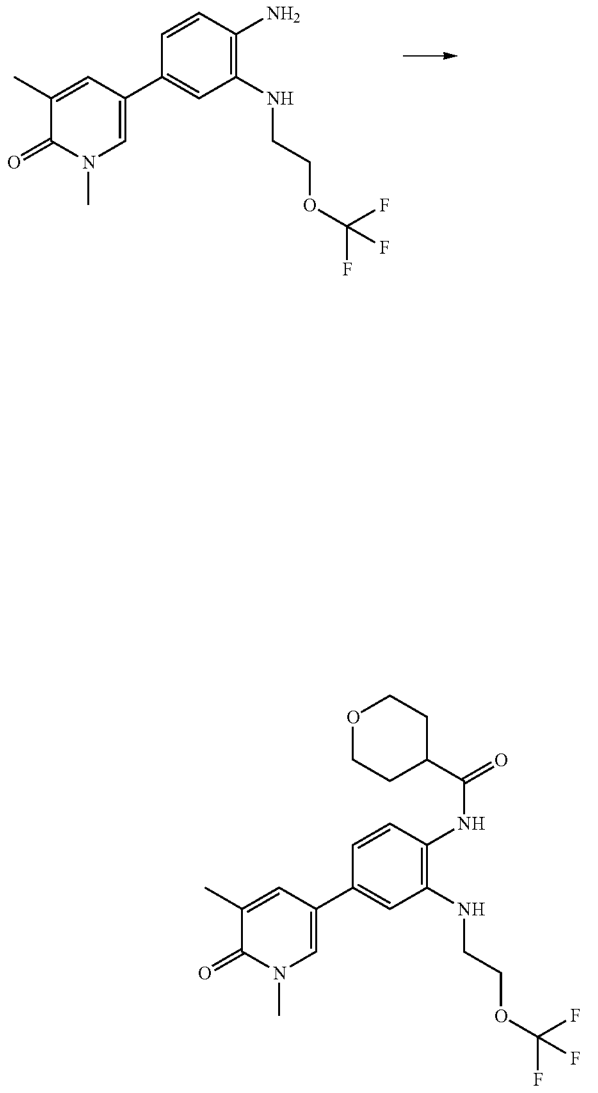

A stirred solution of tetrahydro-2H-pyran-4-carboxylic acid (6.4 g, 49.2 mmol) in DCM (200 mL) was added T3P™ (50% in EtOAc) (23.0 g, 61.5 mmol) at rt and reaction mixture was stirred for 20 min. A solution of Intermediate 8 (14.0 g, 41.1 mmol) and DIPEA (10.6 g, 82 mmol) in DCM (20 mL) was then added and the reaction mixture was stirred at rt for 8 h. After completion, the reaction mixture was concentrated under reduced pressure and the product was extracted using EtOAc (300 mL×3). The combined organic layer was washed with water (150 mL), brine (150 mL), dried over anhydrous $Na_2SO_4$, filtered and concentrated. The resulting product was triturated with $Et_2O$ and dried under vacuum to afford the title compound (13.0 g, 63%) as a solid. $[M+H]^+$ 454.35.

Step 2: Preparation of 1,3-dimethyl-5-(2-(tetrahydro-2H-pyran-4-yl)-1-(2-(trifluoromethoxy)ethyl)-1H-benzo[d]imidazol-6-yl)pyridin-2(1H)-one

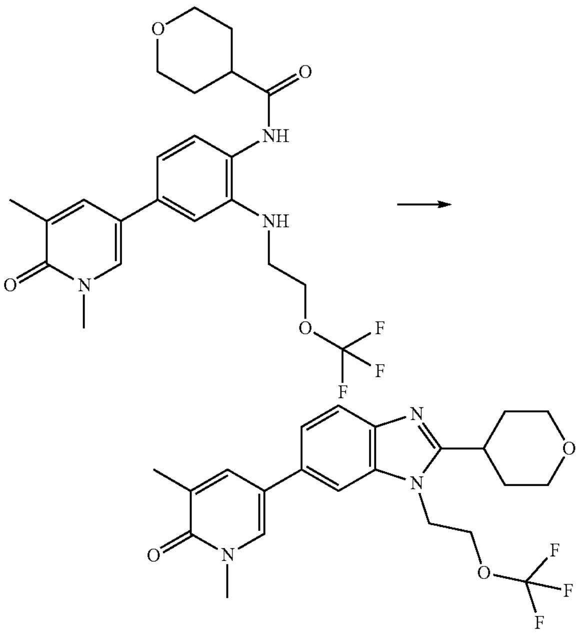

A stirred solution of N-(4-(1,5-dimethyl-6-oxo-1,6-dihydropyridin-3-yl)-2-((2-(trifluoromethoxy) ethyl)amino)phenyl)tetrahydro-2H-pyran-4-carboxamide (13.0 g, 28.7 mmol) in acetic acid (320 mL) was heated at 100° C. for 14 h. After completion, the acetic acid was evaporated under vacuum. A saturated $NaHCO_3$ solution (500 mL) was added to the residue to neutralize any acid left and the mixture was extracted using EtOAc (300 mL). The organic layer was washed with brine (150 mL), dried over anhydrous $Na_2SO_4$, filtered and concentrated. The crude product was purified by silica gel chromatography using 4% MeOH in DCM as eluent to afford 11.0 g of product, which was further crystallized in toluene to afford Compound 1 (6.6 g, 53%) as a solid. $^1H$ NMR (500 MHz, $CDCl_3$) δ 7.81 (d, J=8.3 Hz, 1H), 7.56 (dd, J=2.6, 1.1 Hz, 1H), 7.41 (d, J=2.5 Hz, 1H), 7.34 (dd, J=8.3, 1.7 Hz, 1H), 7.29-7.28 (m, 1H), (4.54 (t, J=5.4 Hz, 2H), 4.35 (t, J=5.3 Hz, 2H), 4.17 (dd, J=11.7, 2.6 Hz, 2H), 3.67 (s, 3H), 3.60 (td, J=11.9, 1.9 Hz, 2H), 3.21-3.00 (m, 1H), 2.28 (s, 3H), 2.38-2.16 (m, 2H), 1.87 (d, J=11.4 Hz, 2H). MS (ESI) $[M+H]^+$ 436.2.

Example 2: 5-[2-cyclopropyl-3-[2-(trifluoromethoxy)ethyl]benzimidazol-5-yl]-1,3-dimethylpyridin-2-one (Compound 2)

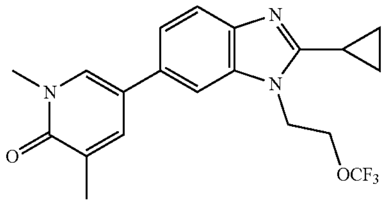 [SMILES: Cc1cc(-c2ccc3nc(C4CC4)n(CCOC(F)(F)F)c3c2)cn(C)c1=O]

Procedure A

Step 1: Preparation of 6-bromo-2-cyclopropyl-1-[2-(trifluoromethoxy)ethyl]benzimidazole

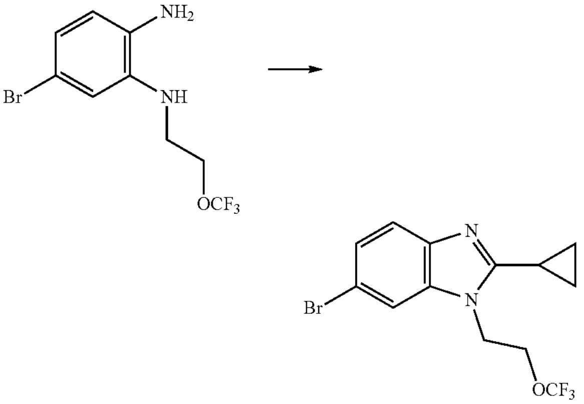

To a solution of 4-bromo-N2-[2-(trifluoromethoxy)ethyl]benzene-1,2-diamine (Intermediate 1, 150 mg, 0.50 mmol) in MeOH (4 mL), cyclopropanecarbaldehyde (35 mg, 0.502 mmol) was added quickly, followed by slow addition of acetic acid (0.143 mL, 2.51 mmol) and then the reaction mixture was stirred at rt for 18 h. The solution was evaporated under reduced pressure and then diluted with EtOAc (20 mL) and saturated $NaHCO_3$ (10 mL). The phases were separated and aqueous phase was extracted with EtOAc (3×15 mL). The combined organic phases were washed with brine, dried over Na2SO4, filtered and evaporated under reduced pressure. The material was purified by flash chromatography on silica gel using a mixture of EtOAc in hexane as eluent to provide title compound (88 mg, 45%). MS (ESI) $[M+H]^+$ 349.0, 351.0.

Step 2: Preparation of Compound 2

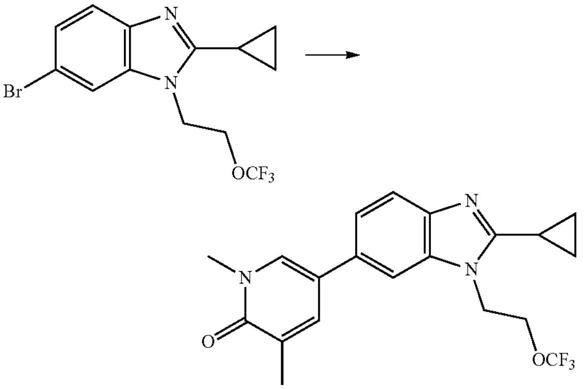

A solution of 6-bromo-2-cyclopropyl-1-[2-(trifluoromethoxy)ethyl]benzimidazole (88 mg, 0.252 mmol), 1,3-dimethyl-5-(4,4,5,5-tetramethyl-1,3,2-dioxaborolan-2-yl) pyridin-2-one (prepared as in US20130053362, 63 mg, 0.252 mmol) in DME (2 mL) and water (0.1 mL) was degassed by bubbling $N_2$ for 10 min. To the mixture, $Cs_2CO_3$ (172 mg, 0.529 mmol) and $Pd(PPh_3)_4$ (29 mg, 0.025 mmol) were then added and then degassed by bubbling $N_2$ for 10 min. The resulting mixture was heated to 85° C. for 3 h and then cooled to rt. The mixture was diluted with saturated $NaHCO_3$ (10 mL) and EtOAc (10 mL), and the aqueous phase was extracted with EtOAc (3×10 mL). The combined organic phases were dried over $MgSO_4$, filtered, and evaporated under reduced pressure. The material was purified by flash chromatography on silica gel using a mixture of EtOAc in hexane as eluent, and followed by preparative HPLC to provide Compound 2 (56 mg, 57%). $^1H$ NMR (500 MHz, $CDCl_3$) δ 7.66 (d, J=8.2 Hz, 1H), 7.55-7.48 (m, 1H), 7.37 (d, J=2.5 Hz, 1H), 7.29-7.25 (m, 1H), 7.25-7.23 (m, 1H), 4.59 (t, J=5.5 Hz, 2H), 4.34 (t, J=5.5 Hz, 2H), 3.62 (s, 3H), 2.23 (s, 3H), 2.07-1.90 (m, 1H), 1.33-1.22 (m, 2H), 1.17-1.09 (m, 2H). $[M+H]^+$ 392.2.

Procedure B

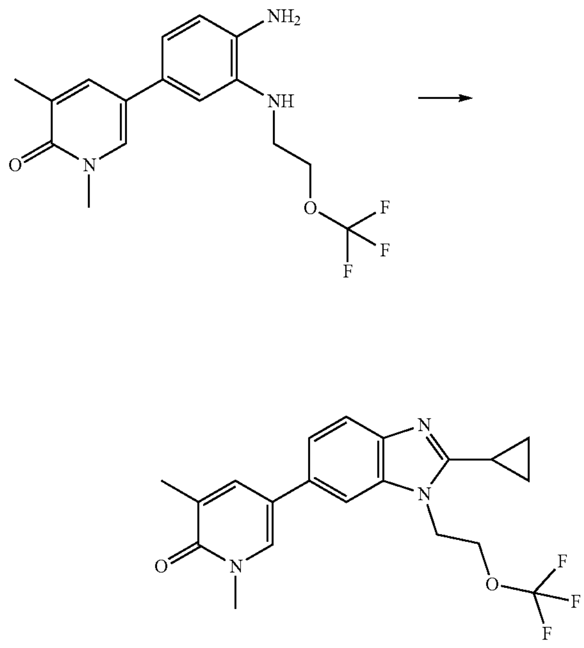

A solution of Intermediate 8 (14.0 g, 41.0 mmol) and cyclopropanecarbaldehyde (3.44 g, 49.0 mmol) in acetic acid (560 mL) was stirred at rt for 14 h. After completion of the reaction, the solvent was evaporated under reduced pressure. A saturated $NaHCO_3$ solution (1 L) was added to the residue to neutralize any acid present and the product was extracted using EtOAc (150 mL×3). The combined organic layer was washed with brine (500 mL), dried over anhydrous $Na_2SO_4$ and concentrated. The crude product was purified by silica gel chromatography using 3% MeOH in DCM as eluent. The combined fractions were concentrated under reduced pressure to afford 5.2 g of a light yellow solid, which was further crystallized (in two batches) in acetone to afford Compound 2 (total 4.68 g, 30%) as a white solid. $^1H$ NMR (500 MHz, $CDCl_3$) δ 7.66 (d, J=8.2 Hz, 1H), 7.55-7.48 (m, 1H), 7.37 (d, J=2.5 Hz, 1H), 7.29-7.25 (m, 1H), 7.25-7.23 (m, 1H), 4.59 (t, J=5.5 Hz, 2H), 4.34 (t, J=5.5 Hz, 2H), 3.62 (s, 3H), 2.23 (s, 3H), 2.07-1.90 (m, 1H), 1.33-1.22 (m, 2H), 1.17-1.09 (m, 2H). $[M+H]^+$ 392.2.

Example 3: 1,3-dimethyl-5-[3-[2-(trifluoromethoxy)ethyl]benzimidazol-5-yl]pyridin-2-one (Compound 3)

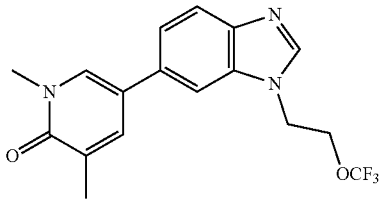

Step 1: Preparation of 6-bromo-1-[2-(trifluoromethoxy)ethyl]benzimidazole

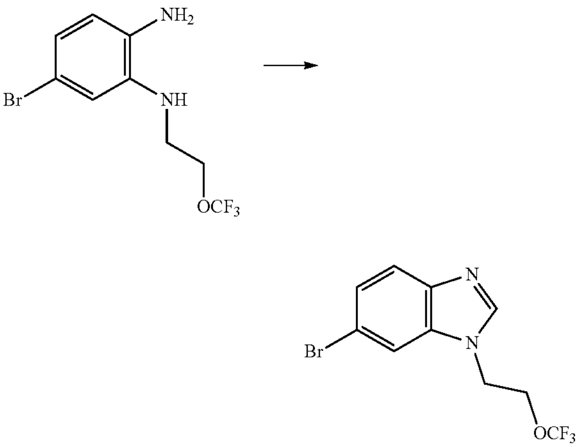

4-bromo-N2-[2-(trifluoromethoxy)ethyl]benzene-1,2-diamine (Intermediate 1, 150 mg, 0.502 mmol) was dissolved in triethyl orthoformate (10 mL) and the solution was stirred for 5 min. pTSA (10 mg, 0.05 mmol) was then added and the mixture was stirred at rt for 18 h. The solution was then diluted with EtOAc (30 mL) and the organic phase was washed with saturated $NaHCO_3$ (5 mL). The aqueous layer was extracted with EtOAc (2×20 mL). The combined organic layers were dried over $Na_2SO_4$, filtered, and under reduced pressure to afford title compound, which was used in the next step without any further purification (100 mg, 65%). MS (ESI) $[M+H]^+$ 309.1, 311.1.

Step 2: Preparation of Compound 3

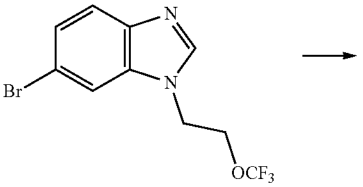

-continued

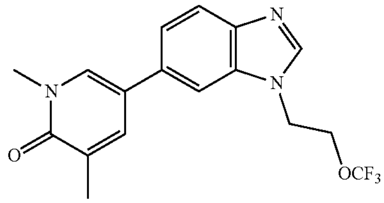 [SMILES: Cc1cc(-c2ccc3ncn(CCOC(F)(F)F)c3c2)cn(C)c1=O]

A solution of 6-bromo-1-[2-(trifluoromethoxy)ethyl]benzimidazole (50 mg, 0.162 mmol), 1,3-dimethyl-5-(4,4,5,5-tetramethyl-1,3,2-dioxaborolan-2-yl)pyridin-2-one (prepared using described procedure in US20130053362, 48 mg, 0.194 mmol) in DME (2 mL) and water (0.1 mL) was degassed by bubbling $N_2$ for 10 min. $Cs_2CO_3$ (111 mg, 0.340 mmol) and $Pd(PPh_3)_4$ (19 mg, 0.016 mmol) were then added and the mixture was degassed by bubbling $N_2$ for 10 min. The resulting mixture was heated to 85° C. for 3 h and then cooled to rt. The mixture was diluted with saturated $NaHCO_3$ (10 mL) and EtOAc (30 mL), and the aqueous phase was extracted with EtOAc (3x10 mL). The combined organic phases were dried over $Na_2SO_4$, filtered, and concentrated under reduced pressure. The material was purified by flash chromatography on silica gel using a mixture of EtOAc in hexane as eluent and then MeOH in DCM, and followed by preparative HPLC to provide Compound 3 (56 mg, 38%). $^1$H NMR (500 MHz, $CDCl_3$) δ 7.95 (s, 1H), 7.84 (d, J=8.4 Hz, 1H), 7.57-7.52 (m, 1H), 7.41 (d, J=2.5 Hz, 1H), 7.38-7.37 (m, 1H), 7.35 (dd, J=8.4, 1.7 Hz, 1H), 4.52 (t, J=5.2 Hz, 2H), 4.34 (t, J=5.2 Hz, 2H), 3.65 (s, 3H), 2.25 (s, 3H). MS (ESI) $[M+H]^+$ 352.4.

Example 4: 5-[2-(1-acetyl-4-piperidyl)-3-[2-(trifluoromethoxy)ethyl]benzimidazol-5-yl]-1,3-dimethylpyridin-2-one (Compound 4)

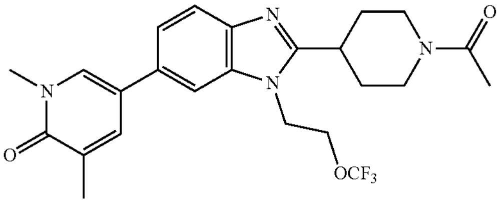 [SMILES: CC(=O)N1CCC(c2nc3ccc(-c4cc(C)c(=O)n(C)c4)cc3n2CCOC(F)(F)F)CC1]

Step 1: Preparation of 1-[4-[6-bromo-1-[2-(trifluoromethoxy)ethyl]benzimidazol-2-yl]-1-piperidyl]ethanone

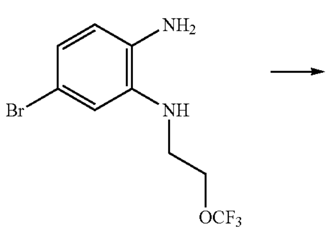

-continued

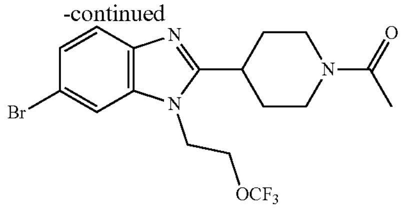

To a solution of 4-bromo-N2-[2-(trifluoromethoxy)ethyl]benzene-1,2-diamine (Intermediate 1, 140 mg, 0.468 mmol) in DCM (5 mL) and 1-acetylpiperidine-4-carbonyl chloride (93.1 mg, 0.491 mmol) was added at rt and the reaction mixture was stirred at rt for 2 h and then quenched by addition of water. The mixture was diluted in EtOAc (50 mL) and saturated $NaHCO_3$ (10 mL) was added. The phases were separated and aqueous phase was extracted with EtOAc (2x20 mL). The combined organic phases were washed with brine, dried over $Na_2SO_4$, filtered and evaporated under reduced pressure to afford the amide, which was used in the next step without any further purification. MS (ESI) $[M+H]^+$ 454.0.

The above compound in toluene (10 mL) and pTSA (80 mg, 0.468 mmol) was added and the mixture was heated to 110° C. for 18 h. The mixture was then cooled and evaporated under reduced pressure. The residue was diluted in EtOAc (50 mL) and saturated $NaHCO_3$ (10 mL) was added. The phases were separated and aqueous phase was extracted with EtOAc (2x20 mL). The combined organic phases were washed with brine, dried over $Na_2SO_4$, filtered and evaporated under reduced pressure. The material was purified by flash chromatography on silica gel using EtOAc in hexane as eluent to provide title compound (140 mg, 64%). MS (ESI) $[M+H]^+$ 434.0, 436.0.

Step 2: Preparation of Compound 4

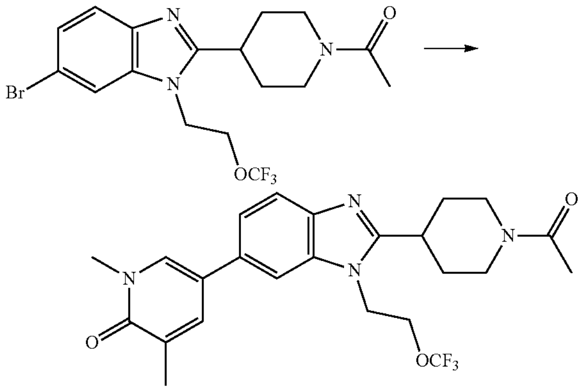

A mixture of 1,3-dimethyl-5-(4,4,5,5-tetramethyl-1,3,2-dioxaborolan-2-yl)pyridin-2-one (prepared using described procedure in US20130053362, 54.8 mg, 0.246 mmol), 1-[4-[6-bromo-1-[2-(trifluoromethoxy)ethyl]benzimidazol-2-yl]-1-piperidyl]ethanone (89 mg, 0.21 mmol), $Pd(PPh_3)_4$ (23.7 mg, 0.02 mmol), $Cs_2CO_3$ (140 mg, 0.43 mmol) in a mixture of DME (2 mL) and water (0.2 mL) was heated at 85° C. for 2 h. The mixture was then cooled and concentrated under reduced pressure. To the residue, EtOAc (30 mL) was added followed by saturated $NaHCO_3$ (20 mL). The phases were separated and the aqueous phase was extracted with EtOAc (2×30 mL). The combined organic phases were washed with brine, dried over $Na_2SO_4$, filtered and evaporated under reduced pressure. The material was purified by preparative HPLC to provide Compound 4 (20 mg, 21%). $^1$H NMR (500 MHz, MeOD) δ 7.85 (dd, J=11.1, 1.5 Hz, 2H), 7.71 (d, J=1.4 Hz, 1H), 7.65 (d, J=8.4 Hz, 1H), 7.45 (dd, J=8.4, 1.5 Hz, 1H), 4.75 (t, J=4.9 Hz, 2H), 4.69 (d, J=13.3 Hz, 1H), 4.45 (t, J=4.9 Hz, 2H), 4.10 (d, J=13.5 Hz, 1H), 3.66 (s, 3H), 3.46-3.31 (m, 2H), 2.80 (td, J=13.0, 2.4 Hz, 1H), 2.21 (s, 3H), 2.16 (s, 3H), 2.07-2.00 (m, 3H), 2.00-1.93 (m, 1H). MS (ESI) $[M+H]^+$ 477.3.

Example 5: 1,3-dimethyl-5-[2-methyl-3-[2-(trifluoromethoxy)ethyl]benzimidazol-5-yl]pyridin-2-one (Compound 5)

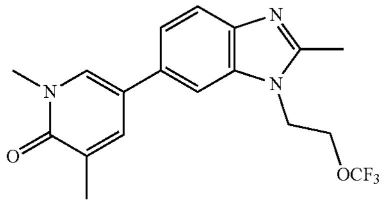 [SMILES: Cc1cc(-c2ccc3nc(C)n(CCOC(F)(F)F)c3c2)cn(C)c1=O]

Step 1: Preparation of 6-bromo-2-methyl-1-[2-(trifluoromethoxy)ethyl]benzimidazole

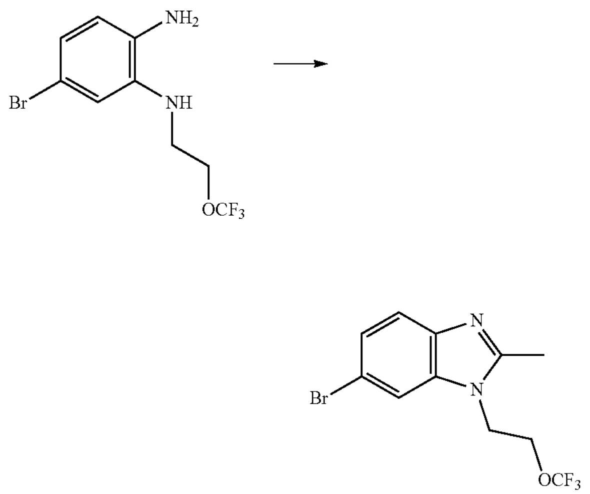

To a solution of Intermediate 1 (67 mg, 0.224 mmol) in trimethyl orthoacetate (1.25 mL) was added a 6 N HCl (37 μL, 0.224 mmol) and the reaction mixture was stirred at rt for 1 h. The mixture was then diluted with DCM (40 mL) and was washed with saturated $NaHCO_3$ (10 mL). The aqueous layer was extracted with DCM (2×20 mL), and the combined organic layers were dried over $Na_2SO_4$, filtered, and evaporated under reduced pressure. The material was purified by flash chromatography on silica gel using a mixture of EtOAc in hexane as eluent to provide title compound (44 mg, 55%). MS (ESI) $[M+H]^+$ 323.0, 325.0.

Step 2: Preparation of Compound 5

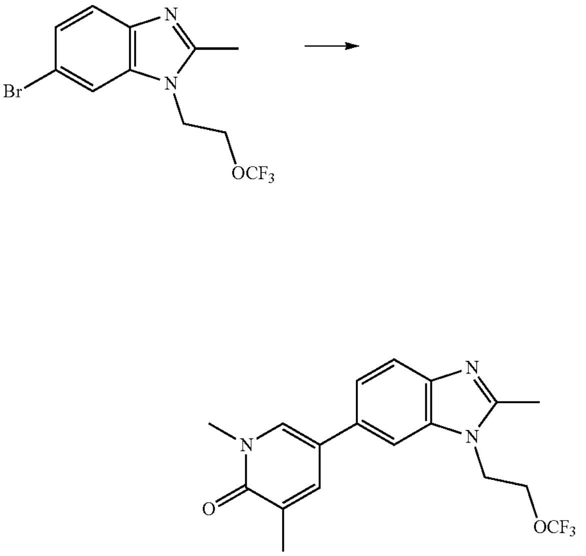

A solution of 6-bromo-2-methyl-1-[2-(trifluoromethoxy)ethyl]benzimidazole (44 mg, 0.136 mmol), 1,3-dimethyl-5-(4,4,5,5-tetramethyl-1,3,2-dioxaborolan-2-yl)pyridin-2-one (prepared using described procedure in US20130053362, 41 mg, 0.163 mmol) in DME (2 mL) and water (0.1 mL) was degassed by bubbling $N_2$ for 10 min. $Cs_2CO_3$ (93 mg, 0.286 mmol) and $Pd(PPh_3)_4$ (16 mg, 0.014 mmol) were then added and the mixture was degassed by bubbling $N_2$ for 10 min. The resulting mixture was heated to 85° C. for 3 h and then cooled to rt. The mixture was diluted with saturated $NaHCO_3$ (10 mL) and EtOAc (30 mL), and the aqueous phase was extracted with EtOAc (3×10 mL). The combined organic phases were dried over $Na_2SO_4$, filtered, and evaporated under reduced pressure. The material was purified by flash chromatography on silica gel using a mixture of EtOAc in hexane as eluent and then MeOH in DCM, and followed by preparative HPLC to provide Compound 5 (7.8 mg, 16%). $^1$H NMR (500 MHz, $CDCl_3$) δ 7.71 (d, J=8.3 Hz, 1H), 7.56-7.50 (m, 1H), 7.39 (d, J=2.6 Hz, 1H), 7.29 (ddd, J=8.3, 1.6, 0.8 Hz, 1H), 7.24 (d, J=1.2 Hz, 1H), 4.46 (t, J=5.3 Hz, 2H), 4.31 (t, J=5.3 Hz, 2H), 3.64 (s, 3H), 2.65 (s, 3H), 2.25 (d, J=0.5 Hz, 3H). MS (ESI) $[M+H]^+$ 366.2.

Example 6: 5-[2-cyclobutyl-3-[2-(trifluoromethoxy)ethyl]benzimidazol-5-yl]-1,3-dimethyl-pyridin-2-one (Compound 6)

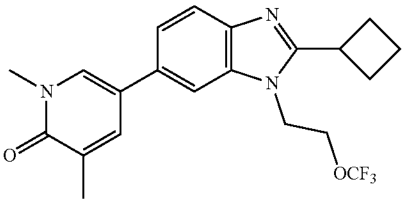 [SMILES: Cc1cc(-c2ccc3nc(C4CCC4)n(CCOC(F)(F)F)c3c2)cn(C)c1=O]

Step 1: Preparation of 6-bromo-2-cyclobutyl-1-[2-(trifluoromethoxy)ethyl]benzimidazole

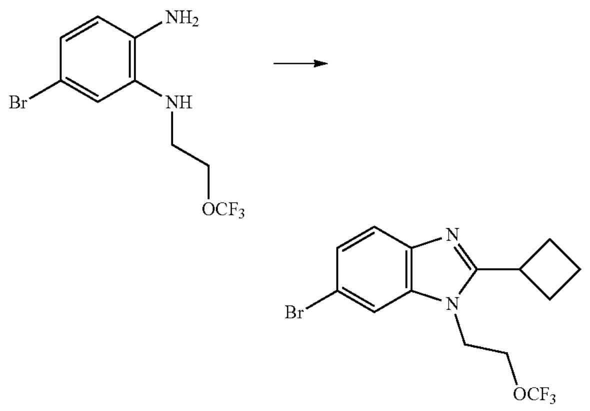

To a solution of Intermediate 1 (86 mg, 0.288 mmol) in DMF (2 mL), DIPEA (0.1 mL, 0.575 mmol), cyclobutanecarboxylic acid (0.04 mL, 0.374 mmol) and HATU (0.109 g, 0.288 mmol) were added and the resulting mixture was stirred at rt for 1 h. The solution was concentrated under reduced pressure and to the residue, EtOAc (20 mL) and saturated $NaHCO_3$ (10 mL) were added. The phases were separated and aqueous phase was extracted with EtOAc (2×10 mL). The combined organic layers were washed with brine, dried over $Na_2SO_4$, filtered and concentrated under reduced pressure to afford amide, which was used in the next step without any further purification. MS (ESI) $[M+H]^+$ 383.1, 383.3.

The above residue in toluene (6 mL), pTSA (49 mg, 0.288) was added and the mixture was heated to 100° C. for 18 h. The mixture was cooled and then concentrated under reduced pressure. To the residue, EtOAc (20 mL) and saturated $NaHCO_3$ (10 mL) were added. The phases were separated and the aqueous phase was extracted with EtOAc (2×20 mL). The combined organic phases were washed with brine, dried over $Na_2SO_4$, filtered and concentrated under reduced pressure to afford title compound, which was used in the next step without any further purification. MS (ESI) $[M+H]^+$ 363.0, 365.0.

Step 2: Preparation of Compound 6

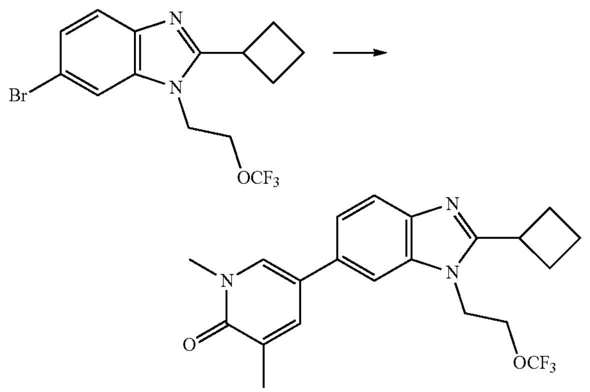

To a solution of 6-bromo-2-cyclobutyl-1-[2-(trifluoromethoxy)ethyl]benzimidazole (50 mg, 0.162 mmol) and 1,3-dimethyl-5-(4,4,5,5-tetramethyl-1,3,2-dioxaborolan-2-yl)pyridin-2-one (prepared using described procedure in US20130053362, 48 mg, 0.194 mmol) in DME (2 mL) and water (0.1 mL) was degassed by bubbling $N_2$ for 10 min. $Cs_2CO_3$ (111 mg, 0.340 mmol) and $Pd(PPh_3)_4$ (19 mg, 0.016 mmol) were then added and the mixture was degassed by bubbling $N_2$ for 10 more min. The resulting mixture was heated to 85° C. for 3 h and then cooled to rt. To the mixture, saturated aqueous $NaHCO_3$ (10 mL) and EtOAc (30 mL) were added, and the aqueous phase was extracted with EtOAc (3×10 mL). The combined organic phases were dried over $Na_2SO_4$, filtered, and concentrated under reduced pressure. The material was purified by flash chromatography on silica gel using a mixture of EtOAc in hexane and then MeOH in DCM as eluent. The mixture was further purified with preparative HPLC to afford Compound 6 (56 mg, 38%). $^1H$ NMR (500 MHz, $CDCl_3$) δ 7.82-7.78 (m, 1H), 7.60-7.51 (m, 1H), 7.40 (d, J=2.3 Hz, 1H), 7.31 (dd, J=8.3, 1.7 Hz, 1H), 7.27-7.22 (m, 1H), 4.40 (t, J=5.5 Hz, 2H), 4.26 (t, J=5.5 Hz, 2H), 3.81-3.70 (m, 1H), 3.65 (s, 3H), 2.74-2.52 (m, 2H), 2.52-2.34 (m, 2H), 2.24 (s, 3H), 2.22-1.94 (m, 2H). MS (ESI) $[M+H]^+$ 406.1.

Example 7: 5-[2-cyclopropyl-3-(2-methoxyethyl)benzimidazol-5-yl]-1,3-dimethyl-pyridin-2-one (Compound 7)

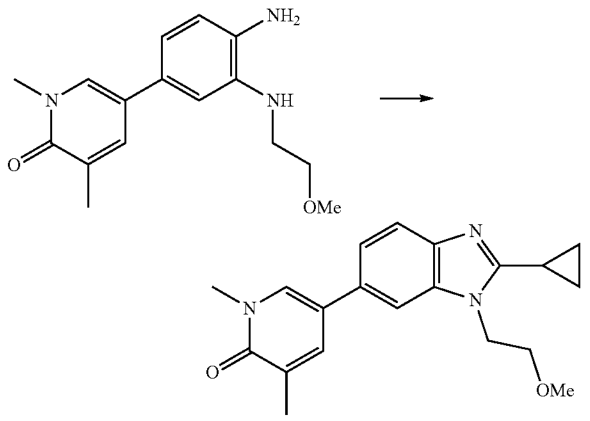

To a solution of Intermediate 2 (80 mg, 0.278 mmol) in MeOH (4 mL), cyclopropanecarbaldehyde (0.021 mL, 0.278 mmol) was added followed by a dropwise addition of acetic acid (0.08 mL, 1.39 mmol) and the resulting mixture was stirred at rt for 18 h. The solution was concentrated under reduced pressure and then EtOAc (20 mL) and saturated $NaHCO_3$ (10 mL) were added. The phases were separated and the aqueous phase was extracted with EtOAc (2×30 mL). The combined organic phases were washed with brine, dried over $Na_2SO_4$, filtered and evaporated under reduced pressure. The material was purified by flash chromatography on silica using a mixture of EtOAc in hexane as eluent, and followed by preparative HPLC to provide Compound 7 (13 mg, 14%). $^1H$ NMR (500 MHz, $CDCl_3$) δ 7.65 (dd, J=8.3, 0.4 Hz, 1H), 7.55 (dd, J=2.6, 1.2 Hz, 1H), 7.39 (d, J=2.2 Hz, 1H), 7.28 (d, J=1.2 Hz, 1H), 7.24 (dd, J=8.3, 1.7 Hz, 1H), 4.45 (t, J=5.7 Hz, 2H), 3.86-3.68 (m, 2H), 3.64 (s, 3H), 3.32

(s, 3H), 2.25 (d, J=0.8 Hz, 3H), 2.17-1.99 (m, 1H), 1.31-1.16 (m, 2H), 1.18-1.00 (m, 2H). MS (ESI) $[M+H]^+$ 338.2.

Example 8: 5-[3-(2-methoxyethyl)-2-methyl-benzimidazol-5-yl]-1,3-dimethylpyridin-2-one (Compound 8)

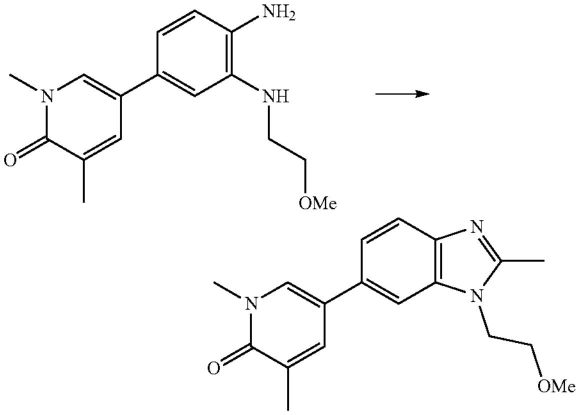

To a solution of Intermediate 2 (49 mg, 0.171 mmol) in trimethyl orthoacetate (1 mL) was added 6 N HCl (0.028 mL, 0.171 mmol) and the resulting mixture was stirred at rt for 2 h. To the mixture, DCM (40 mL) was added and the organic layer was washed with saturated $NaHCO_3$ (10 mL). The aqueous layer was back-extracted with DCM (2×20 mL), and the combined organic layers were dried $Na_2SO_4$, filtered, and concentrated under reduced pressure. The material was purified by preparative HPLC to provide Compound 8 (24 mg, 41%). $^1$H NMR (500 MHz, $CDCl_3$) δ 7.74 (d, J=8.5 Hz, 1H), 7.55 (d, J=1.3 Hz, 1H), 7.41 (d, J=2.4 Hz, 1H), 7.34-7.27 (m, 2H), 4.33 (t, J=5.2 Hz, 2H), 3.72 (t, J=5.3 Hz, 2H), 3.66 (s, 3H), 3.29 (s, 3H), 2.65 (d, J=23.0 Hz, 3H), 2.25 (s, 3H). MS (ESI) $[M+H]^+$: 312.2

Example 9: 5-[3-(2-methoxyethyl)-2-tetrahydropyran-4-yl-benzimidazol-5-yl]-1,3-dimethyl pyridin-2-one (Compound 9)

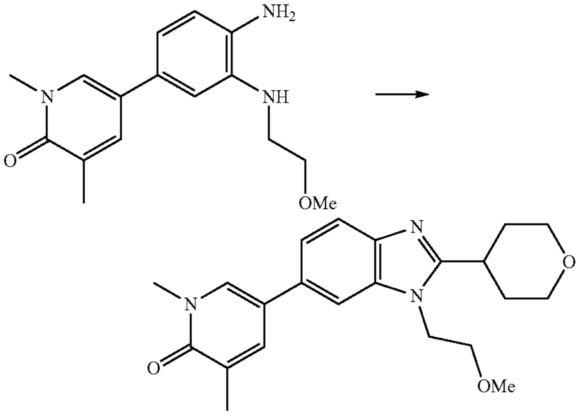

To a solution of Intermediate 2 (56 mg, 0.195 mmol) in DCM (5 mL) and tetrahydropyran-4-carbonyl chloride (30 mg, 0.21 mmol) was added and the resulting mixture was stirred for 1 h at rt. To the mixture, water was added followed by EtOAc (50 mL) and saturated $NaHCO_3$ (10 mL). The phases were separated and the aqueous phase was extracted with EtOAc (2×20 mL). The combined organic phases were washed with brine, dried $Na_2SO_4$, filtered and concentrated under reduced pressure to afford amide, which was used in the next step without any further purification. MS (ESI) $[M+H]^+$ 400.2.

The above compound in toluene (5 mL), pTSA (33 mg, 0.195 mmol) was added and the mixture was heated to 110° C. for 18 h. The solution was cooled to rt and then concentrated under reduced pressure. To the residue, EtOAc (50 mL) and saturated $NaHCO_3$ (10 mL) were added. The phases were separated and the aqueous phase was extracted with EtOAc (2×20 mL). The combined organic phases were washed with brine, dried over $Na_2SO_4$, filtered and concentrated under reduced pressure. The material was purified by flash chromatography on silica gel using a mixture of EtOAc in hexane and then MeOH in EtOAc as eluent. The material was purified again by preparative HPLC to provide Compound 9 (17 mg, 20%). $^1$H NMR (500 MHz, $CDCl_3$) δ 7.82-7.76 (m, 1H), 7.56 (dd, J=2.5, 1.1 Hz, 1H), 7.40 (d, J=2.3 Hz, 1H), 7.29 (dd, J=6.7, 1.8 Hz, 2H), 4.38 (t, J=5.3 Hz, 2H), 4.13 (dd, J=11.5, 3.1 Hz, 2H), 3.72 (t, J=5.3 Hz, 2H), 3.65 (s, 3H), 3.57 (td, J=12.0, 1.7 Hz, 2H), 3.28 (s, 3H), 3.26-3.18 (m, 1H), 2.25 (s, 3H), 2.23-2.15 (m, 2H), 1.90-1.81 (m, 2H). MS (ESI) $[M+H]^+$ 382.2.

Example 10: 5-[3-[(1R)-2-methoxy-1-methyl-ethyl]-2-tetrahydropyran-4-yl-benzimidazol-5-yl]-1,3-dimethyl-pyridin-2-one (Compound 10)

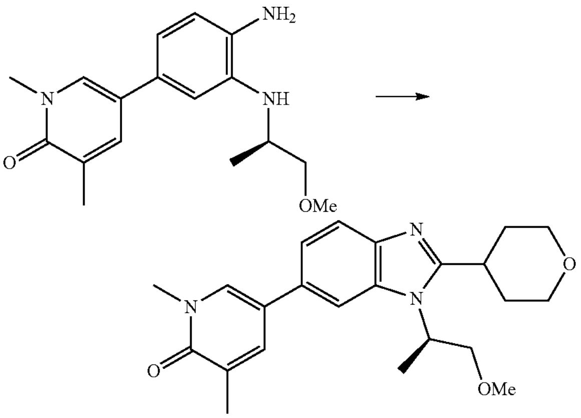

To a solution of Intermediate 3 (50 mg, 0.166 mmol) in DCM (1.5 mL) and tetrahydropyran-4-carbonyl chloride (22 μL, 0.174 mmol) was added at rt and the reaction mixture was stirred for 2 h. To the mixture, EtOAc (50 mL) and saturated $NaHCO_3$ (10 mL) were added. The phases were separated and the aqueous phase was extracted with EtOAc (2×20 mL). The combined organic phases were washed with brine, dried over $Na_2SO_4$, filtered and concentrated under reduced pressure to afford amide, which was used in the next step without further purification. MS (ESI) $[M+H]^+$ 414.2.

To a solution of the above compound in toluene (2 mL) was added pTSA (29 mg, 0.166 mmol) and the resulting mixture was heated to 110° C. for 20 h. The mixture was then cooled and concentrated under reduced pressure. To the residue, EtOAc (50 mL) and saturated $NaHCO_3$ (10 mL) were added. The phases were separated and the aqueous phase was extracted with EtOAc (2×20 mL). The combined organic phases were washed with brine, dried over $Na_2SO_4$, filtered and concentrated under reduced pressure. The material was purified over by flash chromatography over silica gel using a mixture of EtOAc in hexane as eluent, and followed by preparative HPLC to provide Compound 10 (6.9 mg, 11%). $^1$H NMR (500 MHz, $CDCl_3$) δ 7.77 (d, J=8.3 Hz, 1H), 7.51 (dd, J=2.5, 1.1 Hz, 1H), 7.42 (d, J=1.2 Hz, 1H), 7.36 (d, J=2.3 Hz, 1H), 7.25 (d, J=1.7 Hz, 1H), 4.78-4.68 (m, 1H), 4.17-4.09 (m, 2H), 3.91 (dd, J=9.7, 8.1 Hz, 1H), 3.78 (dd, J=9.8, 5.2 Hz, 1H), 3.65 (s, 3H), 3.63-3.55 (m, 2H), 3.27 (s, 3H), 3.20-3.09 (m, 1H), 2.26 (s, 3H), 2.24-2.11 (m, 2H), 1.98 (dd, J=13.5, 1.5 Hz, 1H), 1.84 (ddd, J=13.5, 3.6, 2.0 Hz, 1H), 1.70 (d, J=7.2 Hz, 3H). $[M+H]^+$ 396.2.

Example 11: 5-[3-[(1R)-2-methoxy-1-methyl-ethyl]-2-methyl-benzimidazol-5-yl]-1,3-dimethyl pyridin-2-one (Compound 11)

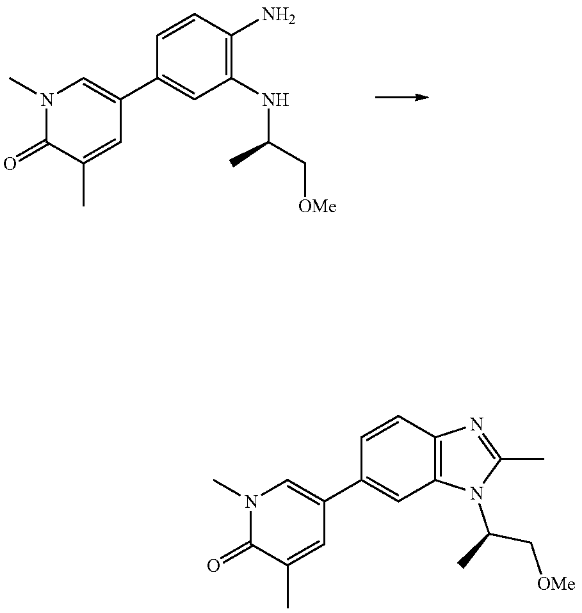

Intermediate 3 (50 mg, 0.166 mmol) was dissolved in trimethyl orthoacetate (2 mL) and the mixture was stirred for 5 min. p-TSA (3.2 mg, 0.017 mmol) was then added and the mixture was stirred at rt for 2 h. To the mixture, EtOAc (30 mL) and saturated $NaHCO_3$ (10 mL) were added. The phases were separated and the aqueous phase was extracted with EtOAc (2×20 mL). The combined organic phases were washed with brine, dried over $Na_2SO_4$, filtered and concentrated under reduced pressure. The material was purified by flash chromatography on silica gel using a mixture of EtOAc in hexane as eluent, and followed by preparative HPLC to provide Compound 11 (8 mg, 15%). $^1$H NMR (500 MHz, $CDCl_3$) δ 7.68 (d, J=8.3 Hz, 1H), 7.52 (s, 1H), 7.39 (s, 1H), 7.36 (d, J=2.3 Hz, 1H), 7.23 (dd, J=8.3, 1.5 Hz, 1H), 4.68 (dd, J=12.7, 7.4 Hz, 1H), 3.87 (dd, J=9.7, 8.1 Hz, 1H), 3.74 (dd, J=9.8, 5.1 Hz, 1H), 3.64 (s, 3H), 3.28 (s, 3H), 2.64 (s, 3H), 2.25 (s, 3H), 1.68 (d, J=7.2 Hz, 3H). MS (ESI) $[M+H]^+$ 326.1.

Example 12: 5-[3-[(1R)-2-methoxy-1-methyl-ethyl]benzimidazol-5-yl]-1,3-dimethyl-pyridin-2-one (Compound 12)

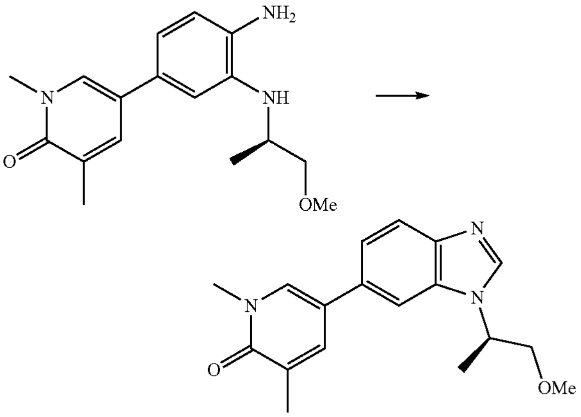

Intermediate 3 (50 mg, 0.17 mmol) was dissolved in triethyl orthoformate (2 mL) and the mixture was stirred for 5 min. p-TSA (3.2 mg, 0.017 mmol) was then added and the reaction mixture was stirred at rt for 16 h. To the mixture, EtOAc (30 mL) and saturated $NaHCO_3$ (10 mL) were added. The phases were separated and the aqueous phase was extracted with EtOAc (2×20 mL). The combined organic phases were washed with brine, dried over $Na_2SO_4$, filtered and concentrated under reduced pressure. The material was purified by flash chromatography on silica gel using a mixture of EtOAc in hexane as eluent, and followed by preparative HPLC to provide Compound 12 (33 mg, 64%). $^1$H NMR (500 MHz, $CDCl_3$) δ 8.06 (s, 1H), 7.80 (d, J=8.3 Hz, 1H), 7.54 (dd, J=2.5, 1.1 Hz, 1H), 7.40 (d, J=2.1 Hz, 2H), 7.29 (dd, J=8.3, 1.6 Hz, 1H), 4.72-4.62 (m, 1H), 3.71 (ddd, J=14.4, 9.8, 5.2 Hz, 2H), 3.63 (s, 3H), 3.32 (s, 3H), 2.23 (s, 3H), 1.66 (d, J=7.0 Hz, 3H). MS (ESI) $[M+H]^+$ 312.2.

Example 13: 5-[2-cyclopropyl-3-[2-(trifluoromethoxy)ethyl]benzimidazol-5-yl]-1-methyl-3-(trifluoromethyl)pyridin-2-one (Compound 13)

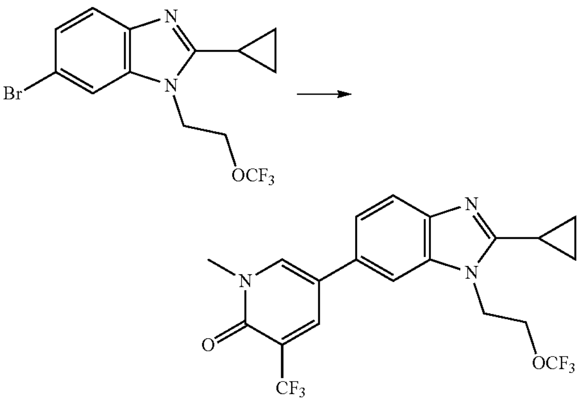

A solution of 6-bromo-2-cyclopropyl-1-[2-(trifluoromethoxy)ethyl]benzimidazole (Example 2, Step 1; 50 mg, 0.143 mmol) and Intermediate 4 (43 mg, 0.143 mmol) in DME (2 mL) and water (0.1 mL) was degassed by bubbling for 10 min. $Cs_2CO_3$ (98 mg, 0.30 mmol) and $Pd(PPh_3)_4$ (16 mg, 0.014 mmol) were then added and the mixture was degassed for 10 more min. The resulting mixture was heated to 85° C. for 3 h and then cooled to rt. To the mixture, saturated $NaHCO_3$ (10 mL) and EtOAc (10 mL) were added, and the aqueous phase was extracted with EtOAc (3×10 mL). The combined organic phases were dried over $MgSO_4$, filtered, and concentrated under reduced pressure. The material was purified over by flash chromatography over silica gel using a mixture of EtOAc in hexane as eluent, and followed by preparative HPLC to provide Compound 13 (9 mg, 14%). $^1$H NMR (500 MHz, MeOD) δ 8.33-8.24 (m, 2H), 7.71 (d, J=1.3 Hz, 1H), 7.60 (dt, J=6.8, 3.4 Hz, 1H), 7.44 (dd, J=8.4, 1.8 Hz, 1H), 4.79 (t, J=5.0 Hz, 2H), 4.48 (t, J=5.0 Hz, 2H), 3.71 (s, 3H), 2.31-2.09 (m, 1H), 1.23-1.12 (m, 4H) MS (ESI) $[M+H]^+$ 446.2.

Example 14: 5-(2-cyclopropyl-3-propylbenzimidazol-5-yl)-3-ethyl-1-methylpyridin-2-one (Compound 14)

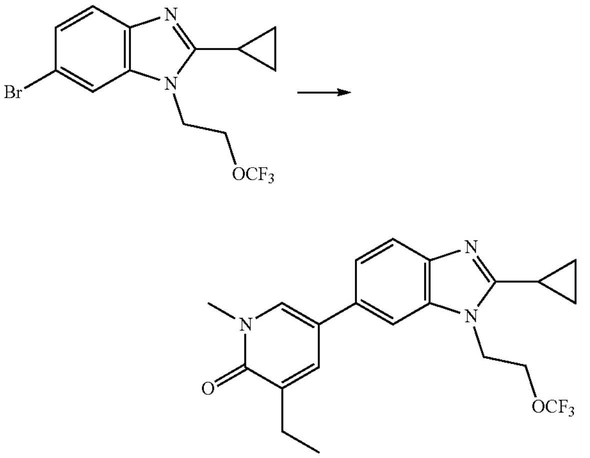

To a solution of 6-bromo-2-cyclopropyl-1-[2-(trifluoromethoxy)ethyl]benzimidazole (Example 2, Step 1, 50 mg, 0.143 mmol) in dioxane (1.2 ml) was added $Cs_2CO_3$ (116.6 mg, 0.36 mmol), Intermediate 5 (53.5 mg, 0.215 mmol), $Pd(PPh_3)_4$ (16.6 mg, 0.014 mmol) and water (0.1 ml). The reaction mixture was degassed by bubbling $N_2$ and then the resulting mixture was heated to 80° C. for 18 h. The mixture was cooled to rt then concentrated under reduced pressure. To the residue, EtOAc (20 ml) was added and the organic layer was washed with water (5 ml). The organic phase was dried over $Na_2SO_4$, filtered and concentrated under reduced pressure. The material was purified over by flash chromatography over silica gel using a mixture of EtOAc in hexane as eluent, and followed by preparative HPLC to provide Compound 14 (8.5 mg, 15%). $^1$H NMR (500 MHz, $CDCl_3$) δ 7.69 (d, J=8.3 Hz, 1H), 7.50 (d, J=2.4 Hz, 1H), 7.38 (d, J=2.5 Hz, 1H), 7.28 (dd, J=8.3, 1.6 Hz, 1H), 7.25 (m, 1H), 4.60 (t, J=5.5 Hz, 2H), 4.36 (t, J=5.5 Hz, 2H), 3.65 (s, 3H), 2.66 (q, J=7.4 Hz, 2H), 2.00 (dd, J=9.0, 4.1 Hz, 1H), 1.27 (dt, J=14.9, 6.1 Hz, 5H), 1.19-1.10 (m, 2H). MS (ESI) $[M+H]^+$ 406.2.

Example 15: 5-[2-cyclopropyl-3-[(1R)-2-methoxy-1-methylethyl]benzimidazol-5-yl]-1,3-dimethyl pyridin-2-one (Compound 15)

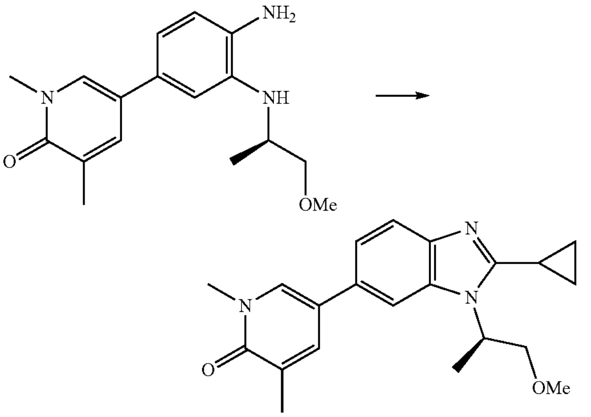

Intermediate 3 (63 mg, 0.21 mmol) was dissolved in MeOH (2 mL) and cyclopropanecarbaldehyde (16 μL, 0.21 mmol) was added quickly. Acetic acid (60 μL, 1.05 mmol) was then added dropwise and the mixture was stirred 3 h at rt. The solution was concentrated under reduced pressure and the material was purified by flash chromatography on silica gel using a mixture of EtOAc in hexane as eluent, and then followed by preparative HPLC to provide Compound 15 (21 mg, 29%). 1H NMR (500 MHz, CDC13) δ 7.68-7.64 (m, 1H), 7.52 (dd, J=2.5, 1.2 Hz, 1H), 7.39 (d, J=1.2 Hz, 1H), 7.36 (d, J=2.3 Hz, 1H), 7.21 (dd, J=8.3, 1.7 Hz, 1H), 5.07-4.97 (m, 1H), 3.92 (dd, J=9.8, 7.7 Hz, 1H), 3.80 (dd, J=9.8, 5.5 Hz, 1H), 3.64 (s, 3H), 3.31 (s, 3H), 2.25 (s, 3H), 2.08-2.01 (m, 1H), 1.70 (d, J=7.2 Hz, 3H), 1.32-1.26 (m, 1H), 1.17-1.12 (m, 1H), 1.12-1.06 (m, 2H). MS (ESI) $[M+H]^+$ 352.2.

Example 16: 5-[2-cyclopropyl-3-[(1S)-2-methoxy-1-methylethyl]benzimidazol-5-yl]-1,3-dimethyl pyridin-2-one (Compound 17)

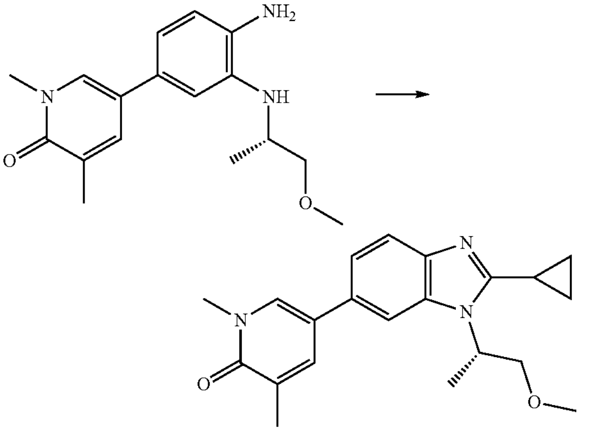

Intermediate 7 (100 mg, 0.332 mmol) was dissolved in MeOH (3 mL) and cyclopropanecarbaldehyde (25 μL, 0.332 mmol) was added quickly. Acetic acid (95 μL, 1.66 mmol)

was then added dropwise and the mixture was stirred at rt for 20 h. The mixture was concentrated under reduced pressure and then purified by flash chromatography on silica gel using a mixture of EtOAc in hexane as eluent and followed by preparative HPLC purification to provide Compound 17 (33 mg, 29%) as a solid. $^1$H NMR (500 MHz, $CDCl_3$) δ 7.65 (d, J=8.2 Hz, 1H), 7.51 (dd, J=2.5, 1.1 Hz, 1H), 7.38 (d, J=1.2 Hz, 1H), 7.35 (d, J=2.4 Hz, 1H), 7.20 (dd, J=8.3, 1.7 Hz, 1H), 5.05-4.96 (m, 1H), 3.91 (dd, J=9.8, 7.7 Hz, 1H), 3.79 (dd, J=9.8, 5.5 Hz, 1H), 3.62 (s, 3H), 3.30 (s, 3H), 2.23 (s, 3H), 2.07-2.00 (m, 1H), 1.69 (d, J=7.2 Hz, 3H), 1.31-1.25 (m, 1H), 1.16-1.10 (m, 1H), 1.10-1.05 (m, 2H). MS (ESI) $[M+H]^+$ 352.2.

Example 17: 5-[3-[(1S)-2-methoxy-1-methylethyl]-2-tetrahydropyran-4-yl-benzimidazol-5-yl]-1,3-dimethylpyridin-2-one (Compound 18)

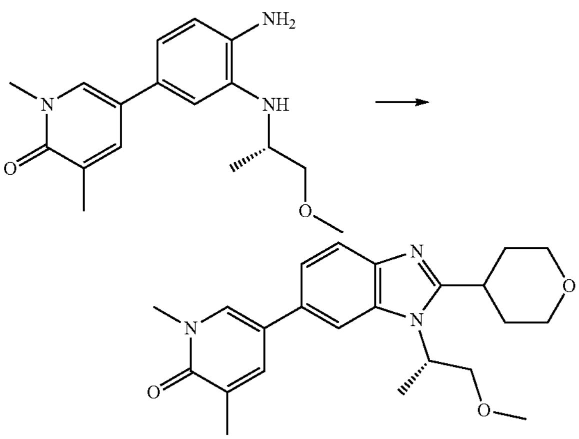

Intermediate 7 (100 mg, 0.33 mmol) was dissolved in DCM (3 mL) and tetrahydropyran-4-carbonyl chloride (52 mg, 0.348 mmol) was added at rt. The reaction mixture was stirred for 3 h and then quenched by addition of water. The mixture diluted in DCM (50 mL) and saturated $NaHCO_3$ (10 mL) was added. The phases were separated and the aqueous phase was extracted with DCM (2×20 mL). The combined organic phases were washed with brine, dried over $Na_2SO_4$, filtered and concentrated under reduced pressure to afford amide, which was used in the next step without further purification.

The above amide in toluene (3 mL) and pTSA (57 mg, 0.332 mmol) was added and the mixture was heated to 110° C. After 20 h, the uncyclized product was still observed and more pPTSA (57 mg, 0.332 mmol) was added and the mixture was heated to 120° C. for 4 h. The mixture was then cooled and concentrated under reduced pressure. The residue was diluted in EtOAc (50 mL) and saturated $NaHCO_3$ (10 mL) was added. The phases were separated and the aqueous phase was extracted with EtOAc (2×20 mL). The combined organic phases were washed with brine, dried over $Na_2SO_4$, filtered and concentrated under reduced pressure. The material was purified by flash chromatography on silica gel using a mixture of EtOAc in hexane as eluent to afford Compound 18 (6.9 mg, 11%) as solid. $^1$H NMR (500 MHz, $CDCl_3$) δ 7.76 (dd, J=8.3, 0.4 Hz, 1H), 7.51 (dd, J=2.5, 1.2 Hz, 1H), 7.42 (d, J=1.2 Hz, 1H), 7.36 (d, J=2.3 Hz, 1H), 7.26-7.24 (m, 1H), 4.78-4.68 (m, 1H), 4.17-4.08 (m, 2H), 3.91 (dd, J=9.7, 8.1 Hz, 1H), 3.78 (dd, J=9.8, 5.2 Hz, 1H), 3.65 (s, 3H), 3.62-3.55 (m, 2H), 3.26 (s, 3H), 3.18-3.09 (m, 1H), 2.25 (s, 3H), 2.24-2.10 (m, 2H), 2.01-1.95 (m, 1H), 1.88-1.81 (m, 1H), 1.70 (d, J=7.2 Hz, 3H). MS (ESI) $[M+H]^+$ 396.2.

Example 18: 3-cyclopropyl-5-[2-cyclopropyl-3-[2-(trifluoromethoxy)ethyl]benzimidazol-5-yl]-1-methylpyridin-2-one (Compound 19)

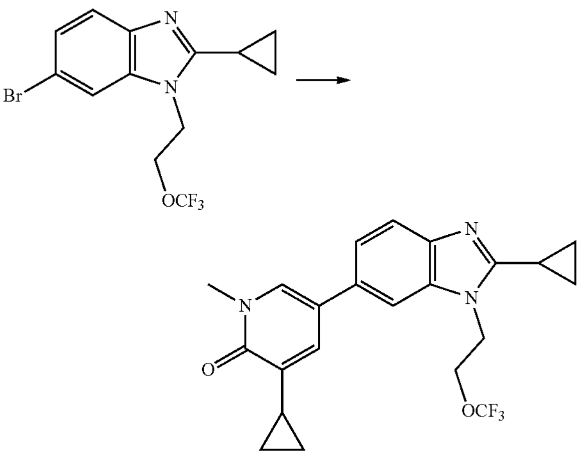

To a solution of 6-bromo-2-cyclopropyl-1-[2-(trifluoromethoxy)ethyl]benzimidazole (Example 2, step 1; 50 mg, 0.143 mmol) in DME (2 mL) was added 3-cyclopropyl-1-methyl-5-(4,4,5,5-tetramethyl-1,3,2-dioxaborolan-2-yl) pyridin-2-one (prepared as in WO2015058160, 59 mg, 0.215 mmol), $Cs_2CO_3$, (116 mg, 0.358 mmol), water (0.2 mL) and $Pd(PPh_3)_4$ (16 mg, 0.014 mmol) and the reaction mixture was degassed by bubbling for 5 min before being heated to 90° C. for 18 h. The reaction mixture was cooled to rt, diluted with EtOAc (10 mL) and water (10 mL). The organic phase was separated and then washed with additional water (2×10 mL). The organic phase was collected, dried over $Na_2SO_4$, filtered and concentrated under reduced pressure. The material was purified using a mixture of MeOH in DCM as eluent and followed by preparative HPLC purification to afford Compound 19 (22.7 mg, 38%) as solid. $^1$H NMR (500 MHz, $CDCl_3$) δ 7.66 (dd, J=8.3, 0.5 Hz, 1H), 7.32 (d, J=2.5 Hz, 1H), 7.23 (dd, J=8.3, 1.7 Hz, 1H), 7.21 (d, J=1.1 Hz, 1H), 7.16 (d, J=2.2 Hz, 1H), 4.58 (t, J=5.5 Hz, 2H), 4.34 (t, J=5.5 Hz, 2H), 3.64 (s, 3H), 2.26-2.14 (m, 1H), 1.98 (ddd, J=8.3, 4.7, 3.3 Hz, 1H), 1.29-1.23 (m, 2H), 1.14 (ddd, J=11.0, 6.8, 4.2 Hz, 2H), 0.98 (ddd, J=8.5, 6.3, 4.4 Hz, 2H), 0.72-0.63 (m, 2H). MS (ESI) $[M+H]^+$ 418.2.

Example 19: 5-[2-cyclopropyl-3-[2-(trifluoromethoxy)ethyl]benzimidazol-5-yl]-1-methyl-3-(methyl amino)pyridin-2-one (Compound 20)

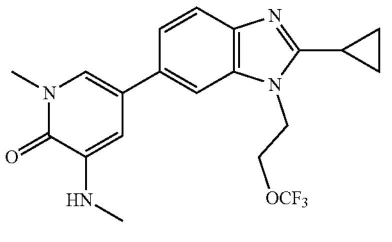 [SMILES: CNc1cc(-c2ccc3nc(C4CC4)n(CCOC(F)(F)F)c3c2)cn(C)c1=O]

Step 1: Preparation of tert-butyl N-methyl-N-[1-methyl-2-oxo-5-(4,4,5,5-tetramethyl-1,3,2-dioxaborolan-2-yl)-3-pyridyl]carbamate

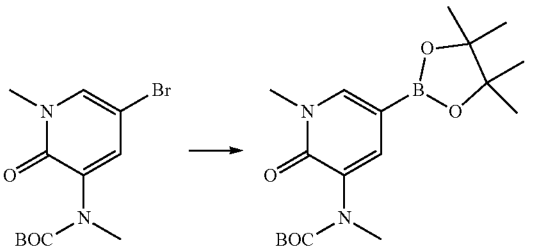

4,4,4',4',5,5,5',5'-octamethyl-2,2'-bi(1,3,2-dioxaborolane) (380 mg, 1.49 mmol), $PdCl_2(dppf)$ (51 mg, 0.062 mmol) and KOAc (306 mg, 3.12 mmol) were added to a solution of tert-butyl N-(5-bromo-1-methyl-2-oxo-3-pyridyl)-N-methyl-carbamate (prepared using described procedure in WO2015058160, 396 mg, 1.25 mmol) in dioxane (3 mL) under $N_2$. The mixture was degassed by bubbling $N_2$ for 5 min and then the reaction mixture was heated to 90° C. in a sealed tube for 18 h. The mixture was cooled to rt and diluted with EtOAc (10 ml) and water (10 ml). The organic phase was separated and dried over $Na_2SO_4$, filtered and concentrated under reduced pressure. The material was purified by flash chromatography on silica gel using a mixture of EtOAc in hexane as eluent to afford title compound (125 mg, 28%) as a solid. $^1H$ NMR (500 MHz, $CDCl_3$) δ 7.68 (d, J=1.9 Hz, 1H), 7.53 (s, 1H), 3.56 (s, 3H), 3.10 (s, 3H), 1.33-1.16 (m, 21H).

Step 2: Preparation of tert-butyl N-[5-[2-cyclopropyl-3-[2-(trifluoromethoxy)ethyl]benzimidazol-5-yl]-1-methyl-2-oxo-3-pyridyl]-N-methyl-carbamate

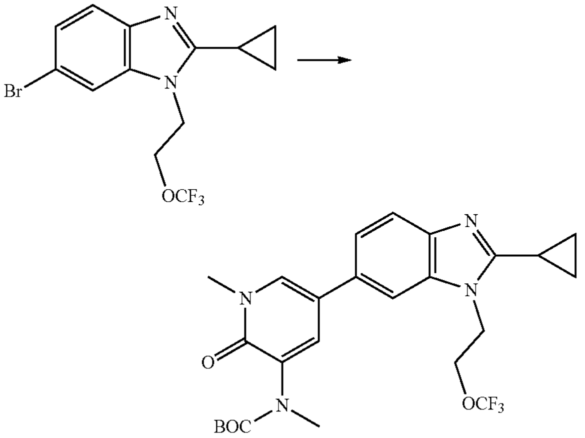

To a solution of 6-bromo-2-cyclopropyl-1-[2-(trifluoromethoxy)ethyl]benzimidazole (Example 2, step 1, 50 mg, 0.143 mmol) in DME (2 mL) was added tert-butyl N-methyl-N-[1-methyl-2-oxo-5-(4,4,5,5-tetramethyl-1,3,2-dioxaborolan-2-yl)-3-pyridyl]carbamate (78 mg, 0.215 mmol), $Cs_2CO_3$ (116 mg, 0.358 mmol) and $Pd(PPh_3)_4$ (17 mg, 0.014 mmol) and the reaction mixture was degassed by bubbling $N_2$ for 5 min and then the reaction mixture was heated in a sealed tube at 90° C. for 18 h. The mixture was cooled to rt, diluted with EtOAc (10 mL) and water (10 mL). The organic phase was collected, dried over $Na_2SO_4$, filtered and concentrated under reduced pressure. The material was purified by flash chromatography on silica gel using a mixture of EtOAc in hexane as eluent to afford title compound (65 mg, 89%) as a solid. $^1H$ NMR (500 MHz, $CDCl_3$) δ 7.64-7.55 (m, 2H), 7.38 (d, J=2.5 Hz, 1H), 7.19 (dt, J=9.9, 4.0 Hz, 2H), 4.53 (t, J=5.4 Hz, 2H), 4.28 (t, J=5.4 Hz, 2H), 3.57 (s, 3H), 3.12 (s, 3H), 1.96-1.85 (m, 1H), 1.25-1.12 (m, 11H), 1.12-1.01 (m, 2H). MS (ESI) $[M+H]^+$ 507.2.

Step 3: Preparation of Compound 20

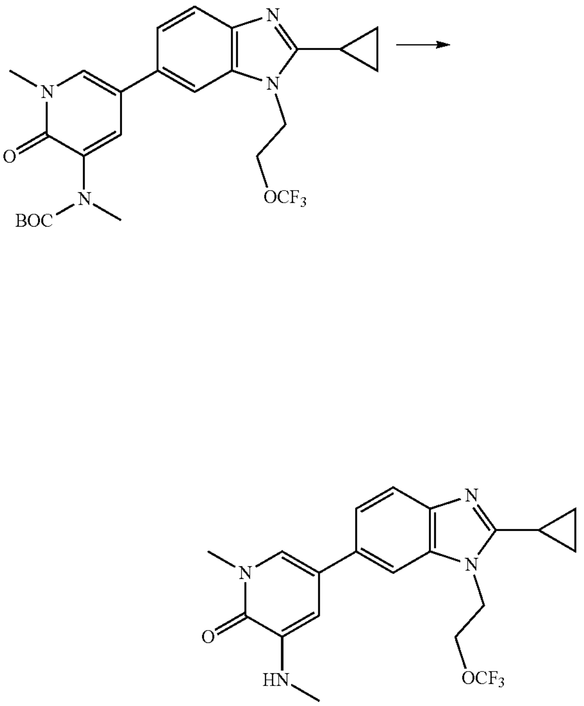

To a solution of tert-butyl N-[5-[2-cyclopropyl-3-[2-(trifluoromethoxy)ethyl]benzimidazol-5-yl]-1-methyl-2-oxo-3-pyridyl]-N-methyl-carbamate (67 mg, 0.132 mmol) in DCM (5 mL) was added TFA (0.10 mL, 1.32 mmol) and the reaction mixture was stirred at rt for 2 h. The mixture was quenched with saturated $NaHCO_3$ (5 mL) and solid $NaHCO_3$ was added until the effervescence ended. The organic phase was diluted with EtOAc (10 mL) and water (10 mL). The phases were separated and the organic phase was collected, dried over $Na_2SO_4$, filtered and concentrated under reduced pressure. The material was purified by flash chromatography on silica gel using a mixture of MeOH in DCM as eluent and followed by preparative HPLC purification to afford Compound 20 (10.7 mg, 20%) as a solid. $^1H$ NMR (500 MHz, $CDCl_3$) δ 7.68 (dd, J=8.3, 0.5 Hz, 1H), 7.33 (dd, J=8.3, 1.7 Hz, 1H), 7.30 (d, J=1.1 Hz, 1H), 6.83 (d, J=2.2 Hz, 1H), 6.43 (d, J=2.1 Hz, 1H), 5.11 (d, J=5.4 Hz, 1H), 4.60 (t, J=5.5 Hz, 2H), 4.36 (t, J=5.6 Hz, 2H), 3.65 (s, 3H), 2.91 (d, J=5.3 Hz, 3H), 1.99 (dd, J=9.0, 4.1 Hz, 1H), 1.32-1.21 (m, 2H), 1.19-1.09 (m, 2H). MS (ESI) $[M+H]^+$ 407.22.

Example 20: 5-[3-(2-methoxypropyl)-2-methylbenzimidazol-5-yl]-1,3-dimethylpyridin-2-one (Compounds 21a and 21b)

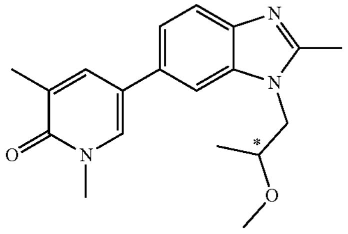

To a solution of Intermediate 6 (100 mg, 0.332 mmol) in trimethyl orthoacetate (3 mL), was added 6 N aqueous HCl (0.055 mL, 0.332 mmol) and the reaction mixture was stirred at rt for 2 h. The mixture was then diluted with DCM (40 mL) and washed with saturated $NaHCO_3$ (10 mL). The aqueous layer was extracted with DCM (2×20 mL) and the combined organic layers were dried over $Na_2SO_4$, filtered, and concentrated under reduced pressure. The material was purified by flash chromatography on silica gel using a mixture of MeOH in DCM as eluent, followed by SFC purification (AD 10×250 mm, 5 μm isocratic 15% MeOH+0.1% $NH_4OH$, 10 mL/min, 100 bar, 35° C.) to afford Compound 21a (11.1 mg) and Compound 21b (4.3 mg) as solids.

Compound 21a: Retention time=11.75 min; $^1$H NMR (500 MHz, $CDCl_3$) δ 7.61 (d, J=8.4 Hz, 1H), 7.48 (dd, J=2.4, 1.1 Hz, 1H), 7.32 (d, J=2.4 Hz, 1H), 7.18 (dd, J=10.7, 2.6 Hz, 2H), 4.04 (qd, J=14.9, 6.1 Hz, 2H), 3.64 (ddd, J=8.0, 6.2, 4.1 Hz, 1H), 3.58 (s, 3H), 3.12 (s, 3H), 2.56 (d, J=14.4 Hz, 3H), 2.18 (s, 3H), 1.19 (t, J=7.5 Hz, 3H). MS (ESI) $[M+H]^+$ 326.2.

Compound 21b: Retention time=13.12 min; $^1$H NMR (500 MHz, $CDCl_3$) δ 7.61 (d, J=8.4 Hz, 1H), 7.48 (dd, J=2.4, 1.1 Hz, 1H), 7.32 (d, J=2.4 Hz, 1H), 7.18 (dd, J=10.7, 2.6 Hz, 2H), 4.04 (qd, J=14.9, 6.1 Hz, 2H), 3.64 (ddd, J=8.0, 6.2, 4.1 Hz, 1H), 3.58 (s, 3H), 3.12 (s, 3H), 2.56 (d, J=14.4 Hz, 3H), 2.18 (s, 3H), 1.19 (t, J=7.5 Hz, 3H). MS (ESI) $[M+H]^+$ 326.2.

Example 21: 5-[3-(2-methoxypropyl)benzimidazol-5-yl]-1,3-dimethylpyridin-2-one (Compounds 22a and 22b)

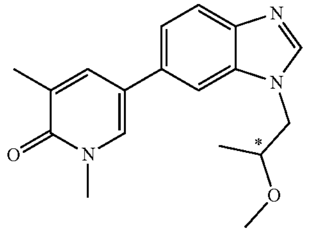 [SMILES: COC(C)Cn1cnc2ccc(-c3cc(C)c(=O)n(C)c3)cc21]

A solution of Intermediate 6 (154.0 mg, 0.511 mmol) in formic acid (1 mL) was heated for 1 h at 40° C. The mixture was cooled to rt and poured into saturated $NaHCO_3$ (10 mL), and additional solid $NaHCO_3$ was added until a pH of 7 was reached. The aqueous layer was extracted with DCM (3×10 mL) and the combined organic layers were dried over $MgSO_4$, filtered and concentrated under reduced pressure. The material was purified by flash chromatography on silica gel using a mixture of MeOH in DCM as eluent, followed by SFC purification (1A 10×250 mm, 5 μm Isocratic 30% EtOH+0.1% $NH_4OH$, 10 mL/min 100 bar @35° C.) afforded Compound 22a (24.8 mg; 24%) and Compound 22b (31.2 mg; 30%) as solids.

Compound 22a: Retention time=12.65 min; $^1$H NMR (500 MHz, $CDCl_3$) δ 7.90 (s, 1H), 7.74 (d, J=8.4 Hz, 1H), 7.49 (dd, J=2.5, 1.1 Hz, 1H), 7.33 (dd, J=15.2, 1.8 Hz, 2H), 7.24 (dd, J=8.4, 1.7 Hz, 1H), 4.11 (qd, J=14.7, 5.6 Hz, 2H), 3.69-3.61 (m, 1H), 3.59 (d, J=15.1 Hz, 3H), 3.19 (s, 3H), 2.18 (s, 3H), 1.16 (d, J=6.2 Hz, 3H). MS (ESI) $[M+H]^+$ 312.2.

Compound 22b: Retention time=16.75 min; $^1$H NMR (500 MHz, $CDCl_3$) δ 7.90 (s, 1H), 7.74 (d, J=8.4 Hz, 1H), 7.49 (dd, J=2.5, 1.1 Hz, 1H), 7.33 (dd, J=15.2, 1.8 Hz, 2H), 7.24 (dd, J=8.4, 1.7 Hz, 1H), 4.11 (qd, J=14.7, 5.6 Hz, 2H), 3.69-3.61 (m, 1H), 3.59 (d, J=15.1 Hz, 3H), 3.19 (s, 3H), 2.18 (s, 3H), 1.16 (d, J=6.2 Hz, 3H). MS (ESI) $[M+H]^+$ 312.2.

Example 22: Preparation of 5-[2-cyclopropyl-3-(2-methoxypropyl)benzimidazol-5-yl]-1,3-dimethylpyridin-2-one (Compounds 23a and 23b)

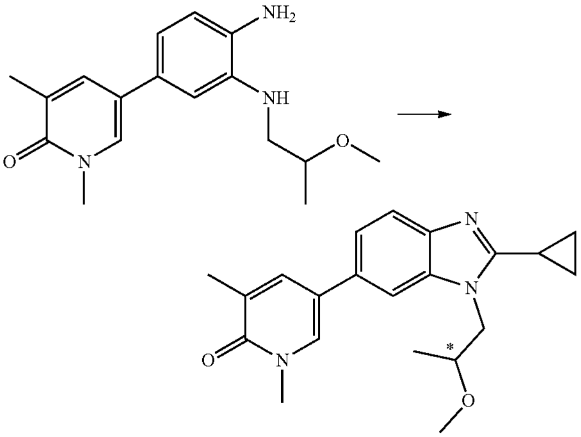

Intermediate 6 (73 mg, 0.242 mmol) was dissolved in MeOH (2 mL) and cyclopropanecarbaldehyde (20 μL, 0.266 mmol) was added quickly. Acetic acid (69 μL, 1.211 mmol) was then added dropwise and the mixture was stirred at rt for 3 h. The mixture was concentrated under reduced pressure and then purified by flash chromatography on silica gel using a mixture of MeOH in DCM as eluent to afford title compound. The isomers of Compound 23 were separated by semi-preparative SFC (conditions: ID 10×250 mm, 5 μM Isocratic 30% IPA+0.1% $NH_4OH$, 10 mL/min 100 Bar) to provide Compound 23a (9 mg, 11%) and Compound 23b (9 mg, 11%) as solids.

Compound 23a: Retention time=23.40; $^1$H NMR (500 MHz, $CDCl_3$) δ 7.66 (dd, J=8.3, 0.5 Hz, 1H), 7.55 (dd, J=2.5, 1.2 Hz, 1H), 7.39 (d, J=2.3 Hz, 1H), 7.29-7.21 (m, 2H), 4.33 (dd, J=14.9, 7.9 Hz, 1H), 4.19 (dd, J=14.9, 4.3 Hz, 1H), 3.78 (ddd, J=7.9, 6.2, 4.4 Hz, 1H), 3.65 (s, 3H), 3.24 (s, 3H), 2.25 (s, 3H), 2.11 (tt, J=8.3, 5.0 Hz, 1H), 1.36-1.32 (m, 1H), 1.32-1.25 (m, 3H), 1.21-1.09 (m, 3H). MS (ESI) $[M+H]^+$ 352.2.

Compound 23b: Retention time=26.11; $^1H$ NMR (500 MHz, $CDCl_3$) δ 7.66 (d, J=8.3 Hz, 1H), 7.55 (dd, J=2.5, 1.1 Hz, 1H), 7.39 (d, J=2.3 Hz, 1H), 7.29-7.22 (m, 2H), 4.33 (dd, J=14.9, 7.9 Hz, 1H), 4.19 (dd, J=14.9, 4.3 Hz, 1H), 3.78 (ddd, J=7.9, 6.2, 4.4 Hz, 1H), 3.65 (s, 3H), 3.24 (s, 3H), 2.25 (s, 3H), 2.17-2.08 (m, 1H), 1.34 (ddd, J=9.0, 4.8, 2.4 Hz, 1H), 1.27 (t, J=8.3 Hz, 3H), 1.19-1.06 (m, 3H). MS (ESI) $[M+H]^+$ 352.3.

Example 23: 5-[3-[(1R)-2-methoxy-1-methyl-ethyl]-2-(trifluoromethyl)benzimidazol-5-yl]-1,3-dimethylpyridin-2-one (Compound 26)

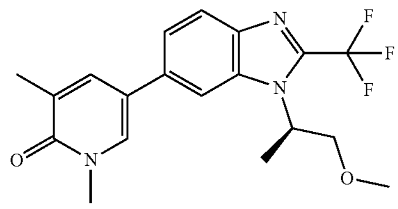 [SMILES: COC[C@@H](C)n1c(C(F)(F)F)nc2ccc(-c3cc(C)c(=O)n(C)c3)cc21]

A solution of Intermediate 3 (134 mg, 0.445 mmol) in TFA (1.5 mL) was heated to 70° C. for 18 h in a sealed tube. The reaction mixture was cooled to rt and poured into saturated $NaHCO_3$ (20 mL) then additional solid $NaHCO_3$ was added until a pH of ~8 was reached. The aqueous mixture was extracted with EtOAc (2×20 mL) and the combined organic layer was washed with brine (20 mL), dried over $MgSO_4$, filtered and concentrated under reduced pressure. The material obtained was purified by flash chromatography on silica gel using a mixture of MeOH in DCM as eluent, followed by trituration with $Et_2O$ to afford Compound 26 (76.3 mg, 45%) as a solid. $^1H$ NMR (500 MHz, $CDCl_3$) δ 7.91 (d, J=8.5 Hz, 1H), 7.65 (d, J=1.2 Hz, 1H), 7.54 (d, J=1.3 Hz, 1H), 7.48-7.38 (m, 2H), 4.97 (m, 1H), 3.98 (dd, J=10.2, 7.0 Hz, 1H), 3.83 (dd, J=10.2, 5.3 Hz, 1H), 3.69 (s, 3H), 3.36 (s, 3H), 2.29 (s, 3H), 1.76 (d, J=7.1 Hz, 3H). MS (ESI) $[M+H]^+$ 380.2.

Example 24: 5-[2-(3,3-difluorocyclobutyl)-3-[2-(trifluoromethoxy)ethyl]benzimidazol-5-yl]-1,3-dimethylpyridin-2-one (Compound 27)

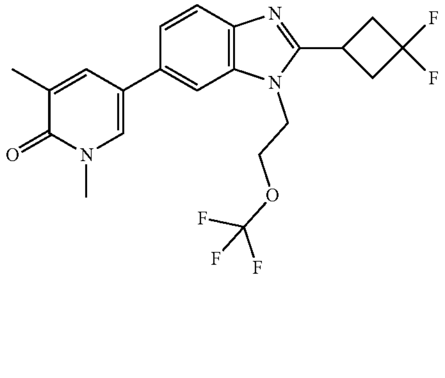 [SMILES: Cc1cc(-c2ccc3nc(C4CC(F)(F)C4)n(CCOC(F)(F)F)c3c2)cn(C)c1=O]

Step 1: Preparation of N-(4-(1,5-dimethyl-6-oxo-1,6-dihydropyridin-3-yl)-2-((2-(trifluoromethoxy)ethyl)amino)phenyl)-3,3-difluorocyclobutancarboxamide

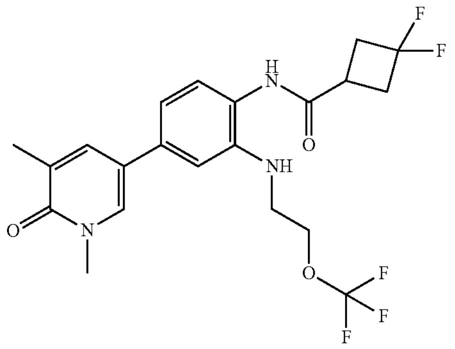 [SMILES: Cc1cc(-c2ccc(NC(=O)C3CC(F)(F)C3)c(NCCOC(F)(F)F)c2)cn(C)c1=O]

To a solution of Intermediate 8 (57.3 mg, 0.168 mmol) in DCM (5 mL), 3,3-difluorocyclobutanecarbonyl chloride (25.9 mg, 0.168 mmol) was added and the reaction mixture was stirred for 1 h at rt. The mixture was diluted with water and EtOAc (10 mL) was added. The organic layer was separated and washed with saturated $NaHCO_3$ (10 mL) and then brine (20 mL). The organic layer was dried over $Na_2SO_4$, filtered and concentrated under reduced pressure to afford the title compound, which was used in the next step without further purification.

Step 2: Preparation of Compound 27

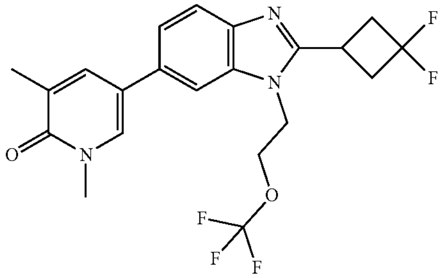 [SMILES: Cc1cc(-c2ccc3nc(C4CC(F)(F)C4)n(CCOC(F)(F)F)c3c2)cn(C)c1=O]

To a solution of N-(4-(1,5-dimethyl-6-oxo-1,6-dihydropyridin-3-yl)-2-((2-(trifluoromethoxy) ethyl)amino)phenyl)-3,3-difluorocyclobutancarboxamide (directly from previous step) in toluene (5 mL), pTSA (31.9 mg, 0.168 mmol) was added and the reaction mixture was heated under reflux for 18 h. The mixture was cooled to rt, diluted with EtOAc (10 mL), and washed with saturated $NaHCO_3$ (2×10 mL) and brine (10 mL). The organic layer was dried over $Na_2SO_4$, filtered and concentrated under reduced pressure. The material was purified by flash chromatography on silica gel using a mixture of MeOH in DCM as eluent and then preparative HPLC to afford Compound 27 (10.6 mg, 14%) as a solid. $^1H$ NMR (500 MHz, $CDCl_3$) δ 7.72 (d, J=8.4 Hz, 1H), 7.47 (d, J=1.3 Hz, 1H), 7.33 (d, J=2.2 Hz, 1H), 7.27 (dd, J=8.4, 1.6 Hz, 1H), 7.22-7.17 (m, 1H), 4.38 (t, J=5.1 Hz, 2H), 4.23 (t, J=5.1 Hz, 2H), 3.59 (d, J=7.9 Hz, 3H), 3.48 (td, J=8.6, 2.1 Hz, 1H), 3.17 (m, 2H), 3.04-2.92 (m, 2H), 2.19 (d, J=7.6 Hz, 3H). MS (ESI) $[M+H]^+$ 442.3.

Example 25: 1,3-dimethyl-5-[2-(3-methoxycyclobutyl)-3-(2-(trifluoromethoxy)ethyl)benzimidazol-5-yl)]pyridin-2-one (Compounds 28a and 28b)

Compound 28a

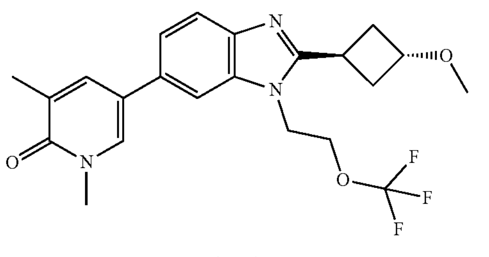

(trans)

Compound 28b

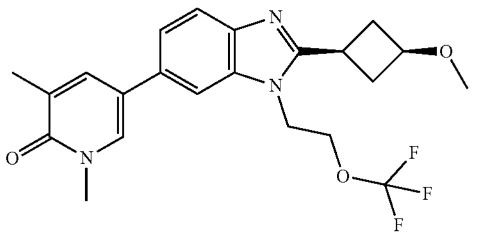

(cis)

Step 1: Preparation of N-(4-(1,5-dimethyl-6-oxo-1,6-dihydropyridin-3-yl)-2-((2-(trifluoromethoxy)ethyl)amino)phenyl)-3-methoxycyclobutane-1-carboxamide

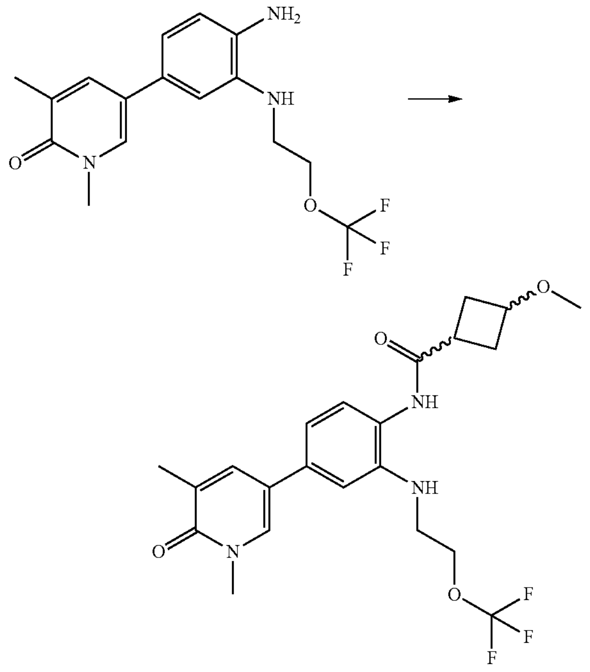

To a stirred solution of 3-methoxycyclobutane-1-carboxylic acid (0.148 g, 1.1432 mmol) in DCM (4 mL) was added HATU (0.501 g, 1.3191 mmol). The reaction was allowed to stir for 10 min at rt, followed by the addition of Intermediate 8 (0.3 g, 0.8794 mmol) and DIPEA (0.3 mL, 1.7580 mmol) in DCM (1 mL). The reaction mixture was the stirred for 4 h at rt. The reaction mixture was diluted with saturated aqueous $NaHCO_3$ (25 mL) and the product was extracted with DCM (20 mL×3). The combined organic layers were washed with brine (30 mL), dried over anhydrous $Na_2SO_4$, filtered and concentrated under reduced pressure. The product obtained was purified by silica gel column chromatography using 3-5% MeOH in DCM as eluent. Fractions were combined and concentrated to provide the title compound (0.04 g, 93%). $[M+H]^+$ 454.35.

Step 2: Preparation of Compounds 28a and 28b

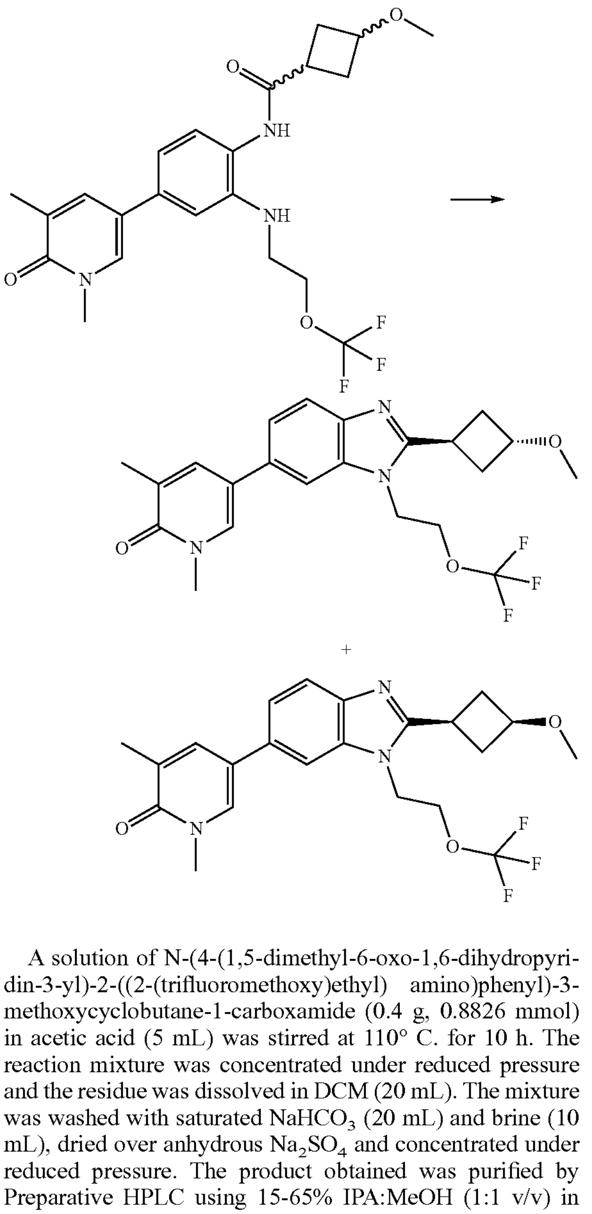

A solution of N-(4-(1,5-dimethyl-6-oxo-1,6-dihydropyridin-3-yl)-2-((2-(trifluoromethoxy)ethyl) amino)phenyl)-3-methoxycyclobutane-1-carboxamide (0.4 g, 0.8826 mmol) in acetic acid (5 mL) was stirred at 110° C. for 10 h. The reaction mixture was concentrated under reduced pressure and the residue was dissolved in DCM (20 mL). The mixture was washed with saturated $NaHCO_3$ (20 mL) and brine (10 mL), dried over anhydrous $Na_2SO_4$ and concentrated under reduced pressure. The product obtained was purified by Preparative HPLC using 15-65% IPA:MeOH (1:1 v/v) in hexane containing 0.3% DEA as modifier to afford Compound 28a (trans) (0.07 g) and Compound 28b (cis) (0.210 g), 73%. Cis/trans assessment was achieved through NMR analysis including selective irradiation.

Compound 28a (trans): 1H NMR (400 MHz, $CDCl_3$) δ ppm 7.81 (d, J=8.4 Hz, 1H), 7.56 (d, J=1.2 Hz, 1H), 7.42 (d, J=2.4 Hz, 1H), 7.34 (dd, J=1.2 and 8.4 Hz, 1H), 7.24 (s, 1H), 4.70-4.34 (m, 2H), 4.33-4.27 (m, 3H), 3.81-3.76 (m, 1H), 3.67 (s, 3H), 3.34 (s, 3H), 2.86-2.79 (m, 2H), 2.57-2.50 (m, 2H), 2.27 (s, 3H). $[M+H]^+$ 436.36

Compound 28b (cis): 1H NMR (400 MHz, $CDCl_3$) δ 7.81 (d, J=8.4 Hz, 1H), 7.56 (t, J=1.2 Hz, 1H), 7.41 (d, J=2.4 Hz, 1H), 7.31 (dd, J=1.6 Hz and 8.4 Hz, 1H), 7.26 (d, J=1.2 Hz, 1H), 4.43-4.42 (m, 2H), 4.30-4.28 (t, J=5.6 Hz, 2H), 4.05-4.00 (m, 1H), 3.66 (s, 3H), 3.32 (s, 3H), 3.26-3.21 (m, 1H), 2.84-2.78 (m, 2H), 2.60-2.53 (m, 2H), 2.27 (s, 3H). $[M+H]^+$ 436.36

Example 26: 1,3-dimethyl-5-[2-tetrahydrofuran-3-yl-3-[2-(trifluoromethoxy)ethyl]benzimidazol-5-yl]pyridin-2-one (Compounds 29a and 29b)

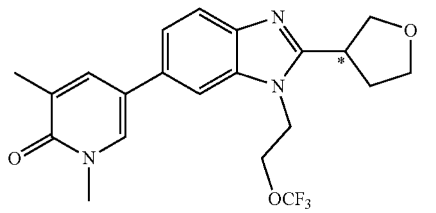 [SMILES: Cc1cc(-c2ccc3nc(C4CCOC4)n(CCOC(F)(F)F)c3c2)cn(C)c1=O]

Tetrahydrofuran-3-carbaldehyde (26 mg, 0.258 mmol) was added quickly to a solution of Intermediate 8 (88 mg, 0.258 mmol) in MeOH (2 mL). Acetic acid (0.074 mL, 1.29 mmol) was then added dropwise and the reaction mixture was stirred for 18 h at rt. The mixture was concentrated under reduced pressure and diluted with EtOAc (20 mL) and saturated $NaHCO_3$ (10 mL). The phases were separated and the aqueous layer was extracted with EtOAc (2×10 mL). The combined organic layers were washed with brine, dried over $Na_2SO_4$, filtered and concentrated under reduced pressure. The material was purified by flash chromatography on silica gel using a mixture of EtOAc in hexane as eluent to afford the Compound 29 in racemic form (90 mg). The product was then purified over reverse phase HPLC followed by SFC purification (IC 10×250 mm, 5 μm Isocratic 45% IPA+0.1% $NH_4OH$, 10 mL/min 100 Bar) to provide Compound 29a (1.24 mg) and Compound 29b (1.24 mg).

Compound 29a: Retention time=14.56 min; $^1H$ NMR (500 MHz, $CDCl_3$) δ 7.77 (d, J=8.8 Hz, 1H), 7.56-7.51 (m, 1H), 7.39 (d, J=2.4 Hz, 1H), 7.32 (dd, J=8.4, 1.7 Hz, 1H), 7.27-7.25 (m, 1H), 4.56-4.48 (m, 2H), 4.32 (t, J=5.3 Hz, 2H), 4.27 (t, J=8.1 Hz, 1H), 4.19-4.13 (m, 1H), 4.12-4.07 (m, 1H), 4.04 (dd, J=14.8, 8.0 Hz, 1H), 3.69-3.61 (m, 1H), 3.65 (s, 3H), 2.63-2.35 (m, 2H), 2.25 (s, 3H). MS (ESI) $[M+H]^+$ 422.2.

Compound 29b: Retention time=17.09 min; $^1H$ NMR (500 MHz, $CDCl_3$) δ 7.77 (d, J=8.3 Hz, 1H), 7.54 (dd, J=2.5, 1.1 Hz, 1H), 7.39 (d, J=2.4 Hz, 1H), 7.32 (dd, J=8.4, 1.7 Hz, 1H), 7.27-7.25 (m, 1H), 4.56-4.49 (m, 2H), 4.32 (t, J=5.3 Hz, 2H), 4.27 (t, J=8.1 Hz, 1H), 4.20-4.13 (m, 1H), 4.08 (t, J=16.7, 8.4 Hz, 1H), 4.04 (dd, J=15.4, 7.3 Hz, 1H), 3.70-3.60 (m, 1H), 3.65 (s, 3H), 2.55-2.35 (m, 2H), 2.25 (s, 3H). MS (ESI) $[M+H]^+$ 422.2.

Example 27: 1,3-dimethyl-5-[2-tetrahydrofuran-2-yl-3-[2-(trifluoromethoxy)ethyl]benzimidazol-5-yl]pyridin-2-one (Compounds 30a and 30b)

Procedure A

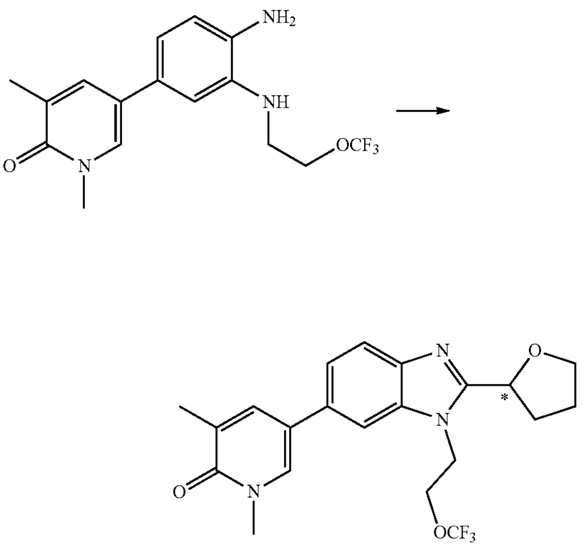

Intermediate 8 (98 mg, 0.287 mmol) was dissolved in MeOH (2 mL) and tetrahydrofuran-2-carbaldehyde (29 mg, 0.287 mmol) was added quickly. Acetic acid (82 μL, 1.44 mmol) was then added dropwise and the mixture was stirred at rt for 18 h. The mixture was then concentrated under reduced pressure and then diluted with EtOAc (20 mL) and saturated $NaHCO_3$ (10 mL). The phases were separated and the aqueous phase was extracted with EtOAc (2×10 mL). The combined organic phases were washed with brine, dried over $Na_2SO_4$, filtered and concentrated under reduced pressure. The material was purified by flash chromatography on silica gel using a mixture of EtOAc hexane and then EtOAc/MeOH as eluent to afford title compound. The material was then purified by preparative HPLC and then the isomers of Compound 30 were separated by semi-preparative SFC (conditions: ID 10×250 mm, 5 μM Isocratic 30% IPA+0.1% $NH_4OH$, 10 mL/min 100 Bar) to provide Compound 30a (2.41 mg) and Compound 30b (1.95 mg) as solids.

Compound 30a: Retention time=8.00; $^1H$ NMR (500 MHz, $CDCl_3$) δ 7.77 (d, J=8.3 Hz, 1H), 7.55 (s, 1H), 7.38 (d, J=13.6 Hz, 2H), 7.31 (d, J=8.3 Hz, 1H), 5.20 (t, J=6.7 Hz, 1H), 4.80-4.62 (m, 1H), 4.62-4.45 (m, 1H), 4.39 (t, J=5.4 Hz, 2H), 4.04-3.79 (m, 2H), 3.65 (s, 3H), 2.96-2.81 (m, 1H), 2.51-2.32 (m, 1H), 2.25 (s, 3H), 2.23-2.13 (m, 1H), 2.13-2.03 (m, 1H). MS (ESI) $[M+H]^+$ 422.2.

Compound 30b: Retention time=10.56; $^1H$ NMR (500 MHz, $CDCl_3$) δ 7.77 (d, J=8.3 Hz, 1H), 7.58-7.52 (m, 1H), 7.38 (dd, J=12.4, 1.7 Hz, 2H), 7.31 (dd, J=8.4, 1.7 Hz, 1H), 5.20 (dd, J=7.2, 6.3 Hz, 1H), 4.77-4.66 (m, 1H), 4.62-4.52 (m, 1H), 4.39 (dd, J=6.3, 4.8 Hz, 2H), 3.99-3.86 (m, 2H), 3.65 (s, 3H), 2.95-2.84 (m, 1H), 2.46-2.35 (m, 1H), 2.25 (s, 3H), 2.23-2.13 (m, 1H), 2.14-2.00 (m, 1H). MS (ESI) $[M+H]^+$ 422.2.

Procedure B: Preparation of Compound 30a

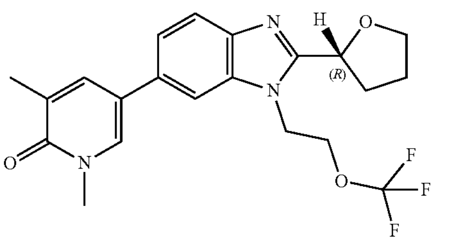

Step 1: Preparation of (R)—N-(4-(1,5-dimethyl-6-oxo-1,6-dihydropyridin-3-yl)-2-((2-(trifluoro methoxy)ethyl)amino)phenyl)tetrahydrofuran-2-carboxamide

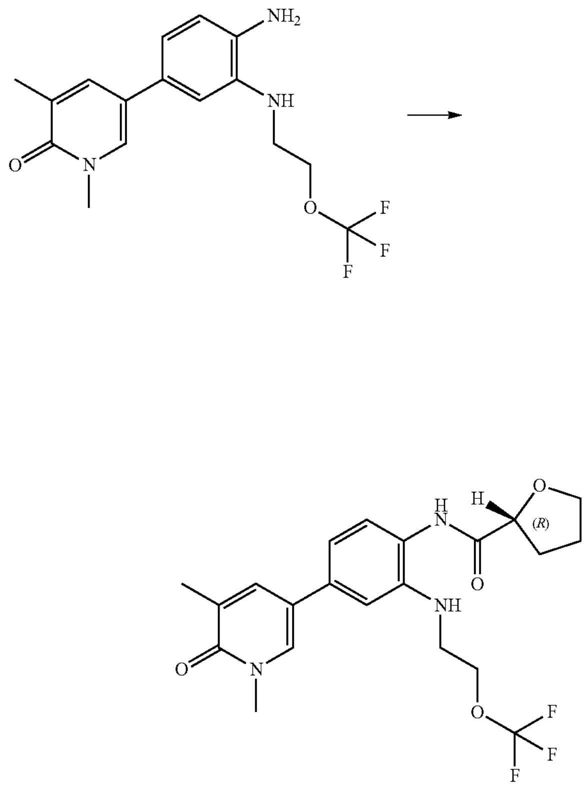

DIPEA (0.454 g, 3.52 mmol) was added to a stirred solution of (R)-tetrahydrofuran-2-carboxylic acid (0.153 g, 1.32 mmol) and HATU (0.669 g, 1.76 mmol) in DCM (6 mL), followed by Intermediate 8 (0.3 g, 0.88 mmol), and the reaction was stirred at rt for 5 h. After completion, the reaction mixture was poured into water (30 mL) and extracted with EtOAc (20 mL×3). The combined EtOAc layer was washed with brine (30 mL), dried over anhydrous $Na_2SO_4$ and concentrated under reduced pressure. The crude product was purified by silica gel chromatography using 3% MeOH in DCM as eluent to afford the title compound (0.31 g, 77%) as a solid. $[M+H]^+$ 440.30.

Step 2: Preparation of Compound 30a

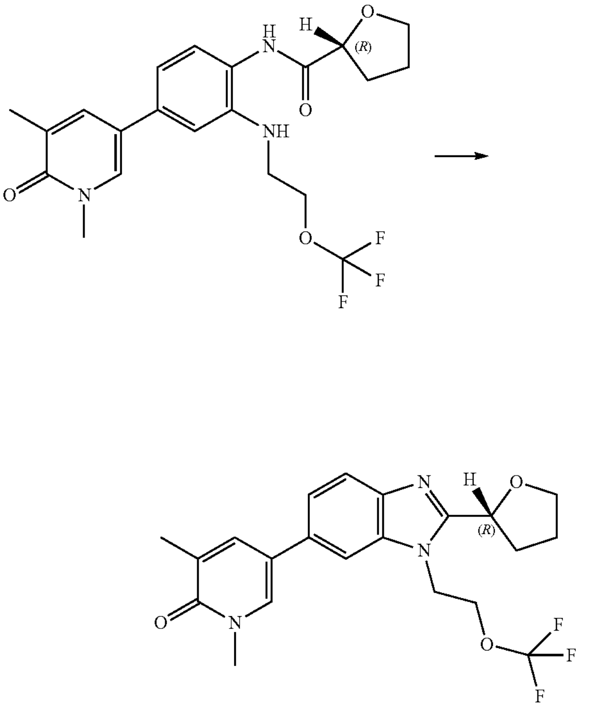

A solution of (R)—N-(4-(1,5-dimethyl-6-oxo-1,6-dihydropyridin-3-yl)-2-((2-(trifluoromethoxy)ethyl) amino)phenyl)tetrahydrofuran-2-carboxamide (0.31 g, 0.71 mmol) in acetic acid (10 mL) was stirred at rt and then heated at 100° C. for 14 h. After completion, the solvent was evaporated under reduced pressure and EtOAc (50 mL) was added. The obtained organic layer was washed with saturated $NaHCO_3$ (30 mL), brine (30 mL), dried over anhydrous $Na_2SO_4$, filtered and concentrated under reduced pressure. The crude product was purified by silica gel chromatography using 4% MeOH in DCM as eluent to afford Compound 30a (0.178 g, 59%) as a solid. $^1H$ NMR (400 MHz, DMSO) δ ppm 7.99 (d, J=2.4 Hz, 1H), 7.81 (d, J=1.2 Hz, 1H), 7.79 (d, J=1.2 Hz, 1H), 7.64 (d, J=8.4 Hz, 1H), 7.42 (dd, J=1.6 and 8.4 Hz, 1H), 5.26 (t, J=7.2 Hz, 1H), 4.82-4.75 (m, 2H), 4.51-4.48 (m, 2H), 3.88-3.78 (m, 2H), 3.54 (s, 3H), 2.74-2.66 (m, 1H), 2.26-2.19 (m, 1H), 2.11 (s, 3H), 2.09-2.01 (m, 1H), 1.99-1.94 (m, 1H). $[M+H]^+$ 422.20.

Procedure C: Preparation of Compound 30b

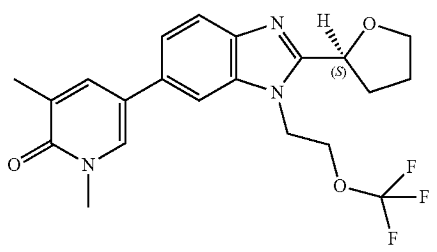

Step 1: Preparation of (S)—N-(4-(1,5-dimethyl-6-oxo-1,6-dihydropyridin-3-yl)-2-((2-(trifluoro methoxy)ethyl)amino)phenyl)tetrahydrofuran-2-carboxamide

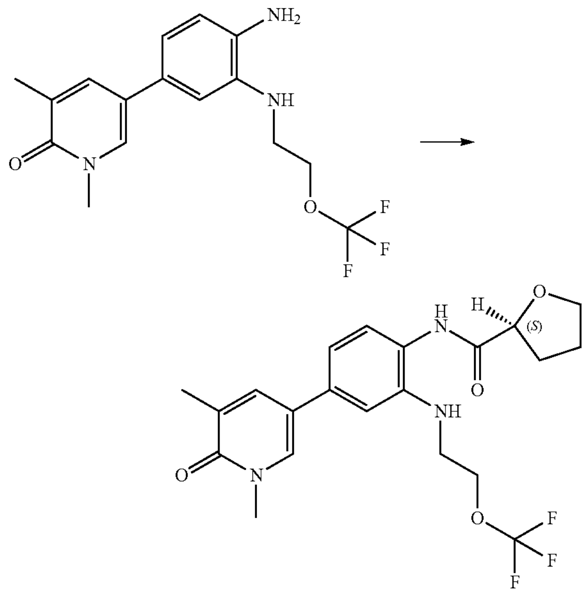

Step 1 of Procedure B above was followed, except for the use of (S)-tetrahydrofuran-2-carboxylic acid. Purification afforded the title compound (0.32 g, 78%) as a solid. $[M+H]^+$ 440.

Step 2: Preparation of Compound 30b

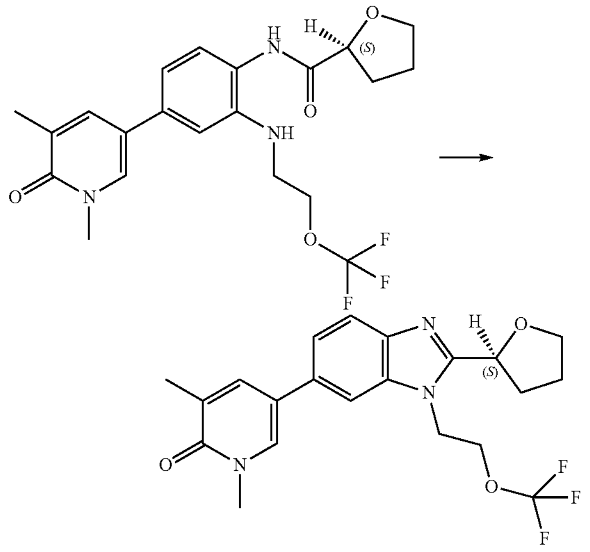

Step 2 of Procedure B above was followed, except for the use of (S)—N-(4-(1,5-dimethyl-6-oxo-1,6-dihydropyridin-3-yl)-2-((2-(trifluoromethoxy)ethyl)amino)phenyl)tetrahydrofuran-2-carboxamide (0.32 g, 0.73 mmol). Purification afforded Compound 30b (0.178 g, 58%) as a solid. $^1H$ NMR (400 MHz, DMSO) δ ppm 7.99 (d, J=2.4 Hz, 1H), 7.81 (s, 1H), 7.79 (s, 1H), 7.65 (d, J=8.8 Hz, 1H), 7.42 (dd, J=1.6 and 8.4 Hz, 1H), 5.27 (t, J=13.2 Hz, 1H), 4.78-4.67 (m, 2H), 4.51 (d, J=4.4 Hz, 2H), 3.86-3.78 (m, 2H), 3.54 (s, 3H), 2.72-2.67 (m, 1H), 2.26-2.22 (m, 1H), 2.11 (s, 3H), 2.09-2.05 (m, 1H), 2.01-1.97 (m, 1H). $[M+H]^+$ 422.40.

Example 28: 1,3-dimethyl-5-(2-(4-methyltetrahydro-2H-pyran-4-yl)-1-(2-(trifluoromethoxy)ethyl)-1H-benzo[d]imidazol-6-yl)pyridin-2 (1H)-one (Compound 31)

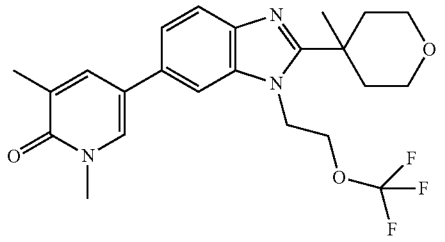 [SMILES: Cc1cc(-c2ccc3nc(C4(C)CCOCC4)n(CCOC(F)(F)F)c3c2)cn(C)c1=O]

Step 1: Preparation of N-(4-(1,5-dimethyl-6-oxo-1,6-dihydropyridin-3-yl)-2-((2-(trifluoromethoxy) ethyl)amino)phenyl)-4-methyltetrahydro-2H-pyran-4-carboxamide

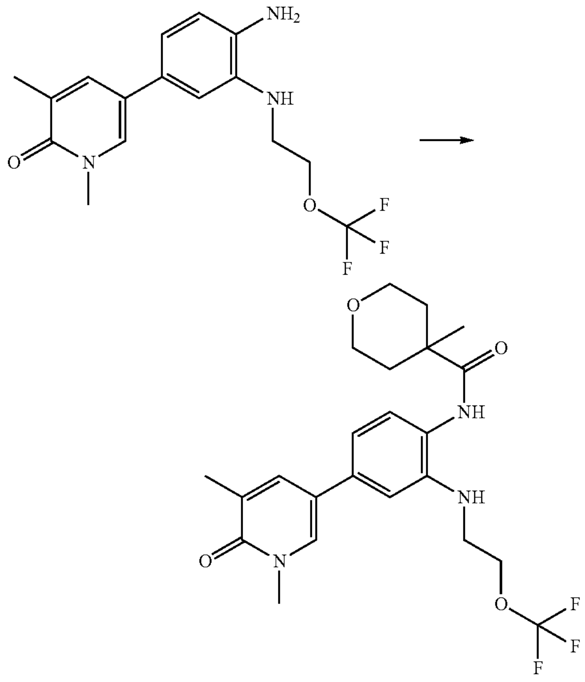

HATU (1.11 g, 2.92 mmol) was added to rt stirred solution of 4-methyltetrahydro-2H-pyran-4-carboxylic acid (0.31 g, 2.19 mmol) in DCM (5 mL) and the reaction mixture was stirred for 20 min. A solution of Intermediate 8 (0.5 g, 1.46 mmol) and DIPEA (0.56.g, 4.39 mmol) in DCM (5 mL) was added and the reaction mixture was stirred at rt for 16 h. The solvent was then evaporated under reduced pressure and the product was extracted using DCM (20 mL×3). The combined organic layers were washed with water (50 mL) and brine (50 mL), and dried over anhydrous $Na_2SO_4$, filtered and concentrated to dryness. The resulting product was triturated with $Et_2O$ and dried under vacuum to afford the title compound (0.35 g, 51%). M+2 469.49

Step 2: Preparation of Compound 31

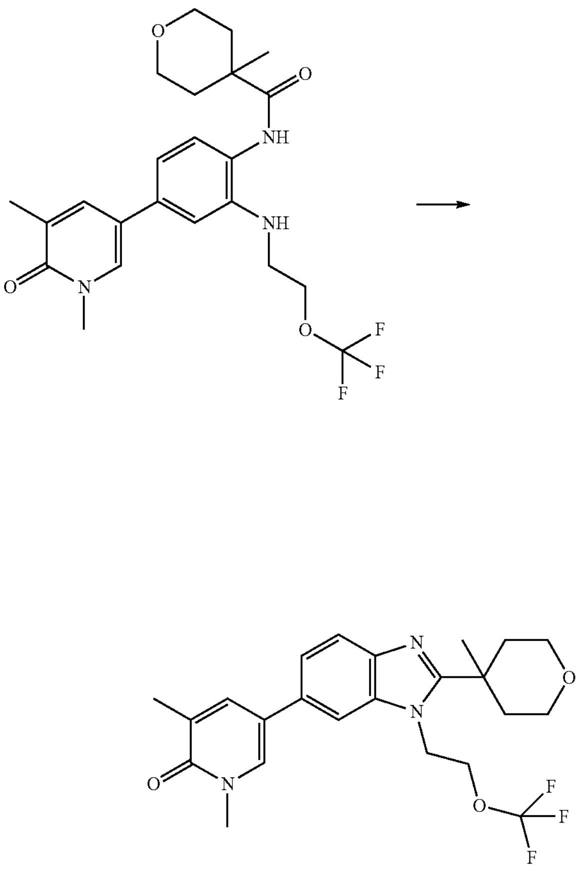

A stirred solution of N-(4-(1,5-dimethyl-6-oxo-1,6-dihydropyridin-3-yl)-2-((2-(trifluoromethoxy) ethyl)amino)phenyl)-4-methyltetrahydro-2H-pyran-4-carboxamide (0.35 g, 0.74 mmol) in acetic acid (2 mL) was heated at 100° C. for 3 h under microwave irradiation. After completion of the reaction, acetic acid was evaporated under reduced pressure. The residue obtained was neutralized with saturated $NaHCO_3$ (50 mL) and extracted using EtOAc (100 mL). The organic layer was washed with brine (50 mL), dried over anhydrous $Na_2SO_4$ and concentrated under reduced pressure. The crude product was purified by silica gel chromatography using 1.5% MeOH in DCM as eluent. Fractions were combined and concentrated to dryness to afford a semi-purified product, which was subjected to preparative HPLC purification using 35% MeCN in water to afford Compound 31 (0.04 g, 12%) as a solid. $^1H$ NMR (400 MHz, MeOH) δ ppm 7.90 (s, 1H), 7.87 (s, 1H), 7.73 (s, 1H), 7.71 (s, 1H), 7.48 (dd, J=1.6 and 1.2 Hz, 1H), 4.87 (t, J=11.2 Hz, 2H), 4.54 (t, J=10.8 Hz, 2H), 3.89-3.84 (m, 2H), 3.77-3.72 (m, 2H), 3.70 (s, 3H), 2.54-2.50 (m, 2H), 2.24 (s, 3H), 1.96-1.89 (m, 2H), 1.55 (s, 3H). $[M+H]^+$ 450.47.

Example 29: 1,3-dimethyl-5-[2-tetrahydropyran-4-yl-3-(3,3,3-trifluoropropyl)benzimidazol-5-yl]pyridin-2-one (Compound 34)

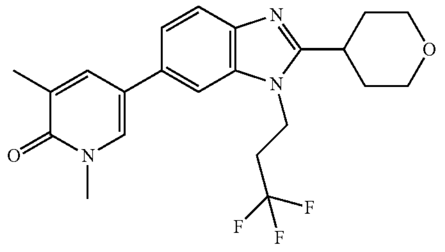 [SMILES: Cc1cc(-c2ccc3nc(C4CCOCC4)n(CCC(F)(F)F)c3c2)cn(C)c1=O]

Step 1: Preparation of N-(4-(1,5-dimethyl-6-oxo-1,6-dihydropyridin-3-yl)-2-(3,3,3-trifluoroprop-1-ylamino)phenyl)tetrahydropyran-4-carboxamide

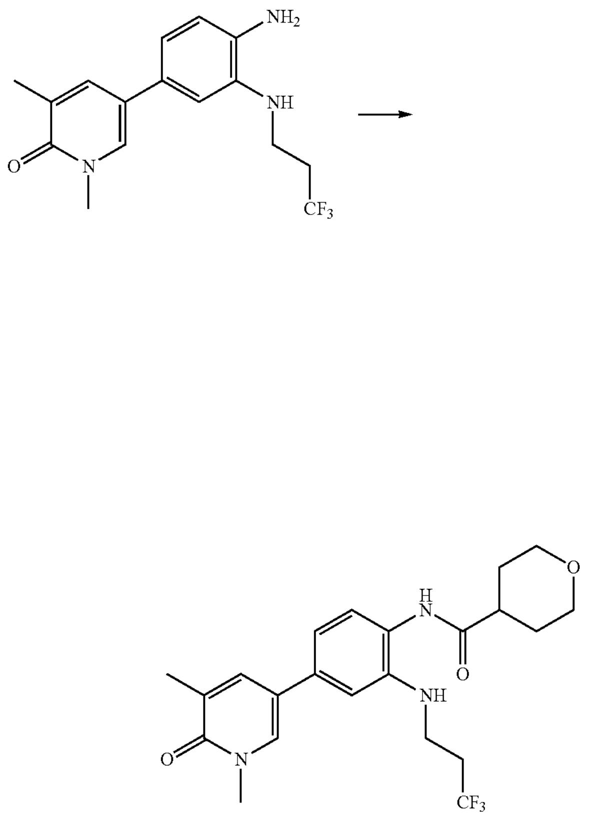

To a solution of Intermediate 10 (244 mg, 0.75 mmol) in DCM (5 mL), tetrahydropyran-4-carbonyl chloride (111 mg, 0.75 mmol) was added and the reaction mixture was stirred for 1 h at rt. The mixture was diluted with water and then EtOAc (5 mL) was added. The organic layer was separated and washed with saturated $NaHCO_3$ (2×10 mL) and then brine (20 mL). The organic layer was dried over $Na_2SO_4$, filtered and concentrated under reduced pressure to afford amide compound, which was used in the next step without further purification.

Step 2: Preparation of Compound 34

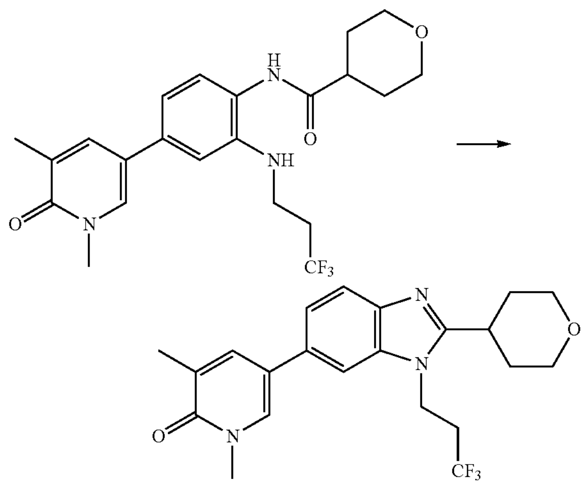

To a solution of N-(4-(1,5-dimethyl-6-oxo-1,6-dihydropyridin-3-yl)-2-(3,3,3-trifluoroprop-1-ylamino)phenyl)tetrahydropyran-4-carboxamide (directly from previous step) in toluene (5 mL), pTSA (143 mg, 0.75 mmol) was added and the reaction mixture was heated under reflux for 18 h. The mixture was then cooled to rt, diluted with EtOAc (5 ml) and washed with saturated $NaHCO_3$ (2×10 mL) and brine (10 mL). The organic layer was dried over $Na_2SO_4$, filtered and concentrated under reduced pressure. The material was purified by flash chromatography on silica gel using a mixture of EtOAc in hexane as eluent, followed by trituration with $Et_2O$ to afford Compound 34 (167 mg, 53%) as a solid. $^1$H NMR (500 MHz, $CDCl_3$) δ 7.80 (d, J=8.3 Hz, 1H), 7.56 (d, J=1.3 Hz, 1H), 7.42 (d, J=2.5 Hz, 1H), 7.34 (dd, J=8.4, 1.6 Hz, 1H), 7.29-7.23 (m, 1H), 4.52-4.42 (m, 2H), 4.22-4.14 (m, 2H), 3.68 (s, 3H), 3.62 (dd, J=11.8, 10.2 Hz, 2H), 3.14-3.02 (m, 1H), 2.69 (dd, J=16.6, 8.9 Hz, 2H), 2.33-2.20 (m, 5H), 1.88 (d, J=13.3 Hz, 2H). MS (ESI) $[M+H]^+$ 420.2.

Example 30: 5-[3-(2-methoxypropyl)-2-tetrahydropyran-4-yl-benzimidazol-5-yl]-1,3-dimethyl pyridin-2-one (Compounds 35a and 35b)

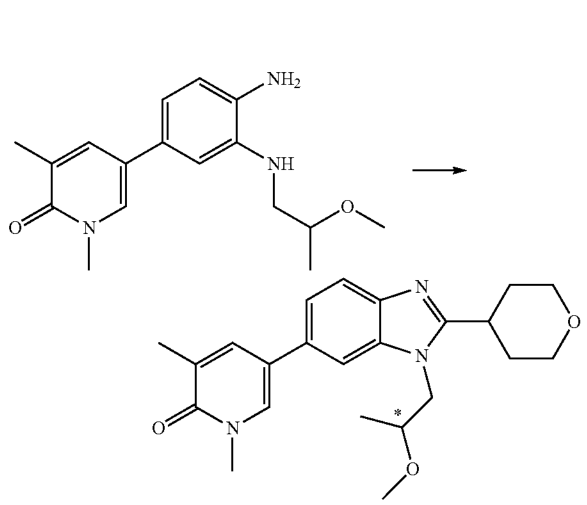

Intermediate 6 (120 mg, 0.39 mmol) was dissolved in DCM (5 ml) and tetrahydropyran-4-carbonyl chloride (50 mg, 0.39 mmol) was added and the reaction mixture was stirred for 1 h. The mixture was diluted by the addition of water and EtOAc (10 mL). The organic phase was separated and washed with saturated $NaHCO_3$ (10 mL) and then brine (20 mL). The organic phase was collected, dried over $Na_2SO_4$, filtered and concentrated to afford amide, which was used in the next step with further purification.

To the above amide in toluene (5 mL) was added pTSA (75 mg, 0.39 mmol) and the mixture was heated to reflux for 18 h. The mixture was cooled to rt, diluted with EtOAc (10 mL) then washed with saturated $NaHCO_3$ (2×10 mL) and brine (10 mL). The organic phase was collected, dried over $Na_2SO_4$, filtered and concentrated under reduced pressure. The material was purified by flash chromatography on silica gel using a mixture of MeOH in DCM as eluent and followed by preparative HPLC purification to afford title compound. The isomers of Compound 35 were separated using Semi-Preparative SFC (IC 10×250 mm, 5 um Isocratic 55% MeOH+0.1% NH4OH, 10 mL/min 100 Bar) to provide Compound 35a (22.5 mg, 14%) and Compound 35b (14.9 mg, 10%) as solids.

Compound 35a: Retention time=15.23, $^1$H NMR (500 MHz, $CDCl_3$) δ 7.76 (dd, J=8.2, 0.6 Hz, 1H), 7.54 (dd, J=2.5, 1.1 Hz, 1H), 7.39 (d, J=2.4 Hz, 1H), 7.28 (dd, J=8.2, 1.7 Hz, 2H), 4.22-4.06 (m, 4H), 3.71 (ddd, J=8.3, 6.2, 3.7 Hz, 1H), 3.65 (s, 3H), 3.58 (tdd, J=11.8, 6.1, 2.1 Hz, 2H), 3.24 (tt, J=11.6, 3.7 Hz, 1H), 3.16 (s, 3H), 2.35-2.22 (m, 4H), 2.15 (ddd, J=25.2, 12.1, 4.3 Hz, 1H), 1.85 (dd, J=44.7, 13.4 Hz, 2H), 1.28 (t, J=10.5 Hz, 3H). MS (ESI) $[M+H]^+$ 396.2.

Compound 35b: Retention time=17.47, $^1$H NMR (500 MHz, $CDCl_3$) δ 7.75 (dd, J=8.2, 0.6 Hz, 1H), 7.53 (dd, J=2.5, 1.2 Hz, 1H), 7.38 (d, J=2.3 Hz, 1H), 7.30-7.23 (m, 2H), 4.22-4.05 (m, 4H), 3.69 (ddd, J=8.3, 6.2, 3.8 Hz, 1H), 3.64 (s, 3H), 3.63-3.52 (m, 2H), 3.29-3.18 (m, 1H), 3.15 (s, 3H), 2.30-2.22 (m, 4H), 2.20-2.09 (m, 1H), 1.84 (dd, J=45.4, 14.2 Hz, 2H), 1.28 (d, J=6.2 Hz, 3H). MS (ESI) $[M+H]^+$ 396.3.

Example 31: 3-chloro-1-methyl-5-[2-tetrahydropyran-4-yl-3-[2-(trifluoromethoxy)ethyl]benzimidazol-5-yl]pyridin-2-one (Compound 36)

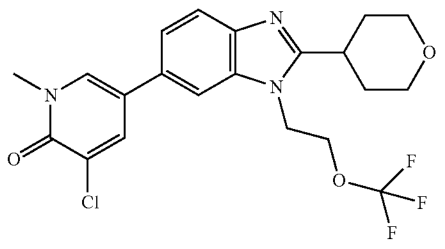 [SMILES: Cn1cc(-c2ccc3nc(C4CCOCC4)n(CCOC(F)(F)F)c3c2)cc(Cl)c1=O]

$Na_2CO_3$ (48.5 mg, 0.458 mmol), $Pd(PPh_3)_4$ (8.82 mg, 0.008 mmol), and Intermediate 9 (61.69 mg, 0.229 mmol) were added to a solution of 6-bromo-2-tetrahydropyran-4-yl-1-[2-(trifluoromethoxy)ethyl]benzimidazole (Example 1, step 1; 60 mg, 0.153 mmol) in a mixture of water (1 mL) and dioxane (5 mL). The resulting mixture was degassed by bubbling nitrogen for 15 min and then heated for 16 h at 110° C. The mixture was then cooled, filtered through Celite™ and extracted with EtOAc (3×50 mL). The organic layer was dried over $Na_2SO_4$, filtered and concentrated under reduced pressure. The material was purified by flash chromatography on silica gel using a gradient (0-20%) of MeOH in EtOAc as eluent, followed by preparative HPLC to afford Compound 36 (20 mg, 40%) as a solid. $^1$H NMR (500 MHz, $CDCl_3$) δ 7.87 (d, J=2.5 Hz, 1H), 7.83-7.78 (m, 1H), 7.47 (d, J=2.5 Hz, 1H), 7.30 (dd, J=8.3, 1.7 Hz, 1H), 7.25 (d, J=1.2 Hz, 1H), 4.52 (t, J=5.3 Hz, 2H), 4.32 (t, J=5.3 Hz, 2H), 4.15 (dd, J=11.7, 2.5 Hz, 2H), 3.71 (s, 3H), 3.63-3.55 (m, 2H), 3.13 (tt, J=11.8, 3.8 Hz, 1H), 2.30-2.18 (m, 2H), 1.85 (dd, J=13.4, 1.7 Hz, 2H).

Example 32: 5-(2-benzyl-1-(2-methoxyethyl)-1H-benzo[d]imidazol-6-yl)-1,3-dimethylpyridin-2(1H)-one (Compound 37)

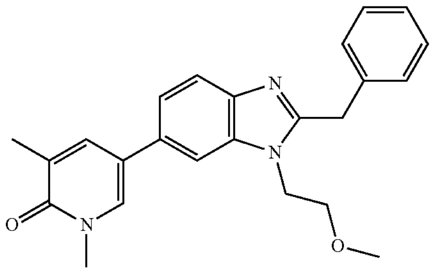 [SMILES: COCCn1c(Cc2ccccc2)nc2ccc(-c3cc(C)c(=O)n(C)c3)cc21]

Step 1: Preparation of 5-bromo-N-(2-methoxyethyl)-2-nitroaniline

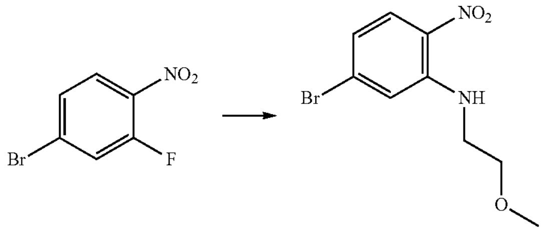

TEA (0.9 mL, 5.90 mmol) was added to a rt stirred solution of 4-bromo-2-fluoro-1-nitrobenzene (1 g, 4.54 mmol) and 2-methoxyethan-1-amine (0.5 g, 5.54 mmol) in ethanol (5 mL) and the reaction mixture was heated at 80° C. for 3 h. The resulting mixture was poured into water (50 mL) and extracted with EtOAc (30 mL×3). The combined EtOAc layers were washed with brine (30 mL), dried over anhydrous $Na_2SO_4$ and concentrated under reduced pressure. The crude product was purified by silica gel chromatography using 20% EtOAc in hexane as eluent. Product fractions were combined and concentrated to dryness to afford the title compound (1.1 g, 89%) as a solid. $^1$H NMR (400 MHz, DMSO) δ ppm 8.22 (t, J=4.8 Hz, 1H), 7.99 (d, J=2 Hz, 1H), 7.31 (d, J=2 Hz, 1H), 7.86 (dd, $J_1$, $J_2$=2 Hz, 1H), 3.60-3.51 (m, 4H), 3.32 (d, J=9.6 Hz, 3H).

Step 2: Preparation of 5-bromo-N$^1$-(2-methoxyethyl)benzene-1,2-diamine

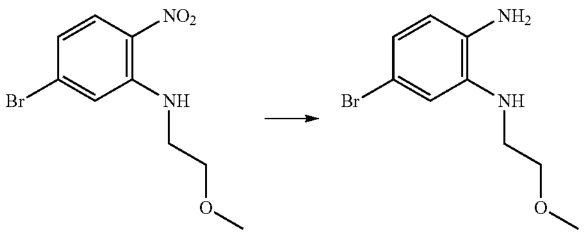

To a rt stirred solution of 5-bromo-N-(2-methoxyethyl)-2-nitroaniline (1.1 g, 4.00 mmol) in MeOH (25 mL) was added sodium dithionite (5.99 g, 48.00 mmol) followed by water (10 mL) and the reaction mixture was heated at 50° C. for 3 h. The resulting mixture was then poured into water (30 mL) and extracted with EtOAc (20 mL×3). The combined EtOAc layers were washed with brine (25 mL), dried over anhydrous $Na_2SO_4$ and concentrated under reduced pressure. The crude material was purified by silica gel chromatography using 15% EtOAc in hexane as eluent. Product fractions were combined and concentrated to dryness to afford the title compound (0.60 g, 62%) as a solid. $M^{+2}$ 247.12.

Step 3: Preparation of 2-benzyl-6-bromo-1-(2-methoxyethyl)-1H-benzo[d]imidazole

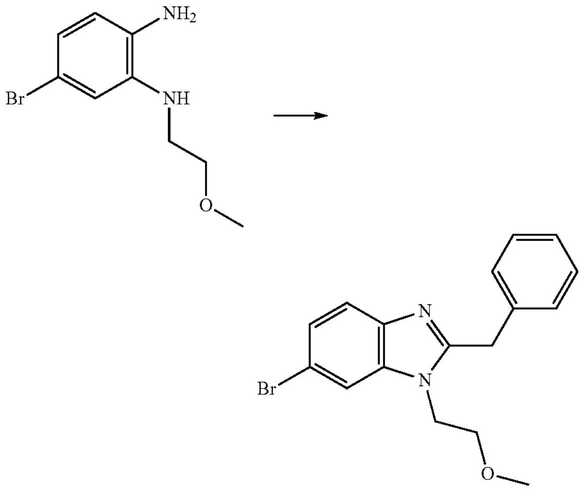

A solution of 5-bromo-N$^1$-(2-methoxyethyl)benzene-1,2-diamine (0.30 g, 1.22 mmol) and 2-phenylacetaldehyde (0.18 g, 1.46 mmol) in acetic acid (10 mL) was stirred at rt for 14 h. After completion, the solvent was evaporated under reduced pressure. The residue was neutralized with saturated aqueous $NaHCO_3$ (20 mL) and extracted with EtOAc (25 mL×3). The combined organic layers were washed with brine (20 mL), dried over anhydrous $Na_2SO_4$ and concentrated under reduced pressure. The crude material was purified by silica gel chromatography using 15% EtOAc in hexane as eluent. Product fractions were combined and concentrated to dryness to afford the title compound (0.15 g, 36%) as a solid. $[M+H]^+$ 345.24.

Step 4: Preparation of Compound 37

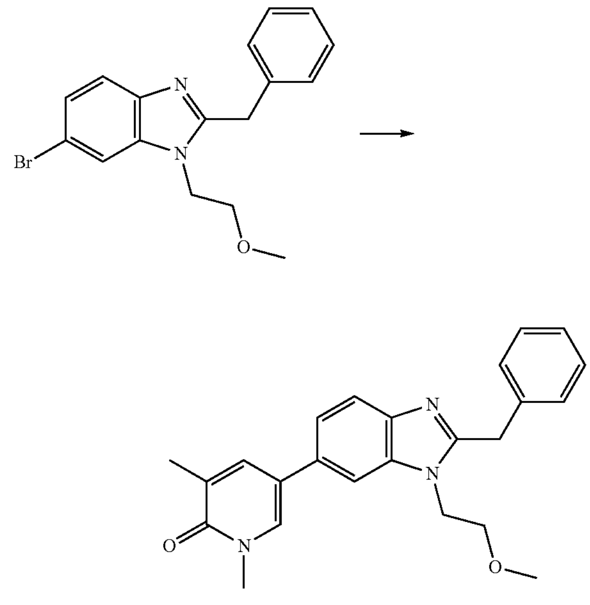

A stirred solution of 2-benzyl-6-bromo-1-(2-methoxyethyl)-1H-benzo[d]imidazole (0.15 g, 0.43 mmol) and 1,3-dimethyl-5-(4,4,5,5-tetramethyl-1,3,2-dioxaborolan-2-yl)pyridin-2 (1H)-one (0.14 g, 0.56 mmol) in 1,4-dioxane (5 mL) was purged with nitrogen for 10 minutes, followed by the addition of $Na_2CO_3$ (0.14 g, 1.30 mmol) in water (0.5 mL). The resulting mixture was purged again with nitrogen for 10 minutes. $Pd(PPh_3)_4$ (0.025 g, 0.02 mmol) was added and the reaction mixture was heated at 90° C. for 5 h. The solvent was then evaporated under reduced pressure and the residue was extracted with EtOAc (20 mL×3). The combined organic layers were washed with water (20 mL), brine (20 mL), dried over anhydrous $Na_2SO_4$ and concentrated under reduced pressure. The crude material was purified by flash chromatography using 1.5% MeOH in DCM as eluent. Fractions were combined and concentrated to dryness to afford Compound 37 (0.08 g, 38%) as a solid. $^1$H NMR (400 MHz, DMSO) δ ppm 7.97 (d, J=2 Hz, 1H), 7.80 (s, 1H), 7.70 (s, 1H), 7.57 (d, J=8.4 Hz, 1H), 7.38-7.24 (m, 6H), 4.38 (t, J=5 Hz, 2H), 4.31 (s, 2H), 3.53-3.51 (m, 5H), 3.16 (s, 3H), 2.10 (s, 3H). $[M+H]^+$ 387.48.

Example 33: 5-(2-cyclohexyl-1-(2-methoxyethyl)-1H-benzo[d]imidazol-6-yl)-1,3-dimethylpyridin-2(1H)-one (Compound 38)

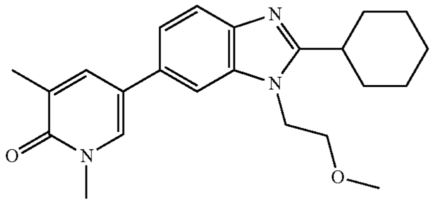 [SMILES: COCCn1c(C2CCCCC2)nc2ccc(-c3cc(C)c(=O)n(C)c3)cc21]

Step 1: Preparation of 6-bromo-2-cyclohexyl-1-(2-methoxyethyl)-1H-benzo[d]imidazole

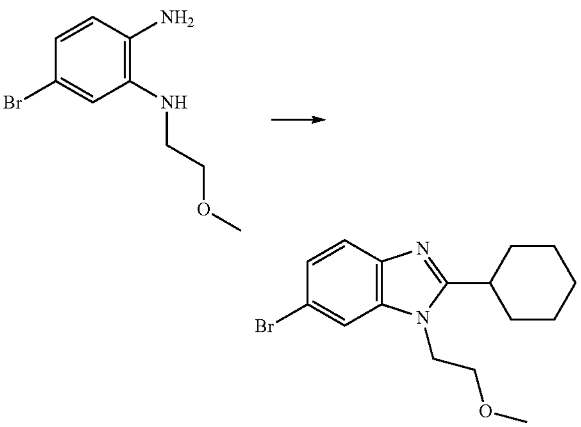

A solution of 5-bromo-N$^1$-(2-methoxyethyl)benzene-1,2-diamine (Example 32, step 2, 0.30 g, 1.22 mmol) and cyclohexanecarbaldehyde (0.16 g, 1.46 mmol) in acetic acid (10 mL) was stirred at rt for 14 h. After completion, the solvent was the evaporated under vacuum. The residue was neutralized with saturated aqueous $NaHCO_3$ (20 mL) and extracted with EtOAc (25 mL×3). The combined organic layers were washed with brine (20 mL), dried over anhydrous $Na_2SO_4$ and concentrated under reduced pressure. The crude material was purified by silica gel chromatography using 15% EtOAc in hexane as eluent. Fractions were combined and concentrated to dryness to afford the title compound (0.16 g, 38%) as a solid. $M^{+2}$ 339.26.

Step 2: Preparation of Compound 38

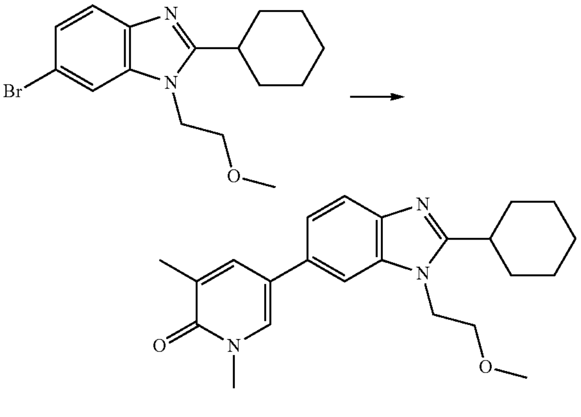

A stirred solution of 6-bromo-2-cyclohexyl-1-(2-methoxyethyl)-1H-benzo[d]imidazole (0.16 g, 0.47 mmol) and 1,3-dimethyl-5-(4,4,5,5-tetramethyl-1,3,2-dioxaborolan-2-yl)pyridin-2 (1H)-one (0.15 g, 0.62 mmol) in 1,4-dioxane (5 mL) was purged with nitrogen for 10 minutes, followed by the addition of $Na_2CO_3$ (0.15 g, 1.42 mmol) in water (0.5 mL). The resulting mixture was purged again with nitrogen for 10 minutes. $Pd(PPh_3)_4$ (0.028 g, 0.02 mmol) was added and the reaction mixture was heated at 90° C. for 14 h. The solvent was evaporated under reduced pressure and the residue was extracted using EtOAc (20 mL×3). The combined organic layers were washed with water (20 mL), brine (20 mL), dried over anhydrous $Na_2SO_4$ and concentrated under reduced pressure. The crude material was purified by silica gel chromatography using 1.3% MeOH in DCM as eluent. Product fractions were combined and concentrated to dryness to afford Compound 38 (0.1 g, 56%) as a solid. $^1$H NMR (400 MHz, DMSO) δ 7.97 (d, J=2.4 Hz, 1H), 7.80 (s, 1H), 7.69 (d, J=1.2 Hz, 1H), 7.54 (d, J=8.4 Hz, 1H), 7.34 (dd, $J_1$, $J_2$=1.6 Hz, 1H), 4.43 (t, J=5 Hz, 2H), 3.65 (t, J=5 Hz, 2H), 3.54 (s, 3H), 3.20 (s, 3H), 3.01-2.95 (m, 1H), 2.11 (s, 3H), 1.90-1.83 (m, 4H), 1.80-1.59 (m, 3H), 1.46-1.26 (m, 3H). $[M+H]^+$ 380.

Example 34: (R)-5-(1-(2-ethoxypropyl)-2-(tetrahydro-2H-pyran-4-yl)-1H-benzo[d]imidazol-6-yl)-1,3-dimethylpyridin-2(1H)-one (Compound 39)

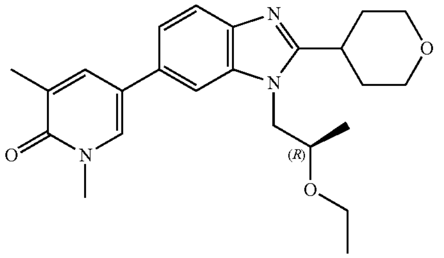

Step 1: Preparation of (R)-5-bromo-N-(2-ethoxypropyl)-2-nitroaniline

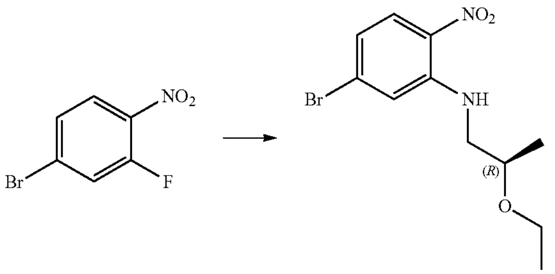

A stirred solution of 4-bromo-2-fluoro-1-nitrobenzene (0.6 g, 2.73 mmol) and Intermediate 11 (0.57 g, 5.45 mmol) in ethanol (10 mL) was stirred for 10 min at rt. TEA (1.3 mL, 8.19 mmol) was added dropwise and the reaction mixture was heated at 70° C. for 8 h. The reaction mixture was then diluted with water (100 mL) and extracted with EtOAc (100 mL×3). The combined organic layers were washed with brine (30 mL), dried over anhydrous $Na_2SO_4$, filtered and concentrated under reduced pressure. The crude material was purified by silica gel chromatography using a gradient of 1-3% EtOAc in hexanes as eluent. Fractions were combined and concentrated under reduced pressure to afford the title compound (0.275 g, 32%) as a solid. $^1$H NMR (400 MHz, DMSO) δ 8.30 (t, J=4.8 Hz, 1H), 7.98 (d, J=9.2 Hz, 1H), 7.33 (d, J=1.6 Hz, 1H), 6.83 (dd, J=2 and 9.2 Hz, 1H), 3.72-3.67 (m, 1H), 3.63-3.50 (m, 2H), 3.44-3.36 (m, 1H), 3.26-3.20 (m, 1H), 1.16-1.13 (m, 6H).

Step 2: Preparation of (R)-5-bromo-$N^1$-(2-ethoxypropyl)benzene-1,2-diamine

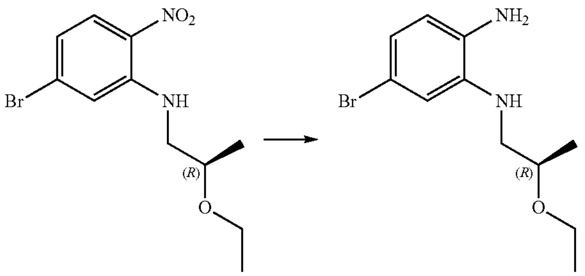

Sodium dithionite (1.51 g, 11.87 mmol) was added to a rt suspension of (R)-5-bromo-N-(2-ethoxypropyl)-2-nitroaniline (0.3 g, 0.99 mmol) in MeOH (10 mL) and water (4 mL) and the reaction mixture was heated at 50° C. for 1 h. The resulting mixture was then diluted with water (50 mL) and extracted with DCM (50 mL×3). The combined organic layers were washed with brine (50 mL), dried over anhydrous $Na_2SO_4$, filtered and concentrated under reduced pressure to afford the title compound (0.2 g, 68%) as a solid. $[M+H]^+$ 273.2

Step 3: Preparation of (R)-6-bromo-1-(2-ethoxypropyl)-2-(tetrahydro-2H-pyran-4-yl)-1H-benzo[d]imidazole

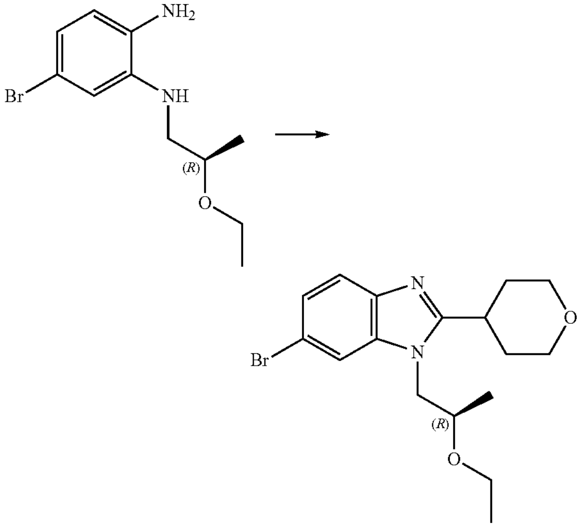

Tetrahydro-2H-pyran-4-carbaldehyde (0.1 g, 0.88 mmol) was added to a rt stirred solution of (R)-5-bromo-$N^1$-(2-ethoxypropyl)benzene-1,2-diamine (0.2 g, 0.73 mmol) in acetic acid (10 mL) and reaction mixture was stirred for 48 h at the same temperature. The reaction mixture was then concentrated, neutralized with saturated $NaHCO_3$ and extracted with EtOAc (50 mL×3). The combined organic layers were washed with brine (50 mL), dried over anhydrous $Na_2SO_4$, filtered and concentrated under reduced pressure. The crude material was purified by silica gel chromatography using a gradient of 35-40% EtOAc in hexanes as eluent. Product fractions were combined and concentrated under reduced pressure to afford the title compound (0.14 g, 49%) as a solid. $[M+H]^+$ 367.24.

Step 4: Preparation of Compound 39

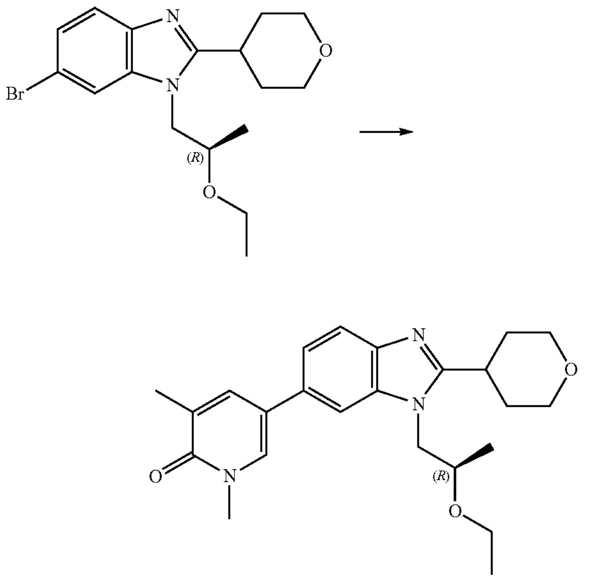

A stirred solution of (R)-6-bromo-1-(2-ethoxypropyl)-2-(tetrahydro-2H-pyran-4-yl)-1H-benzo[d]imidazole (0.14 g, 0.38 mmol) and 1,3-dimethyl-5-(4,4,5,5-tetramethyl-1,3,2-dioxaborolan-2-yl)pyridin-2 (1H)-one (0.145 g, 0.57 mmol) in 1,4-dioxane (3 mL) was purged with nitrogen for 20 min, followed by the addition of $Na_2CO_3$ (0.125 g, 1.14 mmol) in water (0.3 mL). The resulting mixture was purged again with nitrogen for 20 min. $Pd(PPh_3)_4$ (0.025 g, 0.019 mmol) was added and the reaction mixture was heated at 90° C. for 16 h. The reaction mixture was then diluted with water (30 mL) and extracted with EtOAc (30 mL×3). The combined organic layers were washed with brine (30 mL), dried over anhydrous $Na_2SO_4$, filtered and concentrated under reduced pressure. The crude material was purified by silica gel chromatography using a gradient of 3-5% MeOH in DCM as eluent. Product fractions were combined and concentrated to dryness to give 0.09 g of a product, which was further purified by preparative HPLC using 20-55% MeCN in water to afford Compound 39 (0.031 g, 20%) as a solid. $^1H$ NMR (400 MHz, DMSO) δ 7.95 (d, J=2 Hz, 1H), 7.80 (s, 1H), 7.70 (s, 1H), 7.56 (d, J=8.4 Hz, 1H), 7.34 (dd, J=1.6 and 8.4 Hz, 1H), 4.34-4.19 (m, 2H), 4.01-3.92 (m, 2H), 3.76 (s, 1H), 3.53 (s, 3H), 3.51-3.37 (m, 4H), 3.03-2.97 (m, 1H), 2.10 (s, 3H), 2.07-1.96 (m, 1H), 1.82-1.79 (m, 3H), 1.21 (t, J=9.2 Hz, 3H), 0.84 (t, J=6.8 Hz, 3H). $[M+H]^+$ 410.4.

Example 35: (S)-5-(1-(2-ethoxypropyl)-2-(tetrahydro-2H-pyran-4-yl)-1H-benzo[d]imidazol-6-yl)-1,3-dimethylpyridin-2 (1H)-one (Compound 40)

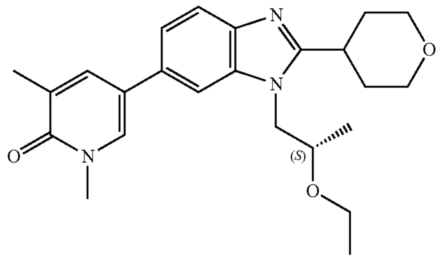

Step 1: Preparation of (S)-5-bromo-N-(2-ethoxypropyl)-2-nitroaniline

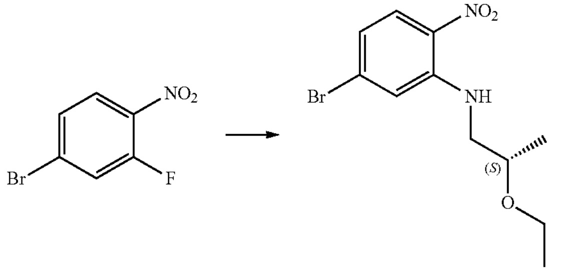

The procedure of Step 1 of Example 34 was followed except for the use of Intermediate 12 (0.57 g, 5.45 mmol). The crude material obtained was purified by silica gel chromatography using a gradient of 1-5% EtOAc in hexanes as eluent. The combined and concentrated fractions afforded the title compound (0.25 g, 30%) as a solid. $^1H$ NMR (400 MHz, DMSO) δ 8.30 (t, J=4.8 Hz, 1H), 7.98 (d, J=9.2 Hz, 1H), 7.33 (d, J=1.6 Hz, 1H), 6.83 (dd, J=2 and 9.2 Hz, 1H), 3.72-3.67 (m, 1H), 3.63-3.50 (m, 2H), 3.44-3.36 (m, 1H), 3.26-3.20 (m, 1H), 1.16 (d, J=6 Hz, 3H), 1.12 (t, J=6.8 Hz, 3H).

Step 2: Preparation of (S)-5-bromo-$N^1$-(2-ethoxypropyl)benzene-1,2-diamine

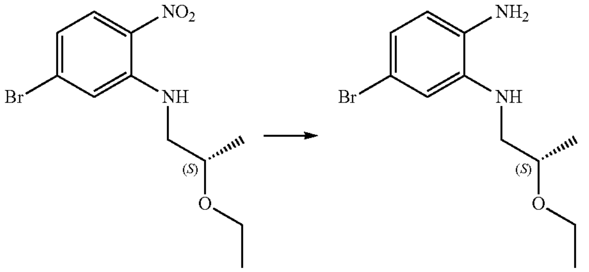

Similarly to the conditions in step 2 of Example 34, sodium dithionite (2.51 g, 19.79 mmol) was added to a rt suspension of (S)-5-bromo-N-(2-ethoxypropyl)-2-nitroaniline (0.5 g, 1.65 mmol) in MeOH (13 mL) and water (6 mL)

and the reaction mixture was heated at 50° C. for 1 h. The reaction mixture was treated as in step 2 of Example 34 to afford the title compound (0.2 g, 31%) as a solid. $[M+H]^+$ 273.2.

Step 3: Preparation of (S)-6-bromo-1-(2-ethoxypropyl)-2-(tetrahydro-2H-pyran-4-yl)-1H-benzo[d]imidazole

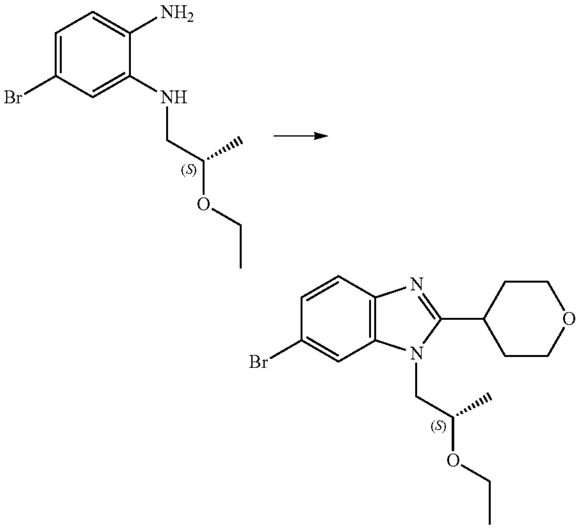

The procedure depicted in step 3 of Example 34, except for the use of (S)-5-bromo-$N^1$-(2-ethoxypropyl)benzene-1,2-diamine. The crude material was purified by silica gel chromatography using a gradient of 30-35% EtOAc in hexanes as eluent. Product fractions were combined and concentrated under reduced pressure to afford the title compound (0.12 g, 42%) as a solid. $[M+H]^+$ 367.24.

Step 4: Preparation of Compound 40

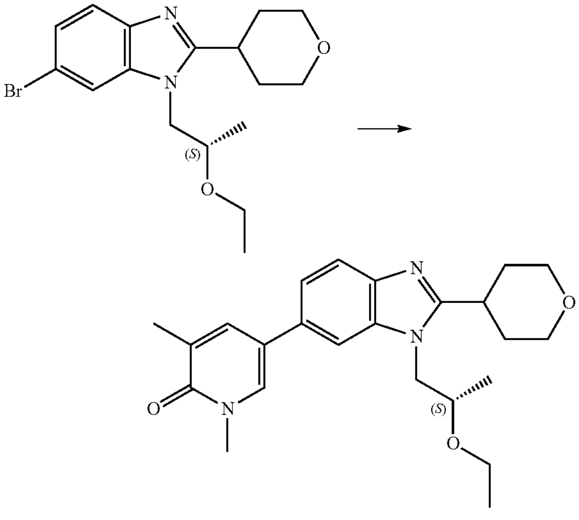

A stirred solution of (S)-6-bromo-1-(2-ethoxypropyl)-2-(tetrahydro-2H-pyran-4-yl)-1H-benzo[d]imidazole (0.12 g, 0.33 mmol) and 1,3-dimethyl-5-(4,4,5,5-tetramethyl-1,3,2-dioxaborolan-2-yl)pyridin-2 (1H)-one (0.13 g, 0.49 mmol) in 1,4-dioxane (2 mL) was purged with nitrogen for 20 min, followed by the addition of $Na_2CO_3$ (0.11 g, 0.98 mmol) in water (0.2 mL). The resulting mixture was purged again with nitrogen for 20 min. $Pd(PPh_3)_4$ (0.02 g, 0.016 mmol) was added and the reaction mixture was heated at 90° C. for 16 h. The resulting mixture was treated and purified as described in step 4 of Example 34 to afford Compound 40 (0.026 g, 19%) as a solid. $^1H$ NMR (400 MHz, DMSO) δ 7.95 (d, J=2 Hz, 1H), 7.80 (d, J=1.6 Hz, 1H), 7.70 (d, J=1.6 Hz, 1H), 7.56 (d, J=8.4 Hz, 1H), 7.34 (dd, J=1.6 and 8.4 Hz, 1H), 4.22-4.20 (m, 2H), 4.01-3.92 (m, 2H), 3.78-3.74 (m, 1H), 3.54 (s, 3H), 3.51-3.36 (m, 4H), 3.03-2.95 (m, 1H), 2.11 (s, 3H), 2.02-1.96 (m, 1H), 1.81-1.78 (m, 3H), 1.21 (t, J=9.2 Hz, 3H), 0.84 (t, J=6.8 Hz, 3H). $[M+H]^+$ 410.4

Example 36: 1,3-dimethyl-5-(2-(tetrahydro-2H-pyran-4-yl)-1-(2-(2,2,2-trifluoroethoxy)ethyl)-1H-benzo[d]imidazol-6-yl)pyridin-2 (1H)-one (Compound 41)

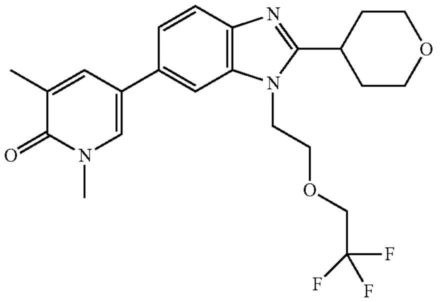 [SMILES: Cc1cc(-c2ccc3nc(C4CCOCC4)n(CCOCC(F)(F)F)c3c2)cn(C)c1=O]

Step 1: Preparation of 5-bromo-2-nitro-N-(2-(2,2,2-trifluoroethoxy)ethyl)aniline

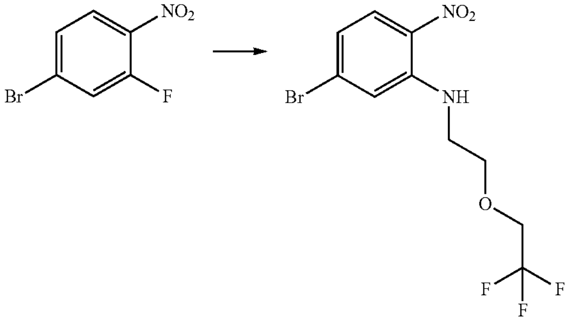 [SMILES: O=[N+]([O-])c1ccc(Br)cc1F ; O=[N+]([O-])c1ccc(Br)cc1NCCOCC(F)(F)F]

TEA (0.6 mL, 1.17 mmol) was added to a stirred rt solution of 4-bromo-2-fluoro-1-nitrobenzene (0.2 g, 0.9 mmol) and 2-(2,2,2-trifluoroethoxy)ethan-1-amine (0.19 g, 1.09 mmol) in ethanol (4 mL) and the reaction mixture was heated at 50° C. for 2 h. The resulting mixture was then poured into water (50 mL) and extracted with EtOAc (40 mL×3). The combined organic layers were washed with brine (30 mL), dried over anhydrous $Na_2SO_4$, filtered and concentrated under reduced pressure. The crude material was purified by silica gel chromatography using 20% EtOAc in hexane as eluent. The fractions were combined and concentrated to afford the title compound (0.3, 96%) as a solid. $^1$H NMR (400 MHz, DMSO) δ ppm 8.25 (d, J=5.6 Hz, 1H), 7.99 (d, J=9.2 Hz, 1H), 7.34 (d, J=2.0 Hz, 1H), 6.86 (dd, J=2.0 and 9.2 Hz, 1H), 4.17-4.10 (m, 2H), 3.83 (t, J=5.2 Hz, 2H), 3.62-3.58 (m, 2H).

Step 2: Preparation of 5-bromo-$N^1$-(2-(2,2,2-trifluoroethoxy)ethyl)benzene-1,2-diamine

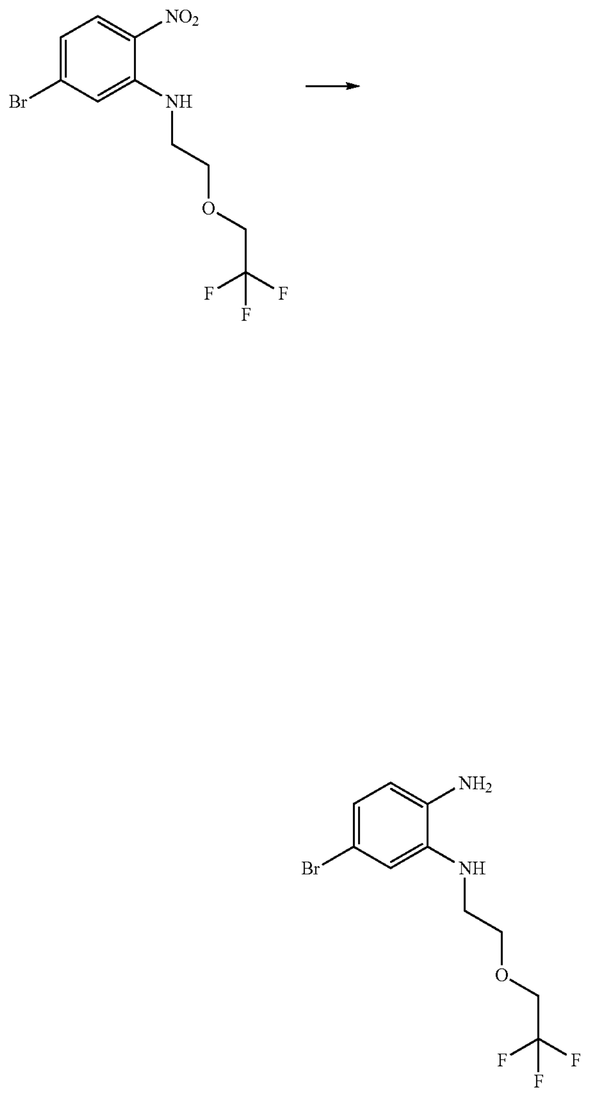

To a stirred rt solution of 5-bromo-2-nitro-N-(2-(2,2,2-trifluoroethoxy)ethyl)aniline (0.3 g, 0.87 mmol) in MeOH (8 mL) was added sodium dithionite (13.32 g, 10.49 mmol) followed by water (3 mL) and the reaction mixture was heated to 50° C. for 3 h. The resulting mixture was poured into water (30 mL) and extracted with EtOAc (20 mL×3). The combined organic layers were washed with brine (25 mL), dried over anhydrous $Na_2SO_4$, filtered and concentrated under reduced pressure. The crude material was purified by silica gel chromatography using 30% EtOAc in hexane as eluent. The fractions were combined and concentrated to afford the title compound (0.2 g, 73%) as a solid. $[M+H]^+$ 313.1, 315.14

Step 3: Preparation of 6-bromo-2-(tetrahydro-2H-pyran-4-yl)-1-(2-(2,2,2-trifluoroethoxy)ethyl)-1H-benzo[d]imidazole

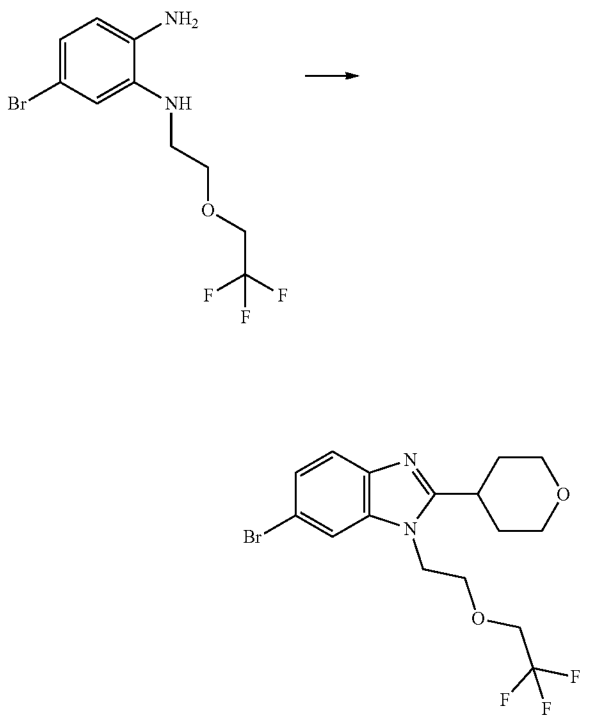

A solution of 5-bromo-$N^1$-(2-(2,2,2-trifluoroethoxy)ethyl)benzene-1,2-diamine (0.2 g, 0.63 mmol) and tetrahydro-2H-pyran-4-carbaldehyde (0.11 g, 0.76 mmol) in acetic acid (10 mL) was stirred at rt for 14 h. The solvent was then evaporated under reduced pressure. The residue was neutralized using saturated aqueous $NaHCO_3$ (20 mL) and extracted with EtOAc (25 mL×3). The combined organic layers were washed with brine (20 mL), dried over anhydrous $Na_2SO_4$, filtered and concentrated under reduced pressure. The crude material was purified by silica gel column chromatography using 15% EtOAc in hexane as eluent. The fractions were combined and concentrated to afford the title compound (0.14 g, 54%) as a solid. $[M+H]^+$ 407.23, 409.23.

Step 4: Preparation of Compound 41

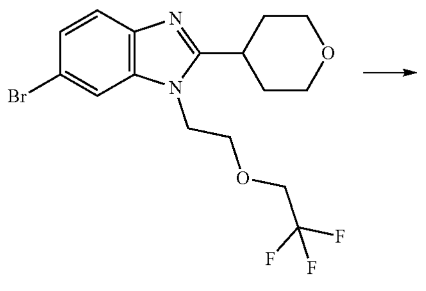

-continued

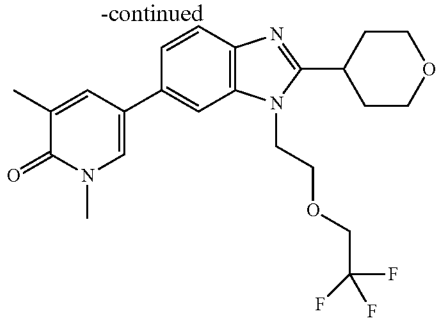

A stirred solution of 6-bromo-2-(tetrahydro-2H-pyran-4-yl)-1-(2-(2,2,2-trifluoroethoxy)ethyl)-1H-benzo[d]imidazole (0.14 g, 0.34 mmol) and 1,3-dimethyl-5-(4,4,5,5-tetramethyl-1,3,2-dioxaborolan-2-yl)pyridin-2 (1H)-one (0.11 g, 0.44 mmol) in 1,4-dioxane (5 mL) was purged with nitrogen for 10 minutes followed by the addition of $Na_2CO_3$ (0.11 g, 1.03 mmol) in water (0.5 mL). The reaction mixture was again purged with nitrogen for 10 minutes. $Pd(PPh_3)_4$ (0.02 g, 0.01 mmol) was added and the reaction mixture was heated to 90° C. for 5 h. The solvent was then evaporated under reduced pressure and the residue was extracted with EtOAc (20 mL×3). The combined organic layers were washed with water (20 mL) and brine (20 mL), dried over anhydrous $Na_2SO_4$, filtered and concentrated under reduced pressure. The crude material was purified by silica gel chromatography using 1.5% MeOH in DCM as eluent. The fractions were combined and concentrated to afford a semi-purified product, which was further purified by preparative HPLC using 35-45% MeCN in water to afford Compound 41 (0.07 g, 45%) as a solid. $^1H$ NMR (400 MHz, DMSO) δ ppm 7.97 (d, J=2.4 Hz, 1H), 7.80 (s, 1H), 7.74 (d, J=1.2 Hz, 1H), 7.58 (d, J=8.4 Hz, 1H), 7.34 (dd, J1.6 and 8.4 Hz, 1H), 4.53 (t, J=4.8 Hz, 2H), 4.09-3.91 (m, 6H), 3.54 (s, 3H), 3.50-3.34 (m, 2H), 3.31-3.28 (m, 1H), 2.11 (s, 3H), 1.91-1.77 (m, 4H). $[M+H]^+$ 450.35.

Example 37: 5-(1-(2-methoxyethyl)-2-((tetrahydro-2H-pyran-4-yl)methyl)-1H-benzo[d]imidazol-6-yl)-1,3-dimethylpyridin-2(1H)-one (Compound 42)

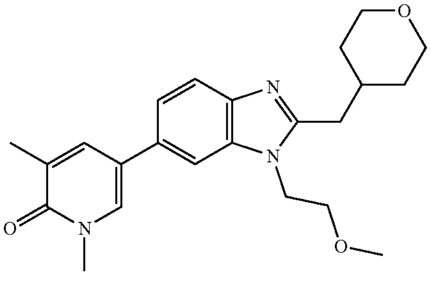 [SMILES: COCCn1c(CC2CCOCC2)nc2ccc(-c3cc(C)c(=O)n(C)c3)cc21]

Step 1: Preparation of 6-bromo-1-(2-methoxyethyl)-2-((tetrahydro-2H-pyran-4-yl)methyl)-1H-benzo[d]imidazole

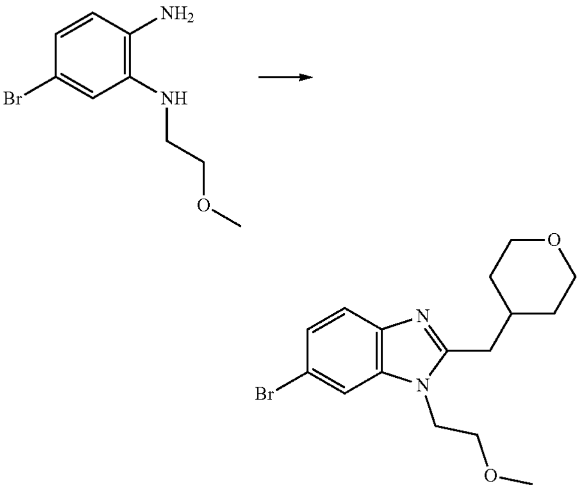

A solution of 5-bromo-$N^1$-(2-methoxyethyl)benzene-1,2-diamine (Example 32, step 2, 0.30 g, 1.22 mmol) and 2-(tetrahydro-2H-pyran-4-yl)acetaldehyde (0.19 g, 1.46 mmol) in acetic acid (10 mL) was stirred at rt for 14 h. After completion of the reaction, the solvent was evaporated under reduced pressure. The residue was neutralized using saturated $NaHCO_3$ (20 mL) and extracted with EtOAc (25 mL×3). The combined organic layers were washed with brine (20 mL), dried over anhydrous $Na_2SO_4$, filtered and concentrated under reduced pressure. The crude material was purified by silica gel chromatography using 10% EtOAc in hexane as eluent to afford the title compound (0.18 g, 42%) as a solid. $[M+H]^+$ 353.2, 355.26.

Step 2: Preparation of Compound 42

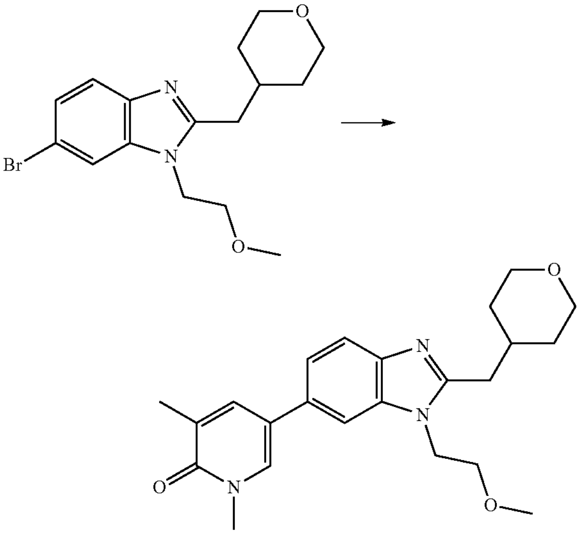

A stirred solution of 6-bromo-1-(2-methoxyethyl)-2-((tetrahydro-2H-pyran-4-yl)methyl)-1H-benzo[d]imidazole (0.18 g, 0.51 mmol) and 1,3-dimethyl-5-(4,4,5,5-tetramethyl-1,3,2-dioxaborolan-2-yl)pyridin-2 (1H)-one (0.16 g, 0.66 mmol) in 1,4-dioxane (5 mL) was purged with nitrogen for 10 minutes, followed by the addition of $Na_2CO_3$ (0.16 g, 1.53 mmol) in water (0.5 mL). The reaction mixture was again purged with nitrogen for 10 minutes. $Pd(PPh_3)_4$ (0.03 g, 0.05 mmol) was added and the reaction mixture was heated to 90° C. for 5 h. The solvent was evaporated under reduced pressure and the residue was extracted using EtOAc (20 mL×3). The combined organic layers were washed with water (20 mL) and brine (20 mL), dried over anhydrous $Na_2SO_4$, filtered and concentrated under reduced pressure. The crude material was purified by silica gel chromatography using 1.3% MeOH in DCM as eluent to afford Compound 42 (0.07 g, 34%) as a solid. $^1H$ NMR (400 MHz, DMSO) δ ppm 7.97 (d, J=2.4 Hz, 1H), 7.80 (s, 1H), 7.69 (s, 1H), 7.55 (d, J=8.4 Hz, 1H), 7.34 (dd, J=1.6 and 8.4 Hz, 1H), 4.41 (t, J=5.2 Hz, 2H), 3.84 (dd, J=2.4 and 11.2 Hz, 2H), 3.65 (t, J=5.2 Hz, 2H), 3.53 (s, 3H), 3.34-3.31 (m, 2H), 3.19 (s, 3H), 2.81 (d, J=6.8 Hz, 2H), 2.23-2.18 (m, 1H), 2.10 (s, 3H), 1.68-1.65 (m, 2H), 1.37-1.27 (m, 2H). $[M+H]^+$ 395.50.

Example 38: 1,3-dimethyl-5-(2-((tetrahydro-2H-pyran-4-yl)methyl)-1-(2-(trifluoromethoxy)ethyl)-1H-benzo[d]imidazol-6-yl)pyridin-2(1H)-one (Compound 43)

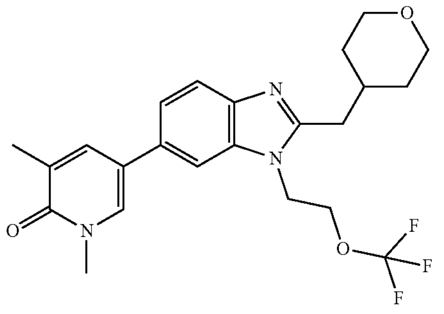 [SMILES: Cc1cc(-c2ccc3nc(CC4CCOCC4)n(CCOC(F)(F)F)c3c2)cn(C)c1=O]

A solution of Intermediate 8 (0.25 g, 0.73 mmol) and 2-(tetrahydro-2H-pyran-4-yl)acetaldehyde (0.11 g, 0.88 mmol) in acetic acid (10 mL) was stirred at rt for 14 h. The resulting mixture was concentrated under reduced pressure and diluted with EtOAc (100 mL), which was washed with saturated aqueous $NaHCO_3$ (30 mL) and brine (30 mL), dried over anhydrous $Na_2SO_4$, filtered and concentrated under reduced pressure. The crude material was purified by silica gel chromatography using 4% MeOH in DCM as eluent to afford Compound 43 (0.98 g, 33%) as a solid. $^1H$ NMR (400 MHz, DMSO) δ ppm 7.97 (d, J=2.4 Hz, 1H), 7.80 (d, J=1.2 Hz, 1H), 7.74 (d, J=1.6 Hz, 1H), 7.58 (d, J=8.4 Hz, 1H), 7.37 (dd, J=1.6 and 8.4 Hz, 1H), 4.63 (t, J=9.6 Hz, 2H), 4.43 (t, J=10 Hz, 2H), 3.84 (dd, J=2.8 and 11.2 Hz, 2H), 3.53 (s, 3H), 3.30 (d, J=1.2 Hz, 2H), 2.80 (d, J=7.2 Hz, 2H), 2.24-2.19 (m, 1H), 2.10 (s, 3H), 1.67 (d, J=10.8 Hz, 2H), 1.37-1.26 (m, 2H). $[M+H]^+$ 450.40.

Example 39: 5-(2-(4,4-difluorocyclohexyl)-1-(2-methoxyethyl)-1H-benzo[d]imidazol-6-yl)-1,3-dimethylpyridin-2(1H)-one (Compound 44)

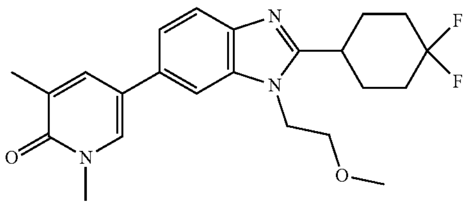 [SMILES: COCCn1c(C2CCC(F)(F)CC2)nc2ccc(-c3cc(C)c(=O)n(C)c3)cc21]

Step 1: Preparation of 6-bromo-2-(4,4-difluorocyclohexyl)-1-(2-methoxyethyl)-1H-benzo [d]imidazole

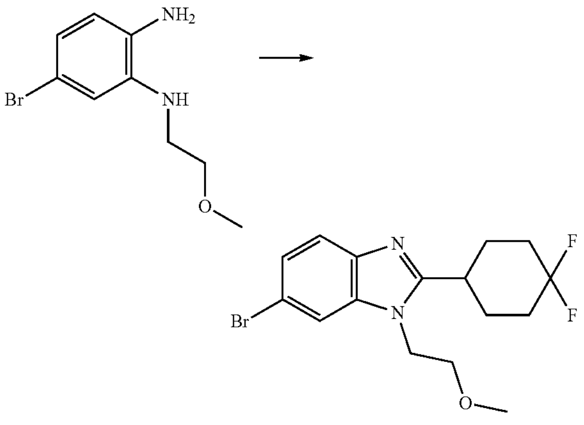

A solution of 5-bromo-N[1]-(2-methoxyethyl)benzene-1,2-diamine (Example 32, step 2, 0.3 g, 1.22 mmol) and 4,4-difluorocyclohexylcarbaldehyde (0.27 g, 1.46 mmol) in acetic acid (10 mL) was stirred at rt for 14 h. The solvent was evaporated under reduced pressure. The residue was neutralized with saturated $NaHCO_3$ (20 mL) and extracted with EtOAc (25 mL×3). The combined organic layers were washed with brine (20 mL), dried over anhydrous $Na_2SO_4$, filtered and concentrated under reduced pressure. The crude material was purified by silica gel chromatography using 25% EtOAc in hexane as eluent. The product fractions were combined and concentrated to dryness to afford the title compound (0.35 g, 77%) as a solid. $[M+H]^+$ 373.2, 375.24.

Step 2: Preparation of Compound 44

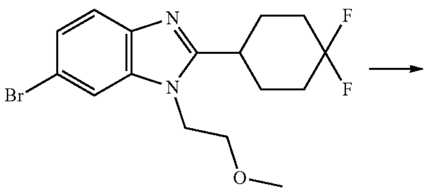

-continued

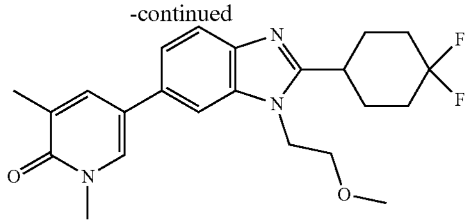

A stirred solution of 6-bromo-2-(4,4-difluorocyclohexyl)-1-(2-methoxyethyl)-1H-benzo[d]imidazole (0.2 g, 0.53 mmol) and 1,3-dimethyl-5-(4,4,5,5-tetramethyl-1,3,2-dioxaborolan-2-yl)pyridin-2 (1H)-one (0.17 g, 0.69 mmol) in 1,4-dioxane (5 mL) was purged with nitrogen for 10 minutes, followed by the addition of $Na_2CO_3$ (0.17 g, 1.60 mmol) in water (0.5 mL). The reaction mixture was purged again with nitrogen for 10 minutes. $Pd(PPh_3)_4$ (0.03 g, 0.02 mmol) was added and the reaction mixture was heated to 90° C. for 5 h. The solvent was then evaporated under reduced pressure and the residue was extracted with EtOAc (20 mL×3). The combined organic layers were washed with water (20 mL) and brine (20 mL), dried over anhydrous $Na_2SO_4$, filtered and concentrated under reduced pressure. The crude material was purified by flash chromatography using 1.5% MeOH in DCM as eluent to afford Compound 44 (0.06 g, 27%) as a solid. $^1H$ NMR (400 MHz, DMSO) δ ppm 7.97 (d, J=2 Hz, 1H), 7.81 (s, 1H), 7.72 (s, 1H), 7.56 (d, J=8.4 Hz, 1H), 7.36 (dd, J=1.2 and 8.4 Hz, 1H), 4.47 (t, J=5 Hz, 2H), 3.67 (t, J=5 Hz, 2H), 3.54 (s, 3H), 3.21 (s, 4H), 2.19-1.88 (m, 11H). $[M+H]^+$ 415.48.

Example 40: 5-(2-cyclopropyl-1-(2-(2,2,2-trifluoroethoxy)ethyl)-1H-benzo[d]imidazol-6-yl)-1,3-dimethylpyridin-2(1H)-one (Compound 45)

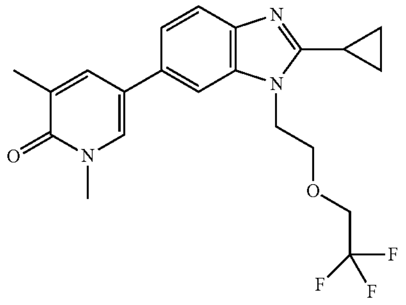 [SMILES: Cc1cc(-c2ccc3nc(C4CC4)n(CCOCC(F)(F)F)c3c2)cn(C)c1=O]

Step 1: Preparation of 1,3-dimethyl-5-(4-nitro-3-((2-(2,2,2-trifluoroethoxy)ethyl)amino)phenyl) pyridin-2(1H)-one

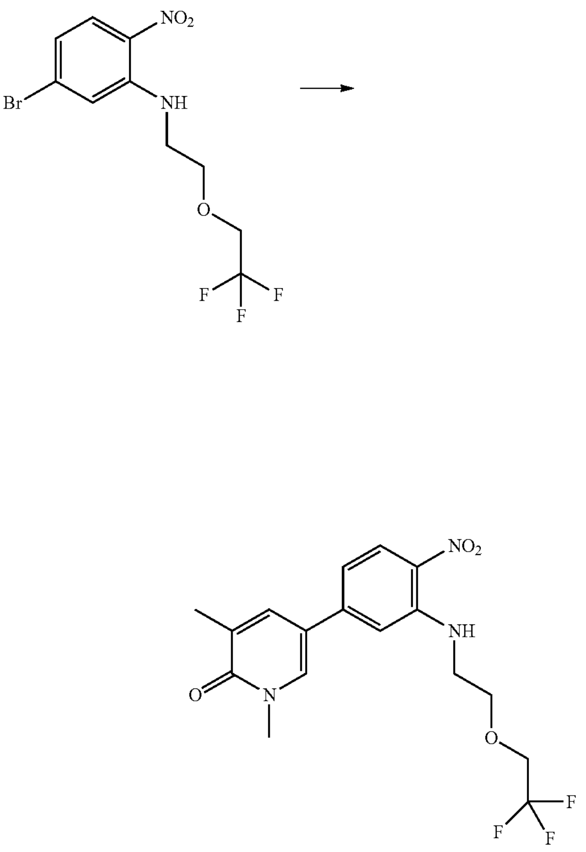

A stirred solution of 5-bromo-2-nitro-N-(2-(2,2,2-trifluoroethoxy)ethyl)aniline (Example 36, Step 1, 0.3 g, 0.87 mmol) and 1,3-dimethyl-5-(4,4,5,5-tetramethyl-1,3,2-dioxaborolan-2-yl)pyridin-2 (1H)-one (0.26 g, 1.04 mmol) in 1,4-dioxane (5 mL) was purged with nitrogen for 10 minutes followed by the addition of $Cs_2CO_3$ (0.71 g, 2.18 mmol) in water (0.5 mL). The mixture was again purged with nitrogen for 10 minutes. $Pd(PPh_3)_4$ (0.10 g, 0.08 mmol) was added and the reaction mixture was heated to 90° C. for 16 h. The solvent was then evaporated under vacuum and the residue was extracted with EtOAc (20 mL×3). The combined organic layers were washed with water (20 mL) and brine (20 mL), dried over anhydrous $Na_2SO_4$, filtered and concentrated under reduced pressure. The crude material was purified by silica gel chromatography using 1.0% MeOH in DCM as eluent. The product fractions were combined and concentrated to dryness to afford the title compound (0.25 g, 74%) as a solid. $[M+H]^+$ 386.54.

Step 2: Preparation of 5-(4-amino-3-((2-(2,2,2-trifluoroethoxy)ethyl)amino)phenyl)-1,3-dimethylpyridin-2(1H)-one

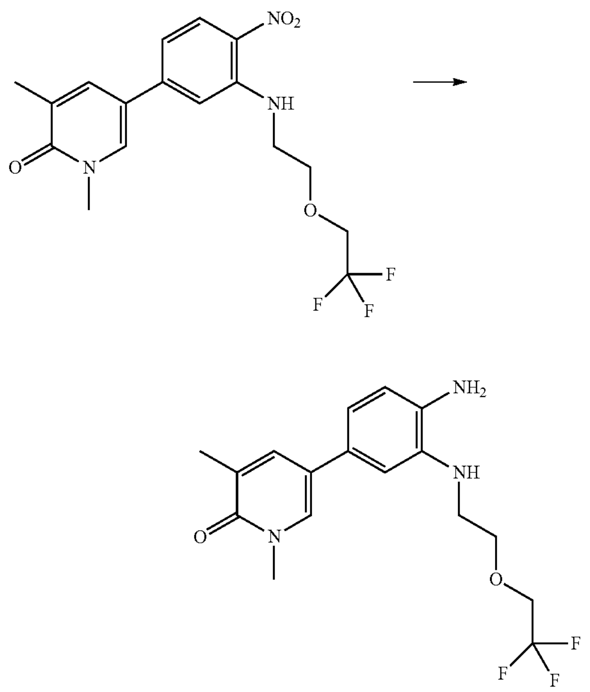

To a stirred solution of 1,3-dimethyl-5-(4-nitro-3-((2-(2,2,2-trifluoroethoxy)ethyl)amino)phenyl) pyridin-2 (1H)-one (0.2 g, 0.51 mmol) in MeOH (8 mL) was added zinc (0.35 g, 10 mmol) followed by acetic acid (0.08 mL, 1.53 mmol) and stirred at rt for 30 min. The resulting mixture was neutralized with $NaHCO_3$, poured into water (40 mL) and extracted with EtOAc (20 mL×3). The combined organic layers were washed with brine (25 mL), dried over anhydrous $Na_2SO_4$, filtered and concentrated under reduced pressure. The crude material was purified by silica gel chromatography using 1.3% MeOH in DCM as eluent. The product fractions were combined and concentrated under reduced pressure to afford the title compound (0.06 g, 92%) as a solid. $[M+H]^+$ 356.29.

Step 3: Preparation of Compound 45

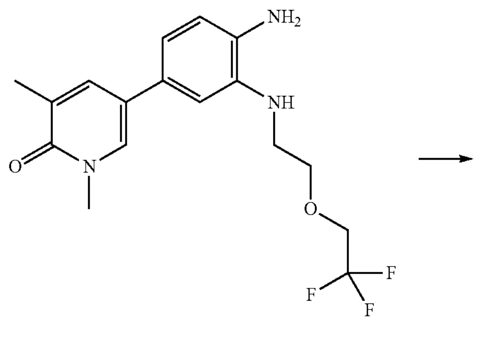

-continued

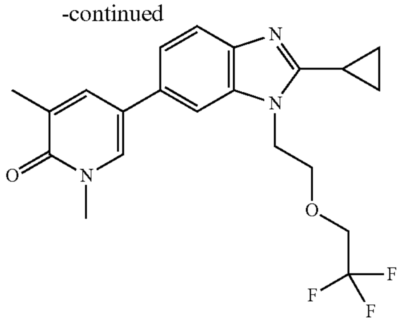

A solution of 5-(4-amino-3-((2-(2,2,2-trifluoroethoxy) ethyl)amino)phenyl)-1,3-dimethylpyridin-2 (1H)-one (0.17 g, 0.47 mmol) and cyclopropanecarbaldehyde (0.04 g, 0.57 mmol) in acetic acid (10 mL) was stirred at rt for 14 h. After completion of the reaction, the solvent was evaporated under vacuum and neutralized using saturated $NaHCO_3$ (20 mL) and extracted with EtOAc (25 mL×3), the organic layer was washed with brine (20 mL), dried over anhydrous $Na_2SO_4$, filtered and concentrated under reduced pressure. The crude material was purified by flash chromatography and the product was eluted in 1.5% MeOH in DCM as gradient to afford Compound 45 (0.06 g) as an off white solid (31% yield). 1H NMR (400 MHz, DMSO) δ ppm 7.95 (s, 1H), 7.79 (s, 1H), 7.69 (s, 1H), 7.47 (d, J=8 Hz, 1H), 7.33 (d, J=8 Hz, 1H), 4.58 (s, 2H), 4.07 (q, J=9.2 Hz, 2H), 3.97 (s, 2H), 3.53 (s, 3H), 2.27-2.25 (m, 1H), 2.10 (s, 3H), 1.05-1.03 (m, 4H). $[M+H]^+$ 405.42.

Example 41: 1,3-dimethyl-5-(2-(tetrahydro-2H-pyran-4-yl)-1-(3,3,3-trifluoro-2-methylpropyl)-1H-benzo[d]imidazol-6-yl)pyridin-2(1H)-one (Compounds 46a and 46b)

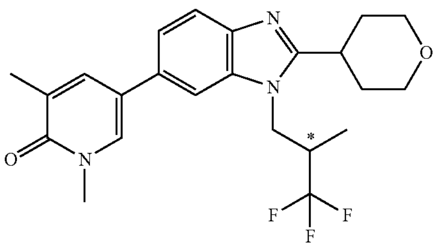 [SMILES: Cc1cc(-c2ccc3nc(C4CCOCC4)n(CC(C)C(F)(F)F)c3c2)cn(C)c1=O]

Step 1: Preparation of 5-bromo-2-nitro-N-(3,3,3-trifluoro-2-methylpropyl)aniline

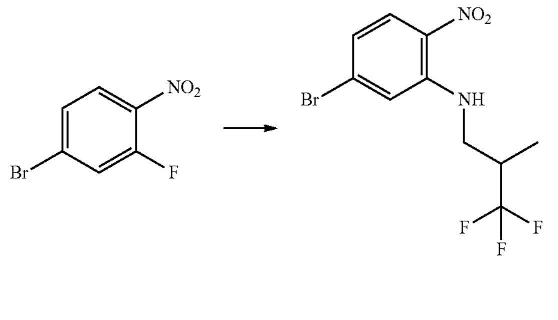 [SMILES: O=[N+]([O-])c1ccc(Br)cc1F ; CC(CNc1cc(Br)ccc1[N+](=O)[O-])C(F)(F)F]

TEA (0.24 mL, 2.48 mmol) was added to a stirred rt solution of 4-bromo-2-fluoro-1-nitrobenzene (0.4 g, 1.83 mmol) and 3,3,3-trifluoro-2-methylpropan-1-amine hydrochloride (0.36 g, 2.20 mmol) in ethanol (8 mL) and the reaction mixture was heated at 70° C. for 8 h. The resulting mixture was diluted with water (100 mL) and extracted with EtOAc (100 mL×3). The combined organic layers were washed with brine (30 mL), dried over anhydrous $Na_2SO_4$, filtered and concentrated under reduced pressure. The crude material was purified by silica gel chromatography using a gradient of 1-3% EtOAc in hexanes as eluent. The product fractions were combined and concentrated to dryness to afford the title compound (0.46 g, 52%) as a solid. $MH^-$326.9.

Step 2: Preparation of 5-bromo-$N^1$-(3,3,3-trifluoro-2-methylpropyl)benzene-1,2-diamine

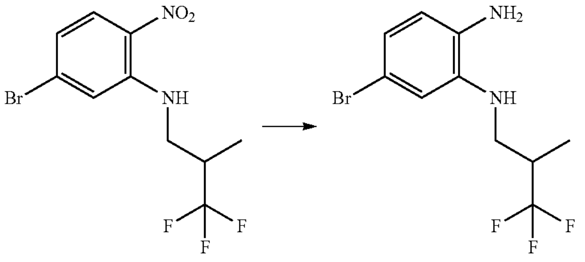 [SMILES: CC(CNc1cc(Br)ccc1[N+](=O)[O-])C(F)(F)F ; CC(CNc1cc(Br)ccc1N)C(F)(F)F]

To a rt suspension of 5-bromo-2-nitro-N-(3,3,3-trifluoro-2-methylpropyl)aniline (0.46 g, 1.40 mmol) in MeOH (8 mL) and water (4 mL) was added sodium dithionite (2.14 g, 16.88 mmol) and the reaction mixture was heated at 50° C. for 1 h. The reaction mixture was diluted with water (50 mL) and extracted with DCM (50 mL×3). The combined organic layers were washed with brine (50 mL), dried over anhydrous $Na_2SO_4$, filtered and concentrated under reduced pressure to afford the title compound (0.3 g, 71%) as a white solid. $[M+H]^+$ 297.1, 299.2.

Step 3: Preparation of 6-bromo-2-(tetrahydro-2H-pyran-4-yl)-1-(3,3,3-trifluoro-2-methylpropyl)-1H-benzo[d]imidazole

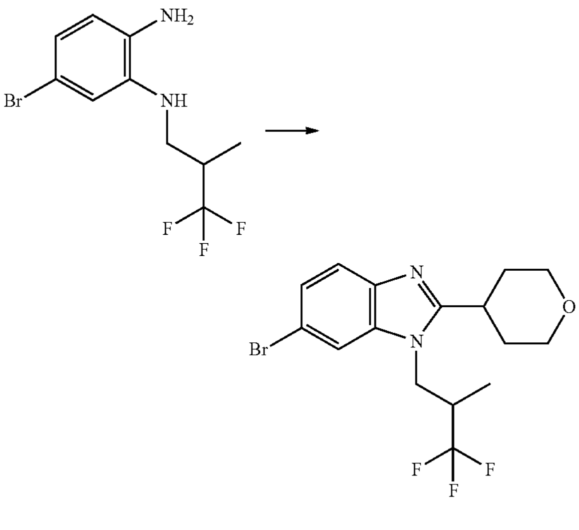

To a stirred solution of 5-bromo-$N^1$-(3,3,3-trifluoro-2-methylpropyl)benzene-1,2-diamine (0.3 g, 1.10 mmol) in acetic acid (5 mL) was added tetrahydro-2H-pyran-4-carbaldehyde (0.13 g, 1.21 mmol) and the reaction mixture was stirred at rt for 48 h. The resulting mixture was concentrated under reduced pressure. Saturated aqueous $NaHCO_3$ was added to the residue and aqueous layer was extracted with EtOAc (50 mL×3). The combined EtOAc layer was washed with brine solution (50 mL), dried over anhydrous $Na_2SO_4$, filtered and concentrated under reduced pressure. The crude material was purified by silica gel chromatography using a gradient of 35-40% EtOAc in hexanes as eluent. The product fractions were combined and concentrated in vacuo to afford the title compound (0.28 g, 70%) as a solid. $[M+H]^+$ 391.1, 393.2.

Step 4: Preparation of Compounds 46a and 46b

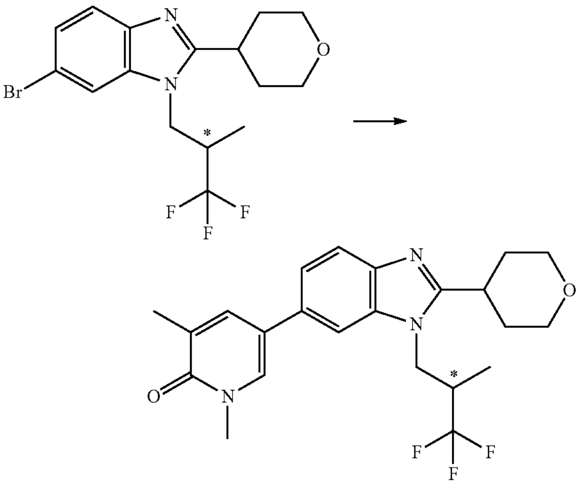

A stirred solution of 6-bromo-2-(tetrahydro-2H-pyran-4-yl)-1-(3,3,3-trifluoro-2-methylpropyl)-1H-benzo[d]imidazole (0.18 g, 0.51 mmol) and 1,3-dimethyl-5-(4,4,5,5-tetramethyl-1,3,2-dioxaborolan-2-yl)pyridin-2 (1H)-one (0.165 g, 0.66 mmol) in 1,4-dioxane (3 mL) was purged with nitrogen for 20 min, followed by the addition of $Na_2CO_3$ (0.162 g, 1.52 mmol) in water (0.3 mL) and purging with nitrogen for another 20 min. $Pd(PPh_3)_4$ (0.030 g, 0.022 mmol) was added and the reaction mixture was heated at 90° C. for 16 h. The resulting mixture was diluted with water (30 mL) and extracted with EtOAc (30 mL×3). The combined organic layers were washed with brine (30 mL), dried over anhydrous $Na_2SO_4$, filtered and concentrated under reduced pressure. The crude material was purified by silica gel chromatography using a gradient of 3-5% MeOH in DCM as eluent. The product fractions were combined and evaporated to dryness to give 0.09 g of Compound 46 as a racemic product. Compound 46 was further purified by chiral preparative HPLC (Chiralpak™ AD-H (250*21) mm, 5μ Column, Flow 70.0 mL/min) using (A) Liquid $CO_2$ (B) 0.3% DEA in IPA; isocratic (A):(B)=85:15 to afford a first fraction (Compound 46a, 0.025 g) and a second fraction (Compound 46b, 0.023 g) as solids (total 21% yield).

Compound 46a: $^1$H NMR (400 MHz, DMSO) 7.98 (d, J=2.4 Hz, 1H), 7.81 (s, 1H), 7.69 (s, 1H), 7.60 (d, J=8.4 Hz, 1H), 7.38 (dd, J=1.6 and 2 Hz, 1H), 4.58 (dd, J=7.6 and 15.2 Hz, 1H), 4.39 (dd, J=7.6 and 15.2 Hz, 1H), 3.97 (t, J=7.8 Hz, 2H), 3.54-3.48 (m, 4H), 3.48 (m, 1H), 3.19-3.15 (m, 2H), 2.11 (s, 3H), 1.98-1.911 (m, 1H), 1.87-1.76 (m, 3H), 1.12 (d, J=7.2 Hz, 3H). $[M+H]^+$ 434.4

Compound 46b: $^1H$ NMR (400 MHz, DMSO) 7.98 (d, J=2.4 Hz, 1H), 7.81 (s, 1H), 7.69 (s, 1H), 7.60 (d, J=8.4 Hz, 1H), 7.38 (dd, J=1.6 and 2 Hz, 1H), 4.58 (dd, J=7.6 and 15.2 Hz, 1H), 4.39 (dd, J=7.6 and 15.2 Hz, 1H), 3.97 (t, J=7.8 Hz, 2H), 3.54-3.48 (m, 4H), 3.48 (m, 1H), 3.19-3.15 (m, 2H), 2.11 (s, 3H), 1.98-1.911 (m, 1H), 1.87-1.76 (m, 3H), 1.12 (d, J=7.2 Hz, 3H). $[M+H]^+$ 434.4

Example 42: (R)-5-(1-(1-ethoxypropan-2-yl)-2-(tetrahydro-2H-pyran-4-yl)-1H-benzo[d]imidazol-6-yl)-1,3-dimethylpyridin-2(1H)-one (Compound 47)

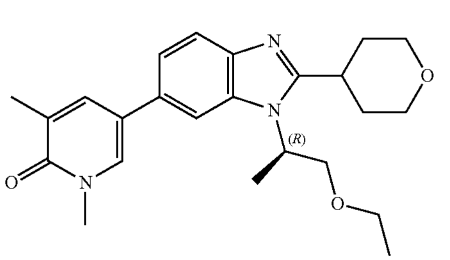

Step 1: Preparation of (R)-2-((5-bromo-2-nitrophenyl)amino)propan-1-ol

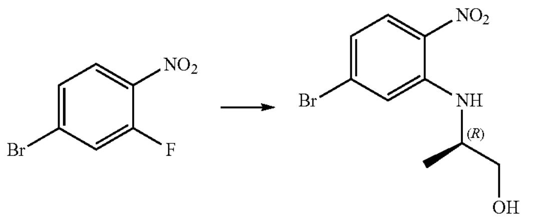

TEA (0.95 mL, 6.82 mmol) was added to a stirred solution of 4-bromo-2-fluoro-1-nitrobenzene (0.5 g, 2.27 mmol) and (R)-2-aminopropan-1-ol (0.34 g, 4.54 mmol) in ethanol (10 mL) and the reaction mixture was heated to 70° C. for 3 h. The resulting mixture was diluted with water (70 mL) and extracted with EtOAc (70 mL×3). The combined organic layers were dried over anhydrous $Na_2SO_4$, filtered and concentrated to dryness under reduced pressure to afford the title compound (0.6 g, 96%) as a solid. $^1H$ NMR (400 MHz, DMSO) δ 8.19 (d, J=7.6 Hz, 1H), 7.99 (d, J=9.2 Hz, 1H), 7.34 (d, J=2 Hz, 1H), 6.83 (dd, J=2 and 9.2 Hz, 1H), 5.08 (bs, 1H), 3.94-3.88 (m, 1H), 3.55-3.34 (m, 2H), 1.18 (dd, J=6.4 and 7.2 Hz, 1H), $[M+H]^+$ 275.13.

Step 2: Preparation of (R)-5-bromo-N-(1-ethoxypropan-2-yl)-2-nitroaniline

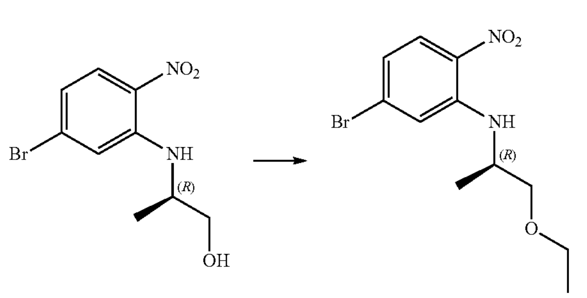

To a 0° C. stirred suspension of (R)-2-((5-bromo-2-nitrophenyl)amino)propan-1-ol (0.6 g, 2.18 mmol) in DMF (10 mL) was added 60% NaH in mineral oil (0.13 g, 3.27 mmol) and stirred at the same temperature for 30 min. Iodoethane (0.26 mL, 3.27 mmol) was added dropwise at 0° C. and the reaction mixture was allowed to stir at rt for 16 h. The reaction mixture was diluted with water (100 mL) and extracted with EtOAc (70 mL×3). The combined organic layers were washed with brine (70 mL), dried over anhydrous $Na_2SO_4$, filtered and concentrated under reduced pressure. The crude material was purified by silica gel chromatography using 10% EtOAc in hexanes as eluent. Fractions were combined and concentrated to dryness to afford the title compound (0.5 g, 75%) as an oil. $^1H$ NMR (400 MHz, DMSO) δ 8.19 (d, J=8 Hz, 1H), 7.98 (d, J=9.2 Hz, 1H), 7.36 (d, J=2 Hz, 1H), 6.83 (dd, J=2 and 9.2 Hz, 1H), 4.11-4.05 (m, 1H), 3.54-3.47 (m, 4H), 1.21 (d, J=6.4 Hz, 3H), 1.13 (t, J=7 Hz, 3H), $[M+H]^+$ 303.14.

Step 3: Preparation of (R)-5-(3-((1-ethoxypropan-2-yl)amino)-4-nitrophenyl)-1,3-dimethylpyridin-2(1H)-one

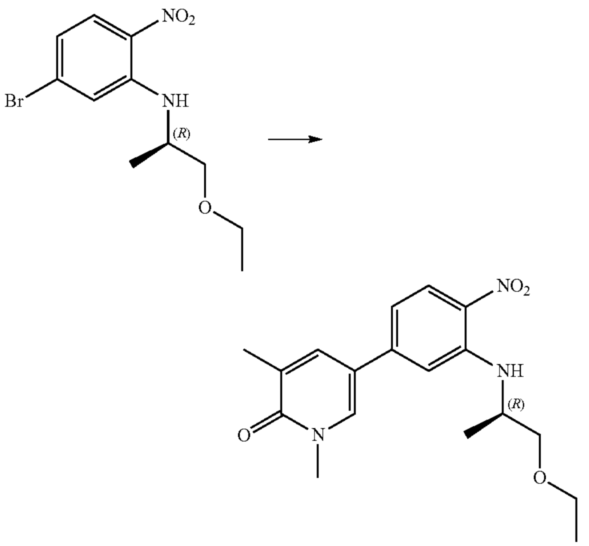

A stirred solution of (R)-5-bromo-N-(1-ethoxypropan-2-yl)-2-nitroaniline (0.5 g, 1.65 mmol) and 1,3-dimethyl-5-(4,4,5,5-tetramethyl-1,3,2-dioxaborolan-2-yl)pyridin-2 (1H)- one (0.49 g, 1.98 mmol) in DME (10 mL) was purged with nitrogen for 15 minutes at rt, followed by the addition of $Cs_2CO_3$ (1.34 g, 4.12 mmol) in water (2 mL) and purging with nitrogen for another 15 minutes. $Pd(PPh_3)_4$ (0.19 g, 0.16 mmol) was added and the reaction mixture was heated to 80° C. for 16 h. The resulting mixture was then filtered through Celite™ and washed with EtOAc (15 mL×3). The combined organic layers were washed with brine (50 mL), dried over anhydrous $Na_2SO_4$, filtered and concentrated under reduced pressure. The crude material was purified by silica gel chromatography using 1-2% MeOH in DCM as eluent. Product fractions were combined and evaporated to dryness to give the title compound (0.5 g, 88%) as a solid, $[M+H]^+$ 346.29

Step 4: Preparation of (R)-5-(4-amino-3-((1-ethoxypropan-2-yl)amino)phenyl)-1,3-dimethyl pyridin-2(1H)-one

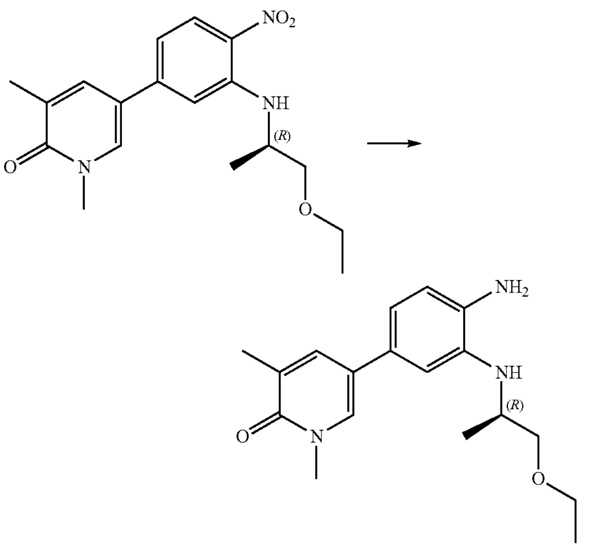

Sodium dithionite (3.34 g, 17.37 mmol) was added to a rt suspension of (R)-5-(3-((1-ethoxypropan-2-yl)amino)-4-nitrophenyl)-1,3-dimethylpyridin-2 (1H)-one (0.5 g, 1.45 mmol) in MeOH (20 mL) and water (10 mL) and the reaction mixture was heated to 50° C. for 1 h. The resulting mixture was diluted with water (50 mL) and extracted with DCM (50 mL×3). The combined DCM layers were washed with brine (50 mL), dried over anhydrous $Na_2SO_4$, filtered and concentrated under reduced pressure to afford the title compound (0.45 g, 94%) as an oil, $[M+H]^+$ 316.34.

Step 5: Preparation of Compound 47

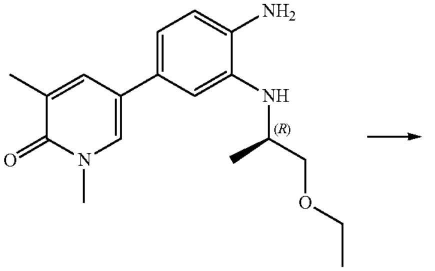

-continued

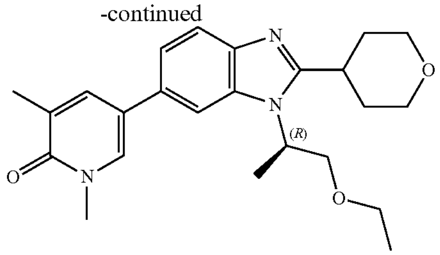

Tetrahydro-2H-pyran-4-carbaldehyde (0.11 g, 0.95 mmol) was added to a stirred solution of (R)-5-(4-amino-3-((1-ethoxypropan-2-yl)amino)phenyl)-1,3-dimethylpyridin-2 (1H)-one (0.25 g, 0.79 mmol) in acetic acid (12 mL) and the reaction mixture was stirred at rt for 48 h. The resulting mixture was then concentrated under reduced pressure, diluted with saturated aqueous $NaHCO_3$ (50 mL) and extracted with EtOAc (30 mL×3). The combined organic layers were washed with brine (50 mL), dried over anhydrous $Na_2SO_4$, filtered and concentrated under reduced pressure. The crude material was purified by silica gel chromatography using 4% MeOH in DCM as eluent. Fractions were combined and concentrated to afford Compound 47 (0.07 g, 22%) as a solid. $^1H$ NMR (400 MHz, MeOD) δ 7.87 (d, J=2.4 Hz, 1H), 7.84 (d, J=0.8 Hz, 1H), 7.78 (d, J=1.2 Hz, 1H), 7.67 (d, J=8.4 Hz, 1H), 7.41 (dd, J=1.6 and 8.4 Hz, 1H), 4.96-4.94 (m, 1H), 4.14-4.07 (m, 3H), 3.86-3.82 (m, 1H), 3.70 (s, 3H), 3.69-3.63 (m, 2H), 3.50-3.45 (m, 1H), 3.41-3.35 (m, 2H), 2.24 (s, 3H), 2.11-2.06 (m, 3H), 1.91-1.87 (m, 1H), 1.73 (d, J=7.2 Hz, 3H), 1.03 (t, J=7.0 Hz, 3H), $[M+H]^+$ 410.64.

Example 43: (S)-5-(1-(1-ethoxypropan-2-yl)-2-(tetrahydro-2H-pyran-4-yl)-1H-benzo[d]imidazol-6-yl)-1,3-dimethylpyridin-2(1H)-one (Compound 48)

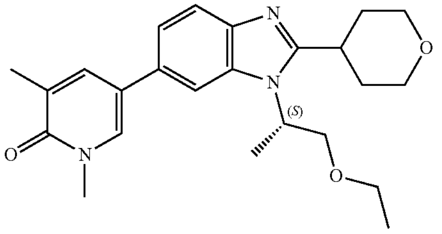

Step 1: Preparation of tert-butyl (S)-(1-ethoxypropan-2-yl)carbamate

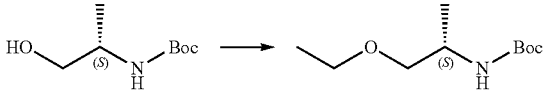

To a stirred 0° C. solution of suspension of tert-butyl (S)-(1-hydroxypropan-2-yl)carbamate (1.4 g, 7.99 mmol) in DMF (14 mL) was added 60% NaH in mineral oil (0.48 g, 11.98 mmol) and the reaction mixture was stirred at this temperature for 30 min. Iodoethane (0.97 mL, 11.98 mmol) was then added dropwise at 0° C. and the reaction was allowed to stir at rt for 16 h. The resulting mixture was then diluted with water (70 mL) and extracted with EtOAc (50 mL×3). The combined organic layers were washed with brine (70 mL), dried over anhydrous $Na_2SO_4$, filtered and concentrated under reduced pressure. The crude material was purified by silica gel chromatography using 20% EtOAc in hexanes as eluent. Fractions were combined and concentrated to dryness to afford the title compound (1.1 g, 68%) as an oil.

Step 2: Preparation of (S)-1-ethoxypropan-2-amine hydrochloride

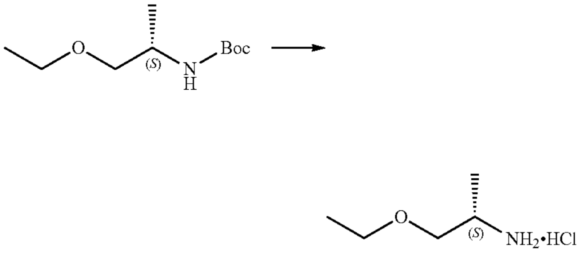

To a 10° C. stirred solution of tert-butyl (S)-(1-ethoxypropan-2-yl)carbamate (1.1 g, 5.41 mmol) in 1,4-dioxane (5 mL) was added 6M HCl in dioxane (11 mL) and the reaction mixture was allowed to stir at rt for 16 h. The resulting mixture was then concentrated under reduced pressure and triturated with EtOAc (5 mL) to afford the title compound (0.7 g, 93%) as a solid.

Step 3: Preparation of (S)-5-bromo-N-(1-ethoxypropan-2-yl)-2-nitroaniline

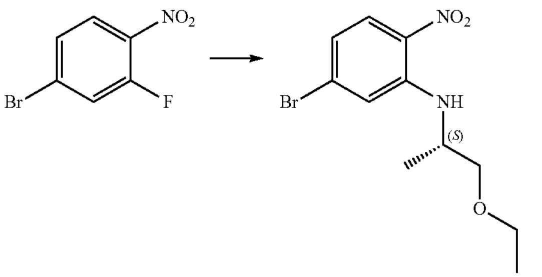

TEA (0.95 mL, 6.82 mmol) was added to a stirred rt solution of 4-bromo-2-fluoro-1-nitrobenzene (0.5 g, 2.27 mmol) and (S)-1-ethoxypropan-2-amine hydrochloride (0.45 g, 3.27 mmol) in ethanol (10 mL) and the reaction mixture was heated to 70° C. for 3 h. The resulting mixture was then diluted with water (70 mL) and extracted with EtOAc (70 mL×3). The combined organic layers were dried over anhydrous $Na_2SO_4$, filtered and concentrated under reduced pressure to afford the title compound (0.65 g, 94%) as an oil. $^1$H NMR (400 MHz, DMSO) δ 8.19 (d, J=8 Hz, 1H), 7.98 (d, J=9.2 Hz, 1H), 7.36 (d, J=2 Hz, 1H), 6.83 (dd, J=2 and 9.2 Hz, 1H), 4.11-4.06 (m, 1H), 3.54-3.47 (m, 4H), 1.21 (d, J=6.4 Hz, 3H), 1.12 (t, J=6.8 Hz, 3H), $[M+H]^+$ 303.14.

Step 4: Preparation of (S)-5-(3-((1-ethoxypropan-2-yl)amino)-4-nitrophenyl)-1,3-dimethylpyridin-2(1H)-one

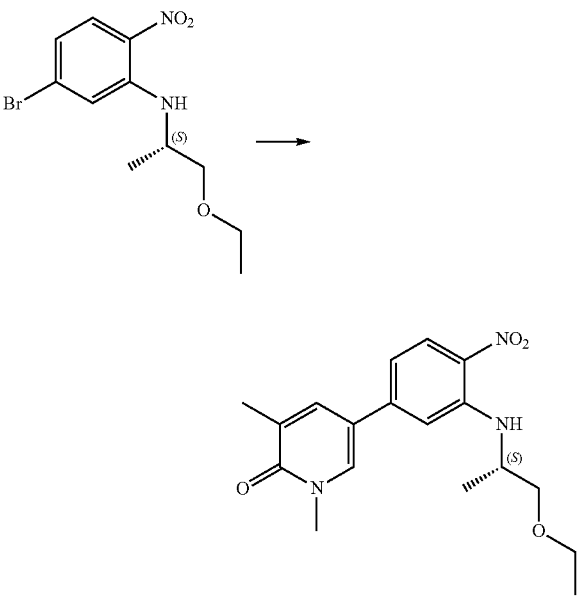

A stirred solution of (S)-5-bromo-N-(1-ethoxypropan-2-yl)-2-nitroaniline (0.65 g, 2.14 mmol) and 1,3-dimethyl-5-(4,4,5,5-tetramethyl-1,3,2-dioxaborolan-2-yl)pyridin-2(1H)-one (0.64 g, 2.57 mmol) in DME (13 mL) was purged with nitrogen for 15 minutes at rt, followed by the addition of $Cs_2CO_3$ (1.75 g, 5.36 mmol) in water (2 mL) and purging with nitrogen for another 15 minutes. $Pd(PPh_3)_4$ (0.19 g, 0.16 mmol) was added and the reaction mixture was heated to 80° C. for 16 h. The resulting mixture was then filtered through Celite™ and washed with EtOAc (15 mL×3). The combined organic layers were washed with brine (50 mL), dried over anhydrous $Na_2SO_4$, filtered and concentrated under reduced pressure. The crude material was purified by silica gel chromatography using 2% MeOH in DCM as eluent. Product fractions were combined and evaporated to dryness to give the title compound (0.7 g, 94%) as a solid, $[M+H]^+$ 346.29.

Step 5: Preparation of (S)-5-(4-amino-3-((1-ethoxypropan-2-yl)amino)phenyl)-1,3-dimethyl pyridin-2(1H)-one

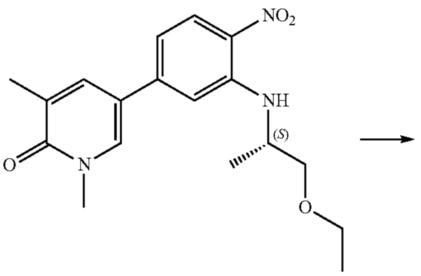

-continued

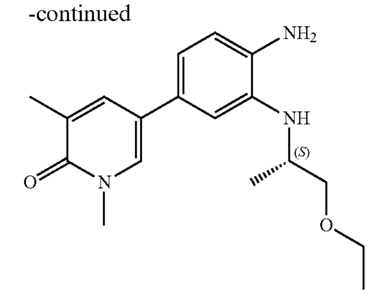

Sodium dithionite (4.67 g, 24.32 mmol) was added to a rt suspension of (S)-5-(3-((1-ethoxypropan-2-yl)amino)-4-nitrophenyl)-1,3-dimethylpyridin-2 (1H)-one (0.7 g, 2.03 mmol) in MeOH (20 mL) and water (10 mL) and the reaction mixture was heated to 50° C. for 1 h. The resulting mixture was diluted with water (50 mL) and extracted with DCM (50 mL×3). The combined DCM layers were washed with brine (50 mL), dried over anhydrous $Na_2SO_4$, filtered and concentrated under reduced pressure to afford the title compound (0.6 g, 94%) as an oil, $[M+H]^+$ 316.34.

Step 6: Preparation of Compound 48

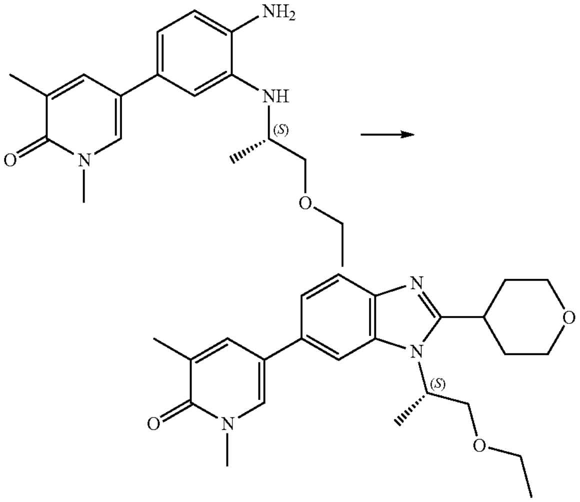

Tetrahydro-2H-pyran-4-carbaldehyde (0.13 g, 1.14 mmol) was added to a stirred solution of (S)-5-(4-amino-3-((1-ethoxypropan-2-yl)amino)phenyl)-1,3-dimethylpyridin-2 (1H)-one (0.3 g, 0.95 mmol) in acetic acid (15 mL) and the reaction mixture was stirred at rt for 48 h. The resulting mixture was then concentrated under reduced pressure, diluted with saturated aqueous $NaHCO_3$ (60 mL) and extracted with EtOAc (40 mL×3). The combined organic layers were washed with brine (50 mL), dried over anhydrous $Na_2SO_4$, filtered and concentrated under reduced pressure. The crude material was purified by silica gel chromatography using 4% MeOH in DCM as eluent. Fractions were combined and concentrated to afford Compound 48 (0.08 g, 21%) as a solid. $^1H$ NMR (400 MHz, MeOD) δ 7.88 (d, J=2.4 Hz, 1H), 7.84 (d, J=0.8 Hz, 1H), 7.78 (d, J=1.2 Hz, 1H), 7.68 (d, J=8.4 Hz, 1H), 7.42 (dd, J=1.6 and 8.4 Hz, 1H), 4.96-4.95 (m, 1H), 4.14-4.07 (m, 3H), 3.86-3.82 (m, 1H), 3.70 (s, 3H), 3.69-3.63 (m, 2H), 3.50-3.46 (m, 1H), 3.40-3.35 (m, 2H), 2.24 (s, 3H), 2.11-2.05 (m, 3H), 1.91-1.87 (m, 1H), 1.73 (d, J=6.8 Hz, 3H), 1.03 (t, J=7.0 Hz, 3H). $[M+H]^+$ 410.64.

Example 44: 5-(1-(2-isopropoxyethyl)-2-(tetrahydro-2H-pyran-4-yl)-1H-benzo[d]imidazole-6-yl)-1,3-dimethylpyridin-2(1H)-one (Compound 49)

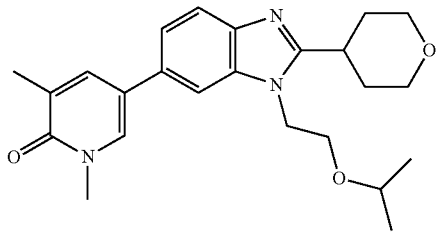 [SMILES: Cc1cc(-c2ccc3nc(C4CCOCC4)n(CCOC(C)C)c3c2)cn(C)c1=O]

Step 1: Preparation of 5-bromo-N-(2-isopropoxyethyl)-2-nitroaniline

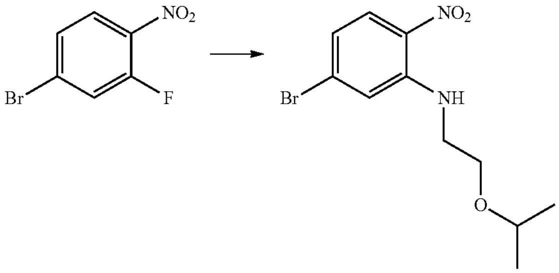 [SMILES: O=[N+]([O-])c1ccc(Br)cc1F ; CC(C)OCCNc1cc(Br)ccc1[N+](=O)[O-]]

TEA (0.3 g, 2.95 mmol) was added to a rt stirred solution of 4-bromo-2-fluoro-1-nitrobenzene (0.5 g, 2.27 mmol) and 2-isopropoxyethan-1-amine hydrochloride (0.38 g, 2.72 mmol) in ethanol (8 mL) and the reaction mixture was heated at 70° C. for 6 h. The resulting mixture was then diluted with water (100 mL) and extracted with EtOAc (100 mL×3). The combined EtOAc layers were washed with brine (50 mL), dried over anhydrous $Na_2SO_4$, filtered and concentrated under reduced pressure. The crude material was purified by silica gel chromatography using a gradient of 10-30% EtOAc in hexane as eluent. Fractions were combined and evaporated to dryness to afford the title compound (0.6 g, 57%) as a solid, $[M+H]^+$ 303.2, 305.2.

Step 2: Preparation of 5-bromo-N1-(2-isopropoxyethyl)benzene-1,2-diamine

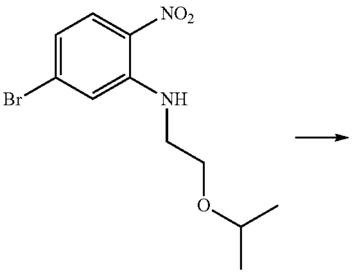

-continued

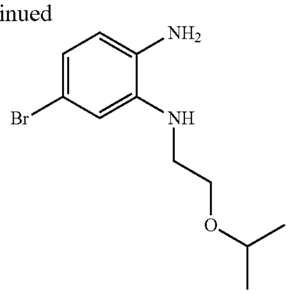

Sodium dithionite (3 g, 23.76 mmol) was added to a rt suspension of 5-bromo-N-(2-isopropoxyethyl)-2-nitroaniline (0.6 g, 1.98 mmol) in MeOH (10 mL) and water (4 mL) and the reaction mixture was heated at 50° C. for 1 h. The resulting mixture was diluted with water (50 mL) and extracted with EtOAc (50 mL×3). The combined organic layers were washed with brine (50 mL), dried over anhydrous $Na_2SO_4$, filtered and concentrated in vacuo to afford the title compound (0.54 g, 58%) as a solid, $M^{+2}$ 275.23.

Step 3: Preparation of 6-bromo-1-(2-isopropoxyethyl)-2-(tetrahydro-2H-pyran-4-yl)-1H-benzo[d]imidazole

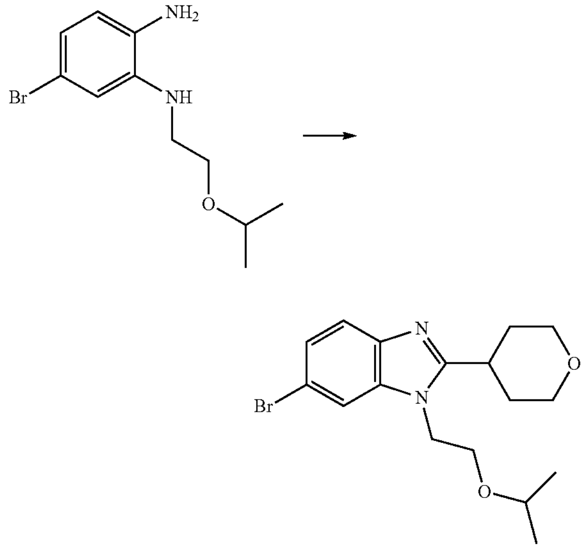

Tetrahydro-2H-pyran-4-carbaldehyde (0.25 g, 2.2 mmol) was added to a stirred rt solution of 5-bromo-$N^1$-(2-isopropoxyethyl)benzene-1,2-diamine (0.5 g, 1.83 mmol) in acetic acid (6 mL) and the reaction mixture was stirred for 48 h at the same temperature. The resulting mixture was concentrated, saturated aqueous $NaHCO_3$ (60 mL) was added to the residue and the aqueous layer was extracted with EtOAc (50 mL×3). The combined organic layers were washed with brine (50 mL), dried over anhydrous $Na_2SO_4$, filtered and concentrated in vacuo. The crude material was purified by silica gel chromatography using a gradient of 35-40% EtOAc in hexane as eluent. The fractions were combined and the concentrated to dryness to afford the title compound (0.28 g, 42%) as a white solid. $M^{+2}$ 369.24

Step 4: Preparation of Compound 49

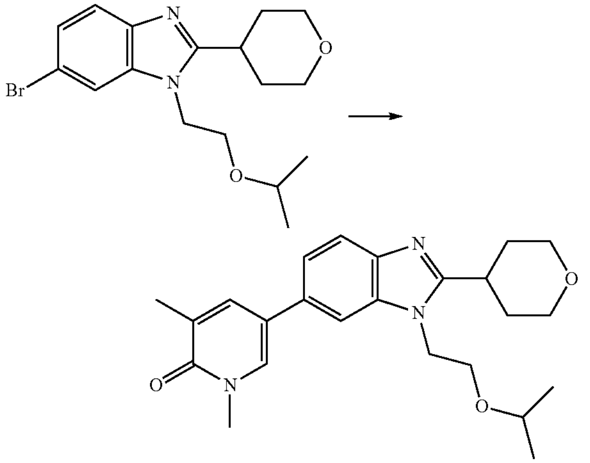

A stirred solution of 6-bromo-1-(2-isopropoxyethyl)-2-(tetrahydro-2H-pyran-4-yl)-1H-benzo[d]imidazole (0.27 g, 0.74 mmol) and 1,3-dimethyl-5-(4,4,5,5-tetramethyl-1,3,2-dioxaborolan-2-yl)pyridin-2 (1H)-one (0.24 g, 0.97 mmol) in 1,4-dioxane (4 mL) was purged with nitrogen for 20 min, followed by the addition of $NaHCO_3$ (0.29 g, 2.24 mmol) in water (0.3 mL) and purging with nitrogen for another 20 min. $Pd(PPh_3)_4$ (0.025 g, 0.022 mmol) was added at rt and the reaction mixture was heated at 90° C. for 16 h. The resulting mixture was diluted with water (30 mL) and extracted with EtOAc (30 mL×3). The combined organic layers were washed with brine (30 mL), dried over anhydrous $Na_2SO_4$, filtered and concentrated in vacuo. The crude material was purified by silica gel chromatography using 2-3% MeOH in DCM as eluent. Fractions were combined and concentrated to give 0.13 g, which was further purified by preparative HPLC using 20-60% MeCN in water to afford Compound 49 (0.075 g, 25%) as a solid. $^1H$ NMR (400 MHz, DMSO) 7.97 (s, 1H), 7.81 (s, 1H), 7.71 (s, 1H), 7.57 (d, J=8 Hz, 1H), 7.35 (d, J=8 Hz, 1H), 4.43 (s, 2H), 3.97 (d, J=10 Hz, 2H), 3.69 (s, 2H), 3.53 (s, 3H), 3.51-3.42 (m, 3H), 3.35-3.32 (m, 1H), 2.10 (s, 3H), 1.94-1.80 (m, 4H), 0.95 (d, J=6 Hz, 6H). $[M+H]^+$ 410.4.

Example 45: (R)-5-(1-(1-methoxypropan-2-yl)-2-((tetrahydro-2H-pyran-4-yl)methyl)-1H-benzo[d]imidazol-6-yl)-1,3-dimethylpyridin-2(1H)-one (Compound 50)

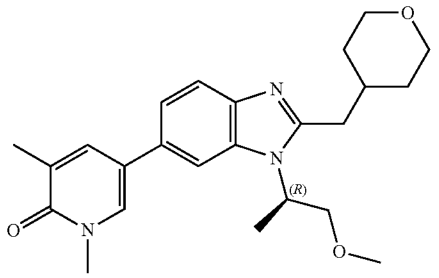

Step 1: Preparation of (R)-5-bromo-N-(1-methoxy-propan-2-yl)-2-nitroaniline

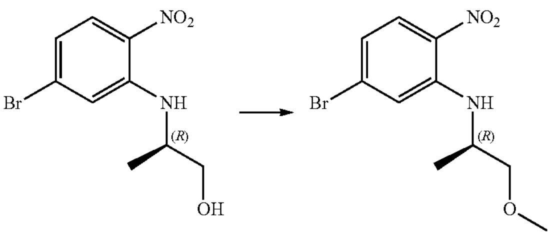

To a stirred 0° C. suspension of (R)-2-((5-bromo-2-nitrophenyl)amino)propan-1-ol (Example 42, Step 1, 0.6 g, 2.18 mmol) in DMF (12 mL) was added 60% NaH in mineral oil (0.13 g, 3.27 mmol) and the reaction mixture was stirred at this temperature for 30 minutes. Iodomethane (0.2 mL, 3.27 mmol) was then added dropwise at 0° C. and the mixture was allowed to stir at rt for 16 h. The resulting mixture was then diluted with water (100 mL) and extracted with EtOAc (70 mL×3). The combined organic layers were washed with brine (70 mL), dried over anhydrous $Na_2SO_4$, filtered and concentrated in vacuo to afford the title compound (0.6 g, 95%) as an oil, $M^{+2}$ 291.18.

Step 2: Preparation of (R)-5-(3-((1-methoxypropan-2-yl)amino)-4-nitrophenyl)-1,3-dimethyl pyridin-2(1H)-one

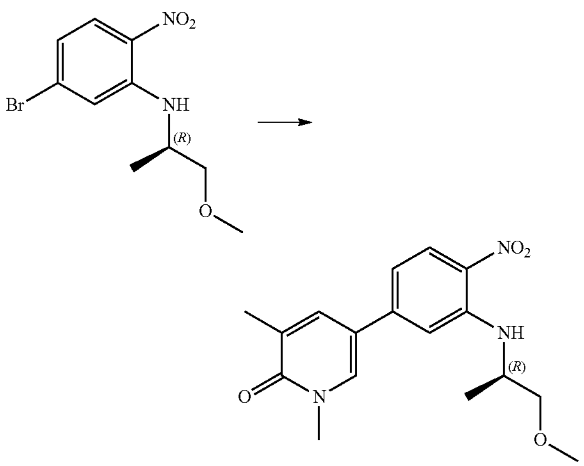

A stirred solution of (R)-5-bromo-N-(1-methoxypropan-2-yl)-2-nitroaniline (0.6 g, 2.07 mmol) and 1,3-dimethyl-5-(4,4,5,5-tetramethyl-1,3,2-dioxaborolan-2-yl)pyridin-2(1H)-one (0.62 g, 2.49 mmol) in DME (12 mL) was purged with nitrogen for 15 minutes at rt, followed by the addition of $Cs_2CO_3$ (1.69 g, 5.19 mmol) in water (3 mL) and purging with nitrogen for another 15 minutes. $Pd(PPh_3)_4$ (0.24 g, 0.21 mmol) was added and the reaction mixture was heated to 80° C. for 4 h. The resulting mixture was then filtered through Celite™ and washed with EtOAc (15 mL×3). The combined organic layers were washed with brine (50 mL), dried over anhydrous $Na_2SO_4$, filtered and concentrated in vacuo. The crude material was purified by silica gel chromatography using 1-2% MeOH in DCM as eluent. Fractions were combined and their solvent was evaporated to dryness to afford the title compound (0.4 g, 58%) as a solid, $[M+H]^+$ 332.29.

Step 3: Preparation of (R)-5-(4-amino-3-((1-methoxypropan-2-yl)amino)phenyl)-1,3-dimethylpyridin-2(1H)-one

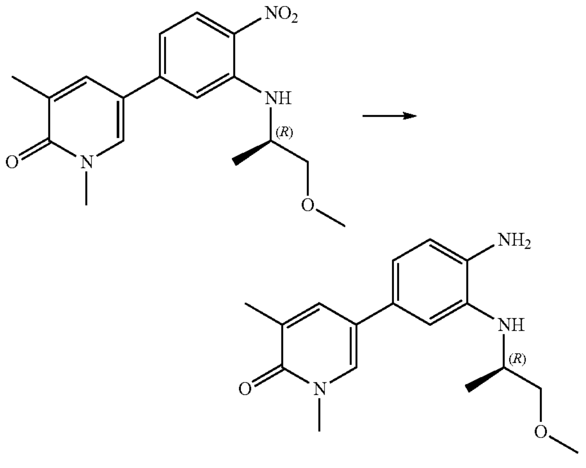

Sodium dithionite (2.8 g, 14.48 mmol) was added to a rt suspension of (R)-5-(3-((1-methoxypropan-2-yl)amino)-4-nitrophenyl)-1,3-dimethylpyridin-2 (1H)-one (0.4 g, 1.21 mmol) in MeOH (15 mL) and water (8 mL) and the reaction mixture was heated at 50° C. for 1 h. The resulting mixture was diluted with water (50 mL) and extracted with DCM (50 mL×3). The combined DCM layers were washed with brine (50 mL), dried over anhydrous $Na_2SO_4$, filtered and concentrated to dryness to afford the title compound (0.3 g, 82%) as a solid, $[M+H]^+$ 302.39.

Step 4: Preparation of Compound 50

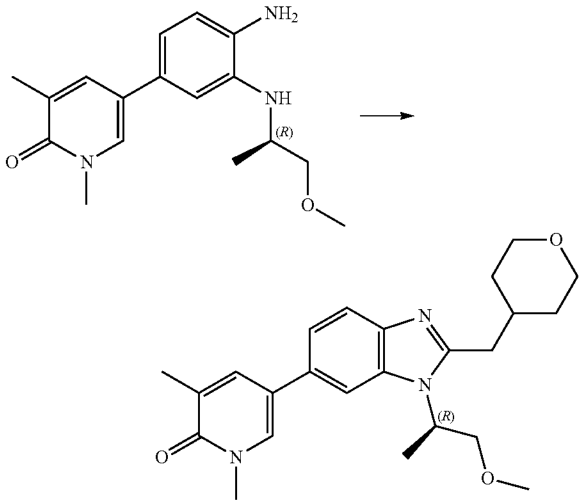

To a stirred solution of (R)-5-(4-amino-3-((1-methoxy-propan-2-yl)amino)phenyl)-1,3-dimethylpyridin-2 (1H)-one (0.15 g, 0.5 mmol) in acetic acid (5 mL) was added 2-(tetrahydro-2H-pyran-4-yl)acetaldehyde (0.076 g, 0.6 mmol). The reaction mixture was stirred at rt for 24 h. The resulting mixture was concentrated under vacuum, diluted with saturated $NaHCO_3$ (50 mL) and extracted with EtOAc (30 mL×3). The combined organic layers were washed with brine (50 mL), dried over anhydrous $Na_2SO_4$, filtered and concentrated under reduced pressure. The crude material was purified by flash chromatography using 3% MeOH in DCM as eluent. Fractions were collected and evaporated to dryness to afford Compound 50 (0.05 g, 24%) as a solid. $^1H$ NMR (400 MHz, MeOD) δ 7.87 (d, J=2.4 Hz, 1H), 7.84 (s, 1H), 7.77 (s, 1H), 7.64 (d, J=8.4 Hz, 1H), 7.41 (dd, J=1.6 and 8.4 Hz, 1H), 4.96-4.94 (m, 1H), 4.10 (t, J=9.8 Hz, 1H), 3.95 (d, J=11.6 Hz, 2H), 3.78 (dd, J=4.4 and 10.4 Hz, 1H), 3.70 (s, 3H), 3.48-3.41 (m, 2H), 3.27 (s, 3H), 2.92 (d, J=7.2 Hz, 2H), 2.25-2.22 (m, 4H), 1.71 (d, J=7.2 Hz, 3H), 1.68-1.64 (m, 2H), 1.50-1.44 (m, 2H). $[M+H]^+$ 410.64.

Example 46: (R)-5-(2-(3,3-difluorocyclobutyl)-1-(1-methoxypropan-2-yl)-1H-benzo[d]imidazol-6-yl)-1,3-dimethylpyridin-2(1H)-one (Compound 51)

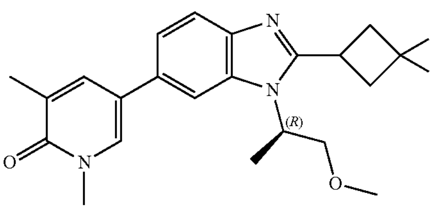

Step 1: Preparation of (R)—N-(4-(1,5-dimethyl-6-oxo-1,6-dihydropyridin-3-yl)-2-((1-methoxy propan-2-yl)amino)phenyl)-3,3-difluorocyclobutane-1-carboxamide

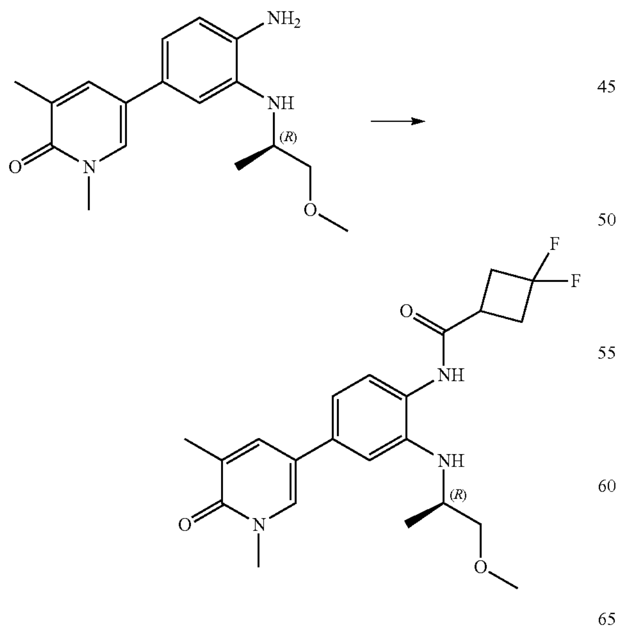

To a stirred 0° C. solution of 3,3-difluorocyclobutane-1-carboxylic acid (0.1 g, 0.75 mmol) in DCM (2 mL) was added HATU (0.28 g, 0.75 mmol) and the reaction was stirred at this temperature for 30 minutes under nitrogen. A solution of (R)-5-(4-amino-3-((1-methoxypropan-2-yl)amino)phenyl)-1,3-dimethylpyridin-2 (1H)-one (Example 45, Step 3, 0.15 g, 0.5 mmol) in DCM (1 mL) was then added dropwise at 0° C. followed by DIPEA (0.26 mL, 1.5 mmol) and the mixture was allowed to stir at rt for 2 h. The resulting mixture was diluted with water (50 mL) and extracted with DCM (30 mL×3). The combined organic layers were washed with brine (50 mL), dried over anhydrous $Na_2SO_4$, filtered and concentrated under reduced pressure to afford the title compound (0.2 g, 100%) as an oil, $[M+H]^+$ 420.35. The product was used in next step without further purification.

Step 2: Preparation of Compound 51

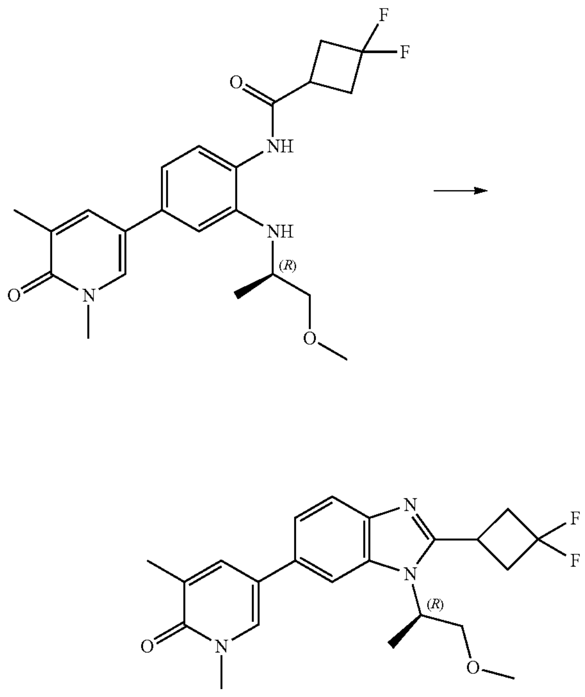

A stirred solution of (R)—N-(4-(1,5-dimethyl-6-oxo-1,6-dihydropyridin-3-yl)-2-((1-methoxy propan-2-yl)amino)phenyl)-3,3-difluorocyclobutane-1-carboxamide (0.2 g, 0.048 mmol) in acetic acid (5 mL) was heated to 110° C. for 16 h. The resulting mixture was concentrated under vacuum, neutralized with saturated $NaHCO_3$ (100 mL) and extracted with EtOAc (30 mL×3). The combined organic layers were washed with brine (50 mL), dried over anhydrous $Na_2SO_4$, filtered and concentrated under reduced pressure. The crude material was purified by flash chromatography using 2% MeOH in DCM as eluent. Fractions were combined and evaporated to dryness to afford Compound 51 (0.06 g, 31%) as a solid. $^1H$ NMR (400 MHz, DMSO-d6) δ 7.98 (d, J=2.4 Hz, 1H), 7.80 (d, J=1.2 Hz, 1H), 7.74 (d, J=0.8 Hz, 1H), 7.63 (d, J=8.4 Hz, 1H), 7.41 (dd, J=1.6 and 8.4 Hz, 1H), 4.72-4.71 (m, 1H), 3.98 (t, J=9.6 Hz, 1H), 3.77 (dt, J=8.4 and 2.8 Hz, 1H), 3.68-3.65 (m, 1H), 3.55 (s, 3H), 3.18 (s, 3H), 3.14-3.05 (m, 4H), 2.11 (s, 3H), 1.58 (d, J=7.2 Hz, 3H). $[M+H]^+$ 410.64.

Example 47: (R)-5-(2-(3,3-difluorocyclobutyl)-1-(1-ethoxypropan-2-yl)-1H-benzo[d]imidazol-6-yl)-1,3-dimethylpyridin-2(1H)-one (Compound 52)

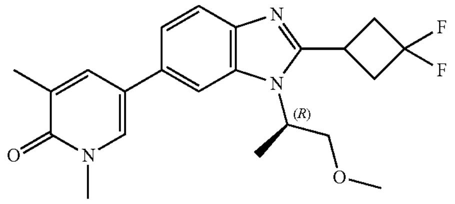

Step 1: Preparation of (R)—N-(4-(1,5-dimethyl-6-oxo-1,6-dihydropyridin-3-yl)-2-((1-ethoxypropan-2-yl)amino)phenyl)-3,3-difluorocyclobutane-1-carboxamide

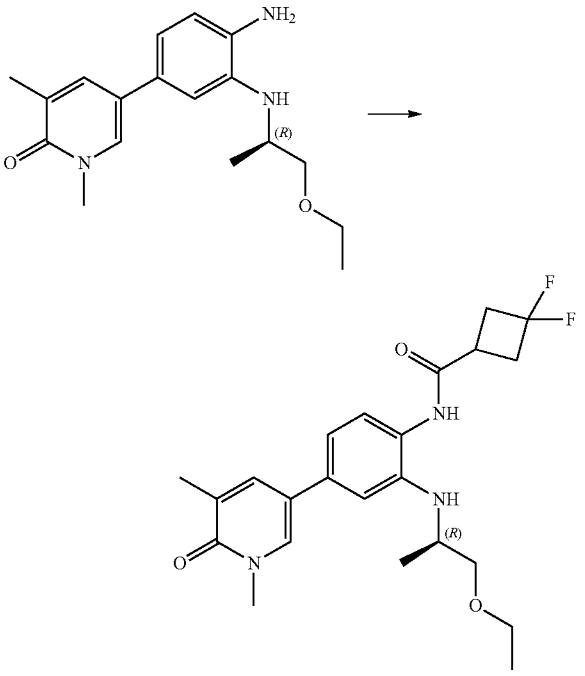

HATU (0.36 g, 0.95 mmol) was added to a stirred 0° C. solution of 3,3-difluorocyclobutane-1-carboxylic acid (0.13 g, 0.95 mmol) in DCM (3 mL) at the reaction mixture was stirred at this temperature for 30 minutes under nitrogen. A solution of (R)-5-(4-amino-3-((1-ethoxypropan-2-yl)amino) phenyl)-1,3-dimethylpyridin-2 (1H)-one (Example 42, Step 4, 0.2 g, 0.63 mmol) in DCM (2 mL) was then added dropwise at 0° C. followed by DIPEA (0.26 mL, 1.5 mmol) and the mixture was allowed to stir at rt for 2 h. The resulting mixture was diluted with water (50 mL) and extracted with DCM (30 mL×3). The combined organic layers were washed with brine (50 mL), dried over anhydrous $Na_2SO_4$, filtered and concentrated under reduced pressure to afford the title compound (0.3 g, 100%) as an oil, $[M+H]^+$ 434.40. The product was used in next step without further purification.

Step 2: Preparation of Compound 52

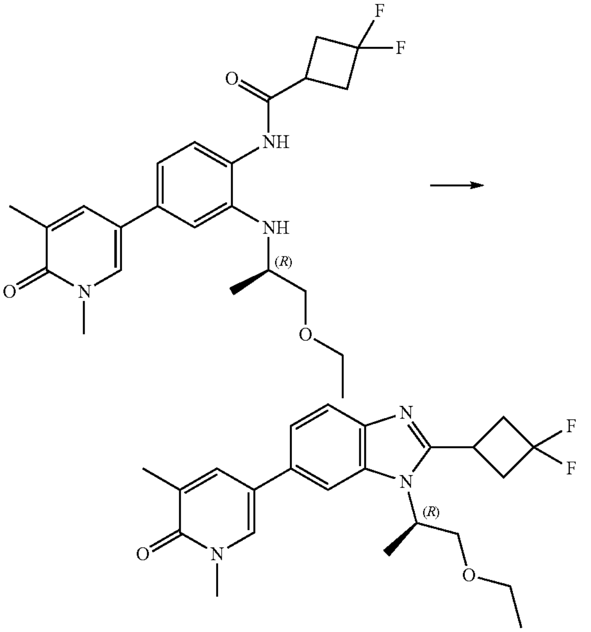

A stirred solution of (R)—N-(4-(1,5-dimethyl-6-oxo-1,6-dihydropyridin-3-yl)-2-((1-ethoxypropan-2-yl)amino)phenyl)-3,3-difluorocyclobutane-1-carboxamide (0.3 g, 0.069 mmol) in acetic acid (10 mL) was heated to 110° C. for 16 h. The resulting mixture was concentrated under vacuum, neutralized with saturated $NaHCO_3$ (150 mL) and extracted with EtOAc (50 mL×3). The combined organic layers were washed with brine (50 mL), dried over anhydrous $Na_2SO_4$, filtered and concentrated under reduced pressure. The crude material was purified by flash chromatography using 2% MeOH in DCM as eluent. Fractions were combined and evaporated to dryness to afford Compound 52 (0.07 g, 24%) as a solid. $^1H$ NMR (400 MHz, DMSO-d6) δ 7.98 (d, J=1.2 Hz, 1H), 7.80 (s, 1H), 7.75 (s, 1H), 7.63 (d, J=8.4 Hz, 1H), 7.41 (d, J=8.4 Hz, 1H), 4.70-4.69 (m, 1H), 4.00 (t, J=9.6 Hz, 1H), 3.77 (t, J=7.4 Hz, 1H), 3.73-3.69 (m, 1H), 3.54 (s, 3H), 3.42-3.40 (m, 1H), 3.31-3.29 (m, 1H), 3.12-3.10 (m, 4H), 2.11 (s, 3H), 1.58 (d, J=7.2 Hz, 3H), 0.97 (t, J=7.0 Hz, 3H). $[M+H]^+$ 416.40.

Example 48: (S)-5-(2-(3,3-difluorocyclobutyl)-1-(2-ethoxypropyl)-1H-benzo[d]imidazol-6-yl)-1,3-dimethylpyridin-2(1H)-one (Compound 53)

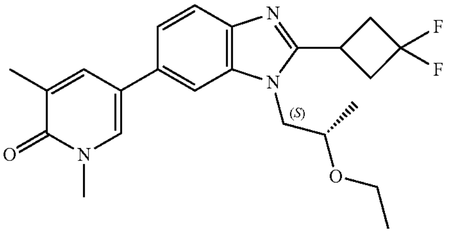

Step 1: Preparation of (S)-5-(3-((2-ethoxypropyl)amino)-4-nitrophenyl)-1,3-dimethylpyridin-2(1H)-one

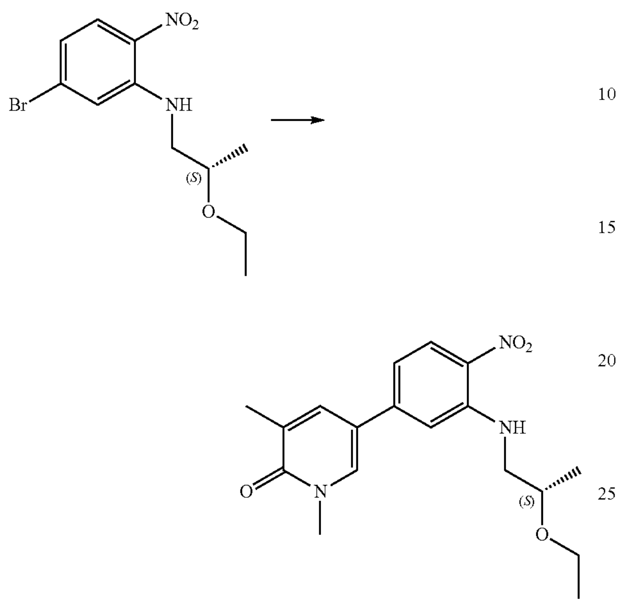

A stirred solution of (S)-5-bromo-N-(2-ethoxypropyl)-2-nitroaniline (Example 35, Step 1, 0.5 g, 1.65 mmol) and 1,3-dimethyl-5-(4,4,5,5-tetramethyl-1,3,2-dioxaborolan-2-yl)pyridin-2 (1H)-one (0.49 g, 1.98 mmol) in DME (10 mL) was purged at rt with nitrogen for 15 minutes followed by the addition of $Cs_2CO_3$ (1.34 g, 4.12 mmol) in water (3 mL) and purging with nitrogen for another 15 minutes. $Pd(PPh_3)_4$ (0.19 g, 0.16 mmol) was then added and the reaction mixture was heated to 80° C. for 16 h. The resulting mixture was filtered through Celite™ and washed with EtOAc (15 mL×3). The organic layer was washed with brine (50 mL), dried over anhydrous $Na_2SO_4$, filtered and concentrated under reduced pressure. The crude material was purified by silica gel chromatography using 1-2% MeOH in DCM as eluent. Product fractions were combined and evaporated to dryness to give the title compound (0.5 g, 88%) as a solid, $[M+H]^+$ 346.29.

Step 2: Preparation of (S)-5-(4-amino-3-((2-ethoxypropyl)amino)phenyl)-1,3-dimethylpyridin-2(1H)-one

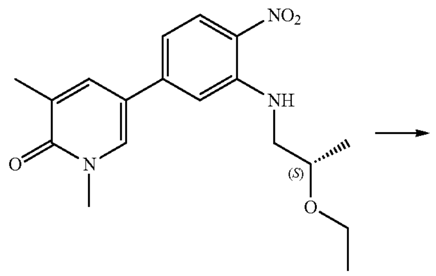

-continued

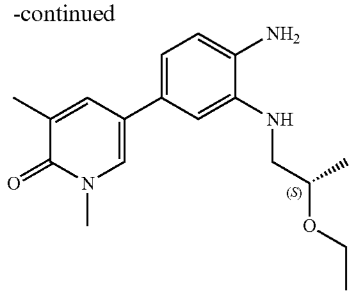

Sodium dithionite (3.33 g, 17.4 mmol) was added to a rt suspension of (S)-5-(3-((2-ethoxypropyl)amino)-4-nitrophenyl)-1,3-dimethylpyridin-2 (1H)-one (0.5 g, 1.45 mmol) in MeOH (20 mL) and water (10 mL) and the reaction mixture was heated to 50° C. for 1 h. The resulting mixture was diluted with water (50 mL) and extracted with DCM (50 mL×3). The combined DCM layers were washed with brine (50 mL), dried over anhydrous $Na_2SO_4$, filtered and concentrated under reduced pressure to afford the title compound (0.4 g, 88%) as an oil, $[M+H]^+$ 316.34.

Step 3: Preparation of (S)—N-(4-(1,5-dimethyl-6-oxo-1,6-dihydropyridin-3-yl)-2-((2-ethoxypropyl)amino)phenyl)-3,3-difluorocyclobutane-1-carboxamide

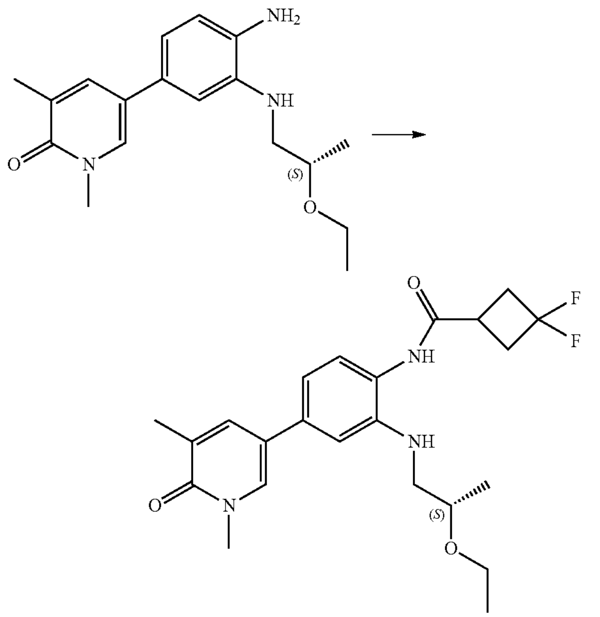

HATU (0.36 g, 0.95 mmol) was added to a stirred 0° C. solution of 3,3-difluorocyclobutane-1-carboxylic acid (0.13 g, 0.95 mmol) in DCM (2 mL) and the reaction was stirred at this temperature for 30 minutes under nitrogen. A solution of (S)-5-(4-amino-3-((2-ethoxypropyl)amino)phenyl)-1,3-dimethylpyridin-2 (1H)-one (0.2 g, 0.63 mmol) in DCM (2 mL) was then added dropwise at 0° C. followed by DIPEA (0.13 mL, 1.90 mmol) and the mixture was allowed to stir at rt for 2 h. The resulting mixture was diluted with water (50 mL) and extracted with DCM (30 mL×2). The combined organic layers were washed with brine (50 mL), dried over anhydrous $Na_2SO_4$, filtered and concentrated under reduced pressure to afford the title compound (0.2 g, 73%) as an oil, $[M+H]^+$ 434.4 The product was used in the next step without further purification.

Step 4: Preparation of Compound 53

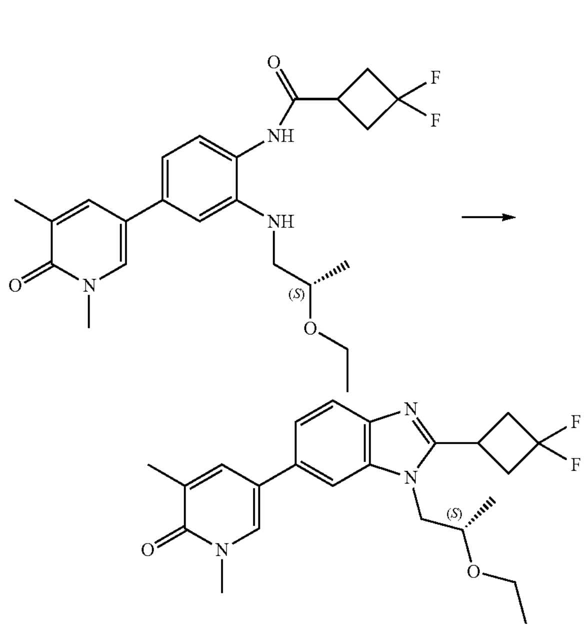

A solution of (S)—N-(4-(1,5-dimethyl-6-oxo-1,6-dihydropyridin-3-yl)-2-((2-ethoxypropyl)amino) phenyl)-3,3-difluorocyclobutane-1-carboxamide (0.2 g, 0.048 mmol) in acetic acid (6 mL) was heated to 110° C. for 16 h. The reaction mixture was then concentrated under reduced pressure, neutralized with saturated aqueous $NaHCO_3$ (120 mL) and extracted with EtOAc (30 mL×3). The combined organic layers were washed with brine (50 mL), dried over anhydrous $Na_2SO_4$, filtered and concentrated under reduced pressure. The crude material was purified by flash chromatography using 1-2% MeOH in DCM as eluent. Product fractions were combined and evaporated to dryness to afford Compound 53 (0.1 g, 52%) as a solid. $^1H$ NMR (400 MHz, DMSO-d6) δ 7.97 (d, J=2.4 Hz, 1H), 7.81 (d, J=1.2 Hz, 1H), 7.73 (d, J=1.6 Hz, 1H), 7.62 (d, J=8.4 Hz, 1H), 7.38 (dd, J=1.6 and 8.4 Hz, 1H), 4.28 (dd, J=3.6 and 15.2 Hz, 1H), 4.16 (dd, J=8.8 and 14.8 Hz, 1H), 3.87-3.82 (m, 1H), 3.77-3.72 (m, 1H), 3.54 (s, 3H), 3.45-3.39 (m, 1H), 3.15-2.97 (m, 5H), 2.11 (s, 3H), 1.19 (d, J=6 Hz, 3H), 0.83 (t, J=6.8 Hz, 3H). $[M+H]^+$ 416.20.

Example 49: (R)-5-(2-(3,3-difluorocyclobutyl)-1-(2-ethoxypropyl)-1H-benzo[d]imidazol-6-yl)-1,3-dimethylpyridin-2(1H)-one (Compound 54)

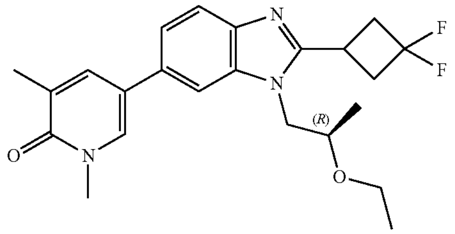

Step 1: Preparation of (R)-5-(3-((2-ethoxypropyl) amino)-4-nitrophenyl)-1,3-dimethylpyridin-2(1H)-one

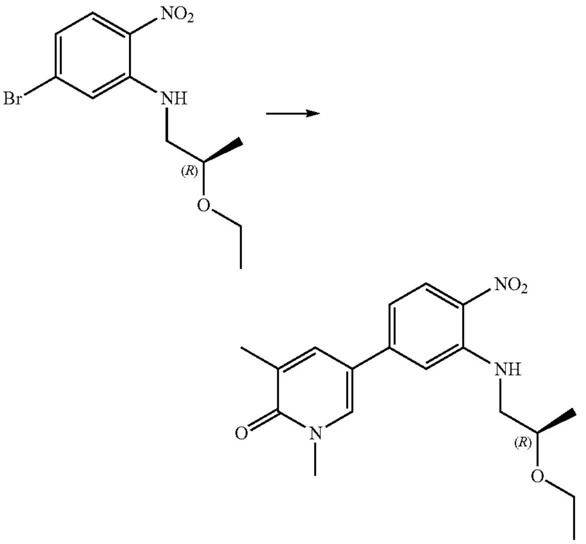

The reaction and isolation procedure depicted in Step 1 of Example 48 was followed except for the use of (R)-5-bromo-N-(2-ethoxypropyl)-2-nitroaniline (Example 34, Step 1, 0.5 g, 1.65 mmol) to afford the title compound (0.5 g, 88%) as a solid, $[M+H]^+$ 346.29.

Step 2: Preparation of (R)-5-(4-amino-3-((2-ethoxypropyl)amino)phenyl)-1,3-dimethylpyridin-2(1H)-one

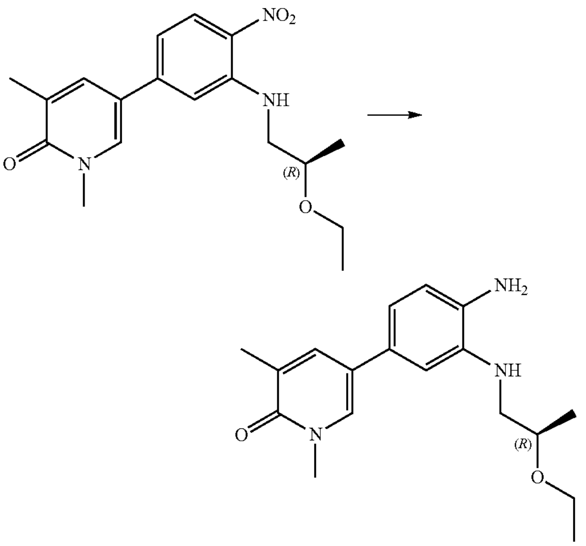

The procedure of Example 48 (step 2) was followed except for the use of (R)-5-(3-((2-ethoxypropyl)amino)-4-nitrophenyl)-1,3-dimethylpyridin-2 (1H)-one (0.5 g, 1.45 mmol) as starting material, to afford the title compound (0.4 g, 88%) as an oil, $[M+H]^+$ 316.34.

Step 3: Preparation of (R)—N-(4-(1,5-dimethyl-6-oxo-1,6-dihydropyridin-3-yl)-2-((2-ethoxypropyl)amino)phenyl)-3,3-difluorocyclobutane-1-carboxamide

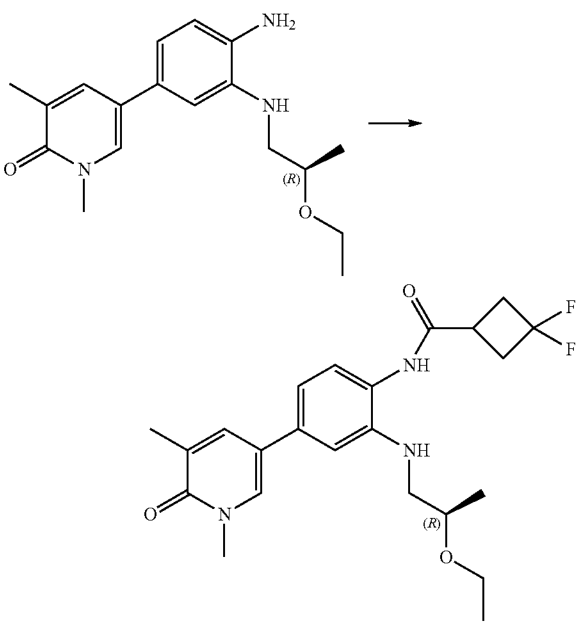

Step 3 of the procedure of Example 48 was followed except for the use of the isomer (R)-5-(4-amino-3-((2-ethoxypropyl)amino)phenyl)-1,3-dimethylpyridin-2 (1H)-one (0.2 g, 0.63 mmol) and afforded the title compound (0.2 g, 73%) as an oil, $[M+H]^+$ 434.3. The product was used in the next step without further purification.

Step 4: Preparation of Compound 54

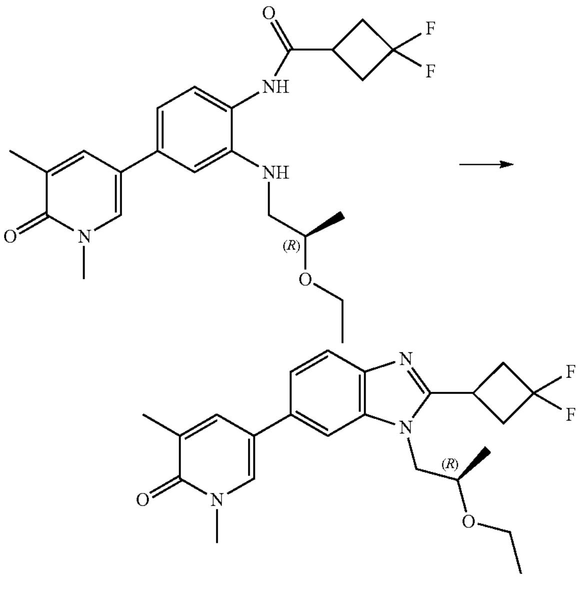

The procedure described in step 4 of Example 48 was followed except for the use of (R)—N-(4-(1,5-dimethyl-6-oxo-1,6-dihydropyridin-3-yl)-2-((2-ethoxypropyl)amino)phenyl)-3,3-difluorocyclo butane-1-carboxamide (0.2 g, 0.048 mmol). Isolation of the product by flash chromatography (1-2% MeOH in DCM) afforded Compound 54 (0.1 g, 52%) as a solid. $^1$H NMR (400 MHz, DMSO-d6) δ 7.97 (d, J=2.4 Hz, 1H), 7.81 (t, J=1.2 Hz, 1H), 7.73 (d, J=1.2 Hz, 1H), 7.62 (d, J=8.4 Hz, 1H), 7.38 (dd, J=1.6 and 8.4 Hz, 1H), 4.28 (dd, J=3.2 and 2.8 Hz, 1H), 4.16 (dd, J=8.8 and 8.4 Hz, 1H), 3.87-3.82 (m, 1H), 3.77-3.72 (m, 1H), 3.54 (s, 3H), 3.45-3.39 (m, 1H), 3.15-2.97 (m, 5H), 2.12 (s, 3H), 1.19 (d, J=6.4 Hz, 3H), 0.83 (t, J=7.0 Hz, 3H). $[M+H]^+$ 416.20.

Example 50: (S)-5-(2-(4,4-difluorocyclohexyl)-1-(2-ethoxypropyl)-1H-benzo[d]imidazol-6-yl)-1,3-dimethylpyridin-2(1H)-one (Compound 55)

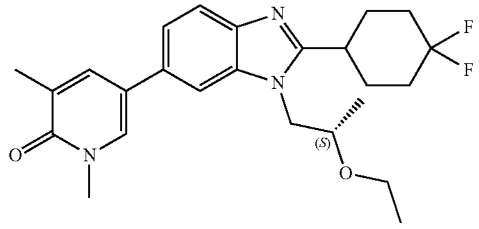

Step 1: Preparation of (S)—N-(4-(1,5-dimethyl-6-oxo-1,6-dihydropyridin-3-yl)-2-((2-ethoxypropyl)amino)phenyl)-4,4-difluorocyclohexane-1-carboxamide

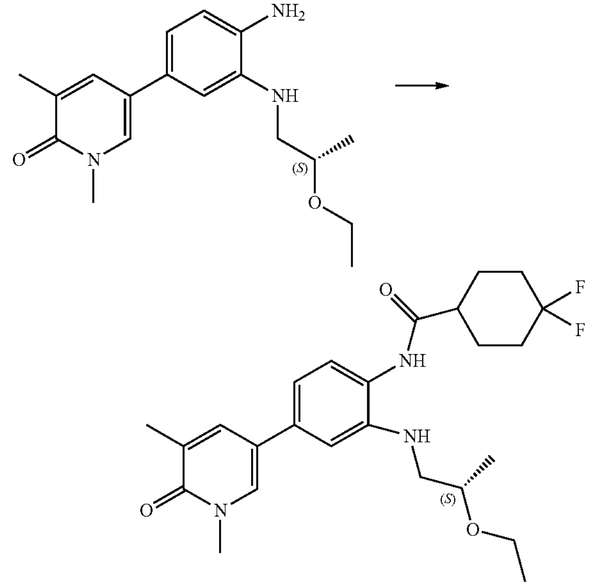

HATU (0.36 g, 0.95 mmol) was added to a stirred 0° C. solution of 4,4-difluorocyclohexane-1-carboxylic acid (0.13 g, 0.95 mmol) in DCM (3 mL) and the reaction was stirred at this temperature for 30 minutes under nitrogen. A solution of (S)-5-(4-amino-3-((2-ethoxypropyl)amino)phenyl)-1,3-dimethylpyridin-2 (1H)-one (Example 48, Step 2, 0.2 g, 0.63 mmol) in DCM (2 mL) was the added dropwise at 0° C.

followed by DIPEA (0.33 mL, 1.90 mmol) and the reaction mixture was allowed to stir at rt for 2 h. The resulting mixture was then diluted with water (50 mL) and extracted with DCM (30 mL×3). The combined organic layers were washed with brine (50 mL), dried over anhydrous $Na_2SO_4$, filtered and concentrated under reduced pressure. The crude material was then purified by flash chromatography using 2% MeOH in DCM as eluent. Product fractions were combined and evaporated to dryness to afford the title compound (0.2 g, 68%) as a solid, $[M+H]^+$ 462.46.

Step 2: Preparation of Compound 55

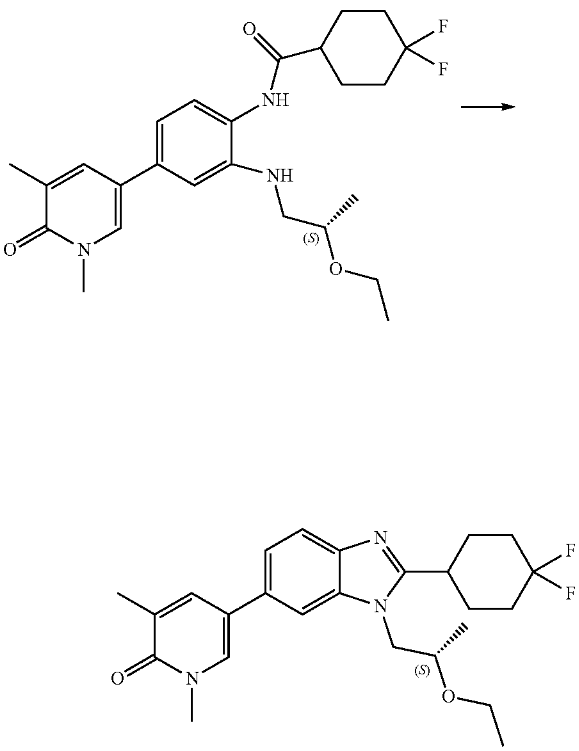

A solution of (S)—N-(4-(1,5-dimethyl-6-oxo-1,6-dihydropyridin-3-yl)-2-((2-ethoxypropyl)amino) phenyl)-4,4-difluorocyclohexane-1-carboxamide (0.2 g, 0.043 mmol) in acetic acid (5 mL) was heated at 110° C. for 16 h. The resulting mixture was concentrated under reduced pressure, neutralized with saturated aqueous $NaHCO_3$ (100 mL) and extracted with EtOAc (50 mL×3). The combined organic layers were washed with brine (50 mL), dried over anhydrous $Na_2SO_4$, filtered and concentrated under reduced pressure. The crude material was purified by flash chromatography using 2% MeOH in DCM as eluent. Product fractions were combined and concentrated to dryness to afford Compound 55 (0.07 g, 24%) as a solid. $^1H$ NMR (400 MHz, DMSO-d6) δ 7.96 (d, J=2.4 Hz, 1H), 7.80 (d, J=1.2 Hz, 1H), 7.71 (d, J=1.2 Hz, 1H), 7.56 (d, J=8.4 Hz, 1H), 7.35 (dd, J=1.2 and 2 Hz, 1H), 4.34-4.21 (m, 2H), 3.80-3.75 (m, 1H), 3.54 (s, 3H), 3.46-3.38 (m, 1H), 3.32-3.27 (m, 1H), 3.05-2.98 (m, 1H), 2.23-2.16 (m, 2H), 2.11 (s, 3H), 2.06-1.80 (m, 6H), 1.20 (d, J=6 Hz, 3H), 0.86 (t, J=6.8 Hz, 3H). $[M+H]^+$ 444.51.

Example 51: (S)-5-(2-(4,4-difluorocyclohexyl)-1-(1-methoxypropan-2-yl)-1H-benzo[d]imidazol-6-yl)-1,3-dimethylpyridin-2(1H)-one (Compound 56)

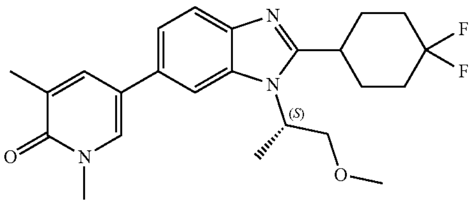

Step 1: Preparation of tert-butyl (S)-(1-methoxypropan-2-yl)carbamate

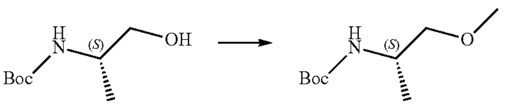

To a stirred 0° C. solution of tert-butyl (S)-(1-hydroxypropan-2-yl)carbamate (1.0 g, 5.71 mmol) in DMF (10 mL) was added 60% NaH in mineral oil (0.34 g, 8.57 mmol) and the reaction was stirred at this temperature for 30 min. Iodomethane (0.54 mL, 8.57 mmol) was added dropwise at 0° C. and the reaction mixture was allowed to stir at rt for 6 h. The resulting mixture was diluted with water (100 mL) and extracted with EtOAc (50 mL×3). The combined organic layers were washed with brine (50 mL), dried over anhydrous $Na_2SO_4$, filtered and concentrated under reduced pressure. The crude material was purified by silica gel chromatography using 10% EtOAc in hexanes as eluent. Product fractions were combined and concentrated in vacuo to afford the title compound (0.9 g, 83%) as an oil. $^1H$ NMR (400 MHz, $CDCl_3$) δ 4.71 (s, 1H), 3.83 (s, 1H), 3.40-3.31 (m, 5H), 1.48 (s, 9H), 1.18 (d, J=6.8 Hz, 3H).

Step 2: Preparation of (S)-1-methoxypropan-2-amine hydrochloride

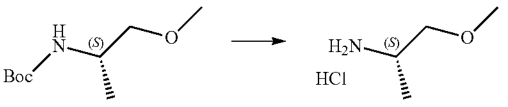

To a rt stirred solution of tert-butyl (S)-(1-methoxypropan-2-yl)carbamate (0.9 g, 4.76 mmol) in DCM (7 mL) was added 4N HCl in dioxane (10 mL) and the reaction mixture was allowed to stir for 8 h. The resulting mixture was concentrated under reduced pressure and triturated with $Et_2O$ (8 mL) to afford the title compound (0.5 g, 84%) as a solid which was used as such without further purification.

Step 3: Preparation of (S)-5-bromo-N-(1-methoxypropan-2-yl)-2-nitroaniline

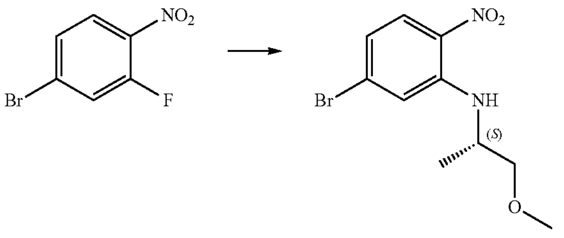

TEA (0.96 mL, 9.54 mmol) was added to a stirred rt solution of 4-bromo-2-fluoro-1-nitrobenzene (0.7 g, 3.18 mmol) and (S)-1-methoxypropan-2-amine hydrochloride (0.48 g, 3.82 mmol) in ethanol (10 mL) and the reaction mixture was heated at 70° C. for 2 h. The resulting mixture was diluted with water (80 mL) and extracted with EtOAc (50 mL×3). The combined organic layers were washed with brine (60 mL), dried over anhydrous $Na_2SO_4$, filtered and concentrated under reduced pressure to afford the title compound (0.6 g, 92%) as a solid, $[M+H]^+$ 289.03.

Step 4: Preparation of (S)-5-bromo-$N^1$-(1-methoxypropan-2-yl)benzene-1,2-diamine

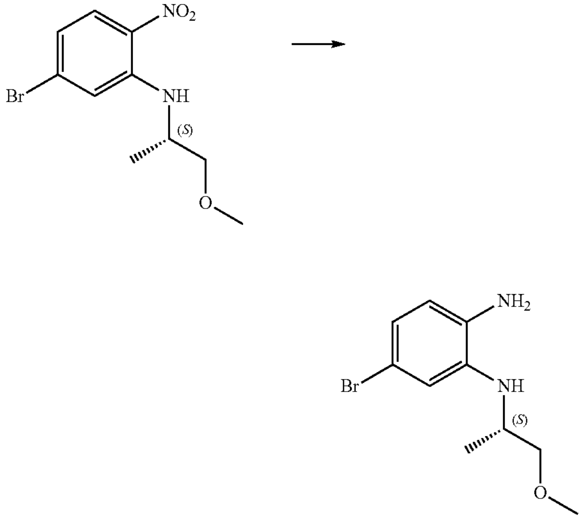

Sodium dithionite (1.62 g, 24.91 mmol) was added to a rt suspension of (S)-5-bromo-N-(1-methoxypropan-2-yl)-2-nitroaniline (0.6 g, 2.07 mmol) in MeOH (10 mL) and water (10 mL) and the reaction mixture was allowed to stir for 2 h. The resulting mixture was diluted with water (60 mL) and extracted with EtOAc (40 mL×3). The combined organic layers were washed with brine (40 mL), dried over anhydrous $Na_2SO_4$, filtered and concentrated under reduced pressure. The crude material was purified by silica gel chromatography using 20% EtOAc in hexanes as eluent. Product fractions were combined and evaporated to dryness to afford the title compound (0.42 g, 78%) as a solid, $[M+H]^+$ 261.04.

Step 5: Preparation of (S)—N-(4-bromo-2-((1-methoxypropan-2-yl)amino)phenyl)-4,4-difluoro cyclohexane-1-carboxamide

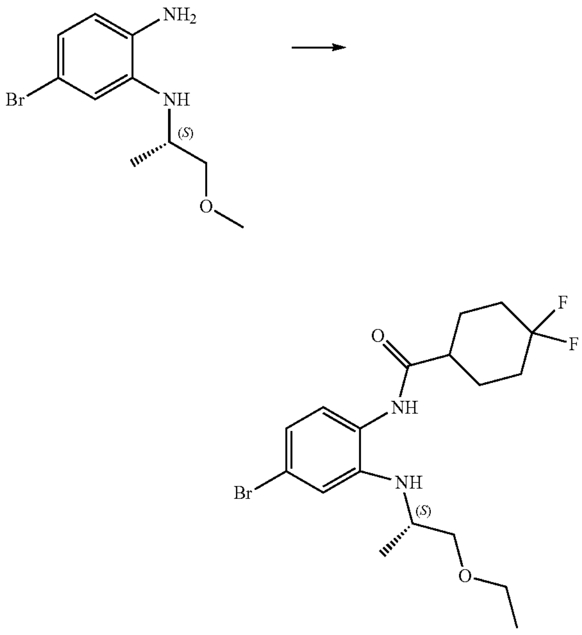

HATU (1.2 g, 3.20 mmol) was added to a stirred 0° C. solution of 4,4-difluorocyclohexane-1-carboxylic acid (0.42 g, 1.62 mmol) in DCM (4 mL) and the reaction mixture was stirred for 30 minutes under nitrogen. A solution of (S)-5-bromo-$N^1$-(1-methoxypropan-2-yl)benzene-1,2-diamine (0.42 g, 1.62 mmol) in DCM (4 mL) was added dropwise at 0° C. followed by DIPEA (0.61 mL, 4.70 mmol) and the reaction mixture was allowed to stir at rt for 6 h. The resulting mixture was diluted with water (80 mL) and extracted with DCM (40 mL×2). The combined organic layers were washed with brine (50 mL), dried over anhydrous $Na_2SO_4$, filtered and concentrated under reduced pressure. The product obtained was triturated with $Et_2O$ (10 mL) to afford the title compound (0.4 g, 50%) as a solid, $[M+H]^+$ 405.24.

Step 6: Preparation of (S)-6-bromo-2-(4,4-difluorocyclohexyl)-1-(1-methoxypropan-2-yl)-1H-benzo[d]imidazole

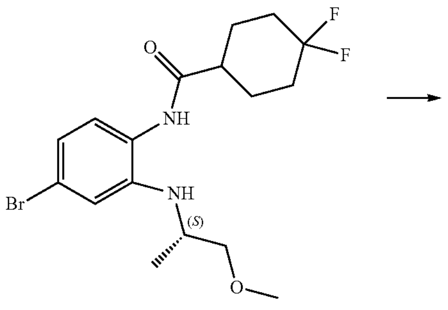

-continued

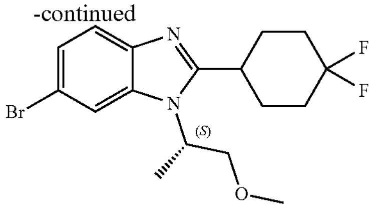

A solution of (S)—N-(4-bromo-2-((1-methoxypropan-2-yl)amino)phenyl)-4,4-difluorocyclohexane-1-carboxamide (0.4 g, 1.04 mmol) in acetic acid (15 mL) was heated at 110° C. for 16 h. The resulting mixture was concentrated under reduced pressure, neutralized with saturated aqueous $NaHCO_3$ (150 mL) and extracted with EtOAc (50 mL×3). The combined organic layers were washed with brine (60 mL), dried over anhydrous $Na_2SO_4$, filtered and concentrated under reduced pressure. The crude material was purified by silica gel chromatography using 15% EtOAc in hexanes as eluent. Product fractions were combined and evaporated to dryness to afford the title compound (0.32 g, 77%) as a solid. $[M+H]^+$ 389.18.

Step 7: Preparation of Compound 56

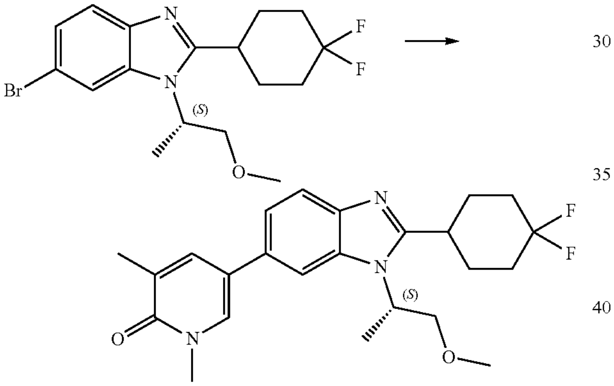

A stirred solution of (S)-6-bromo-2-(4,4-difluorocyclohexyl)-1-(1-methoxypropan-2-yl)-1H-benzo[d]imidazole (0.32 g, 8.30 mmol) and 1,3-dimethyl-5-(4,4,5,5-tetramethyl-1,3,2-dioxaborolan-2-yl)pyridin-2 (1H)-one (0.25 g, 9.94 mmol) in 1,4-dioxane (8 mL) was purged with nitrogen for 15 minutes at rt, followed by the addition of $Cs_2CO_3$ (0.808 g, 24.9 mmol) in water (0.8 mL) and purging with nitrogen for another 15 minutes. $Pd(PPh_3)_4$ (0.095 g, 0.83 mmol) was added and the reaction mixture was heated at 80° C. for 5 h. The resulting mixture was filtered through Celite™ and washed with EtOAc (25 mL×3). The organic layer was washed with brine (50 mL), dried over anhydrous $Na_2SO_4$, filtered and concentrated under reduced pressure. The crude material was purified by preparative HPLC using 45-100% of MeCN in water (with 0.1% $NH_3$ as modifier) to afford Compound 56 (0.054 g, 15%) as a solid. $^1H$ NMR (400 MHz, DMSO) δ ppm 7.96 (d, J=2 Hz, 1H), 7.79 (s, 1H), 7.73 (s, 1H), 7.58 (d, J=8 Hz, 1H), 7.34 (dd, J=1.2 and 8.4 Hz, 1H), 4.88 (m, 1H), 4.01 (t, J=9.6 Hz, 1H), 3.72 (dd, J=4.8 and 4.4 Hz, 1H), 3.54 (s, 3H), 3.29-3.21 (m, 1H), 3.18 (s, 3H), 2.13-1.86 (m, 11H), 1.61 (d, J=7.2 Hz, 3H). $[M+H]^+$ 430.35.

Example 52: (R)-5-(2-(4,4-difluorocyclohexyl)-1-(1-methoxypropan-2-yl)-1H-benzo[d]imidazol-6-yl)-1,3-dimethylpyridin-2(1H)-one (Compound 57)

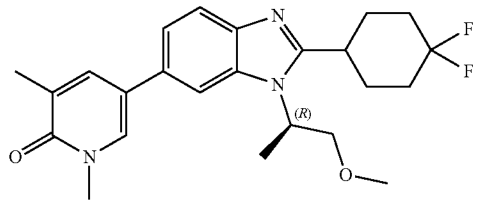

Step 1: Preparation of (R)-5-bromo-N1-(1-methoxypropan-2-yl)benzene-1,2-diamine

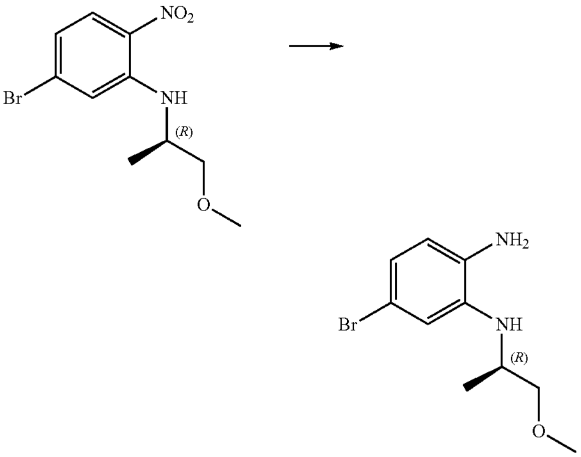

Sodium dithionite (3.5 g, 20 mmol) was added to a rt suspension of (R)-5-bromo-N-(1-methoxypropan-2-yl)-2-nitroaniline (Example 45, step 1, 0.5 g, 1.73 mmol) in MeOH (10 mL) and water (10 mL) and the reaction mixture was stirred for 1 h. The resulting mixture was diluted with water (50 mL) and extracted with EtOAc (30 mL×3). The combined organic layers were washed with brine (50 mL), dried over anhydrous $Na_2SO_4$, filtered and concentrated under reduced pressure. The product was then triturated with $Et_2O$ to afford the title compound (0.4 g, 89%) as a solid, $[M+H]^+$ 261.04.

Step 2: Preparation of (R)—N-(4-bromo-2-((1-methoxypropan-2-yl)amino)phenyl)-4,4-difluoro cyclohexane-1-carboxamide

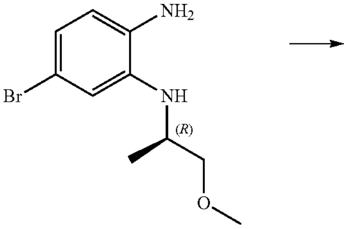

-continued

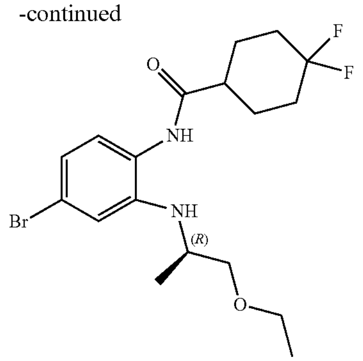

HATU (1.2 g, 3.10 mmol) was added to a stirred 0° C. solution of 4,4-difluorocyclohexane-1-carboxylic acid (0.38 g, 1.55 mmol) in DCM (4 mL) and the reaction mixture was stirred at this temperature for 30 minutes under nitrogen. A solution of (R)-5-bromo-N1-(1-methoxypropan-2-yl)benzene-1,2-diamine (0.4 g, 1.55 mmol) in DCM (4 mL) was the added dropwise at 0° C. followed by DIPEA (0.61 mL, 4.70 mmol). The reaction was allowed to stir at rt for 6 h. The resulting mixture was diluted with water (80 mL) and extracted with DCM (40 mL×2). The combined organic layers were washed with brine (50 mL), dried over anhydrous $Na_2SO_4$, filtered and concentrated under reduced pressure. The product was triturated with $Et_2O$ (15 mL) to afford the title compound (0.42 g, 50%) as a solid, $[M+H]^+$ 407.19.

Step 3: Preparation of (R)-6-bromo-2-(4,4-difluorocyclohexyl)-1-(1-methoxypropan-2-yl)-1H-benzo[d]imidazole

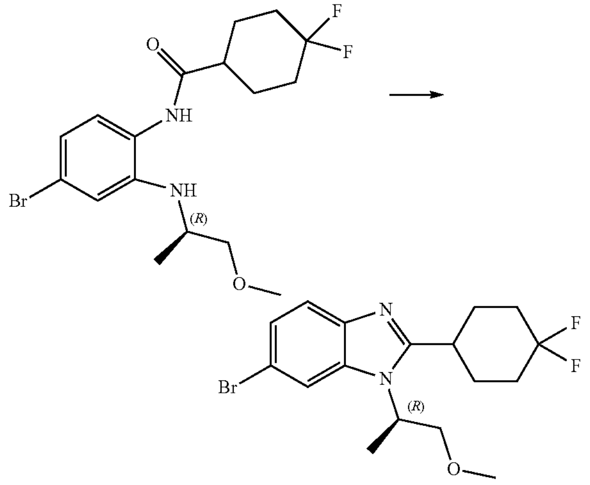

A solution of (R)—N-(4-bromo-2-((1-methoxypropan-2-yl)amino)phenyl)-4,4-difluorocyclohexane-1-carboxamide (0.42 g, 1.04 mmol) in acetic acid (15 mL) was heated to 110° C. for 16 h. The resulting mixture was concentrated under reduced pressure, neutralized with saturated aqueous $NaHCO_3$ (120 mL) and extracted with EtOAc (40 mL×3). The combined organic layers were washed with brine (50 mL), dried over anhydrous $Na_2SO_4$, filtered and concentrated under reduced pressure. The crude material was purified by silica gel chromatography using 20% EtOAc in hexanes as eluent. Product fractions were combined and concentrated to dryness to afford the title compound (0.38 g, 88%) as a solid. $[M+H]^+$ 389.18.

Step 4: Preparation of Compound 57

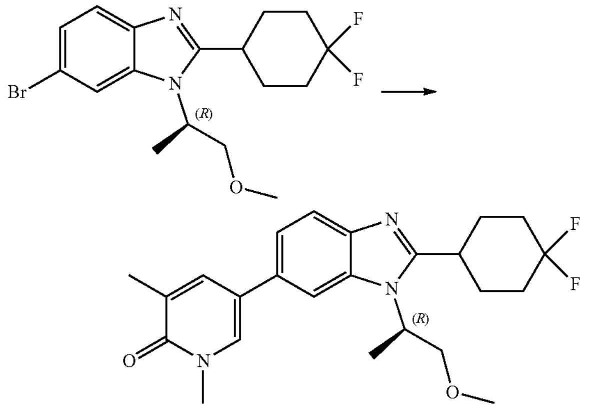

A stirred solution of (R)-6-bromo-2-(4,4-difluorocyclohexyl)-1-(1-methoxypropan-2-yl)-1H-benzo[d]imidazole (0.38 g, 0.984 mmol) and 1,3-dimethyl-5-(4,4,5,5-tetramethyl-1,3,2-dioxaborolan-2-yl)pyridin-2 (1H)-one (0.29 g, 1.18 mmol) in 1,4-Dioxan (8 mL) was purged with nitrogen for 15 minutes at rt followed by the addition of $Cs_2CO_3$ (0.96 g, 2.95 mmol) in water (0.8 mL) and purging with nitrogen for another 15 minutes. $Pd(PPh_3)_4$ (0.1 g, 0.098 mmol) was added and the reaction mixture was heated at 80° C. for 5 h. The resulting mixture was filtered through Celite™ and washed with EtOAc (30 mL×3). The organic layer was washed with brine (60 mL), dried over anhydrous $Na_2SO_4$, filtered and concentrated under reduced pressure. The crude material was purified by silica gel chromatography using 3% MeOH in DCM as eluent. Product fractions were combined and concentrated in vacuo to afford Compound 57 (0.11 g, 26%) as a solid. $^1H$ NMR (400 MHz, DMSO) δ ppm 7.96 (d, J=2.4 Hz, 1H), 7.79 (d, J=1.6 Hz, 1H), 7.73 (d, J=1.2 Hz, 1H), 7.58 (d, J=8.4 Hz, 1H), 7.34 (dd, J=1.6 and 8.4 Hz, 1H), 4.90 (m, 1H), 4.01 (t, J=10 Hz, 1H), 3.73 (dd, J=4.8 and 10.4 Hz, 1H), 3.54 (s, 3H), 3.21-3.18 (m, 4H), 2.14-1.86 (m, 11H), 1.60 (d, J=7.2 Hz, 3H). $[M+H]^+$ 430.40.

Example 53: (R)-5-(2-(4,4-difluorocyclohexyl)-1-(2-methoxypropyl)-1H-benzo[d]imidazol-6-yl)-1,3-dimethylpyridin-2 (1H)-one (Compound 58)

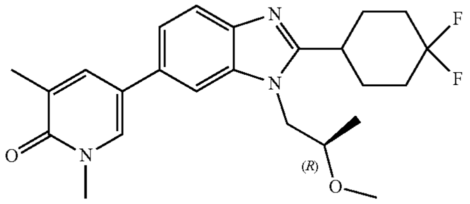

Step 1: Preparation of (R)-5-bromo-N-(2-methoxypropyl)-2-nitroaniline

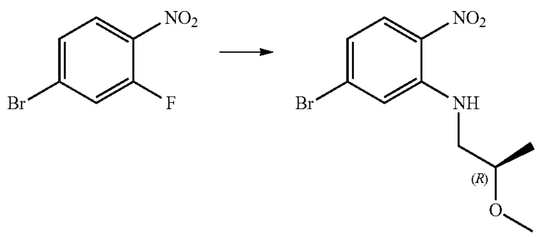

TEA (0.95 mL, 6.82 mmol) was added to a stirred solution of 4-bromo-2-fluoro-1-nitrobenzene (0.5 g, 2.27 mmol) and (R)-2-methoxypropan-1-amine hydrochloride (0.343 g, 2.73 mmol) in ethanol (10 mL) and the reaction mixture was heated to 70° C. for 2 h. The resulting mixture was then diluted with water (50 mL) and extracted with EtOAc (50 mL×3). The combined organic layers were dried over anhydrous $Na_2SO_4$, filtered and concentrated under reduced pressure to afford the title compound (0.65 g, 99%) as a solid.

Step 2: Preparation of (R)-5-bromo-$N^1$-(2-methoxypropyl)benzene-1,2-diamine

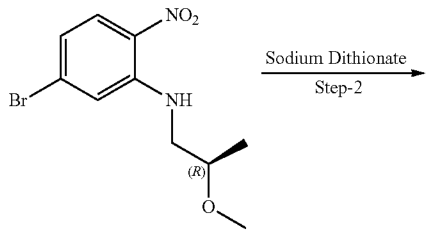

2

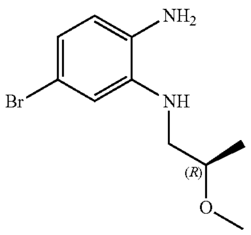

3

Sodium dithionite (4.7 g, 26.98 mmol) was added to a rt stirred suspension of (R)-5-bromo-N-(2-methoxypropyl)-2-nitroaniline (0.65 g, 2.25 mmol) in MeOH (10 mL) and water (10 mL) and the reaction mixture was heated at 50° C. for 15 min. The resulting mixture was concentrated under reduced pressure, neutralized with saturated aqueous $NaHCO_3$ (250 mL) and extracted with EtOAc (100 mL×3). The combined organic layers were washed with brine (50 mL), dried over anhydrous $Na_2SO_4$, filtered and concentrated under reduced pressure to afford the title compound (0.45 g, 59%) as a solid, $[M+H]^+$ 261.03.

Step 3: Preparation of (R)—N-(4-bromo-2-((2-methoxypropyl)amino)phenyl)-4,4-difluoro cyclohexane-1-carboxamide

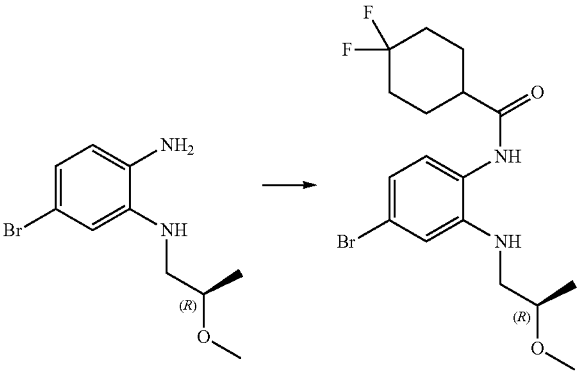

HATU (0.99 g, 2.61 mmol) was added to a 0° C. stirred solution of 4,4-difluorocyclohexane-1-carboxylic acid (0.428 g, 2.61 mmol) in DCM (5 mL) and the reaction mixture was stirred for 30 min. A solution of (R)-5-bromo-N1-(2-methoxypropyl)benzene-1,2-diamine (0.45 g, 1.74 mmol) and DIPEA (0.9 mL, 5.21 mmol) in DCM (5 mL) was added at rt and the reaction was stirred for 2 h. The resulting mixture was diluted with water (100 mL) and extracted with DCM (50 mL×3). The combined organic layers were washed with brine (50 mL), dried over anhydrous $Na_2SO_4$, filtered and concentrated under reduced pressure to afford the title compound (0.7 g, 75%) as a semisolid, $[M+H]^+$ 405.35.

Step 4: Preparation of (R)-6-bromo-2-(4,4-difluorocyclohexyl)-1-(2-methoxypropyl)-1H-benzo[d]imidazole

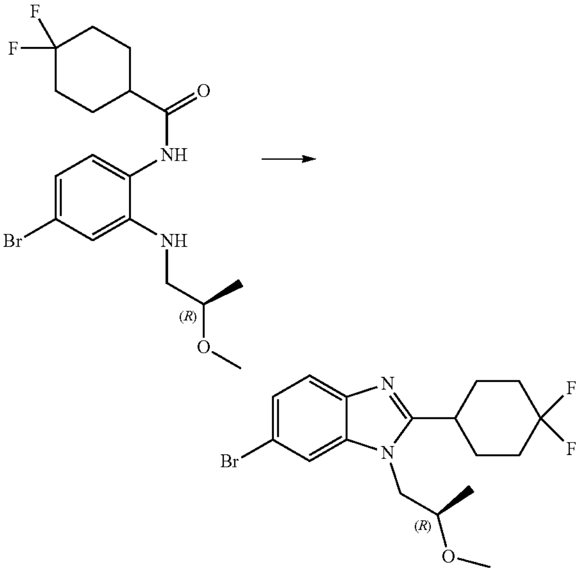

A solution of (R)—N-(4-bromo-2-((2-methoxypropyl) amino)phenyl)-4,4-difluorocyclohexane-1-carboxamide (0.7 g, 1.73 mmol) in acetic acid (10 mL) was heated to 100°

C. for 16 h. The resulting mixture was basified with saturated aqueous $NaHCO_3$ (150 mL) and extracted with EtOAc (100 mL×3). The combined organic layers were washed with brine (50 mL), dried over anhydrous $Na_2SO_4$, filtered and concentrated under reduced pressure. The crude product was purified by silica gel chromatography using a gradient of 20-40% EtOAc in hexane. Product fractions were combined and evaporated to dryness to afford the title compound (0.4 g, 36%) as a semisolid, $[M+H]^+$ 387.23.

Step 5: Preparation of Compound 58

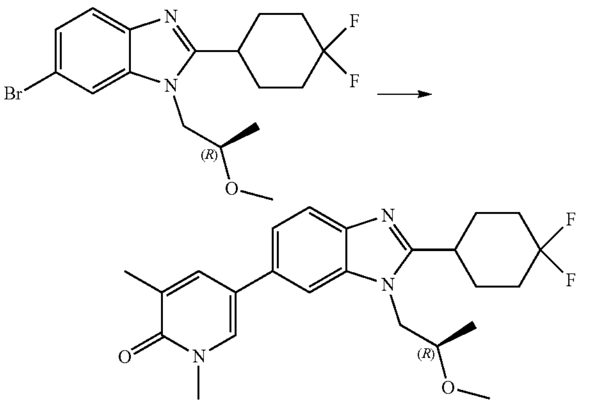

A stirred solution of (R)-6-bromo-2-(4,4-difluorocyclohexyl)-1-(2-methoxypropyl)-1H-benzo[d]imidazole (0.4 g, 1.03 mmol) and 1,3-dimethyl-5-(4,4,5,5-tetramethyl-1,3,2-dioxaborolan-2-yl)pyridin-2 (1H)-one (0.386 g, 1.55 mmol) in 1,4-dioxane (5 mL) was purged with nitrogen for 15 minutes at rt, followed by the addition of $Na_2CO_3$ (0.329 g, 3.10 mmol) in water (1 mL) and purging with nitrogen for another 15 minutes. $Pd(PPh_3)_4$ (0.06 g, 0.05 mmol) was added and the reaction mixture was stirred at 100° C. for 6 h. The resulting mixture was concentrated under reduced pressure. The crude material was purified by silica gel chromatography using 1-2% MeOH in DCM as eluent. Product fractions were combined and evaporated to dryness to afford Compound 58 (0.08 g, 18%) as a solid. $^1H$ NMR (400 MHz, DMSO) δ ppm 7.96 (d, J=2.4 Hz, 1H), 7.79 (s, 1H), 7.71 (s, 1H), 7.56 (d, J=8.4 Hz, 1H), 7.35 (dd, J=1.6 and 8.4 Hz, 1H), 4.35-4.24 (m, 2H), 3.72-3.67 (m, 1H), 3.54 (s, 3H), 3.27-3.23 (m, 1H), 3.08 (s, 3H), 2.19-2.17 (m, 2H), 2.12 (s, 3H), 2.08-1.91 (m, 4H), 1.90-1.84 (m, 2H), 1.19 (d, J=6.4 Hz, 3H), $[M+H]^+$ 430.40.

Example 54: (S)-5-(2-(4,4-difluorocyclohexyl)-1-(2-methoxypropyl)-1H-benzo[d]imidazol-6-yl)-1,3-dimethylpyridin-2 (1H)-one (Compound 59)

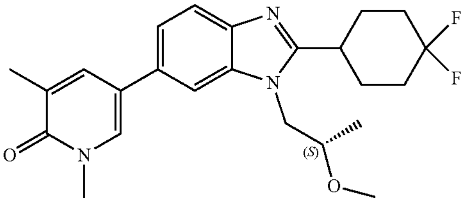

Step 1: Preparation of (S)-5-bromo-N-(2-methoxypropyl)-2-nitroaniline

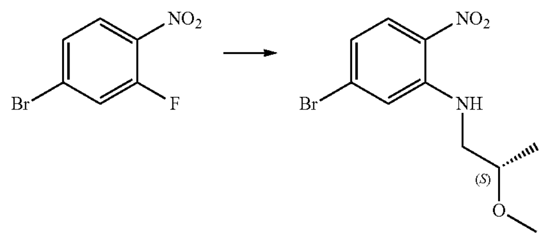

The procedure of Example 53, step 1, was followed except for the use of (S)-2-methoxypropan-1-amine hydrochloride (0.343 g, 2.73 mmol) to afford the title compound (0.65 g, 99%) as a solid, $[M+H]^+$ 289.08.

Step 2: Preparation of (S)-5-bromo-$N^1$-(2-methoxypropyl)benzene-1,2-diamine

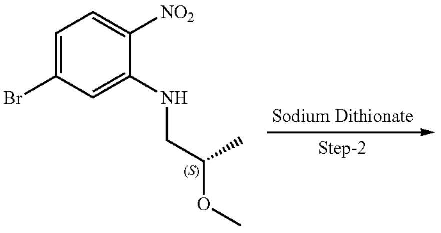

2

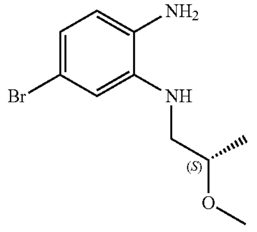

3

The procedure of Example 53, step 2, was followed except for the use of the enantiomer (S)-5-bromo-N-(2-methoxypropyl)-2-nitroaniline, to afford the title compound (0.45 g, 59%) as a solid, $[M+H]^+$ 261.0.

Step 3: Preparation of (S)—N-(4-bromo-2-((2-methoxypropyl)amino)phenyl)-4,4-difluoro cyclohexane-1-carboxamide

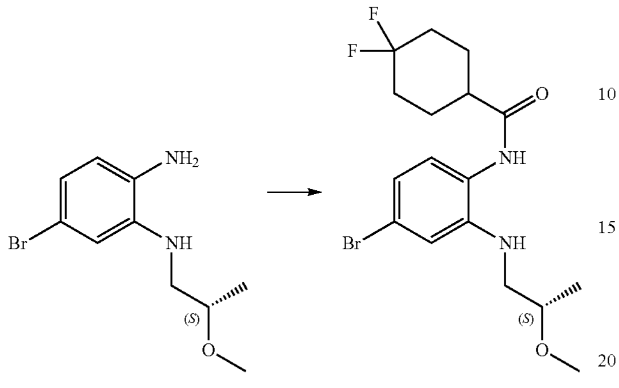

The procedure of Example 53, step 3, was followed except for the use of (S)-5-bromo-$N^1$-(2-methoxypropyl) benzene-1,2-diamine (0.45 g, 1.74 mmol), and afforded the title compound (0.7 g, 75%) as a semisolid, $[M+H]^+$ 405.35.

Step 4: Preparation of (S)-6-bromo-2-(4,4-difluoro-cyclohexyl)-1-(2-methoxypropyl)-1H-benzo[d]imidazole

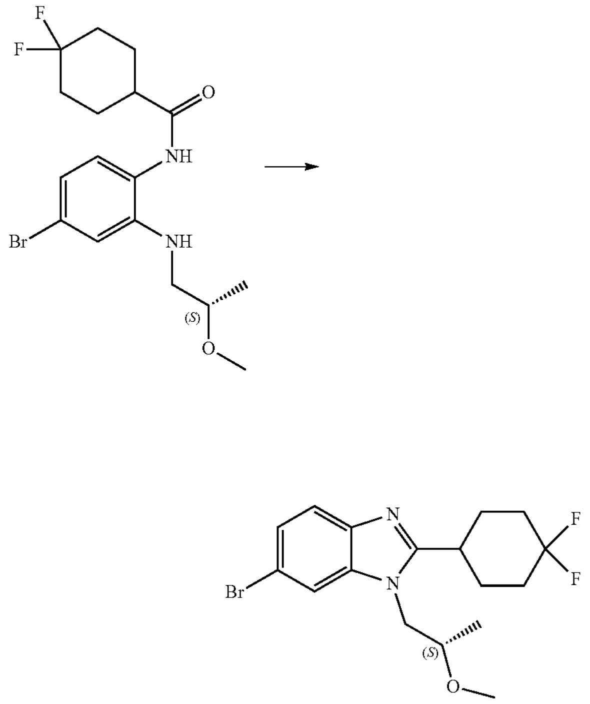

The procedure of Example 53, step 4, was followed except for the use of (S)—N-(4-bromo-2-((2-methoxypropyl)amino)phenyl)-4,4-difluorocyclohexane-1-carboxamide. Purification afforded the title compound (0.5 g, 64%) as a semisolid, $[M+H]^+$ 387.23.

Step 5: Preparation of Compound 59

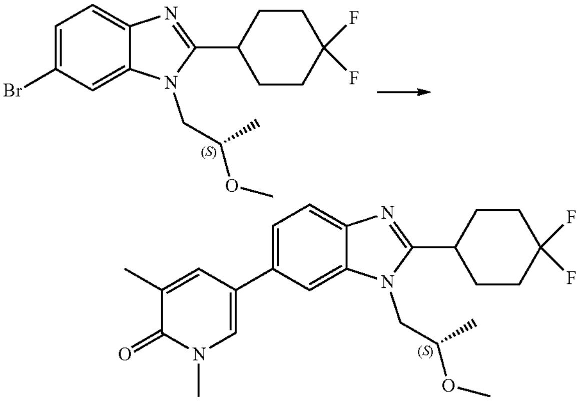

The procedure of Example 53, step 5, was followed except for the use of (S)-6-bromo-2-(4,4-difluorocyclohexyl)-1-(2-methoxypropyl)-1H-benzo[d]imidazole (0.5 g, 1.29 mmol). The quantities of the other reagents were adapted in proportion. Purification afforded Compound 59 (0.085 g, 15%) as a solid. $^1H$ NMR (400 MHz, DMSO) δ ppm 7.96 (d, J=2.0 Hz, 1H), 7.79 (s, 1H), 7.71 (s, 1H), 7.56 (d, J=8.4 Hz, 1H), 7.35 (dd, J=1.2 and 8.4 Hz, 1H), 4.35-4.24 (m, 2H), 3.71-3.67 (m, 1H), 3.54 (s, 3H), 3.27-3.23 (m, 1H), 3.08 (s, 3H), 2.33-2.17 (m, 2H), 2.11 (s, 3H), 2.08-2.03 (m, 1H), 1.99-1.91 (m, 4H), 1.88-1.82 (m, 1H), 1.24-1.17 (m, 3H), $[M+H]^+$ 430.2.

Example 55: 5-(1-(2-ethoxyethyl)-2-(tetrahydro-2H-pyran-4-yl)-1H-benzo[d]imidazol-6-yl)-1,3-dimethylpyridin-2 (1H)-one (Compound 60)

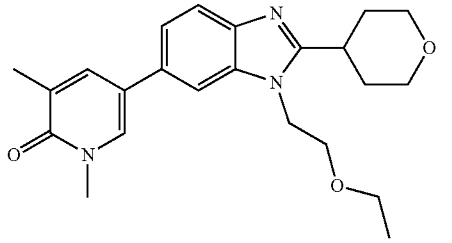 [SMILES: CCOCCn1c(C2CCOCC2)nc2ccc(-c3cc(C)c(=O)n(C)c3)cc21]

Step 1: Preparation of 2-((5-bromo-2-nitrophenyl)amino)ethanol

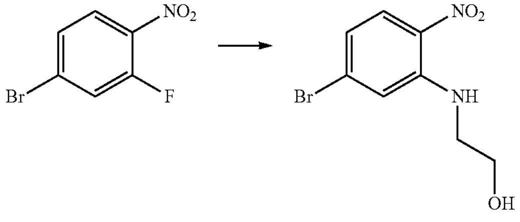 [SMILES: O=[N+]([O-])c1ccc(Br)cc1F ; O=[N+]([O-])c1ccc(Br)cc1NCCO]

TEA (2.9 mL, 20.55 mmol) was added to a rt stirred solution of 4-bromo-2-fluoro-1-nitrobenzene (1.5 g, 6.85 mmol) and 2-aminoethan-1-ol (0.51 g, 8.22 mmol) in ethanol (15 mL) and the reaction mixture was heated at 80° C. for 2 h. The resulting mixture was then diluted with water (100 mL) and extracted with EtOAc (40 mL×3). The combined organic layers were dried over anhydrous $Na_2SO_4$, filtered and concentrated under reduced pressure to afford the title compound (1.7 g, 95%) as an oil. $[M+H]^+$ 262.94.

Step 2: Preparation of 5-bromo-N-(2-ethoxyethyl)-2-nitroaniline

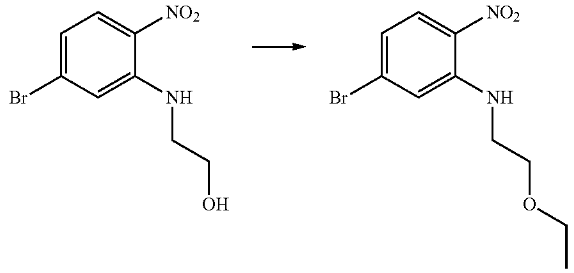 [SMILES: O=[N+]([O-])c1ccc(Br)cc1NCCO ; CCOCCNc1cc(Br)ccc1[N+](=O)[O-]]

To a stirred 0° C. solution of suspension of 2-((5-bromo-2-nitrophenyl)amino)ethan-1-ol (1.7 g, 6.54 mmol) in DMF (15 mL) was added 60% NaH in mineral oil (0.24 g, 9.81 mmol) and the mixture stirred at this temperature for 30 min. Iodoethane (0.8 mL, 9.81 mmol) was then added dropwise at 0° C. and the reaction mixture was allowed to stir at rt for 16 h. The resulting mixture was diluted with water (100 mL) and extracted with EtOAc (40 mL×3). The combined organic layers were washed with brine (50 mL), dried over anhydrous $Na_2SO_4$, filtered and concentrated under reduced pressure. The crude material was purified by silica gel chromatography using 20% EtOAc as eluent. Product fractions were combined and concentrated to dryness to afford the title compound (1.7 g, 93%) as an oil. $^1$H NMR (400 MHz, DMSO) δ ppm 8.26 (t, J=4.8 Hz, 1H), 7.99 (d, J=9.2 Hz, 1H), 7.33 (d, J=1.6 Hz, 1H), 6.85 (dd, J=2 and 9.2 Hz, 1H), 3.60 (t, J=5.2 Hz, 2H), 3.54-3.43 (m, 4H), 1.13 (t, J=7.2 Hz, 3H), $[M+H]^+$ 289.1.

Step 3: Preparation of 5-bromo-N1-(2-ethoxyethyl)benzene-1,2-diamine

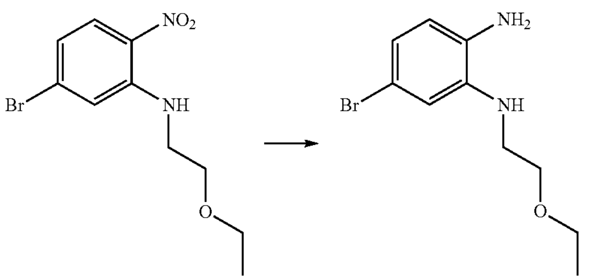 [SMILES: CCOCCNc1cc(Br)ccc1[N+](=O)[O-] ; CCOCCNc1cc(Br)ccc1N]

Sodium dithionite (13.99 g, 72.91 mmol) was added to a rt suspension of 5-bromo-N-(2-ethoxyethyl)-2-nitroaniline (1.75 g, 6.08 mmol) in MeOH (30 mL) and water (15 mL) and the reaction mixture was heated at 50° C. for 10 min. The resulting mixture was diluted with water (200 mL) and extracted with DCM (50 mL×3). The combined DCM layers were washed with brine (50 mL), dried over anhydrous $Na_2SO_4$, filtered and concentrated under reduced pressure to afford the title compound (1 g, 64%) as an oil, $[M+H]^+$ 2=261.26.

Step 4: Preparation of 6-bromo-1-(2-ethoxyethyl)-2-(tetrahydro-2H-pyran-4-yl)-1H-benzo[d]imidazole

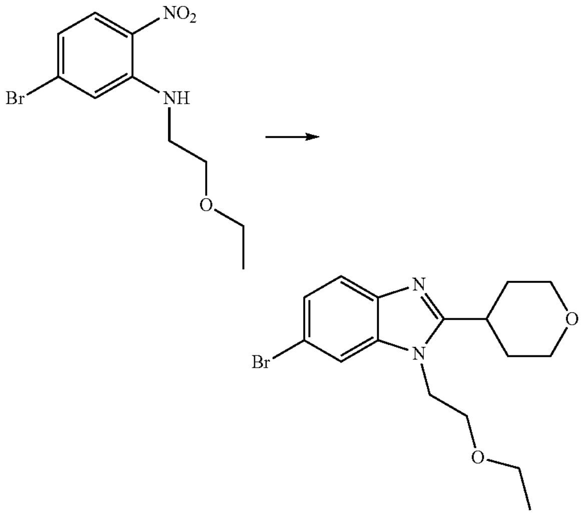

To a stirred solution of 5-bromo-N1-(2-methoxyethyl)benzene-1,2-diamine (0.3 g, 1.16 mmol) in acetic acid (5 mL) was added tetrahydro-2H-pyran-4-carbaldehyde (0.14 g, 1.16 mmol) and the reaction was stirred at rt for 12 h. The resulting mixture was concentrated under reduced pressure, diluted with saturated aqueous $NaHCO_3$ (60 mL) and extracted with EtOAc (40 mL×3). The combined organic layers were washed with brine (50 mL), dried over anhydrous $Na_2SO_4$, filtered and concentrated under reduced pressure. The crude material was purified by silica gel chromatography using 3% MeOH in DCM as eluent. Product fractions were combined and concentrated in vacuo to afford the title compound (0.21 g, 51%) as an oil. $[M+H]^+$ 353.15.

Step 5: Preparation of Compound 60

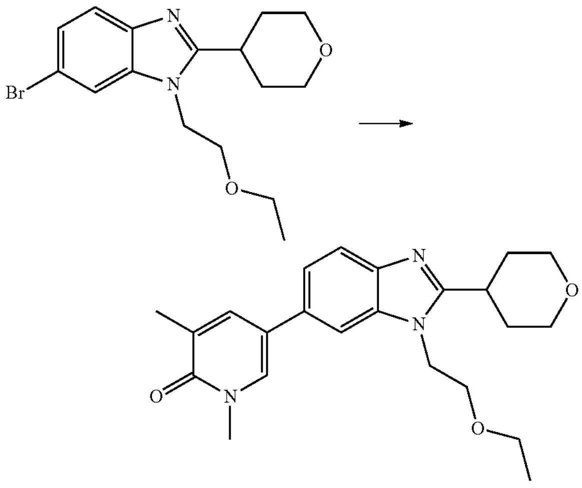

A stirred solution of 6-bromo-1-(2-ethoxyethyl)-2-(tetrahydro-2H-pyran-4-yl)-1H-benzo[d]imidazole (0.21 g, 0.60 mmol) and 1,3-dimethyl-5-(4,4,5,5-tetramethyl-1,3,2-dioxaborolan-2-yl) pyridin-2 (1H)-one (0.2 g, 0.77 mmol) in 1,4-dioxane (4 mL) was purged with nitrogen for 10 minutes, followed by the addition of $Na_2CO_3$ (0.19 g, 1.8 mmol) in water (0.5 mL) and purging with nitrogen for another 10 min. $Pd(PPh_3)_4$ (0.035 g, 0.03 mmol) was then added and the reaction mixture was heated at 100° C. for 3 h. The resulting mixture was diluted with EtOAc (100 mL), washed with water (40 mL×2) and brine (30 mL), dried over anhydrous $Na_2SO_4$, filtered and concentrated under reduced pressure. The crude material was purified using flash chromatography using 1.5-2% MeOH in DCM as eluent. Product fractions were combined and evaporated to dryness to afford Compound 60 (0.09 g, 39%) as a solid. $^1H$ NMR (400 MHz, DMSO) δ ppm 7.97 (d, J=2 Hz, 1H), 7.80 (s, 1H), 7.72 (s, 1H), 7.58 (d, J=8.4 Hz, 1H), 7.37 (dd, J=1.6 and 8.4 Hz, 1H), 4.46 (t, J=4.8 Hz, 2H), 3.99 (d, J=10.5 Hz, 2H), 3.70 (t, J=4.8 Hz, 2H), 3.54-3.46 (m, 5H), 3.40-3.32 (m, 3H), 2.11 (s, 3H), 1.95-1.80 (m, 4H), 1.01 (t, J=7.2 Hz, 3H). $MH^+$ 396.43.

Example 56: 5-(2-(4,4-difluorocyclohexyl)-1-(2-ethoxyethyl)-1H-benzo[d]imidazol-6-yl)-1,3-dimethylpyridin-2 (1H)-one (Compound 61)

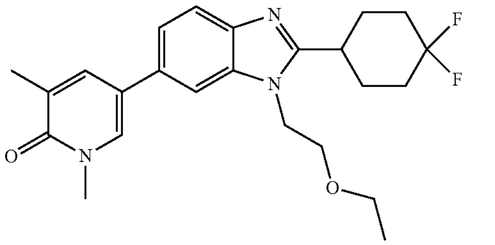 [SMILES: CCOCCn1c(C2CCC(F)(F)CC2)nc2ccc(-c3cc(C)c(=O)n(C)c3)cc21]

Step 1: Preparation of N-(4-bromo-2-((2-ethoxyethyl)amino)phenyl)-4,4-difluorocyclohexane-1-carboxamide

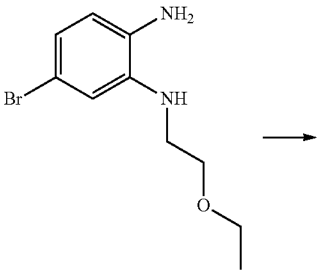

-continued

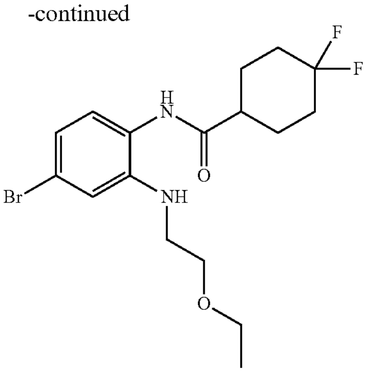

HATU (0.66 g, 1.74 mmol) was added to a stirred 0° C. solution of 4,4-difluorocyclohexane-1-carboxylic acid (0.3 g, 1.16 mmol) in DCM (4 mL) under nitrogen atmosphere. A solution of 5-bromo-N[1]-(2-ethoxyethyl)benzene-1,2-diamine (Example 55, Step 3, 0.20 g, 1.22 mmol) and DIPEA (0.6 mL, 3.48 mmol) in DCM (2 mL) was added then dropwise and the reaction mixture was stirred for 3 h at 0° C. The resulting mixture was diluted with saturated $NaHCO_3$ (25 mL) and the product was extracted with DCM (20 mL×3). The combined organic layers were washed with brine (30 mL), dried over anhydrous $Na_2SO_4$, filtered and concentrated under reduced pressure. The crude material was purified by silica gel chromatography using a gradient of 3-5% MeOH in DCM as eluent. Product fractions were combined and concentrated to afford the title compound (0.33 g, 65%) as an oil. $[M+H]^+$ 405.2, 407.24.

Step 2: Preparation of 6-bromo-2-(4,4-difluorocyclohexyl)-1-(2-ethoxyethyl)-1H-benzo[d]imidazole

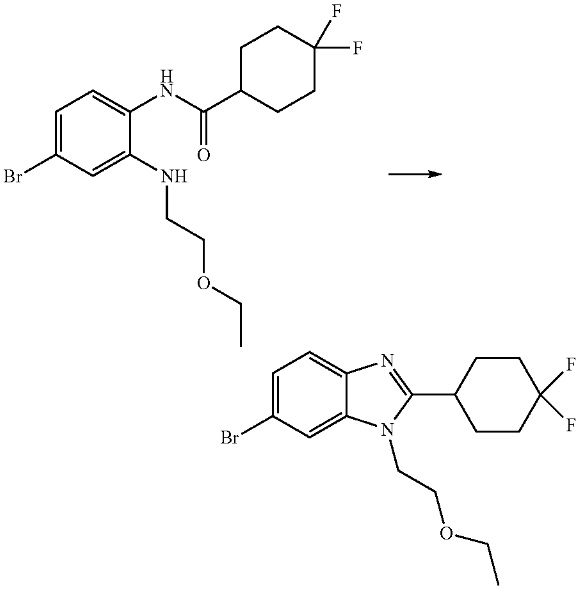

A solution of N-(4-bromo-2-((2-ethoxyethyl)amino)phenyl)-4,4-difluorocyclohexane-1-carboxamide (0.3 g, 0.74 mmol) in acetic acid (5 mL) was stirred at 100° C. for 12 h. The resulting mixture was evaporated under reduced pressure and the residue was dissolved in DCM (30 mL), washed with saturated $NaHCO_3$ (20 mL×2) and brine (10 mL); dried over anhydrous $Na_2SO_4$, filtered and concentrated under reduced pressure. The crude material was purified by silica gel chromatography using a gradient of 3-5% MeOH in DCM as eluent. Product fractions were combined and concentrated to afford the title compound (0.13 g, 46%) as an oil. $[M+H]^{+2}$ 389.18.

Step 3: Preparation of Compound 61

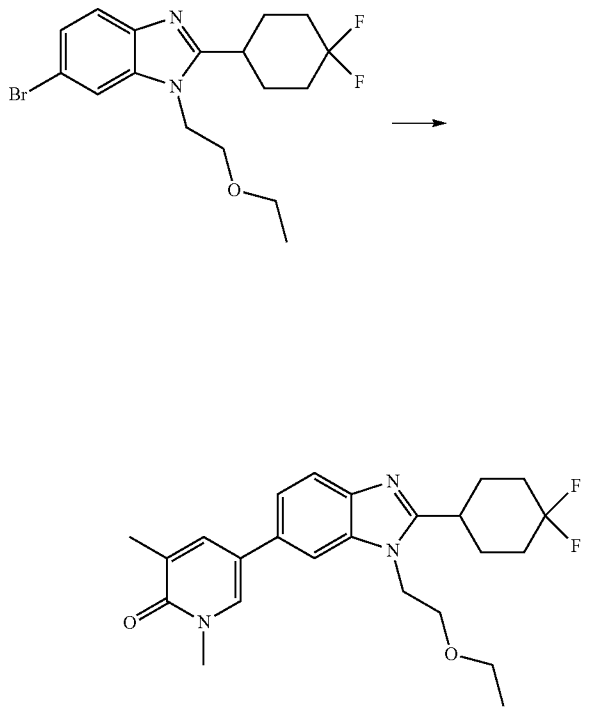 [SMILES: CCOCCn1c(C2CCC(F)(F)CC2)nc2ccc(Br)cc21 ; CCOCCn1c(C2CCC(F)(F)CC2)nc2ccc(-c3cc(C)c(=O)n(C)c3)cc21]

A stirred solution of 6-bromo-2-(4,4-difluorocyclohexyl)-1-(2-ethoxyethyl)-1H-benzo[d]imidazole (0.13 g, 0.34 mmol) and 1,3-dimethyl-5-(4,4,5,5-tetramethyl-1,3,2-dioxaborolan-2-yl)pyridin-2 (1H)-one (0.11 g, 0.44 mmol) in 1,4-dioxane (4 mL) was purged for 10 minutes with nitrogen, followed by the addition of $Na_2CO_3$ (0.11 g, 1.02 mmol) in water (0.5 mL) and purging with nitrogen for another 10 min. $Pd(PPh_3)_4$ (0.02 g, 0.02 mmol) was added and the reaction mixture was heated at 100° C. for 3 h. The resulting mixture was then diluted with EtOAc (60 mL), washed with water (40 mL×2) and brine (30 mL), dried over anhydrous $Na_2SO_4$, filtered and concentrated under reduced pressure. The crude material obtained was purified by flash chromatography using 1.5-1.8% MeOH in DCM as eluent. Product fractions were combined and concentrated to dryness to afford afford Compound 61 (0.088 g, 61%) as a solid. $^1H$ NMR (400 MHz, DMSO) δ 7.97 (d, J=2 Hz, 1H), 7.80 (s, 1H), 7.72 (s, 1H), 7.57 (d, J=8.4 Hz, 1H), 7.38 (d, J=8.4 Hz, 1H), 4.48 (t, J=4.4 Hz, 2H), 3.70 (t, J=4.8 Hz, 2H), 3.54 (s, 3H), 3.40-3.35 (m, 2H), 3.28-2.25 (m, 1H), 2.19-2.17 (m, 2H), 2.11 (s, 3H), 2.02-2.00 (m, 3H), 1.95-1.86 (m, 3H), 1.02 (t, J=7.2 Hz, 3H). $[M+H]^+$ 430.40

Example 57: 5-[2-(3-methoxycyclobutyl)-1-(2-(2,2,2-trifluoroethoxy)ethyl)-1H-benzo[d]imidazol-6-yl]-1,3-dimethylpyridin-2(1H)-one (Compounds 62 and 63)

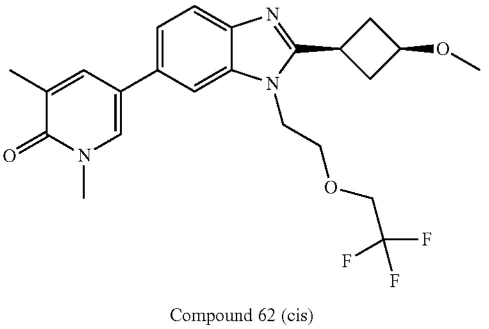

Compound 62 (cis)

+

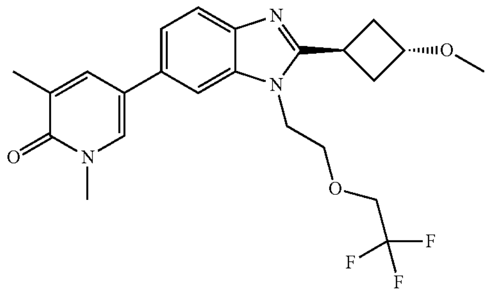

Compound 63 (trans)

Step 1: Preparation of N-(4-(1,5-dimethyl-6-oxo-1,6-dihydropyridin-3-yl)-2-((2-(2,2,2-trifluoro ethoxy) ethyl)amino)phenyl)-3-methoxycyclobutane-1-carboxamide

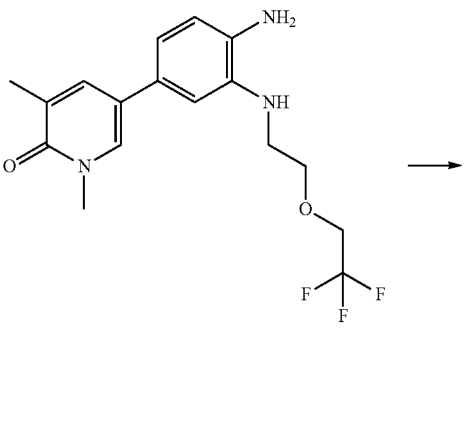

-continued

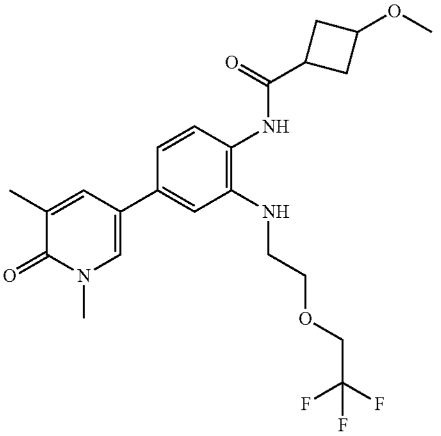

HATU (0.53 g, 1.3929 mmol) was added to a stirred solution of 3-methoxycyclobutane-1-carboxylic acid (0.12 g, 0.9286 mmol) in DCM (5 mL) and the reaction was allowed to stir for 20 min at rt. A solution of 5-(4-amino-3-((2-(2,2,2-trifluoroethoxy)ethyl)amino)phenyl)-1,3-dimethylpyridin-2 (1H)-one (Example 40, Step 2, 0.33 g, 0.9286 mmol) and DIPEA (0.35 mL, 1.8572 mmol) in DCM (1 mL) at rt and the reaction mixture was stirred for 4 h. The resulting mixture was then diluted with saturated aqueous $NaHCO_3$ (25 mL) and the product was extracted with DCM (20 mL×3). The combined organic layers were washed with brine (30 mL), dried over anhydrous $Na_2SO_4$, filtered and concentrated under reduced pressure. The crude material was purified by silica gel chromatography using a gradient of 3-5% MeOH in DCM as eluent. Product fractions were collected and evaporated to afford the title compound (0.4 g, 92%) as an oil. $[M+H]^+$ 468.36

Step 2: Preparation of Compounds 62 and 63

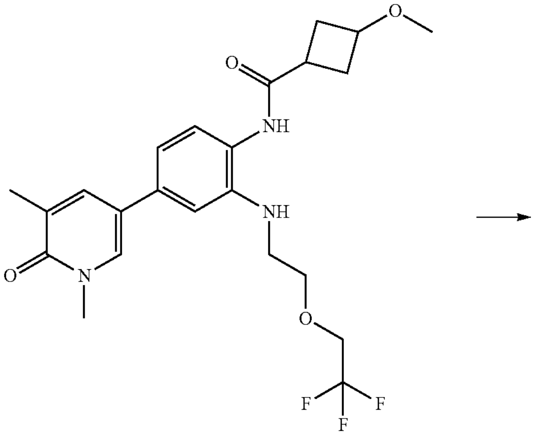

-continued

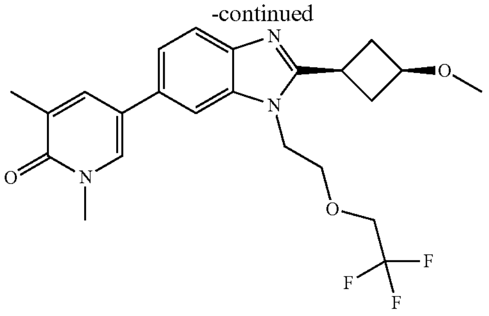

+

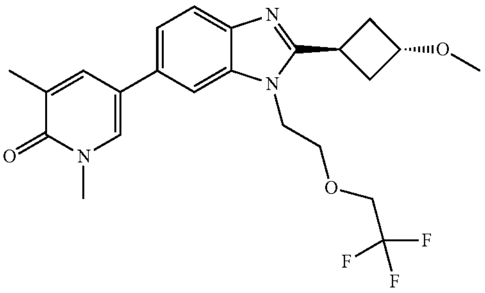

A solution of N-(4-(1,5-dimethyl-6-oxo-1,6-dihydropyridin-3-yl)-2-((2-(2,2,2-trifluoroethoxy)ethyl) amino)phenyl)-3-methoxycyclobutane-1-carboxamide (0.4 g, 0.8561 mmol) in acetic acid (5 mL) was stirred at 100° C. for 12 h. The reaction mixture was concentrated under reduced pressure and the residue was dissolved in DCM (20 mL), washed with saturated $NaHCO_3$ solution (20 mL), brine (10 mL), dried over anhydrous $Na_2SO_4$, filtered and concentrated under reduced pressure. The crude material was purified by silica gel chromatography using 3-5% MeOH in DCM as eluent. Product fractions were combined and concentrated to dryness to afford a mixture of cis and trans isomers (0.4 g) as a solid. The obtained mixture was purified by preparative HPLC using 25% MeCN in water containing 0.1% formic acid as modifier to afford Compound 62 (0.15 g) and Compound 63 (0.062 g) as solids in a combined yield of 55%.

Compound 62 (cis): $^1H$ NMR (400 MHz, $CDCl_3$) δ ppm 7.79 (d, J=8.8 Hz, 1H), 7.57 (d, J=1.2 Hz, 1H), 7.42 (d, J=2.4 Hz, 1H), 7.32-7.28 (m, 2H), 4.34 (t, J=5.2 Hz, 2H), 4.04-4.00 (m, 1H), 3.95 (t, J=9.2 Hz, 2H), 3.76 (q, J=8.4 and 17.2 Hz, 2H), 3.66 (s, 3H), 3.34-3.25 (m, 4H), 2.83-2.76 (m, 2H), 2.58-2.51 (m 2H), 2.27 (s, 3H). $[M+H]^+$ 450.46.

Compound 63 (trans): $^1H$ NMR (400 MHz, $CDCl_3$) δ 7.96 (d, J=2 Hz, 1H), 7.80 (s, 1H), 7.71 (s, 1H), 7.61 (d, J=8.4 Hz, 1H), 7.38 (dd, J=1.2 and 8.4 Hz, 1H), 4.38 (t, J=4.8 Hz, 2H), 4.18-4.15 (m, 1H), 4.05 (q, $J_1$=9.2 and 18.4 Hz, 2H), 3.90 (t, J=4.8 Hz, 2H), 3.85-3.80 (m, 1H), 3.54 (s, 3H), 3.19 (s, 3H), 2.67-2.58 (m, 2H), 2.39-2.33 (m, 2H), 2.11 (s 3H). $[M+H]^+$ 436.36.

Example 58: 5-[1-(2-isopropoxyethyl)-2-(3-methoxycyclobutyl)-1H-benzo[d]imidazol-6-yl]-1,3-dimethylpyridin-2(1H)-one (Compounds 64 and 65)

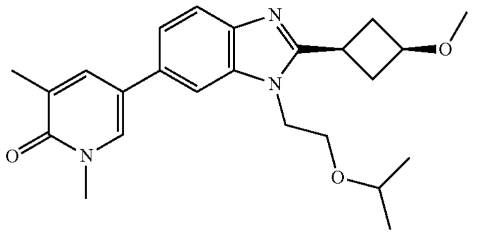

+

Compound 64 (cis)

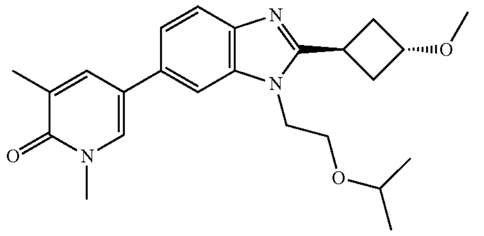

Compound 65 (trans)

Step 1: Preparation of 5-(3-((2-isopropoxyethyl) amino)-4-nitrophenyl)-1,3-dimethylpyridin-2 (1H)-one

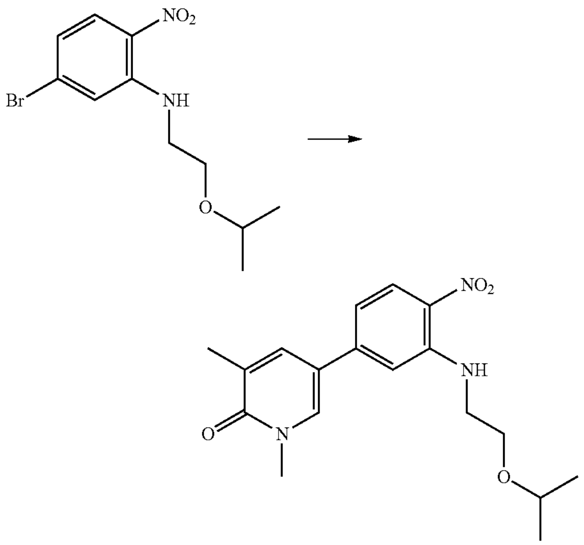

A stirred solution of 5-bromo-N-(2-isopropoxyethyl)-2-nitroaniline (Example 44, Step 1, 0.65 g, 2.14 mmol) and 1,3-dimethyl-5-(4,4,5,5-tetramethyl-1,3,2-dioxaborolan-2-yl)pyridin-2 (1H)-one (0.801 g, 3.22 mmol) in 1,4-dioxane (5 mL) was purged at rt with nitrogen for 15 minutes, followed by the addition of $Na_2CO_3$ (0.682 g, 6.43 mmol) in water (1 mL) and purging with nitrogen for another 15 minutes. $Pd(PPh_3)_4$ (0.124 g, 0.12 mmol) was added and the reaction mixture was heated at 100° C. for 6 h. The resulting mixture was then concentrated under reduced pressure. The crude material was purified by silica gel chromatography using 3-5% MeOH in DCM as eluent. Product fractions were combined and concentrated in vacuo to afford the title compound (0.8 g, 90%) as a semisolid, $[M+H]^+$ 346.25.

Step 2: Preparation of 5-(4-amino-3-((2-isopropoxyethyl)amino)phenyl)-1,3-dimethylpyridin-2(1H)-one

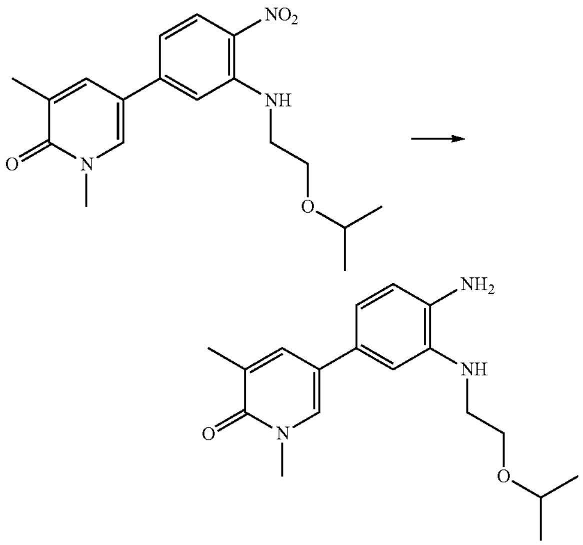

Sodium dithionite (4.84 g, 27.79 mmol) was added to a rt stirred suspension of 5-(3-((2-isopropoxyethyl)amino)-4-nitrophenyl)-1,3-dimethylpyridin-2 (1H)-one (0.8 g, 2.32 mmol) in MeOH (10 mL) and water (10 mL) and the reaction mixture was heated at 50° C. for 15 min. The resulting mixture was concentrated under reduced pressure, basified with saturated $NaHCO_3$ (250 mL) and extracted with EtOAc (100 mL×3). The combined organic layers were washed with brine (50 mL), dried over anhydrous $Na_2SO_4$, filtered and concentrated under reduced pressure. The crude product was purified by silica gel chromatography using 2-4% MeOH in DCM as eluent. Product fractions were combined and concentrated in vacuo to afford the title compound (0.7 g, 96%) as a semisolid, $[M+H]^+$ 316.27.

Step 3: Preparation of N-(4-(1,5-dimethyl-6-oxo-1,6-dihydropyridin-3-yl)-2-((2-isopropoxyethyl) amino)phenyl)-3-methoxycyclobutane-1-carboxamide

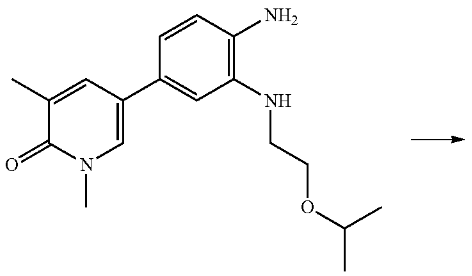

-continued

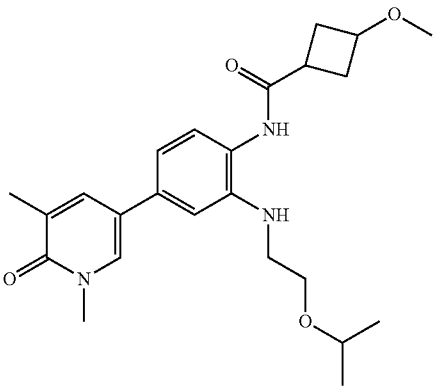

HATU (0.904 g, 2.38 mmol) was added to a 0° C. stirred solution of 3-methoxycyclobutane-1-carboxylic acid (0.248 g, 1.90 mmol) in DCM (5 mL) and the mixture was stirred for 30 min. A solution of 5-(4-amino-3-((2-isopropoxyethyl) amino)phenyl)-1,3-dimethylpyridin-2 (1H)-one (0.5 g, 1.59 mmol) and DIPEA (0.8 mL, 4.76 mmol) in DCM (5 mL) was added at rt and the reaction mixture was stirred for 2 h. The resulting mixture was diluted with water (100 mL) and extracted with DCM (50 mL×3). The combined organic layers were washed with brine (50 mL), dried over anhydrous $Na_2SO_4$, filtered and concentrated under reduced pressure. The crude product was purified by silica gel chromatography using a gradient of 3-10% MeOH in DCM as eluent. Product fractions were combined and concentrated to afford the title compound (0.65 g, 68%) as a semisolid, $[M+H]^+$ 428.45.

Step 4: Preparation of Compounds 64 and 65

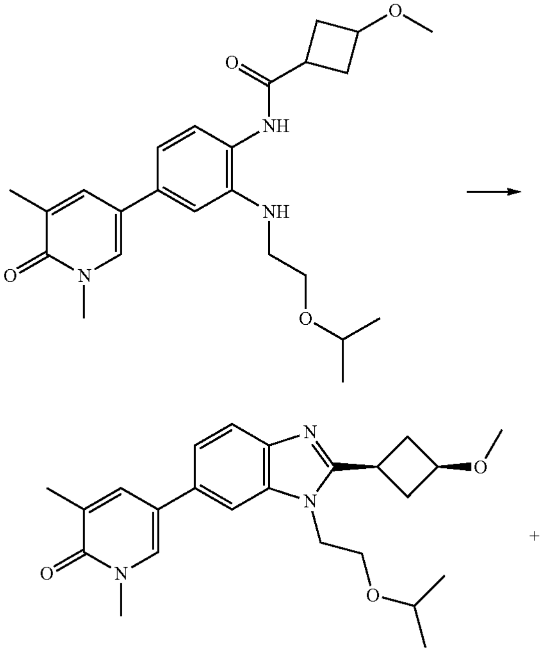

64

-continued

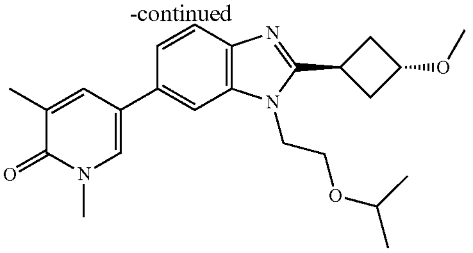

65

A solution of N-(4-(1,5-dimethyl-6-oxo-1,6-dihydropyridin-3-yl)-2-((2-isopropoxyethyl)amino) phenyl)-3-methoxycyclobutane-1-carboxamide (0.65 g, 1.52 mmol) in acetic acid (10 mL) was heated at 100° C. for 16 h. The resulting mixture was basified using saturated aqueous $NaHCO_3$ (300 mL) and extracted with EtOAc (100 mL×3). The combined organic layers were washed with brine (50 mL), dried over anhydrous $Na_2SO_4$, filtered and concentrated under reduced pressure. The crude product was purified by silica gel chromatography using 1-3% MeOH in DCM as eluent. Product fractions were combined and concentrated in vacuo to afford a mixture of cis and trans isomers. The isomer mixture was further purified by preparative HPLC using 18% ACN in water (containing 0.1% formic acid as modifier) to afford Compound 64 (0.08 g) and Compound 65 (0.03 g) as solids in a combined yield of 18%.

Compound 64: $^1H$ NMR (400 MHz, $CDCl_3$) δ ppm 7.78 (d, J=8.4 Hz, 1H), 7.58 (s, 1H), 7.42 (d, J=2.0 Hz, 1H), 7.33 (s, 1H), 7.30 (d, J=2.0 Hz, 1H), 4.26 (t, J=5.4 Hz, 2H), 4.04-4.00 (m, 1H), 3.72 (t, J=5.4 Hz, 2H), 3.67 (s, 3H), 3.51-3.44 (m, 1H), 3.38-3.33 (m, 1H), 3.32 (s, 3H), 2.83-2.77 (m, 2H), 2.58-2.51 (m, 2H), 2.27 (s, 3H), 1.07 (d, J=6.0 Hz, 6H); $[M+H]^+$ 410.44.

Compound 65: $^1H$ NMR (400 MHz, $CDCl_3$) δ ppm 7.78 (d, J=8.4 Hz, 1H), 7.59 (s, 1H), 7.43 (d, J=2.4 Hz, 1H), 7.35 (d, J=1.2 Hz, 1H), 7.31 (d, J=1.6 Hz, 1H), 4.33-4.29 (m, 1H), 4.25 (t, J=5.4 Hz, 2H), 3.89-3.87 (m, 1H), 3.71 (t, J=5.6 Hz, 2H), 3.67 (s, 3H), 3.49-3.46 (m, 1H), 3.34 (s, 3H), 2.85-2.79 (m, 2H), 2.55-2.48 (m, 2H), 2.27 (s, 3H), 1.07 (d, J=6.0 Hz, 6H); $[M+H]^+$ 410.39.

Example 59: (R)-5-(1-(1-isopropoxypropan-2-yl)-2-(tetrahydro-2H-pyran-4-yl)-1H-benzo[d]imidazol-6-yl)-1,3-dimethylpyridin-2(1H)-one (Compound 66)

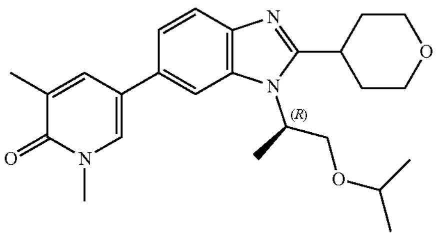

Step 1: Preparation of (R)-5-bromo-N-(1-isopropoxypropan-2-yl)-2-nitroaniline

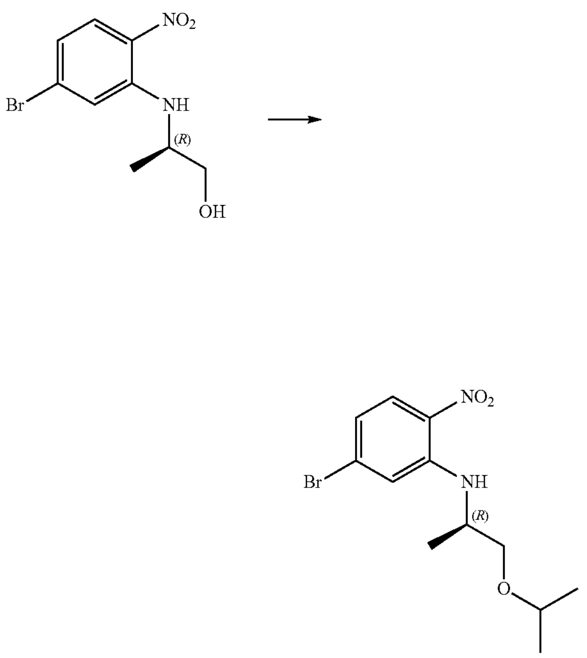

A solution of (R)-2-((5-bromo-2-nitrophenyl)amino)propan-1-ol (Example 42, Step 1, 0.55 g, 2.15 mmol) in DMF (10 mL) was stirred for 10 min at 0° C. NaH 60% in mineral oil (0.30 g, 3.21 mmol) was added and the reaction mixture was stirred for 15 min at the same temperature. 2-Iodopropane (0.50 g, 3.21 mmol) was added at 0° C. and the reaction mixture was heated at 70° C. for 24 h. The resulting mixture was then diluted with water (100 mL) and extracted with EtOAc (100 mL×3). The combined organic layers were washed with brine (30 mL), dried over anhydrous $Na_2SO_4$, filtered and concentrated under reduced pressure. The crude material was purified by silica gel chromatography using a gradient of 10-30% EtOAc in hexanes as eluent. Product fractions were combined and evaporated to dryness to afford the title compound (0.14 g, 19%) as a solid. $[M+H]^+$ 317.1, 319.12.

Step 2: Preparation of (R)-5-(3-((1-isopropoxypropan-2-yl)amino)-4-nitrophenyl)-1,3-dimethyl pyridin-2(1H)-one

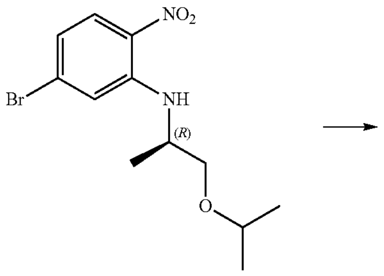

-continued

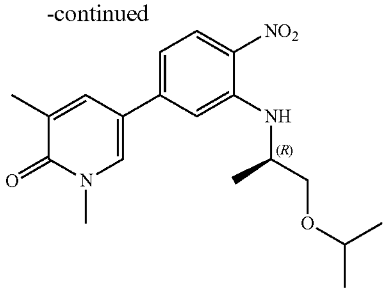

A stirred solution of (R)-5-bromo-N-(1-isopropoxypropan-2-yl)-2-nitroaniline (0.14 g, 0.44 mmol) and 1,3-dimethyl-5-(4,4,5,5-tetramethyl-1,3,2-dioxaborolan-2-yl)pyridin-2 (1H)-one (0.14 g, 0.57 mmol) in DME (5 mL) was purged with nitrogen for 20 min, followed by the addition of $Cs_2CO_3$ (0.42 g, 1.32 mmol) in water (0.3 mL) and purging with nitrogen for another 20 min. $Pd(PPh_3)_4$ (0.025 g, 0.022 mmol) was then added at rt and the reaction mixture was heated at 90° C. for 16 h. The resulting mixture was diluted with water (30 mL) and extracted with EtOAc (30 mL×3). The combined organic layers were washed with brine (30 mL), dried over anhydrous $Na_2SO_4$, filtered and concentrated under reduced pressure. The crude material was purified by silica gel chromatography using 3-5% MeOH in DCM as eluent. Product fractions were combined and evaporated to dryness to afford the title compound (0.16 g, 91%) as a solid. $[M+H]^+$ 360.31.

Step 3: Preparation of (R)-5-(4-amino-3-((1-isopropoxypropan-2-yl)amino)phenyl)-1,3-dimethyl pyridin-2(1H)-one

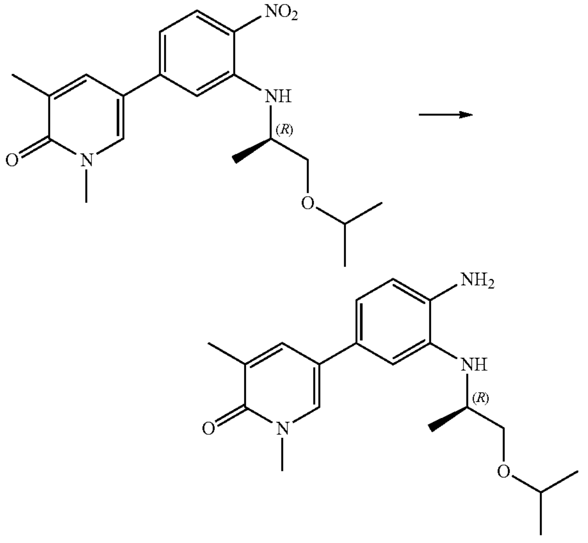

Sodium dithionite (0.68 g, 5.28 mmol) was added to a rt suspension of (R)-5-(3-((1-isopropoxypropan-2-yl)amino)-4-nitrophenyl)-1,3-dimethylpyridin-2 (1H)-one (0.16 g, 0.44 mmol) in MeOH (5 mL) and water (2 mL) and the reaction mixture was heated at 50° C. for 1 h. The resulting mixture was diluted with water (50 mL) and extracted with DCM (50 mL×3). The combined DCM layers were washed with brine (50 mL), dried over anhydrous $Na_2SO_4$, filtered and concentrated under reduced pressure to afford the title compound (0.14 g, 90%) as a solid. $[M+H]^+$ 330.33.

Step 4: Preparation of Compound 66

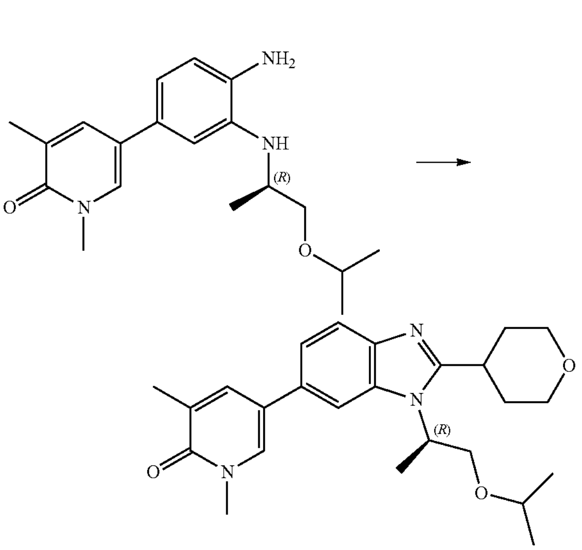

Tetrahydro-2H-pyran-4-carbaldehyde (0.062 g, 0.54 mmol) was added to a rt stirred solution of (R)-5-(4-amino-3-((1-isopropoxypropan-2-yl)amino)phenyl)-1,3-dimethylpyridin-2 (1H)-one (0.15 g, 0.45 mmol) in acetic acid (4 mL) and the reaction mixture was stirred for 48 h at the same temperature. The resulting mixture was concentrated under reduced pressure, diluted with saturated aqueous $NaHCO_3$ (50 mL) and extracted with EtOAc (50 mL×3). The combined organic layers were washed with brine (50 mL), dried over anhydrous $Na_2SO_4$, filtered and concentrated under reduced pressure. The crude material was purified by silica gel chromatography using 1-3% MeOH in DCM as eluent. Product fractions were combined and evaporated to dryness to afford Compound 66 (0.075 g, 41%) as a solid. $^1H$ NMR (400 MHz, CDC13) δ ppm 7.79 (d, J=8.4 Hz, 1H), 7.54 (s, 1H), 7.46 (d, J=0.8 Hz, 1H), 7.38 (d, J=2.4 Hz, 1H), 7.26 (d, J=1.6 Hz, 1H), 4.74-4.69 (m, 1H), 4.16-4.12 (m, 2H), 3.94-3.90 (m, 1H), 3.85-3.82 (m, 1H), 3.67 (s, 3H), 3.64-3.58 (m, 2H), 3.48-3.42 (m, 1H), 3.22-3.15 (m, 1H), 2.27 (s, 3H), 2.24-2.20 (m, 2H), 2.04-2.00 (m, 1H), 1.88-1.84 (m, 1H), 1.73 (d, J=7.2 Hz, 3H), 1.11 (d, J=6 Hz, 3H), 0.94, (d, J=6 Hz, 3H). $[M+H]^+$ 424.39.

Example 60: (S)-5-(1-(2-isopropoxypropyl)-2-(tetrahydro-2H-pyran-4-yl)-1H-benzo[d]imidazol-6-yl)-1,3-dimethylpyridin-2(1H)-one (Compound 67)

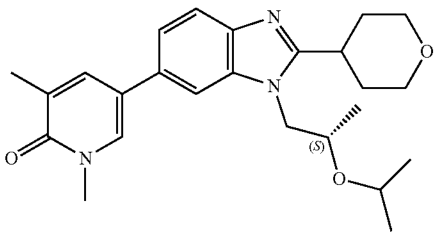

Step 1: Preparation of tert-butyl (S)-(2-isopropoxypropyl)carbamate

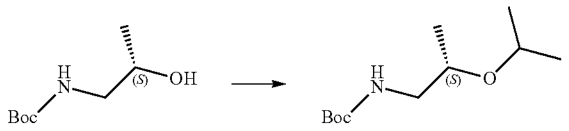

A stirred solution of tert-butyl (S)-(2-hydroxypropyl)carbamate (1 g, 5.71 mmol), 2-iodopropane (1.93 g, 11.42 mmol) and $Cs_2CO_3$ (5.56 g, 17.13 mmol) in DMSO (25 mL) was stirred and heated at 100° C. for 24 h. The resulting mixture was diluted with water (100 mL) and extracted with EtOAc (100 mL×3). The combined organic layers were washed with brine (30 mL), dried over anhydrous $Na_2SO_4$, filtered and concentrated under reduced pressure. The crude material was purified by silica gel chromatography using a gradient of 10-30% EtOAc in hexane as eluent. Product fractions were combined and evaporated to dryness to afford the title compound (0.26 g, 21%) as a solid. $[M+H]^+$ 219.12.

Step 2: Preparation of (S)-2-isopropoxypropan-1-amine

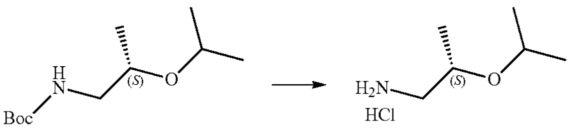

A solution of tert-butyl (S)-(2-isopropoxypropyl)carbamate (0.12 g) in 4 M HCl in dioxane (2 mL) was stirred for 2 h at 0° C. Excess solvent was then evaporated to afford the title compound (0.13 g, 92%) as a solid, which was used as such in the next step without further purification.

Step 3: Preparation of (S)-5-bromo-N-(2-isopropoxypropyl)-2-nitroaniline

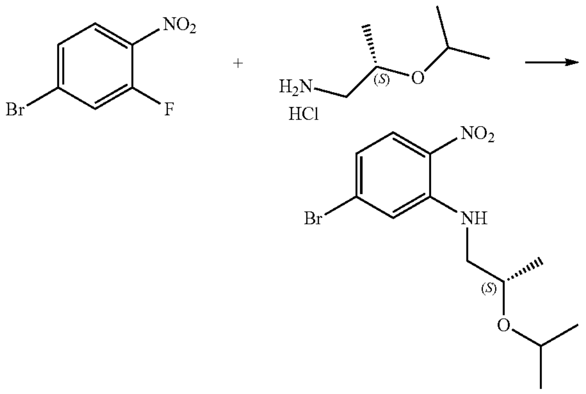

TEA (0.2 mL, 0.95 mmol) was added to a stirred solution of 4-bromo-2-fluoro-1-nitrobenzene (0.16 g, 0.72 mmol) and (S)-2-isopropoxypropan-1-amine hydrochloride (0.13 g, 0.87 mmol) in ethanol (4 mL) and the reaction mixture was heated at 70° C. for 8 h. The resulting mixture was diluted with water (50 mL) and extracted with EtOAc (50 mL×3). The combined organic layers were washed with brine (20 mL), dried over anhydrous $Na_2SO_4$, filtered and concentrated under reduced pressure. The crude material was purified by silica gel chromatography using a gradient of 10-30% EtOAc in hexanes as eluent. Product fractions were combined and evaporated to dryness to afford the title compound (0.24 g, 77%) as a solid. $[M+H]^{+2}$ 319.12.

Step 4: Preparation of (S)-5-(3-((2-isopropoxypropyl)amino)-4-nitrophenyl)-1,3-dimethylpyridin-2 (1H)-one

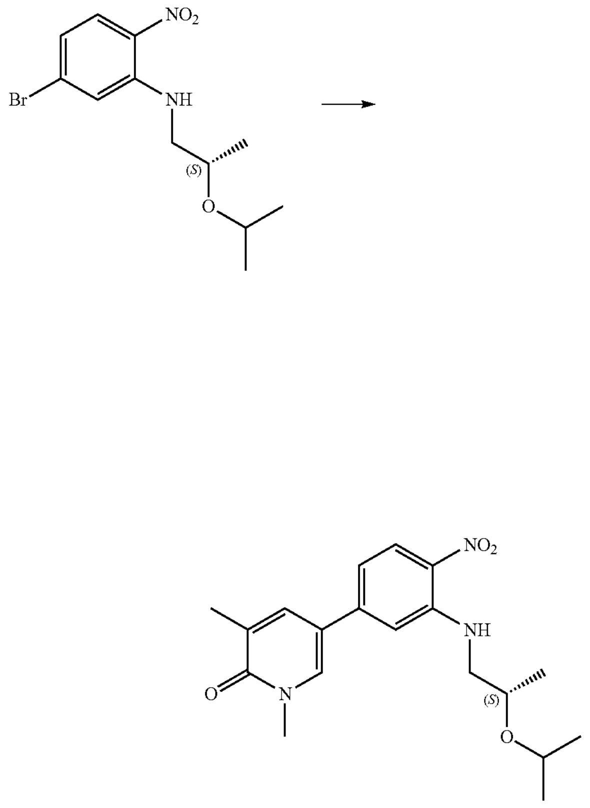

A stirred solution of (S)-5-bromo-N-(2-isopropoxypropyl)-2-nitroaniline (0.24 g, 0.75 mmol) and 1,3-dimethyl-5-(4,4,5,5-tetramethyl-1,3,2-dioxaborolan-2-yl)pyridin-2 (1H)-one (0.24 g, 0.98 mmol) in DME (4 mL) was purged with nitrogen for 20 min, followed by the addition of $Cs_2CO_3$ (0.73 g, 2.27 mmol) in water (0.4 mL) and purging with nitrogen for another 20 min. $Pd(PPh_3)_4$ (0.045 g, 0.037 mmol) was then added and the reaction mixture was heated at 90° C. for 16 h. The resulting mixture was diluted with water (30 mL) and extracted with EtOAc (30 mL×3). The combined organic layers were washed with brine (30 mL), dried over anhydrous $Na_2SO_4$, filtered and concentrated under reduced pressure. The crude material was purified by silica gel chromatography using 3-5% MeOH in DCM as eluent. Product fractions were combined and evaporated to dryness to give the title compound (0.16 g, 48%) as a solid. $[M+H]^+$ 360.31.

Step 5: Preparation of (S)-5-(4-amino-3-((2-isopropoxypropyl)amino)phenyl)-1,3-dimethyl pyridin-2(1H)-one

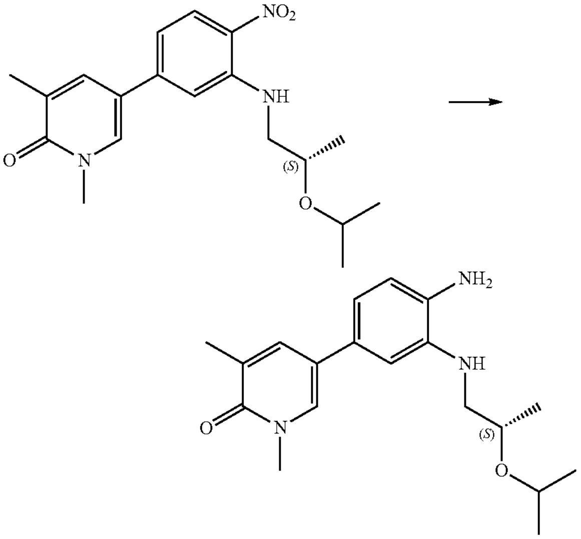

Sodium dithionite (0.68 g, 5.28 mmol) was added to a rt stirred suspension of (S)-5-(3-((2-isopropoxypropyl) amino)-4-nitrophenyl)-1,3-dimethylpyridin-2 (1H)-one (0.16 g, 0.44 mmol) in MeOH (5 mL) and water (2 mL) and the reaction mixture was heated at 50° C. for 1 h. The reaction mixture was then diluted with water (50 mL) and extracted with DCM (50 mL×3). The combined DCM layers were washed with brine (20 mL), dried over anhydrous $Na_2SO_4$, filtered and concentrated under reduced pressure to afford the title compound (0.14 g, 41%) as a solid. $[M+H]^+$ 330.28.

Step 6: Preparation of Compound 67

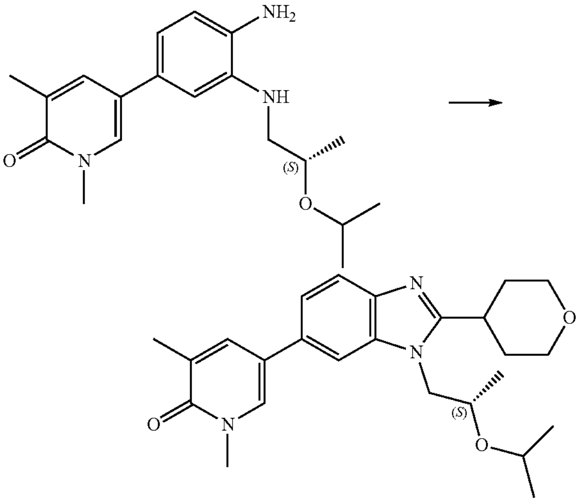

Tetrahydro-2H-pyran-4-carbaldehyde (0.062 g, 0.54 mmol) was added to a stirred rt solution of (S)-5-(4-amino-3-((2-isopropoxypropyl)amino)phenyl)-1,3-dimethylpyridin-2 (1H)-one (0.15 g, 0.45 mmol) in acetic acid (4 mL) and the reaction mixture was stirred for 48 h. The resulting mixture was then evaporated, diluted with saturated aqueous $NaHCO_3$ (50 mL), and extracted with EtOAc (50 mL×3). The combined organic layers were washed with brine (20 mL), dried over anhydrous $Na_2SO_4$, filtered and concentrated under reduced pressure. The crude material was purified by silica gel chromatography using 1-3% MeOH in DCM. Product fractions were combined and evaporated to dryness in vacuo to afford Compound 67 (0.035 g, 39%) as a solid. $^1H$ NMR (400 MHz, $CDCl_3$) δ ppm 7.77 (dd, J=2 and 2.4 Hz, 1H), 7.58 (d, J=1.2 Hz, 1H), 7.42 (d, J=2.4 Hz, 1H), 7.31 (d, J=2.4 Hz, 1H), 7.30 (d, J=1.6 Hz, 1H), 4.20-4.66 (m, 1H), 4.14-4.10 (m, 3H), 3.89-3.84 (m, 1H), 3.67 (s, 3H), 3.65-3.58 (m, 2H), 3.38-3.31 (m, 2H), 2.39-2.31 (m, 1H), 2.27 (s, 3H), 2.13-2.03 (m, 1H), 1.98-1.94 (m, 1H), 1.85-1.82 (m, 1H), 1.32 (d, J=5.2 Hz, 3H), 1.06 (d, J=6.4 Hz, 3H), 0.61, (d, J=6 Hz, 3H).

Example 61: Biological Activity a) In Vitro Bromodomain Inhibition Assay

To measure activity of bromodomain inhibitors, a His-epitope tagged BRD4 BD149-170 is purchased from BPS Bioscience. BRD4 binding and inhibition is assessed by monitoring the engagement of biotinylated H4-tetraacetyl peptide (H4K5/8/12/16; AnaSpec #64989-025) with the target using the AlphaLISA technology (Perkin-Elmer). Specifically, in a 384 well OptiPlate, BRD4 (BD1) (200 nM final) is pre-incubated with either DMSO (final 1.0% DMSO) or a compound dilution series in DMSO. All reagents are diluted in assay buffer containing 50 mM HEPES (pH 7.4), 100 mM NaCl, 0.1% (w/v) BSA, and 0.05% (w/v) CHAPS. After a 30 minute incubation at rt, H4 peptide is added (200 nM final) and the reaction is incubated an additional 30 minutes at rt. Alpha streptavidin donor beads and AlphaLISA nickel chelate acceptor beads are then added to a final concentration of 10 μg/mL each. After one hour, equilibration plates are read on an Envision instrument and $IC_{50}$s calculated using a four parameter non-linear curve fit (results are shown in Table 1).

b) Transcription of Human C-Myc in Human Leukemic MV-4-11 Cells:

The effect of compounds on transcription of human C-Myc gene is monitored in human B-myelomonocytic leukemia cell line MV-4-11 (from American Type Culture Collection (ATCC), Manassas, Virginia, USA) using QuantiGene 2.0 assay kit (Affymetrix, Santa Clara, California, USA).

Typically, 8,000 MV-4-11 cells are plated in sterile 96-well plates (Costar #3598 from Fisher Scientific Canada, Ottawa, Ontario, Canada) in Iscove's medium supplemented with 10% fetal bovine serum, glutamine (2 mM), and penicillin (100 I.U.) and streptomycin (100 μg/mL) (all from Wisent Inc., St. Bruno, Quebec, Canada). Compounds are dissolved in DMSO at 30 mM. A series of 1:3 dilutions are first made in DMSO, and further 1:100 dilutions are made in serum-containing cell culture media. The final concentration of DMSO is 0.1% in cell culture media. After cells are treated with various concentrations of test compound for 4 hours, cells are lysed using Quantigene 2.0 sample processing kit (#QS0100). C-Myc mRNA is detected using a QuantiGene 2.0 assay kit (#QS0009) with gene-specific probe to human C-Myc (#SA-50182) following the manufacturer's recommendations. Luminescene signals are read on Flexstation II microplate reader (Molecular Devices, Sunnyvale, California, USA). Percentage of inhibition of C-Myc transcription is analyzed using EXCEL (2010 version) (results shown in Table 1).

TABLE 1

| Compound No | $IC_{50}$ BRD4 (μM) | $IC_{50}$ MV-4-11 Cell (μM) |
|---|---|---|
| 1 | 0.14 | 0.076 |
| 2 | 0.19 | 0.086 |
| 3 | 0.31 | 0.095 |
| 4 | 0.13 | 0.089 |
| 5 | 0.19 | 0.23 |
| 6 | 0.091 | 0.056 |
| 7 | 0.28 | 0.52 |
| 8 | 0.21 | 0.79 |
| 9 | 0.22 | 0.25 |
| 10 | 0.099 | 0.062 |
| 11 | 0.098 | 0.17 |
| 12 | 0.33 | 0.55 |
| 13 | 0.81 | 0.85 |
| 14 | N/A | 0.25 |
| 15 | 0.10 | 0.24 |
| 17 | N/A | 0.81 |
| 18 | N/A | 0.17 |
| 19 | N/A | 0.87 |
| 20 | N/A | 0.24 |
| 21a | N/A | 0.51 |
| 21b | N/A | 0.59 |
| 22a | N/A | 0.84 |
| 22b | N/A | 0.78 |
| 23a | N/A | 0.25 |
| 23b | N/A | 0.73 |
| 26 | N/A | 0.23 |
| 27 | N/A | 0.092 |
| 28a | N/A | 0.050 |
| 28b | N/A | 0.050 |
| 29a | N/A | 0.22 |
| 29b | N/A | 0.077 |
| 30a | N/A | 0.20 |
| 30b | N/A | 0.087 |
| 31 | N/A | 0.024 |
| 34 | N/A | 0.22 |
| 35a | N/A | 0.18 |
| 35b | N/A | 0.086 |
| 36 | N/A | 0.053 |
| 37 | N/A | 0.49 |
| 38 | N/A | 0.24 |
| 39 | N/A | 0.084 |
| 40 | N/A | 0.027 |
| 41 | N/A | 0.023 |
| 42 | N/A | 0.17 |
| 43 | N/A | 0.027 |
| 44 | N/A | 0.098 |
| 45 | N/A | 0.16 |
| 46a | N/A | 0.22 |
| 46b | N/A | 0.25 |
| 47 | N/A | 0.027 |
| 48 | N/A | 0.26 |
| 49 | N/A | 0.022 |
| 50 | N/A | 0.16 |
| 51 | N/A | 0.062 |
| 52 | N/A | 0.051 |
| 53 | N/A | 0.076 |
| 54 | N/A | 0.17 |
| 55 | N/A | 0.053 |
| 56 | N/A | 0.22 |
| 57 | N/A | 0.072 |
| 58 | N/A | 0.16 |
| 59 | N/A | 0.090 |
| 60 | N/A | 0.017 |
| 61 | N/A | 0.084 |
| 62 | N/A | 0.021 |
| 63 | N/A | 0.017 |
| 64 | N/A | 0.051 |
| 65 | N/A | 0.025 |
| 66 | N/A | 0.018 |
| 67 | N/A | 0.026 |

N/A: not available

Although the invention has been illustrated and described with respect to one or more implementations, equivalent alterations and modifications will occur to others skilled in the art upon the reading and understanding of this specification. In addition, while a particular feature of the invention may have been disclosed with respect to only one of several implementations, such feature may be combined with one or more other features of the other implementations as may be desired and advantageous for any given or particular application.

Accordingly, it is understood that the examples and embodiments described herein are for illustrative purposes only and that various modifications or changes in light thereof will be suggested to persons skilled in the art and are to be included within the spirit and purview of this application and scope of the appended claims. Any publication, document, patent, patent application or publication referred to herein should be construed as incorporated by reference each in their entirety for all purposes.

The invention claimed is:

1. A method of treating a bromodomain-containing protein-mediated disorder in a subject in need thereof, the method comprising administering to the subject a therapeutically effective amount of a compound of Formula I:

Formula I

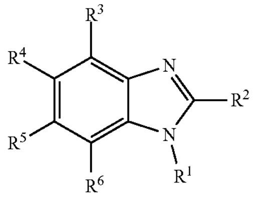

wherein, $R^1$ is:

a) an unsubstituted $C_1$-$C_6$alkyl;

b) a $C_1$-$C_6$alkyl substituted with one or more group(s) selected from halogen, CN, $NO_2$, $C(O)NHR^{11}$, $C(O)N(R^{11})_2$, $CO_2H$, $SO_2R^{11}$, $SO_2NHR^{11}$, and $SO_2N(R^{11})_2$;

c) a $C_2$-$C_6$alkyl group substituted with a group selected from $OR^{11}$, halogenated $OC_1$-$C_6$alkyl, SH, $SR^{11}$, $NH_2$, $NHR^{11}$, $N(R^{11})_2$, $NHC(O)R^{11}$, and $N(R^{11})C(O)R^{11}$; or d) a group selected from $C(O)R^{11}$, $C(O)\ NHR^{11}$, $C(O)N(R^{11})_2$, $SO_2R^{11}$, $SO_2NHR^{11}$, and $SO_2N(R^{11})_2$;

$R^2$ is selected from hydrogen and a substituted or unsubstituted group selected from $C_1$-$C_6$alkyl, $C_2$-$C_6$alkenyl, $C_2$-$C_6$alkynyl, $C_3$-$C_{10}$cycloalkyl, $C_3$-$C_{10}$heterocycloalkyl, $C(O)R^{12}$, $NH_2$, $NHR^{12}$, $N(R^{12})_2$, $C(O)NH_2$, $C(O)NHR^{12}$, $C(O)N(R^{12})_2$, $NHC(O)R^{12}$, $SO_2R^{12}$, $SO_2NHR^{12}$, $SO_2N(R^{12})_2$, $NHSO_2R^{12}$, $N(R^{12})SO_2R^{12}$, $NHSO_2NHR^{12}$, $N(R^{12})SO_2NHR^{12}$, $NHSO_2N(R^{12})_2$, and $N(R^{12})SO_2N(R^{12})_2$;

$R^3$ and $R^6$ are each independently hydrogen or a substituted or unsubstituted group selected from $C_1$-$C_6$alkyl, $C(O)R^{11}$, $NH_2$, $NHR^{11}$, $N(R^{11})_2$, $C(O)NH_2$, $C(O)NHR^{11}$, $C(O)N(R^{11})_2$, $NHC(O)R^{11}$;

$R^4$ is a selected from hydrogen or a substituted or unsubstituted group selected from $C_1$-$C_6$alkyl, $C(O)R^{11}$, $NH_2$, $NHR^{11}$, $N(R^{11})_2$, $C(O)NH_2$, $C(O)NHR^{11}$, $C(O)N(R^{11})_2$, and $NHC(O)R^{11}$;

$R^5$ is a group of Formula II:

Formula II

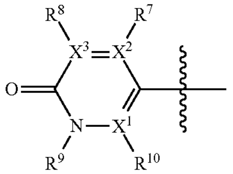

wherein, $R^7$, $R^8$, and $R^{10}$ are each independently selected from hydrogen, halogen, CN, a substituted or unsubstituted $C_1$-$C_6$alkyl or $C_3$-$C_6$cycloalkyl group, $OR^{11}$, $SR^{11}$, $NHR^{11}$, $N(R^{11})_2$, $NHC(O)R^{11}$, and $N(R^{11})C(O)R^{11}$, provided that at least one of $R^7$, $R^8$, and $R^{10}$ is not hydrogen;

$R^9$ is a substituted or unsubstituted $C_1$-$C_3$alkyl or $C_3$-$C_5$cycloalkyl group;

$R^{11}$ is, independently in each occurrence, a substituted or unsubstituted $C_1$-$C_6$alkyl group;

$R^{12}$ is, independently in each occurrence, a substituted or unsubstituted $C_1$-$C_6$alkyl, $C_2$-$C_6$alkenyl, $C_2$-$C_6$alkynyl, $C_3$-$C_{10}$cycloalkyl, and $C_3$-$C_{10}$heterocycloalkyl;

$X^1$, $X^2$, and $X^3$ are each selected from N or C, wherein when $X^1$, $X^2$, or $X^3$ is N, then the $R^7$, $R^8$, or $R^{10}$ attached thereto is absent, provided that at least two of $X^1$, $X^2$, and $X^3$ is C;

wherein each alkyl is a linear or branched acyclic alkyl group, wherein the bromodomain-containing protein-mediated disorder is a hematopoietic neoplasm.

2. The method of claim 1, wherein $R^4$ is selected from hydrogen and substituted or unsubstituted $C_1$-$C_3$alkyl.

3. The method of claim 1, wherein $X^1$, $X^2$, and $X^3$ are all carbon atoms.

4. The method of claim 1, wherein $R^9$ is an unsubstituted $C_1$-$C_3$alkyl or $C_3$-$C_5$cycloalkyl group.

5. The method of claim 4, wherein $R^9$ is selected from methyl, ethyl, n-propyl, isopropyl, and cyclopropyl.

6. The method of claim 1, wherein $R^7$ and $R^{10}$ are each hydrogen; and $R^8$ is selected from methyl, CN, $NHR^{11}$ and a substituted or unsubstituted $C_1$-$C_6$alkyl or $C_3$-$C_6$cycloalkyl group.

7. The method of claim 1, wherein $R^3$ is hydrogen.

8. The method of claim 1, wherein $R^6$ is hydrogen.

9. The method of claim 1, wherein $R^2$ is a substituted or unsubstituted $C_1$-$C_3$alkyl, $C_3$-$C_6$cycloalkyl, or $C_3$-$C_6$heterocycloalkyl group.

10. The method of claim 1, wherein $R^1$ is a branched or linear $C_2$-$C_3$alkyl substituted with a group selected from fluorine, $OC_1$-$C_6$alkyl, and halogenated $OC_1$-$C_6$alkyl.

11. The method of claim 1, wherein $R^1$ is 2-(trifluoromethoxy) ethyl.

12. The method of claim 1, wherein the compound is:

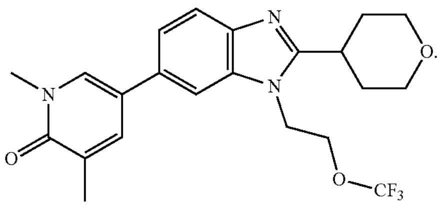 [SMILES: Cc1cc(-c2ccc3nc(C4CCOCC4)n(CCOC(F)(F)F)c3c2)cn(C)c1=O]

13. A method of inhibiting activity of a bromodomain-containing protein in a subject in need thereof, the method comprising contacting the bromodomain-containing protein with a compound of Formula I:

Formula I

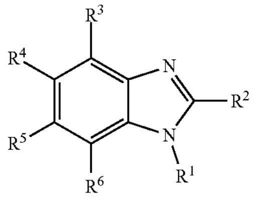

wherein, $R^1$ is:

a) an unsubstituted $C_1$-$C_6$alkyl;

b) a $C_1$-$C_6$alkyl substituted with one or more group(s) selected from halogen, CN, $NO_2$, C(O) $NHR^{11}$, $C(O)N(R^{11})_2$, $CO_2H$, $SO_2R^{11}$, $SO_2NHR^{11}$, and $SO_2N(R^{11})_2$;

c) a $C_2$-$C_6$alkyl group substituted with a group selected from $OR^{11}$, halogenated $OC_1$-$C_6$alkyl, SH, $SR^{11}$, $NH_2$, $NHR^{11}$, $N(R^{11})_2$, $NHC(O)R^{11}$, and $N(R^{11})$ $C(O)R^{11}$; or d) a group selected from $C(O)R^{11}$, C(O) $NHR^{11}$, C(O) $N(R^{11})_2$, $SO_2R^{11}$, $SO_2NHR^{11}$, and $SO_2N(R^{11})_2$;

$R^2$ is selected from hydrogen and a substituted or unsubstituted group selected from $C_1$-$C_6$alkyl, $C_2$-$C_6$alkenyl, $C_2$-$C_6$alkynyl, $C_3$-$C_{10}$cycloalkyl, $C_3$-$C_{10}$heterocycloalkyl, $C(O)R^{12}$, $NH_2$, $NHR^{12}$, $N(R^{12})_2$, $C(O)NH_2$, C(O) $NHR^{12}$, $C(O)N(R^{12})_2$, NHC (O)$R^{12}$, $SO_2R^{12}$, $SO_2NHR^{12}$, $SO_2N(R^{12})_2$, $NHSO_2R^{12}$, $N(R^{12})$ $SO_2R^{12}$, $NHSO_2NHR^{12}$, $N(R^{12})$ $SO_2NHR^{12}$, $NHSO_2N(R^{12})_2$, and $N(R^{12})$ $SO_2N(R^{12})_2$;

$R^3$ and $R^6$ are each independently hydrogen or a substituted or unsubstituted group selected from $C_1$-$C_6$alkyl, $C(O)R^{11}$, $NH_2$, $NHR^{11}$, $N(R^{11})_2$, C(O) $NH_2$, C(O) $NHR^{11}$, $C(O)N(R^{11})_2$, $NHC(O)R^{11}$;

$R^4$ is a selected from hydrogen or a substituted or unsubstituted group selected from $C_1$-$C_6$alkyl, $C(O)R^{11}$, $NH_2$, $NHR^{11}$, $N(R^{11})_2$, C(O) $NH_2$, C(O) $NHR^{11}$, C(O) $N(R^{11})_2$, and $NHC(O)R^{11}$;

$R^5$ is a group of Formula II:

Formula II

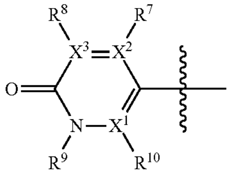

wherein, $R^7$, $R^8$, and $R^{10}$ are each independently selected from hydrogen, halogen, CN, a substituted or unsubstituted $C_1$-$C_6$alkyl or $C_3$-$C_6$cycloalkyl group, $OR^{11}$, $SR^{11}$, $NHR^{11}$, $N(R^{11})_2$, $NHC(O)R^{11}$, and $N(R^{11})$ $C(O)R^{11}$, provided that at least one of $R^7$, $R^8$, and $R^{10}$ is not hydrogen;

$R^9$ is a substituted or unsubstituted $C_1$-$C_3$alkyl or $C_3$-$C_5$cycloalkyl group;

$R^{11}$ is, independently in each occurrence, a substituted or unsubstituted $C_1$-$C_6$alkyl group;

$R^{12}$ is, independently in each occurrence, a substituted or unsubstituted $C_1$-$C_6$alkyl, $C_2$-$C_6$alkenyl, $C_2$-$C_6$alkynyl, $C_3$-$C_{10}$cycloalkyl, and $C_3$-$C_{10}$heterocycloalkyl;

$X^1$, $X^2$, and $X^3$ are each selected from N or C, wherein when $X^1$, $X^2$, or $X^3$ is N, then the $R^7$, $R^8$, or $R^{10}$ attached thereto is absent, provided that at least two of $X^1$, $X^2$, and $X^3$ is C;

wherein each alkyl is a linear or branched acyclic alkyl group.

14. The method of claim 13, wherein $X^1$, $X^2$, and $X^3$ are all carbon atoms.

15. The method of claim 13, wherein $R^1$ is a branched or linear $C_2$-$C_3$alkyl substituted with a group selected from fluorine, $OC_1$-$C_6$alkyl, and halogenated $OC_1$-$C_6$alkyl.

16. The method of claim 13, wherein the compound is:

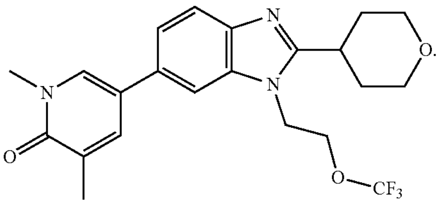 [SMILES: Cc1cc(-c2ccc3nc(C4CCOCC4)n(CCOC(F)(F)F)c3c2)cn(C)c1=O]

* * * * *